US010280219B2

(12) United States Patent
Bedian et al.

(10) Patent No.: US 10,280,219 B2
(45) Date of Patent: May 7, 2019

(54) ANTIBODIES TO M-CSF

(71) Applicants: Amgen Fremont Inc., Thousand Oaks, CA (US); Warner-Lambert Company LLC, Morris Plains, NJ (US)

(72) Inventors: Vahe Bedian, East Lyme, CT (US); Madhav Narasimha Devalaraja, Ann Arbor, MI (US); Ian Foltz, Burnaby (CA); Mary Haak-Frendscho, San Francisco, CA (US); Sirid-Aimee Kellermann, Menlo Park, CA (US); Joseph Edwin Low, Ann Arbor, MI (US); James Leslie Mobley, Brighton, MI (US)

(73) Assignees: AMGEN FREMONT INC., Thousand Oaks, CA (US); WARNER-LAMBERT COMPANY LLC, Morris Plains, NJ (US)

( * ) Notice: Subject to any disclaimer, the term of this patent is extended or adjusted under 35 U.S.C. 154(b) by 0 days.

(21) Appl. No.: 15/614,237

(22) Filed: Jun. 5, 2017

(65) Prior Publication Data
US 2017/0275354 A1 Sep. 28, 2017

Related U.S. Application Data

(60) Division of application No. 14/923,655, filed on Oct. 27, 2015, now Pat. No. 9,718,883, which is a division of application No. 13/458,820, filed on Apr. 27, 2012, now abandoned, which is a continuation of application No. 12/748,602, filed on Mar. 29, 2010, now Pat. No. 8,188,249, which is a continuation of application No. 11/894,560, filed on Aug. 20, 2007, now Pat. No. 7,728,113, which is a continuation of application No. 11/375,221, filed on Mar. 13, 2006, now Pat. No. 7,326,414, which is a continuation of application No. 10/938,353, filed on Sep. 9, 2004, now Pat. No. 7,592,430.

(60) Provisional application No. 60/502,163, filed on Sep. 10, 2003.

(51) Int. Cl.
| | |
|---|---|
| *A61K 39/00* | (2006.01) |
| *A61K 39/395* | (2006.01) |
| *A61K 38/19* | (2006.01) |
| *C07K 16/24* | (2006.01) |
| *G06Q 30/02* | (2012.01) |
| *G06Q 30/06* | (2012.01) |
| *G06Q 40/04* | (2012.01) |
| *G06Q 50/12* | (2012.01) |

(52) U.S. Cl.
CPC .......... *C07K 16/243* (2013.01); *A61K 38/193* (2013.01); *A61K 39/395* (2013.01); *C07K 16/24* (2013.01); *G06Q 30/02* (2013.01); *G06Q 30/0601* (2013.01); *G06Q 40/04* (2013.01); *G06Q 50/12* (2013.01); *A61K 2039/505* (2013.01); *C07K 2317/14* (2013.01); *C07K 2317/21* (2013.01); *C07K 2317/56* (2013.01); *C07K 2317/565* (2013.01); *C07K 2317/73* (2013.01); *C07K 2317/76* (2013.01); *C07K 2317/92* (2013.01); *Y02A 50/412* (2018.01)

(58) Field of Classification Search
CPC ............ A61K 39/395; A61K 2039/505; C07K 16/24; C07K 16/243; C07K 2317/14; C07K 2317/21; C07K 2317/56; C07K 2317/73; C07K 2317/76; C07K 2317/92; C07K 2317/565
See application file for complete search history.

(56) References Cited

U.S. PATENT DOCUMENTS

| | | |
|---|---|---|
| 4,399,216 A | 8/1983 | Axel |
| 4,504,586 A | 3/1985 | Nicolson |
| 4,510,245 A | 4/1985 | Cousens |

(Continued)

FOREIGN PATENT DOCUMENTS

| | | |
|---|---|---|
| EP | 016846 | 4/1987 |
| EP | 0323997 | 7/1989 |

(Continued)

OTHER PUBLICATIONS

Aalberse et al., "IgG4 breaking the rules," Immunology, 105:9-19 (2002).

(Continued)

*Primary Examiner* — Robert S Landsman
*Assistant Examiner* — Bruce D. Hissong
(74) *Attorney, Agent, or Firm* — Haley Guiliano LLP; James F. Haley, Jr.; Brian M. Gummow

(57) ABSTRACT

The present invention relates to antibodies and antigen-binding portions thereof that specifically bind to a M-CSF, preferably human M-CSF, and that function to inhibit a M-CSF. The invention also relates to human anti-M-CSF antibodies and antigen-binding portions thereof. The invention also relates to antibodies that are chimeric, bispecific, derivatized, single chain antibodies or portions of fusion proteins. The invention also relates to isolated heavy and light chain immunoglobulins derived from human anti-M-CSF antibodies and nucleic acid molecules encoding such immunoglobulins. The present invention also relates to methods of making human anti-M-CSF antibodies, compositions comprising these antibodies and methods of using the antibodies and compositions for diagnosis and treatment. The invention also provides gene therapy methods using nucleic acid molecules encoding the heavy and/or light immunoglobulin molecules that comprise the human anti-M-CSF antibodies. The invention also relates to transgenic animals and transgenic plants comprising nucleic acid molecules of the present invention.

12 Claims, 23 Drawing Sheets
Specification includes a Sequence Listing.

(56) References Cited

U.S. PATENT DOCUMENTS

| | | |
|---|---|---|
| 4,634,665 A | 1/1987 | Axel |
| 4,740,461 A | 4/1988 | Kaufman |
| 4,847,201 A | 7/1989 | Kaswasaki |
| 4,868,119 A | 9/1989 | Clark |
| 4,912,040 A | 3/1990 | Kaufman |
| 4,929,700 A | 5/1990 | Halenbeck |
| 4,959,455 A | 9/1990 | Clark |
| 4,968,615 A | 11/1990 | Koszinowki |
| 5,151,510 A | 9/1992 | Stec |
| 5,168,062 A | 12/1992 | Stinski |
| 5,179,017 A | 1/1993 | Axel |
| 5,223,409 A | 6/1993 | Ladner |
| 5,470,569 A | 11/1995 | Kawasaki |
| 5,470,578 A | 11/1995 | Aoki |
| 5,491,065 A | 2/1996 | Halenbeck |
| 5,545,806 A | 8/1996 | Lonberg |
| 5,545,807 A | 8/1996 | Surani |
| 5,569,825 A | 10/1996 | Lonberg |
| 5,573,763 A | 11/1996 | Clark |
| 5,587,458 A | 12/1996 | King |
| 5,591,669 A | 1/1997 | Krimpenfort |
| 5,612,205 A | 3/1997 | Kay |
| 5,625,126 A | 4/1997 | Lonberg |
| 5,633,425 A | 5/1997 | Lonberg |
| 5,643,563 A | 7/1997 | Ladner |
| 5,643,763 A | 7/1997 | Dunn |
| 5,661,016 A | 8/1997 | Lonberg |
| 5,681,719 A | 10/1997 | Ladner |
| 5,721,367 A | 2/1998 | Kay |
| 5,741,957 A | 4/1998 | Deboer |
| 5,747,498 A | 5/1998 | Schnur |
| 5,750,172 A | 5/1998 | Meade |
| 5,756,687 A | 5/1998 | Denman |
| 5,770,429 A | 6/1998 | Lonberg |
| 5,789,215 A | 8/1998 | Berns |
| 5,789,650 A | 8/1998 | Lonberg |
| 5,792,450 A | 8/1998 | Wilson |
| 5,792,783 A | 8/1998 | Tang |
| 5,814,318 A | 9/1998 | Lonberg |
| 5,827,690 A | 10/1998 | Meade |
| 5,834,504 A | 11/1998 | Tang |
| 5,837,229 A | 11/1998 | Ralph |
| 5,837,460 A | 11/1998 | Von Feldt |
| 5,861,510 A | 1/1999 | Piscopio |
| 5,863,949 A | 1/1999 | Robinson |
| 5,877,305 A | 3/1999 | Huston |
| 5,883,113 A | 3/1999 | Tang |
| 5,886,020 A | 3/1999 | Tang |
| 5,916,771 A | 6/1999 | Hon |
| 5,939,598 A | 8/1999 | Kucherlapati |
| 5,959,177 A | 9/1999 | Hein |
| 5,985,615 A | 11/1999 | Jakobovits |
| 5,994,619 A | 11/1999 | Stice |
| 5,998,209 A | 12/1999 | Jokobovits |
| 6,046,037 A | 4/2000 | Hiatt |
| 6,075,181 A | 6/2000 | Kucherlapati |
| 6,091,001 A | 7/2000 | Jakobovits |
| 6,103,224 A | 8/2000 | Ladner |
| 6,114,598 A | 9/2000 | Kucherlapati |
| 6,117,422 A | 9/2000 | Ladner |
| 6,130,364 A | 10/2000 | Jakobovits |
| 6,146,851 A | 11/2000 | Ladner |
| 6,150,584 A | 11/2000 | Jakobovits |
| 6,162,963 A | 12/2000 | Kucherlapati |
| 6,184,354 B1 | 2/2001 | Koths |
| 6,204,020 B1 | 3/2001 | Ladner |
| 6,255,455 B1 | 7/2001 | Siegel |
| 6,255,458 B1 | 7/2001 | Lonberg |
| 6,284,764 B1 | 9/2001 | Kath |
| 6,300,129 B1 | 10/2001 | Lonberg |
| 6,322,779 B1 | 11/2001 | Halenbeck |
| 6,417,429 B1 | 7/2002 | Hein |
| 6,465,449 B1 | 10/2002 | Kath |
| 6,517,529 B1 | 2/2003 | Quinn |
| 6,680,209 B1 | 1/2004 | Buechler |
| 6,720,155 B1 | 4/2004 | Lopez |
| 6,794,132 B2 | 9/2004 | Buechler |
| 6,984,720 B1 | 1/2006 | Korman |
| 7,041,871 B1 | 5/2006 | Lonberg |
| 7,084,260 B1 | 8/2006 | Lonberg |
| 7,115,717 B2 | 10/2006 | Mori |
| 7,135,287 B1 | 11/2006 | Lonberg |
| 7,171,311 B2 | 1/2007 | Dai |
| 7,186,809 B2 | 3/2007 | Pluenneke |
| 7,189,515 B2 | 3/2007 | Buechler |
| 7,192,582 B2 | 3/2007 | Hudson |
| 7,193,064 B2 | 3/2007 | Mikayama |
| 7,262,277 B2 | 8/2007 | Lancaster |
| 7,262,278 B2 | 8/2007 | Tawara |
| 7,271,245 B2 | 9/2007 | Felding |
| 7,273,610 B2 | 9/2007 | Nixon |
| 7,326,414 B2 | 2/2008 | Bedian |
| 7,592,430 B2 | 9/2009 | Bedian |
| 7,728,113 B2 | 6/2010 | Bedian |
| 8,188,249 B2 | 5/2012 | Bedian |
| 2002/0141994 A1 | 10/2002 | Devalaraja |
| 2002/0146753 A1 | 10/2002 | Ditzel |
| 2003/0040605 A1 | 2/2003 | Siegel |
| 2003/0232054 A1 | 12/2003 | Tang |
| 2004/0175379 A1 | 9/2004 | DeVries |
| 2004/0259153 A1 | 12/2004 | Kurosawa |
| 2005/0009136 A1 | 1/2005 | Nixon |
| 2005/0019845 A1 | 1/2005 | Harkins |
| 2005/0054019 A1 | 3/2005 | Michaud |
| 2005/0058649 A1 | 3/2005 | Landes |
| 2005/0080239 A1 | 4/2005 | Ditzel |
| 2005/0084449 A1 | 4/2005 | Landes |
| 2005/0226876 A1 | 10/2005 | Graus |
| 2005/0255532 A1 | 11/2005 | Ruben |
| 2005/0266423 A1 | 12/2005 | Tang |
| 2005/0282252 A1 | 12/2005 | Siegel |
| 2005/0287150 A1 | 12/2005 | Ambrosino |
| 2006/0177440 A1 | 8/2006 | Siegel |
| 2006/0246071 A1 | 11/2006 | Green |
| 2006/0257397 A1 | 11/2006 | Throsby |
| 2007/0065444 A1 | 3/2007 | North |

FOREIGN PATENT DOCUMENTS

| | | |
|---|---|---|
| EP | 0499161 | 8/1992 |
| EP | 0606046 | 7/1994 |
| EP | 0780386 | 6/1997 |
| EP | 0818442 | 1/1998 |
| EP | 0256055 | 2/1998 |
| EP | 0265384 | 4/1998 |
| EP | 0931788 | 7/1999 |
| EP | 0945864 | 9/1999 |
| EP | 1004578 | 5/2000 |
| EP | 1322146 | 6/2003 |
| EP | 1792991 | 6/2007 |
| EP | 1813672 | 8/2007 |
| GB | 2404660 | 2/2005 |
| GB | 2405873 | 3/2005 |
| JP | 05095794 | 4/1993 |
| JP | 6007189 | 1/1994 |
| JP | 6194367 | 7/1994 |
| JP | 6319584 | 11/1994 |
| JP | 2001527386 | 12/2001 |
| JP | 2003527832 | 9/2003 |
| JP | 2004512005 | 4/2004 |
| JP | 2005500832 | 1/2005 |
| JP | 2005507635 | 3/2005 |
| JP | 2005126443 | 5/2005 |
| JP | 2005168497 | 6/2005 |
| JP | 2005185281 | 7/2005 |
| JP | 2005533486 | 11/2005 |
| JP | 2005534281 | 11/2005 |
| JP | 2005537784 | 12/2005 |
| JP | 2005538682 | 12/2005 |
| JP | 2007513633 | 5/2006 |
| JP | 2006517392 | 7/2006 |
| JP | 2006519591 | 8/2006 |
| JP | 2006523083 | 10/2006 |
| JP | 2006523433 | 10/2006 |

(56) References Cited

FOREIGN PATENT DOCUMENTS

| | | |
|---|---|---|
| JP | 2006342173 | 12/2006 |
| JP | 2007514419 | 6/2007 |
| KR | 2006030153 | 4/2006 |
| WO | WO-1990005719 | 5/1990 |
| WO | WO-1990009400 | 8/1990 |
| WO | WO-1991001330 | 2/1991 |
| WO | WO-1991008774 | 6/1991 |
| WO | WO-1991010741 | 7/1991 |
| WO | WO-1991017271 | 11/1991 |
| WO | WO-1992001047 | 1/1992 |
| WO | WO-1992009690 | 6/1992 |
| WO | WO-1992015679 | 9/1992 |
| WO | WO-1992018619 | 10/1992 |
| WO | WO-1992020791 | 11/1992 |
| WO | WO-1993001288 | 1/1993 |
| WO | WO-1993006213 | 4/1993 |
| WO | WO-1993012232 | 6/1993 |
| WO | WO-1994002602 | 2/1994 |
| WO | WO-1995019970 | 7/1995 |
| WO | WO-1995021613 | 8/1995 |
| WO | WO-1996027583 | 9/1996 |
| WO | WO-1996033172 | 10/1996 |
| WO | WO-1996033735 | 10/1996 |
| WO | WO-1996034096 | 10/1996 |
| WO | WO-1997013760 | 4/1997 |
| WO | WO-1997022596 | 6/1997 |
| WO | WO-1997032856 | 9/1997 |
| WO | WO-1998002434 | 1/1998 |
| WO | WO-1998002437 | 1/1998 |
| WO | WO-1998002438 | 1/1998 |
| WO | WO-1998003516 | 1/1998 |
| WO | WO-1998007697 | 2/1998 |
| WO | WO-1998014451 | 4/1998 |
| WO | WO-1998016654 | 4/1998 |
| WO | WO-1998024893 | 6/1998 |
| WO | WO-1998030566 | 7/1998 |
| WO | WO-1998033768 | 8/1998 |
| WO | WO-1998034915 | 8/1998 |
| WO | WO-1998034918 | 8/1998 |
| WO | WO-1998040488 | 9/1998 |
| WO | WO-1998046644 | 10/1998 |
| WO | WO-1998050356 | 11/1998 |
| WO | WO-1998050433 | 11/1998 |
| WO | WO-1998052976 | 11/1998 |
| WO | WO-1998054093 | 12/1998 |
| WO | WO-1999007675 | 2/1999 |
| WO | WO-1999010349 | 3/1999 |
| WO | WO-1999016755 | 4/1999 |
| WO | WO-1999024440 | 5/1999 |
| WO | WO-1999029667 | 6/1999 |
| WO | WO-1999035132 | 7/1999 |
| WO | WO-1999035146 | 7/1999 |
| WO | WO-1999045031 | 9/1999 |
| WO | WO-1999052889 | 10/1999 |
| WO | WO-1999052910 | 10/1999 |
| WO | WO-1999053049 | 10/1999 |
| WO | WO-1999061422 | 12/1999 |
| WO | WO-1999062890 | 12/1999 |
| WO | WO-200009560 | 2/2000 |
| WO | WO-200009561 | 2/2000 |
| WO | WO-200034317 | 6/2000 |
| WO | WO-2000035956 | 6/2000 |
| WO | WO-2000037504 | 6/2000 |
| WO | WO-200100678 | 1/2001 |
| WO | WO-200202641 | 1/2001 |
| WO | WO-200114424 | 3/2001 |
| WO | WO-200125492 | 4/2001 |
| WO | WO-200134177 | 5/2001 |
| WO | WO-200140306 | 6/2001 |
| WO | WO-200154477 | 8/2001 |
| WO | WO-200259340 | 8/2001 |
| WO | WO-200192340 | 12/2001 |
| WO | WO-200264634 | 8/2002 |
| WO | WO-200288186 | 11/2002 |
| WO | WO-200294878 | 11/2002 |
| WO | WO-200319187 | 3/2003 |
| WO | WO-200333538 | 4/2003 |
| WO | WO-200348328 | 6/2003 |
| WO | WO-2003048731 | 6/2003 |
| WO | WO-200355979 | 7/2003 |
| WO | WO-200359282 | 7/2003 |
| WO | WO-200370752 | 8/2003 |
| WO | WO-200379750 | 10/2003 |
| WO | WO-200294880 | 11/2003 |
| WO | WO-2003091413 | 11/2003 |
| WO | WO-2003093313 | 11/2003 |
| WO | WO-2004024750 | 3/2004 |
| WO | WO-2004035603 | 4/2004 |
| WO | WO-2004045512 | 6/2004 |
| WO | WO-2004045532 | 6/2004 |
| WO | WO-2004050017 | 6/2004 |
| WO | WO-2004050032 | 6/2004 |
| WO | WO-2004050838 | 6/2004 |
| WO | WO-2004050850 | 6/2004 |
| WO | WO-2004084823 | 10/2004 |
| WO | WO-2004099251 | 11/2004 |
| WO | WO-2004101790 | 11/2004 |
| WO | WO-2004108078 | 12/2004 |
| WO | WO-2005010048 | 2/2005 |
| WO | WO-2005019266 | 3/2005 |
| WO | WO-2005019267 | 3/2005 |
| WO | WO-2005019270 | 3/2005 |
| WO | WO-2005023177 | 3/2005 |
| WO | WO-2005109266 | 3/2005 |
| WO | WO-2005030124 | 4/2005 |
| WO | WO-2005034733 | 4/2005 |
| WO | WO-2005047325 | 5/2005 |
| WO | WO-2005047331 | 5/2005 |
| WO | WO-2005058815 | 6/2005 |
| WO | WO-2005059106 | 6/2005 |
| WO | WO-2005060642 | 7/2005 |
| WO | WO-2005063819 | 7/2005 |
| WO | WO-2005068503 | 7/2005 |
| WO | WO-2005086713 | 9/2005 |
| WO | WO-2005091805 | 10/2005 |
| WO | WO-2005092926 | 10/2005 |
| WO | WO-2006007850 | 1/2006 |
| WO | WO-2006013107 | 2/2006 |
| WO | WO-2006014498 | 2/2006 |
| WO | WO-2006017538 | 2/2006 |
| WO | WO-2006017759 | 2/2006 |
| WO | WO-2006020258 | 2/2006 |
| WO | WO-2006020706 | 2/2006 |
| WO | WO-2006021210 | 3/2006 |
| WO | WO-2006033386 | 3/2006 |
| WO | WO-2006039644 | 4/2006 |
| WO | WO-2006055809 | 5/2006 |
| WO | WO-2006068953 | 6/2006 |
| WO | WO-2006071441 | 7/2006 |
| WO | WO-2006072564 | 7/2006 |
| WO | WO-2006081139 | 8/2006 |
| WO | WO-2006089232 | 8/2006 |
| WO | WO-2006096461 | 9/2006 |
| WO | WO-2006096488 | 9/2006 |
| WO | WO-2006096489 | 9/2006 |
| WO | WO-2006105338 | 10/2006 |
| WO | WO-2006113643 | 10/2006 |
| WO | WO-2006121422 | 11/2006 |
| WO | WO-2006124269 | 11/2006 |
| WO | WO-2006137931 | 12/2006 |
| WO | WO-2007005874 | 1/2007 |
| WO | WO-2007016240 | 2/2007 |
| WO | WO-2007016285 | 2/2007 |
| WO | WO-2007027713 | 8/2007 |

OTHER PUBLICATIONS

Abd et al., "The role of macrophages in experimental arthritis induced by *Streptococcus agalactiae* sonicate: Actions of macrophage colony-stimulating factor (CSF-1) and other macrophage-modulating agents," Lymphokine and Cytokine Research, 10:43-50 (1991).

(56) References Cited

OTHER PUBLICATIONS

Accession No. IPI00885193, International Protein Index Database (Feb. 25, 2008).
Accession No. Q9UL78, UniProtKB/TrEMBL Database (May 1, 2000).
Aharinejad et al., "Colony-stimulating factor-1 blockade by antisense oligonucleotides and small interfering RNAs suppresses growth of human mammary tumor xenografts in mice," Cancer Research, 64(15):5378-5384 (2004).
Aharinejad et al., "Colony-stimulating factor-1 treatment suppresses growth of human tumor xenografts in mice," Cancer Research, 62:5317-5324 (2002).
Altschul et al., "Basic local alignment search tool," Journal of Molecular Biology, 215(1):403-410(1990).
Altschul et al., "Gapped BLAST and PSI-BLAST: a new generation of protein database search programs," Nucleic Acids Research, 25(17):3389-3402 (1997).
Babcook et al., "A novel strategy for generating monoclonal antibodies from single, isolated lymphocytes producing antibodies of defined specificities," PNAS, 93:7843-7848 (1996).
Barbas et al., "Assembly of combinatorial antibody libraries on phage surfaces: the gene III site," PNAS, 88:7978-7982 (1991).
Bird et al., "Single-chain antigen-binding proteins," Science, 242:423-426 (1988).
Bischof et al., "Exacerbation of acute inflammatory arthritis by the colony-stimulating factors CSF-1 and granulocyte macrophage (GM)-CSF: evidence of macrophage infiltration and local proliferation," Clinical and Experimental Immunology, 119:361-367 (2000).
Bowie et al., "A method to identify protein sequences that fold into a known three-dimensional structure," Science, 253:164-170 (1991).
Burkhardt et al., "Epitope-specific recognition of type II collagen by rheumatoid arthritis antibodies is shared with recognition by antibodies that are arthritogenic in collagen-induced arthritis in the mouse," Arthritis & Rheumatism, 46(9):2339-2348 (2002).
Campbell et al., "The colony-stimulating factors and collagen-induced arthritis: exacerbation of disease by M-CSF and G-CSF and requirement for endogenous M-CSF," Journal of Leukocyte Biology, 68:144-150 (2000).
Casset, F. et al., "A peptide mimetic of an anti-CD4 monoclonal antibody by rational design," Biochemical and Biophysical Research Communications, vol. 307, pp. 198-205.
Chang et al., "Structure-Function Relationships for Human Antibodies to Pneumococcal Capsular Polysaccharide from Transgenic Mice with Human Immunoglobulin Loci," Infection and Immunity, 70(9): 4977-4986 (2002).
Chen, "AAA58995," The National Center for Biotechnology Protein Database, submitted Feb. 18, 1987.
Chiorazzi et al., "AAT86026," The National Center for Biotechnology Protein Database, submitted Mar. 17, 2004.
Chothia et al., "Canonical structures for the hypervariable regions of immunoglobulins," Journal of Molecular Biology, 196:901-917 (1987).
Chothia et al., "Conformations of immunoglobulin hypervariable regions," Nature, 342:877-883 (1989).
Clackson et al., "Making antibody fragments using phage display libraries," Nature, 352:624-628 (1991).
Cook et al., "Blockade of collagen-induced arthritis post-onset by antibody to granulocyte-macrophage colony-stimulating factor (GM-CSF): requirement for GM-CSF in the effector phase of disease," Arthritis Research, 3:293-298 (2001).
Crowe et al., "AAW67409," The National Center for Biotechnology Protein Database, submitted Jul. 14, 2004.
Davies et al., "Antibody VH domains as small recognition units," Biotechnology, 13(5):475-479 (1995).
Ditzel et al., "AAB41048," The National Center for Biotechnology Protein Database, submitted Dec. 20, 1996.
Ditzel et al., "Mapping the protein surface of human immunodeficiency virus type 1 gp120 using human monoclonal antibodies from phage display libraries," J Mol Biol. 267(3):684-95.
Evans et al., "Design of nonpeptidal ligands for a peptide receptor: Cholecystokinin antagonists," Journal of Medicinal Chemistry, 30:1229-1239 (1987).
Fais et al. "CAB51298," The National Center for Biotechnology Protein Database, submitted Jul. 20, 1999.
Fauchere, "Elements for the rational drug design of peptide drugs," Advances in Drug Research, 15:29-69 (1986).
Feldman et al., "Anti-TNFa therapy useful in rheumatoid arthritis and Crohn's disease: analysis of the mechanism of action predicts utility in other diseases," Transplantation Proceedings, 30:4126-4127 (1998).
Fingerle et al., "The novel subset of CD14+/CD16+ blood monocytes is expanded in sepsis patients," Blood, 82(10):3170-3176 (1993).
Frankenberger et al., "Differential cytokine expression in human blood monocyte subpopulations: A polymerase chain reaction analysis," Blood, 87(1):373-377 (1996).
Fuchs et al., "Targeting recombinant antibodies to the surface of *Escherichia coli*: fusion to a peptidoglycan associated lipoprotein," Biotechnology, 9:1369-1372 (1991).
Galfre et al., "Preparation of monoclonal antibodies: strategies and procedures," Methods in Enzymology, 73:3-46 (1981).
Garrard et al., "FAB assembly and enrichment in a monovalent phage display system," Biotechnology, 9:1373-1377 (1991).
Gonnet et al., "Exhaustive matching of the entire protein sequence database," Science, 256:1443-1445 (1992).
Gram et al., "In vitro selection and affinity maturation of antibodies from a naive combinatorial immunoglobulin library," PNAS, 89:3576-3580 (1992).
Green et al., "Antigen-specific human monoclonal antibodies from mice engineered with human lg heavy and light chain YACs," Nature Genetics, 7:13-21 (1994).
Green et al., "Regulation of B cell development by variable gene complexity in mice reconstituted with human immunoglobulin yeast artificial chromosomes," Journal of Experimental Medicine, 188(3):483-495 (1998).
Griffiths et al., "Human anti-self antibodies with high specificity from phage display libraries," The EMBO Journal, 12(2):725-734 (1993).
Griffiths et al., "Isolation of high affinity human antibodies directly from large synthetic repertoires," The EMBO Journal, 13(14):3245-3260 (1994).
Hall et al., "A single amino acid mutation in CDR3 of the 3-14-9 L chain abolished expression of the IDA 10-defined idiotope and antigen binding," Journal of Immunology, 149(5):1605-1612 (1992).
Hamilton, "CSF-1 signal transduction.," Journal Of Leukocyte Biology, 62(2):145-155 (1997).
Hawkins et al., "Selection of phage antibodies by binding affinity mimicking affinity maturation," Journal of Molecular Biology, 226:889-896 (1992).
Hay et al., "Bacteriophage cloning and *Escherichia coli* expression of a human IgM Fab," Hum. Antibod. Hybridomas, 3:81-85 (1992).
Holliger et al., "Diabodies: small bivalent and bispecific antibody fragments," PNAS, 90:6444-6448 (1993).
Holm et al., "Functional mapping and single chain construction of the anti-cytokeratin 8 monoclonal antibody TS1," Molecular Immunology, 44:1075-1084 (2007).
Hoogenboom et al., "Multi-subunit proteins on the surface of filamentous phage: methodologies for displaying antibody (Fab) heavy and light chains," Nucleic Acids Research, 19(15):4133-4137 (1991).
Huang et al., "A majority of Ig H chain cDNA of normal human adult blood lymphocytes resembles cDNA for fetal Ig and natural autoantibodies," J. Immunol. 151:5290-5300 (1993).
Huse et al., "Generation of a large combinatorial library of the immunoglobulin repertoire in phage lambda," Science, 246:1275-1281 (1989).
Huston et al., "Protein engineering of antibody binding sites: recovery of specific activity in an anti-digoxin single-chain Fv analogue produced in *Escherichia coli*," PNAS, 85:5879-5883 (1988).
Ill et al., "Design and construction of a hybrid immunoglobulin domain with properties of both heavy and light chain variable regions," Protein Engineering, 10(8): 949-957 (1997).

(56) References Cited

OTHER PUBLICATIONS

Ishikawa et al., "Macrophage colony-stimulating factor aggravates rather than regenerates emphysematous lungs in mice," Respiration, 73(4):538-545 (2006).
Johnsson et al., "Comparison of methods for immobilization to carboxymethyl dextran sensor surfaces by analysis of the specific activity of monoclonal antibodies," Journal of Molecular Recognition, 8:125-131 (1995).
Johnsson et al., "Immobolization of proteins to a carboxymethyldextran-modified gold surface for biospecific interaction analysis in surface plasmon resonance sensors," Analytical Biochemistry, 198:268-277 (1991).
Jonsson et al., "Introducing a biosensor based technology for real-time biospecific interaction analysis," Ann. Biologie Clinique., 51:19-26 (1993.
Jonsson et al., "Real-time biospecific interaction analysis using surface plasmon resonance and a sensor chip technology," BioTechniques, 11(5):620-627 (1991).
Kawakami et al., "Macrophage-colony stimulating factor inhibits the growth of human ovarian cancer cells in vitro," European Journal of Cancer, 36: 1991-1997 (2000).
Kawanaka et al., "CD14+, CD16+ Blood Monocytes and Joint Inflammation in Rheumatoid Arthritis," Arthritis & Rheumatism, 46(10): 2578-2586 (2002).
Kipps et al., "Molecular characterization of a major autoantibody-associated cross-reactive idiotype in Sjogren's syndrome," J. Immunol. 142(12):4261-8 (1989).
Kipps, "AAA36087," The National Center for Biotechnology Protein Database, submitted Aug. 16, 1989.
Kipps, "AAA36088," The National Center for Biotechnology Protein Database, submitted Aug. 16, 1989.
Klebl et al., "Expression of macrophage-colony stimulating factor in normal and inflammatory bowel disease intestine," Journal of Pathology, 195(5):609-915 (2001).
Kostelny et al., "Formation of a bispecific antibody by the use of leucine zippers," The Journal of Immunology, 148:1547-1553 (1992).
Kreipe et al., "Proliferation, macrophage colony-stimulating factor, and macrophage colony-stimulating factor-receptor expression of alveolar macrophages in active sarcoidosis," Laboratory Investigation, 62(6):697-703 (1990).
Kurosawa, "BAC01758," The National Center for Biotechnology Protein Database, submitted Jun. 25, 2001.
Kurosawa, "BAC01567," The National Center for Biotechnology Protein Database, submitted Jun. 25, 2001.
Kurosawa, "BAC01570," The National Center for Biotechnology Protein Database, submitted Jun. 25, 2001.
Kurosawa, "BAC01589," The National Center for Biotechnology Protein Database, submitted Jun. 25, 2001.
Kurosawa, "BAC01595," The National Center for Biotechnology Protein Database, submitted Jun. 25, 2001.
Laplanche et al., "Phosphorothiolate-modified oligodeoxyribonucleotides, III. NMR and UV spectroscopic studies of the Rp-Rp, Sp-Sp, and Rp-Sp duplexes, [d(GG5AATTCC)]2, derived from diastereomeric O-ethyl phosphorothioates," Nucleic Acids Research, 14(22):9081-9093 (1986).
Le Meur et al., "Macrophage Accumulation at a Site of Renal Inflammation is Dependent on the M-CSF/c-fms Pathway," Journal of Leukocyte Biology, 72: 530-537 (2002).
Lewis et al., "Characterization of humanized anti-TAC, an antibody directed against the interleukin 2 receptor, using electrospray ionization mass spectrometry by direct infuction, LC/MS, and MS/MS," Analytical Chemistry, 66(5):585-595 (1994).
Lieby et al., "AAG30436," The National Center for Biotechnology Protein Database, submitted Sep. 1, 2000.
Lieby et al., "The clonal analysis of anticardiolipin antibodies in a single patient with primary antiphospholipid syndrome reveals an extreme antibody heterogeneity," Blood 97(12):3820-8 (2001).
MacCallum, et al., "Antibody-antigen interactions: Contact analysis and binding site topography," Journal of Molecular Biology, 262:732-745 (1998).
Martin et al., "Evidence for somatic selection of natural autoantibodies," J Exp Med. 175(4):983-91 (1992).
Martin et al., "The affinity-selection of a minibody polypeptide inhibitor of human interleukin-6," The EMBO Journal, 13(22):5303-5309 (1994).
McCafferty et al., "Phage antibodies: filamentous phage displaying antibody variable domains," Nature, 348:552-554 (1990).
McIntosh et al., "Cloning and analysis of IgG kappa and IgG lambda anti-thyroglobulin autoantibodies from a patient with Hashimoto's thyroiditis: evidence for in vivo antigen-driven repertoire selection," J. Immunol. 157(2):927-35 (1996).
McIntosh, "CAA63579," The National Center for Biotechnology Protein Database, submitted Nov. 16, 1995.
McLachlan et al., "AAK68023," The National Center for Biotechnology Protein Database, submitted Sep. 18, 2000.
McQulater et al., "Granulocyte Macrophage Colony-stimulating factor: a new putative therapeutic target in multiple sclerosis," Journal of Experimental Medicine, 194(7):873-881 (2001).
Mendez et al., "Functional transplant of megabase human immunoglobulin loci recapitulates human antibody response in mice," Nature Genetics, 15:146-156 (1997).
Mestas et al., "Of mice and not men: differences between mouse and human immunology," The Journal of Immunology, 172:2731-2738 (2004).
Moss et al., "Proliferation of a subpopulation of human peripheral blood monocytes in the presence of colony stimulating factors may contribute to the inflammatory process in diseases such as rheumatoid arthritis," Immunobiology, 202:18-25 (2000).
Nissim et al., "Antibody fragments from a 'single pot' phage display library as immunochemical reagents," The EMBO Journal, 13(3):692-698 (1994).
Okabe et al., "Production of colony-stimulating factor by sarcoid granulomas in vitro," Japanese Journal of Medicine, 26(1):36-40 (1987).
Pascalis et al., "Grafting of 'abbreviated' complementarity-determining regions containing specificity-determining residues essential for ligand contact to engineer a less immunogenic humanized monoclonal antibody," Journal of Immunology, vol. 169, pp. 3076-3084 (2002).
Paul, Fundamental Immunology, 3rd edition, 292-295 (1993).
Pearson, "Effective protein sequence comparison," Methods in Enzymology, 266:227-258 (1996).
Pearson, "Empirical statistical estimates for sequence similarity searches," Journal of Molecular Biology, 276:71-84 (1998).
Pearson, "Flexible sequence similarity searching with the FASTA3 program package," Methods in Molecular Biology, 132:185-219 (2000).
Pearson, "Rapid and sensitive sequence comparison with FASTP and FASTA," Methods in Enzymolology, 183:63-98 (1990).
Pearson, "Using the FASTA program to search protein and DNA sequence databases," Methods in Molecular Biology, 24:307-331 (1994).
Pereira et al., "Cardiolipin binding a light chain from lupus-prone mice," Biochemistry, 37(5):1430-1437 (1998).
Pichurin et al., "Human monoclonal autoantibodies to B-cell epitopes outside the thyroid peroxidase autoantibody immunodominant region," Thyroid 11(4):301-13 (2001).
Poljak "Production and structure of diabodies," Structure, 2:1121-1123 (1994).
Pratt et al., "Ig V region gene expression in small lymphocytic lymphoma with little or no somatic hypermutation," J. Immunol. 143(2):699-705 (1989).
Pratt, "AAA58911," The National Center for Biotechnology Protein Database, submitted Sep. 20, 1989.
Radoux et al., "A conserved human germline V kappa gene directly encodes rheumatoid factor light chains," J Exp Med. 164: 2119-24 (1986).
Rajavashisth et al., "Heterozygous osteopetrotic (op) mutation reduces atherosclerosis in LDL receptor-deficient mice," Journal of Clinical Investigation, 101(12):2702-2710 (1998).

(56) References Cited

OTHER PUBLICATIONS

Reiter et al., "An antibody single-domain phage display library of a native heavy chain variable region: isolation of functional single-domain VH molecules with a unique interface," Journal of Molecular Biology, 290(3):685-698 (1999).
Rizo et al., "Constrained peptides: models of bioactive peptides and protein substructures," Annual Review of Biochemistry, 61:387-418 (1992).
Rudikoff, S. et al., "Single amino acid substitution altering antigen-binding specificity," Proceedings of the National Academy of Sciences,. vol. 79, pp. 1979-1983 (1982).
Saleh et al., "CD16+ monocytes in patients with cancer: Spontaneous elevation and pharmacologic induction by recombinant human macrophage colony-stimulating factor," Blood, 85(10): 2910-2917 (1995).
Schaeble, "CAA31198," The National Center for Biotechnology Protein Database, submitted Apr. 22, 1991.
Seyedhossein et al., "Colony-stimulating factor-1 antisense treatment suppresses growth of human tumor xenografts in mice," Cancer Research, 62:5317-5324 (2002).
Shibaguchi et al., "BAD16744," The National Center for Biotechnology Protein Database, submitted Apr. 23, 2004.
Songsivilai et al, "Bispecific antibody: a tool for diagnosis and treatment of disease," Clinical and Experimental Immunology, 79: 315-321 (1990).
Stanley et al., "Biology and action of colony-stimulating factor-1," Molecular Reproduction and Development, 46(1):4-10 (1997).
Stec et al., "Automated solid-phase synthesis, separation, and stereochemistry of phosphorothioate analogues of oligodeoxyribonucleotides," Journal of the American Chemical Society, 106(20):6077-6079 (1984).
Stein et al., "Physiochemical properties of phosphorothioate oligodeoxynucleotides," Nucleic Acids Research, 16(8):3209-3221 (1988).
Stollar, "AAA17913," The National Center for Biotechnology Protein Database, submitted Aug. 10, 1993.
Straubinger et al., "The human VK locus. Characterization of a duplicated region encoding 28 different immunoglobulin genes," J Mol Biol. 199(1):23-34 (1988).
Tanaka et al., "Macrophage Colony-stimulating Factor Is Indispensable for both Proliferation and Differentiation of Osteoclast Progenitors," J. Clin. Invest, 91: 257-263.
Thornton et al., "Prediction of progress at last," Nature, 354:105-106 (1991).
Traunecker et al., "Bispecific single chain molecules (Janusins) target cytotoxic lymphocytes on HIV infected cells," The EMBO Journal, 10(12):3655-3659 (1991).
Traunecker et al., "Janusin: new molecular design for bispecific reagents," International Journal of Cancer, 7:51-52 (1992).
Uhlmann et al., "Antisense oligonucleotides: a new therapeutic principle," Chemical Reviews, 90(4):543-584 (1990).
United States Patent and Trademark Office, "Notice of Allowability," U.S. Appl. No. 10/938,353, dated Jul. 24, 2007.
United States Patent and Trademark Office, "Notice of Allowability," U.S. Appl. No. 11/375,221, dated Sep. 17, 2007.
United States Patent and Trademark Office, "Notice of Allowance and Fee(s) Due," U.S. Appl. No. 10/938,353, dated Jan. 14, 2009.
United States Patent and Trademark Office, "Notice of Allowance and Fee(s) Due," U.S. Appl. No. 10/938,353, dated Jul. 24, 2007.
United States Patent and Trademark Office, "Notice of Allowance and Fee(s) Due," U.S. Appl. No. 11/375,221, dated Sep. 17, 2007.
Vajdos, F.F. et al., "Comprehensive functional maps of the antigen-binding site of an anti-ErbB2 antibody obtained with shotgun screening mutagenesis," Journal of Molecular Biology, vol. 320, pp. 414-428 (2002).
Veber et al., "The design of metabolically-stable peptide analogs," TINS, 8(9):392-396 (1985).

Verdrengh et al., "Granulocyte-macrophage colony-stimulating factor in *Staphylococcus aureus* induced arthritis," Infection and Immunity, 66(2):853-855 (1998).
Wagner et al., "V kappa gene segments rearranged in chronic lymphocytic leukemia are distributed over a large portion of the V kappa locus and do not show somatic mutation," Eur J Immunol. 23(2):391-7 (1993).
Wang et al. "AAC18218," The National Center for Biotechnology Protein Database, submitted Apr. 22, 1998.
Wang et al. "AAC18242," The National Center for Biotechnology Protein Database, submitted Apr. 22, 1998.
Wang et al., "Immunoglobulin VH gene expression in human aging," Clin Immunol., 93:132-143 (1999).
Ward et al., "Binding activities of a repertoire of single immunoglobulin variable domains secreted from *Escherichia coli*," Nature, 341:544-546 (1989).
Weber et al., "Differential chemokine receptor expression and function in human monocyte subpopulations," Journal of Leukocyte Biology, 67: 699-704 (2000).
Weitkamp et al., "VH1-46 is the dominant immunoglobulin heavy chain gene segment in rotavirus-specific memory B cells expressing the intestinal homing receptor alpha4beta7," J Immunol. 174(6):3454-60 (2005).
Williams et al., "Anti-tumor necrosis factor ameliorates joint disease in murine collagen-induced arthritis," Proceedings of National Academy of Science of the United States of America, 89:9784-9788 (1992).
Winkler et al., "Changing the antigen binding specificity by single point mutations of an anti-p24 (HIV-1) antibody," Journal of Immunology, 165(8):4505-4514 (2000).
Wu et al., "Myosin-reactive autoantibodies in rheumatic carditis and normal fetus," Clin Immunol Immunopathol. 87(2):184-92 (1998).
Wu, et al., "Humanization of a murine monoclonal antibody by simultaneous optimization of framework and CDR residues," Journal of Molecular Biology, 294:151-162 (1999).
Yang et al., "Co-Expression of macrophage colony-stimulating factor with its receptor in human hepatoma cells and its potential roles," Chinese Journal of Cancer Research, 11(2):79-84 (1999).
Young, "AAD56272," The National Center for Biotechnology Protein Database, submitted Nov. 19, 1997.
Yui et al., "Increased macrophage colony-stimulating factor in neonatal and adult autoimmune MRL-lpr mice," American Journal of Pathology, 139(2):255-261 (1991).
Zebedee et al., "AAA35977," The National Center for Biotechnology Protein Database (1992).
Zebedee et al., "Human combinatorial antibody libraries to hepatitis B surface antigen," Proc Natl Acad Sci U S A. 89(8):3175-9 (1992).
Zhao et al., "Xenogeneic skin graft rejection in M-CSF/macrophage deficient osteopetrotic mice," Xenotransplantation, 10: 232-239 (2003).
Zhao, "AAT84385," The National Center for Biotechnology Protein Database, submitted Mar. 21, 2004.
Zhu et al., "Acquisition of potential N-glycosylation sites in the immunoglobulin variable region by somatic mutation is a distinctive feature of follicular lymphoma," Blood 99:2562-2568 (2002).
Zhu, "AAL13258," The National Center for Biotechnology Protein Database, submitted Jul. 15, 2001.
Ziegler-Heibbrock, "Heterogeneity of human blood monocytes: the CD14+CD16+ subpopulation," Immunology Today, 17(9):424-428 (1996).
Zon et al., "Phosphorothioate oligonucleotides," Oligonucleotides and Analogues: A Practical Approach, 87-108 (F. Eckstein, Ed., Oxford University Press, Oxford England (1991).
Zon et al., "Phosphorothioate oligonucleotides: chemistry, purification, analysis, scale-up and future directions," Anti-Cancer Drug Design, 6:539-568 (1991).
Zemel, et al., "Differences in the biochemical properties of esterolytic antibodies correlate with structural diversity," Molecular Immunology, 31(2):127-137 (1994).

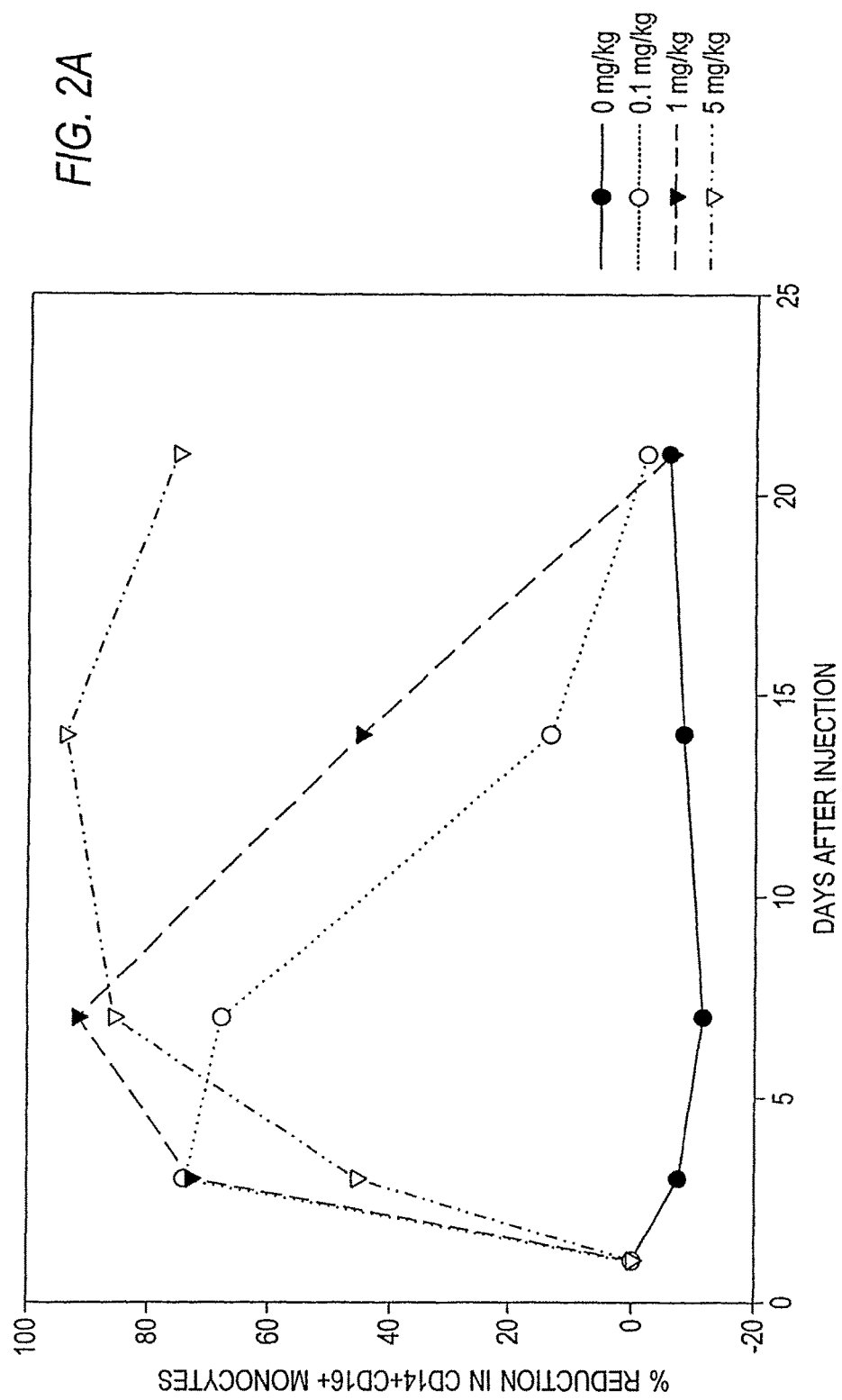

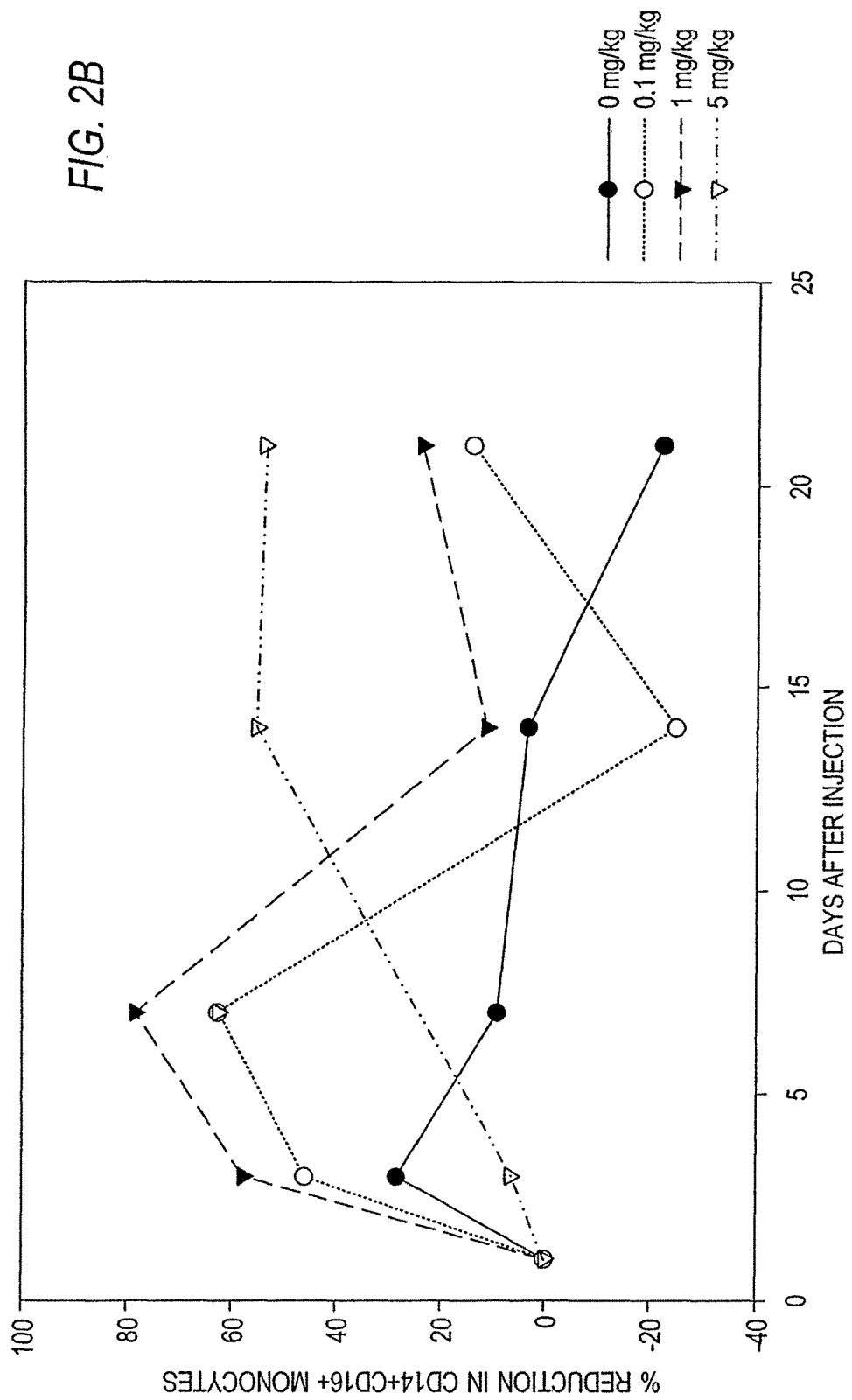

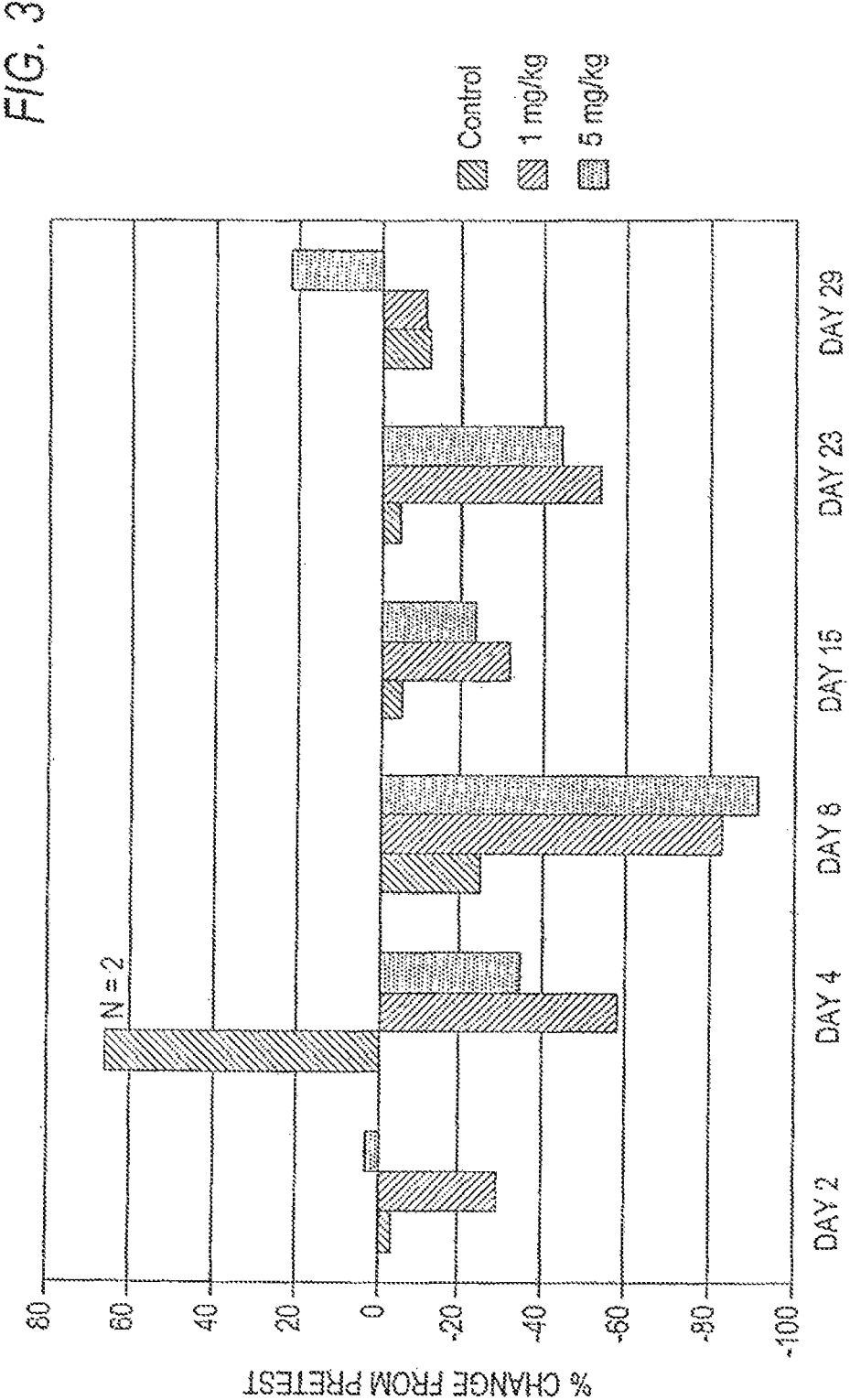

FIG. 4A

Germline V=O12, J=JK3
252

```
Germ  DIQMTQSPSSLSASVGDRVTITC  RASQSISSYLN  WYQQKPGKAPKLLIY  AASSLQS  GVPSRFSGSGSGTDFTLTISSLQPEDFATYYC  QQSYSTPFT
             FR1                 CDR1             FR2          CDR2                FR3                        CDR3

252   --------G--- (residues 21-127 of SEQ ID NO: 4)              -T-----                                ------V---

Germ  FGPGTKVDIK (SEQ ID NO: 103)
            J
```

FIG. 4B

Germline V=O12, J=JK3
88

```
Germ  DIQMTQSPSSLSASVGDRVTITC  RASQSISSYLN  WYQQKPGKAPKLLIY  AASSLQS  GVPSRFSGSGSGTDFTLTISSLQPEDFATYYC  QQSYSTPFT
             FR1                 CDR1             FR2          CDR2                FR3                        CDR3

88    --B--D--- (residues 21-127 of SEQ ID NO: 8)                 -I---

Germ  FGPGTKVDIK (SEQ ID NO: 103)
            J
```

FIG. 4C

Germline V=L2, J=JK3
100

```
Germ  DIVMTQSPATLSVSPGERATLSC  RASQSVSSNLA  WYQQKPGQAPRLLIY  GASTRAT  GIPARFSGSGSGTEFTLTISSLQSEDFAVYYC  QQYNNWPPT
             FR1                 CDR1             FR2          CDR2                FR3                        CDR3

100   -------S--- (residues 21-127 of SEQ ID NO: 12)             -I---

Germ  FGPGTKVDIK (SEQ ID NO: 107)
            J
```

FIG. 4D

Germline V=L15, J=JK3
1.8.3
(residues 23-130 of SEQ ID NO: 18)

```
Germ   DIQMTQSPSSLSASVGDRVTITC RASQGISSWLA WYQQKPGKAPKLLIY AASSLQS GVPSRFSGSGSGTDFTLTISSLQPEDFATYYC QQANSFPFT FGPGTKVDIKR
       FR1                     CDR1       FR2             CDR2    FR3                              CDR3      J
(SEQ ID NO: 109)

Germline V=L15, J=JK4
2.7.3
(residues 23-130 of SEQ ID NO: 20)

```
Germ   DIQMTQSPSSLSASVGDRVTITC RASQGISSWLA WYQQKPGKAPKLLIY AASSLQS GVSRFSGSGSGTDFTLTISSLQPEDFATYYC QQANSFPLT FGGGTKVEIKR
       FR1                     CDR1       FR2             CDR2    FR3                             CDR3      J
(SEQ ID NO: 117)

Germline V=B3, J=JK1
1.120.1

```
Germ   DIVMTQSPDSLAVSLGERATINC KSSQSVLYSSNNKNYLA WYQQKPGQPPKLLIY WASTRES GVPDRFSGSGSGTDFTLTISSLQAEDVAVYYC QQYYSTPWT
       FR1                     CDR1              FR2             CDR2    FR3                              CDR3

1.120.1  ----------(residues 21-134 of SEQ ID NO: 24)         ---I-FF---- --R---- --N---                 ---S---

Germ   FGGGTKVEIKR (SEQ ID NO: 112)
       J
```

FIG. 4G
Germline V=3-11, D=D7-27, J=JH6
252
Germ  QVQLVESGGGLVKPGGSLRLSCAAS GFTFSDYYMS WIRQAPGKGLEWVS YISSSGSTIYYADSVKG RFTISRDNAKNSLYLQMNSLRAEDTAVYYCAR ALGGMDV
         FR1                    CDR1        FR2              CDR2              FR3                              CDR3
252   ---------------------------------------------I---------------------I---G---------------------------------B---------
Germ  RGQGTTVTVSSA (SEQ ID NO: 106)
         FR4
      -------- (residues 20-136 of SEQ ID NO: 2)

FIG. 4H
Germline V=3-7, D=6-13, J=JH4
89
Germ  EVQLVESGGGLVQPGGSLRLSCAAS GFTFSSYAMS WVRQAPGKGLEWVS NIKQDGSEKYYVDSVKG RFTISRDNAKNSLYLQMNSLRAEDTAVYYCAR GIAAAGYFDY
         FR1                    CDR1        FR2              CDR2              FR3                              CDR3
89    ---------------------------------------------------------------------------P---------RAIS
Germ  WGQGTLVTVSSA (SEQ ID NO: 105)
         FR4
      -------- (residues 20-138 of SEQ ID NO: 6)

FIG. 4I
Germline V=3-23, D=D1-26, J=JH4
100
Germ  EVQLLESGGGLVQPGGSLRLSCAAS GFTFSSYAMS WVRQAPGKGLEWVS AISGSGGSTYYADSVKG RFTISRDNSKNTLYLQMNSLRAEDTAVYYCAK ##YSGSYYYFDY
         FR1                    CDR1        FR2              CDR2              FR3                              CDR3
100   -------------------------------------------------R---R---S-----------------F-Y--EG---R--GF---
Germ  WGQGTLVTVSSA (SEQ ID NO: 104)
         FR4
      -------- (residues 20-141 of SEQ ID NO: 10)

FIG. 4J

Germline V=1-11, D=D7-27, J=JH4
3.8.3

```
Germ   QVQLVESGGGLVKPGGSLRLSCAAS GFTFSDYYMS WIRQAPGKGLEWVS YISSSGSTIYYADSVKG RFTISRDNAKNSLYLQMNSLRAEDTAVYYCAR SLTGDY
              FR1                  CDR1         FR2              CDR2                    FR3                    CDR3

3.8.3  ---------- (residues 20-135 of SEQ ID NO: 14)             ----G---

Germ   WGQGTLVTVSSA (SEQ ID NO: 108)
              FR4
```

FIG. 4K

Germline V=3-33, D=D1-26, J=JH4
2.7.3

```
Germ   QVQLVESGGGVVQPGRSLRLSCAAS GYTFSSYGMH WVRQAPGKGLEWVA VIWYDGSNKYYADSVKG RFTISRDNSKNTLYLQMNSLRAEDTAVYYCAR GYSKYDY
              FR1                  CDR1          FR2              CDR2                   FR3                    CDR3

2.7.3  ---------- (residues 20-137 of SEQ ID NO: 18)    R-----           --RV---

Germ   WGQGTLVTVSSA (SEQ ID NO: 110)
              FR4
```

FIG. 4L

Germline V=1-18, D=D4-23, J=JH4
1.120.1

```
Germ   QVQLVQSGAEVKKPGASVKVSCKAS GYTFTSYGIS WVRQAPGQGLEWMG WISAYNGNTNYAQKLQG RVTMTTDTSTSTAYMELRSLRSDDTAVYYCAR SDYGGNYFDY
              FR1                   CDR1         FR2              CDR2                    FR3                     CDR3

1.120.1 ---------- (residues 20-139 of SEQ ID NO: 22)            ----D---                ----R      RA--A-F---

Germ   WGQGTLVTVSSA (SEQ ID NO: 111)
              FR4
```

FIG. 4M

Germline V=A27, J=JK4
8.10.3

```
Germ     EIVLTQSPGTLSLSPGERATLSC RASQSVSSSYLA WYQQKPGQAPRLLIY GASSRAT GIPDRFSGSGSGTDFTLTISRLEPEDFAVYYC
                    FR1              CDR1              FR2           CDR2                  FR3
8.10.3   ---------V---------------  -----------  ---------------  -------  --------------------------
         (residues 21-129 of SEQ ID NO: 44)

Germ     QQYGSSPLT FGGGTKVEIKR (SEQ ID NO: 114)
           CDR3            J
```

FIG. 4N

Germline V=VH3-48, D=D1-26, J=JH4b
8.10.3

```
Germ     EVQLVESGGGLVQPGGSLRLSCAAS GFTFSSYSMN WVRQAPGKGLEWVS YISSSSSTIYYADSVKG RFTISRDNAKNSLYLQMNSLRAEDTAVYYCAR   DPLLA-AMP--
                    FR1                CDR1              FR2                CDR2                    FR3                   CDR3
8.10.3   -----------------------   ---P-I---I---   --------------  --R-----S------   -----------------------------  HHHIVG##FDY
                                                                                                                        CDR3

Germ     WGQGTLVTVSSA (SEQ ID NO: 113)
              J
```

FIG. 4O

Germline V=O12, J=JK3
9.14.4
(residues 23-130 of SEQ ID NO: 28)

```
Germ     DIQMTQSPSSLSASVGDRVTITC RASQSISSYLN WYQQKPGKAPKLLIY AASSLQS GVPSRFSGSGSGTDFTLTISSLQPEDFATYYC  QQSYSTPPT FGPGTKVDIKR
                    FR1              CDR1             FR2           CDR2                  FR3             CDR3             J
9.14.4   -----------------------  ----------  ---------------  -------  ----------------------------- ------------  ---------
         (SEQ ID NO: 103)
```

FIG. 4P

```
Germline V=VH3-11, D=D7-27, J=JH4b
9.14.4     ------------------------------------------------------------------G------
Germ       QVQLVESGGGLVKPGGSLRLSCAAS GFTFSDYYMS WIRQAPGKGLEWVS YISSSGSTIYADSVKG RFTISRDNAKNSLYLQMNSLRAEDTAVYYCAR HLTGDY
                 FR1                  CDR1         FR2             CDR2                   FR3                     CDR3
9.14.4     -------- (residues 20-135 of SEQ ID NO: 38)
Germ       WGQGTLVTVSSA (SEQ ID NO: 116)
                  3
```

FIG. 4Q

```
Germline V=O12, J=JK3
9.7.2      -----------------------T-----------R---1---------T-----L-------------------------------------------
(residues 23-130 of SEQ ID NO: 48)
Germ       DIQMTQSPSSLSASVGDRVTITC RASQSISSYLN WYQQKPGKAPKLLIY AASSLQS GVPSRFSGSGSGTDFTLTISSLQPEDFATYYC QQSYSTPFT FGPGTKVDIKR
(SEQ ID NO: 103)  FR1         CDR1           FR2          CDR2           FR3                              CDR3
                                                                                                              3
```

FIG. 4R

```
Germline V=VH3-11, D=D6-13, J=JH6b
9.7.2      ------------------------------------------------------------------R--G------
Germ       QVQLVESGGGLVKPGGSLRLSCAAS GFTFSDYYMS WIRQAPGKGLEWVS YISSSGSTIYADSVKG RFTISRDNAKNSLYLQMNSLRAEDTAVYYCAR HIAGNDV
                 FR1                  CDR1         FR2             CDR2                   FR3                     CDR3
9.7.2      -------- (residues 20-136 of SEQ ID NO: 46)
Germ       WGQGTTVTVSSA (SEQ ID NO: 115)
                  3
```

FIG. 4S

Germline V=012, J=JK3
9.14.4I
(residues 23-130 of SEQ ID NO: 28)

```
Germ     DIQMTQSPSSLSASVGDRVTITC RASQSISSYLN WYQQKPGKAPKLLIY AASSLQS GVPSRFSGSGSGTDFTLTISSLQPEDFATYYC QQSYSTPFT FGPGTKVDIKR
(SEQ ID NO: 103)  FR1              CDR1                FR2             CDR2              FR3                         CDR3           J
9.14.4I  ---------------------- ---------- --------------- -P-I---- --------------------B----------- -------- -----------
```

FIG. 4T

Germline V=VH3-11, D=D7-27, J=JH4b
9.14.4I

```
Germ     QVQLVESGGGLVKPGGSLRLSCAAS GFTFSDYYMS WIRQAPGKGLEWVS YISSSGSTIYYADSVKG RFTISRDNAKNSLYLQMNSLRAEDTAVYYCAR #LTGDY
                FR1                CDR1           FR2              CDR2                       FR3                   CDR3
                         ---- (residues 20-135 of SEQ ID NO: 26)
9.14.4I  ------------------------- ---------- --------------- ----------------- -----------------------G------- ------

Germ     WGQGTLVTVSSA (SEQ ID NO: 116)
              J
```

FIG. 4U

Germline V=A27, J=JK4
8.10.3F
-R--------

```
Germ     EIVLTQSPGTLSLSPGERATLSC RASQSVSSSYLA WYQQKPGQAPRLLIY GASSRAT GIPDRFSGSGSGTDFTLTISRLEPEDFAVYYC
                FR1                 CDR1           FR2            CDR2                  FR3
                         ---------- (residues 21-129 of SEQ ID NO: 32)
8.10.3F  ----------------------- ------------ --------------- ------- --------------------------------

Germ     QQYGSSPLT FGGGTKVEIKR (SEQ ID NO: 114)
           CDR3         J
```

FIG. 4V

Germline V=VH3-48, D=D1-26, J=JH4b
8.10.3F

```
8.10.3F  EVQLVESGGGLVQPGGSLRLSCAAS GFTFSSYSMN WVRQAPGKGLEWVS YISSSSSTIYYADSVKG RFTISRDNAKNSLYLQMNSLRAEDTAVYYCAR ##IVG##TDY DPILA-ATT---
             FR1                  CDR1            FR2               CDR2                  FR3                    CDR3
8.10.3F  ---------- (residues 20-141 of SEQ ID NO: 39)
Germ     ----R----G----
Germ     WGQGTLVTVSS (SEQ ID NO: 113)
             J
```

FIG. 4W

Germline V=O12, J=JK3
9.7.2IF

```
9.7.2IF  DIQMTQSPSSLSASVGDRVTITC RASQSISSYLN WYQQKPGKAPKLLIY AASSLQS GVPSRFSGSGSGTDFTLTISSLQPEDFATYYC QQSYSTFT FGPGTKVDIKR
(residues 23-130 of SEQ ID NO: 36)   FR1         CDR1           FR2        CDR2         FR3                CDR3       J
Germ     ----T----
Germ     DIQMTQSPSSLSASVGDRVTITC RASQSISSYLN WYQQKPGKAPKLLIY AASSLQS GVPSRFSGSGSGTDFTLTISSLQPEDFATYYC QQSYSTFT FGPGTKVDIKR
(SEQ ID NO: 103)   FR1          CDR1             FR2        CDR2         FR3                CDR3       J
```

FIG. 4X

Germline V=VH3-11, D=D6-13, J=JH6b
9.7.21F

```
9.7.21F  QVQLVESGGGLVKPGGSLRLSCAAS GFTFSDYYMS WIRQAPGKGLEWVS YISSSGSTIYYADSVKG RFTISRDNAKNSLYLQMNSLRAEDTAVYCAR #I#GMDV R-G----
             FR1                   CDR1          FR2              CDR2                   FR3                  CDR3
9.7.21F  ---------- (residues 20-136 of SEQ ID NO: 34)
Germ     WGQGTTVTVSS (SEQ ID NO: 115)
             J
```

FIG. 4Y

Germline V=012, J=JK3
9.7.2C-Ser
(residues 23-130 of SEQ ID NO: 52)

```
Germ     DIQMTQSPSSLSASVGDRVTITC RASQSISSYLN WYQQKPGKAPKLLIY AASSLQS GVPSRFSGSGSGTDFTLTISSLQPEDFATYYC QQSYSTPFT FGPGTKVDIKR
(SEQ ID NO: 103)         FR1                    CDR1                FR2            CDR2                   FR3                        CDR3          J
9.7.2C-Ser                                      ------GP-I-         --S-----                                                         ------------ -
                                                  CDR1              FR2            CDR2                   FR3                        CDR3          J
```

FIG. 4Z

Germline V=VH3-11, D=D6-13, J=JH6b
9.7.2C-Ser

```
Germ     QVQLVESGGGLVKPGGSLRLSCAAS GFTFSDYYMS WIRQAPGKGLEWVS YISSSGSTIYYADSVKG RFTISRDNAKNSLYLQMNSLRAEDTAVYYCA #14GMDV
              FR1                  CDR1            FR2                CDR2                  FR3                     CDR3
9.7.2C-Ser   --------- (residues 20-136 of SEQ ID NO: 50)                                                           ---------  R-G---
Germ     WGQGTTVTVSSA (SEQ ID NO: 115)
              J
```

FIG. 4AA

Germline V=012, J=JK3
9.14.4C-Ser
(residues 23-130 of SEQ ID NO: 56)

```
Germ     DIQMTQSPSSLSASVGDRVTITC RASQSISSYLN WYQQKPGKAPKLLIY AASSLQS GVPSRFSGSGSGTDFTLTISSLQPEDFATYYC QQSYSTPFT FGPGTKVDIKR
(SEQ ID NO: 103)         FR1                    CDR1                FR2            CDR2                   FR3                        CDR3          J
9.14.4C-Ser                                     -P-Z-I--            ----------                                                       ------------ -
                                                  CDR1              FR2            CDR2                   FR3                        CDR3          J
```

FIG. 4BB

Germline V=VH3-11, D=D7-27, J=JH4b
9.14.4C-Ser

```
Germ  QVQLVESGGGLVKPGGSLRLSCAAS GTFSDYYMS WIRQAPGKGLEWVS YISSSGSTIYYADSVKG RFTISRDNAKNSLYLQMNSLRAEDTAVYYCAR SLIGDY
                              FR1                   CDR1         FR2               CDR2                    FR3                   CDR3

9.14.4C-Ser -------------------------- (residues 20-135 of SEQ ID NO: 54)

Germ  WGQGTLVTVSSA (SEQ ID NO: 116)
           J
```

FIG. 4CC

Germline V=A27, J=JK4
8.10.3C-Ser

```
Germ  EIVLTQSPGTLSLSPGERATLSC RASQSVSSSYLA WYQQKPGQAPRLLIY GASSRAT GIPDRFSGSGSGTDFTLTIRRLEPEDFAVYYC
                          FR1                 CDR1                FR2               CDR2                    FR3

Germ  QQYGSSPLT FGGGTKVEIKR (residues 21-129 of SEQ ID NO: 60)
         CDR3           J 8.10.3 ---------- --------- (SEQ ID NO: 114)
```

FIG. 4DD

Germline V=VH3-48, D=D1-26, J=JH4b
8.10.3C-Ser

```
Germ  EVQLVESGGGLVQPGGSLRLSCAAS GFTFSSYSMN WVRQAPGKGLEWVS YISSSSSTIYADSVKG RFTISRDNAKNSLYLQMNSLRDEDTAVYYCAR DPLLA-ATF
                              FR1                   CDR1         FR2               CDR2                    FR3                   CDR3

8.10.3C-Ser -------------------------- (residues 20-141 of SEQ ID NO: 58)

Germ  WGQGTLVTVSSA (SEQ ID NO: 113)
           J
```

FIG. 4EE

Germline V=A27, J=JK4
8.10.3-CG2

Germ    EIVLTQSPGTLSLSPGERATLSC RASQVSSSYLA WYQQKPGQAPRLLIY GASSRAT GIPDRFSGSGSGTDFTLTISRLEPEDFAVYYC
        FR1                     CDR1        FR2             CDR2    FR3

8.10.3-CG2  ---------- (residues 21-129 of SEQ ID NO: 60)

Germ    QQYGSSPLT FGGGTKVEIKR (SEQ ID NO: 114)
        CDR3      J

FIG. 4FF

Germline V=VH3-48, D=D1-26, J=JH4b
8.10.3-CG2

Germ    EVQLVESGGGLVQPGGSLRLSCAAS GFTFSSYSMN WVRQAPGKGLEWVS YISSSSSTIYYADSVKG RFTISRDNAKNSLYLQMNSLRAEDTAVYYCAR DRLLA-AFF----
        FR1                       CDR1       FR2            CDR2              FR3

8.10.3-CG2 ----------G-I---- ------T--- --------------- -----S-------- ---------------------S---------- HHHIVGHHFDY
                                                                                                       CDR3

Germ    WGQGTLVTVSSA (SEQ ID NO: 113)
        J

FIG. 4GG

Germline V=012, J=JK3
9.7.2-CG2

Germ    DIQMTQSPSSLSASVGDRVTITC RASQSISSYLN WYQQKPGKAPKLLIY AASSLQS GVPSRFSGSGSGTDFTLTISSLQPEDFATYYC QQSYSTPFT FGPGTKVDIKR
        FR1                    CDR1         FR2             CDR2    FR3                              CDR3      J (residues 23-130 of SEQ ID NO: 52)

Germ    DIQMTQSPSSLSASVGDRVTITC RASQSISSYLN WYQQKPGKAPKLLIY AASSLQS GVPSRFSGSGSGTDFTLTISSLQPEDATYYC QQSYSTPFT FGPGTKVDIKR
(SEQ ID NO: 103)                CDR1         FR2             CDR2    FR3                              CDR3      J
        FR1

FIG. 4HH

Germline V=VH3-11, D=D6-13, J=JH6b
9.7.2-CG2
(residues 20-136 of SEQ ID NO: 66)

```
Germ     QVQLVESGGGLVKPGGSLRLSCAAS GFTFSDYYMS WIRQAPGKGLEWVS YISSSGSTIYYADSVKG RFTISRDNAKNSLYLQMNSLRAEDTAVYYCA IIHGMDV
(SEQ ID NO: 115)                   FR1                CDR1              FR2               CDR2                           FR3                   CDR3

9.7.2-CG2  --------------------------- ---------- -------------- ----------------- ------------------------------- R-G----

Germ     WGQGTTVTVSSA
              J
```

FIG. 4II

Germline V=O12, J=JK3
9.7.2-CG4
(residues 23-130 of SEQ ID NO: 52)

```
Germ     DIQMTQSPSSLSASVGDRVTITC RASQSISSYLN WYQQKPGKAPKLLIY AASSLQS GVPSRFSGSGSGTDFTLTISSLQPEDFATYYC QQSYSTPFT FGPGTKVDIKR
(SEQ ID NO: 103)              FR1              CDR1              FR2              CDR2                           FR3                   CDR3         J 9.7.2-CG4  ---------------GF-I------ ---------- --------------- --T---- ----------------------------- -------- ----------
```

FIG. 4JJ

Germline V=VH3-11, D=D6-13, J=JH6b
9.7.2-CG4

```
Germ     QVQLVESGGGLVKPGGSLRLSCAAS GFTFSDYYMS WIRQAPGKGLEWVS YISSSGSTIYYADSVKG RFTISRDNAKNSLYLQMNSLRAEDTAVYYCA IIHGMDV
(SEQ ID NO: 115)                   FR1                CDR1              FR2               CDR2                           FR3                   CDR3

9.7.2-CG4 ---------- (residues 20-135 of SEQ ID NO: 70)

Germ     WGQGTTVTVSSA (SEQ ID NO: 115)
              J
```

FIG. 4KK

Germline V=012, J=JK3
9.14.4-CG2
(residues 23-130 of SEQ ID NO: 56)

```
Germ        DIQMTQSPSSLSASVGDRVTITC RASQSISSYLN WYQQKPGKAPKLLIY AASSLQS GVPSRFSGSGSGTDFTLTISSLQPEDFATYYC QQSYSTPFT FGPGTKVDIKA
(SEQ ID NO: 103)      FR1                      CDR1              FR2          CDR2              FR3                          CDR3         J
9.14.4-CG2   ---------------------- ---------- --------------- ------- -P--I--L------------------------ -------- G----------
```

FIG. 4LL

Germline V=VH3-11, D=D7-27, J=JH4b
9.14.4-CG2

```
Germ        QVQLVESGGGLVKPGGSLRLSCAAS GFTFSDYYMS WIRQAPGKGLEWVS YISSSGSTIYYADSVKG RFTISRDNAKNSLYLQMNSLRAEDTAVYYCAR GLTGDY WGQGTLVTVSSA
                  FR1                  CDR1          FR2           CDR2                    FR3                     CDR3       J
(SEQ ID NO: 116)
9.14.4-CG2  ------------------------- ---------- --------------- ----------------- -------------------------------- ------ ------------
            (residues 20-135 of SEQ ID NO: 74)
```

FIG. 4MM

Germline V=012, J=JK3
9.14.4-CG4
(residues 23-130 of SEQ ID NO: 56)

```
Germ        DIQMTQSPSSLSASVGDRVTITC RASQSISSYLN WYQQKPGKAPKLLIY AASSLQS GVPSRFSGSGSGTDFTLTISSLQPEDFATYYC QQSYSTPFT FGPGTKVDIKR
(SEQ ID NO: 103)      FR1                      CDR1              FR2          CDR2              FR3                          CDR3         J
9.14.4-CG4   ---------------------- ---------- --------------- ------- -P--I--L------------------------ -------- G----------
```

FIG. 4NN

Germline V=VK3-11, D=D7-27, J=JH4b
9.14.4-CG4

```
Germ       QVQLVESGGGVVKPGGSLRLSCAAS GFTFSDYYMS WIRQAPGKGLEWVS YISSSGSTIYYADSVKG RFTISRDNAKNSLYLQMNSLRAEDTAVYYCAR #LTGDY
                      FR1                 CDR1            FR2              CDR2                  FR3                   CDR3
9.14.4-CG4 ---------- (residues 20-135 of SEQ ID NO: 78)                                                              -P-I-------    -------   G--------
Germ       RGQGTLVTVSSA (SEQ ID NO: 116)
                  J
```

FIG. 4OO

Germline V=O12, J=JK3
9.14.4-Ser
(residues 23-130 of SEQ ID NO: 28)

```
Germ       DIQMTQSPSSLSASVGDRVTITC RASQSISSYLN WYQQKPGKAPKLLIY AASSLQS GVPSRFSGSGSGTDFTLTISSLQPEDFATYYC QQSYSTPFT FGPGTKVDIKR
(SEQ ID NO: 103)   FR1              CDR1             FR2           CDR2                     FR3                  CDR3        J
```

FIG. 4PP

Germline V=VH3-11, D=D7-27, J=JH4b
9.14.4-Ser

```
Germ       QVQLVESGGGVVKPGGSLRLSCAAS GFTFSDYYMS WIRQAPGKGLEWVS YISSSGSTIYYADSVKG RFTISRDNAKNSLYLQMNSLRAEDTAVYYCAR #LTGDY
                      FR1                 CDR1            FR2              CDR2                  FR3                   CDR3
9.14.4-Ser ---------- (residues 20-135 of SEQ ID NO: 82)                                                              ---------     -------    G--------
Germ       RGQGTLVTVSSA (SEQ ID NO: 116)
                  J
```

FIG. 4QQ

Germline VκO12, J=JK3
9.7.2-Ser ------GP-I ----R---- ----------- -----L---- ----R-----
          FR1        CDR1       FR2        CDR2       FR3        CDR3
(residues 23-130 of SEQ ID NO: 48)

Germ DIQMTQSPSSLSASVGDRVTITC RASQSISSYLN WYQQKPEKAPKLLIY AASSLQS GVPSRFSGSGSGTDFTLTISSLQPEDFATYYC QQSYSTPFT FGPGTKVDIKR
     FR1                    CDR1        FR2             CDR2    FR3                              CDR3       J
(SEQ ID NO: 103) FR1         CDR1        FR2             CDR2    FR3                              CDR3       J

FIG. 4RR

Germline V=VH3-11, D=D6-13, J=JH6b
9.7.2-Ser ----------- --------- --------- ---------- -----L----- --------- -------------- ---------------------------- R-G------
Germ QVQLVESGGGLVKPGGSLRLSCAAS GFTFSDYYMS WIRQAPGKGLEWVS YISSSGSTIYYADSVKG RFTISRDNAKNSLYLQMNSLRAEDTAVYYCA 0I#GMDV
     FR1                       CDR1       FR2            CDR2              FR3                             CDR3
9.7.2-Ser --------- (residues 20-136 of SEQ ID NO: 50)
Germ WGQGTTVTVSSA (SEQ ID NO: 115)
                   J

FIG. 4SS

Germline VκA27, J=JK4
8.10.3-Ser ----R----- --------- -------- -------- --------- ---------- ----------- ---------------- ------------------------ -----Q--
Germ EIVLTQSPGTLSLSPGERATLSC RASQSVSSSYLA WYQQKPGQAPRLLIY GASSRAT GIPDRFSGSGSGTDFTLTISRLEPEDFAVYYC
     FR1                    CDR1         FR2             CDR2    FR3
8.10.3-Ser ----------- (residues 21-129 of SEQ ID NO: 44)
Germ ---------- (SEQ ID NO: 114)
Germ QQYGSSPLT FGGGTKVEIKR (SEQ ID NO: 114)
     CDR3      J

FIG. 4TT

Germline V=VH3-48, D=D1-26, J=JH4b
8.10.3-Ser

| | FR1 | CDR1 | FR2 | CDR2 | FR3 | CDR3 |
|---|---|---|---|---|---|---|
| Germ | EVQLVESGGGLVQPGGSLRLSCAAS | GFTFSSYSMN | WVRQAPGKGLEWVS | YISSSSSTIYYADSVKG | RFTISRDNAKNSLYLQMNSLRAEDTAVYYCAR | DPLLA-ATF--- |
| 8.10.3-Ser | ----------- (residues 20-141 of SEQ ID NO: 90) | | | | | ###IVGH##FDY |
| Germ | WGQGTLVTVSSA (SEQ ID NO: 113) | | | | | |

FIG. 4UU

Germline V=A27, J=JK4
8.10.3-CG4

| | FR1 | CDR1 | FR2 | CDR2 | FR3 |
|---|---|---|---|---|---|
| Germ | EIVLTQSPGTLSLSPGERATLSC | RASQSVSSSYLA | WYQQKPGQAPRLLIY | GASSRAT | GIPDRFSGSGSGTDFTLTISRLEPEDFAVYYC |
| 8.10.3-CG4 | ----------- (residues 21-128 of SEQ ID NO: 60) | | | | |
| Germ | QQYGSSPLT FGGGTKVEIKR (SEQ ID NO: 114) | | | | |

FIG. 4VV

Germline V=VH3-48, D=D1-26, J=JH4b
8.10.3-CG4

| | FR1 | CDR1 | FR2 | CDR2 | FR3 | CDR3 |
|---|---|---|---|---|---|---|
| Germ | EVQLVESGGGLVQPGGSLRLSCAAS | GFTFSSYSMN | WVRQAPGKGLERVS | YISSSSSTIYYADSVKG | RFTISRDNAKMSLYLQMNSLRAEDTAVYYCAR | DPLLA-ATF--- |
| 8.10.3-CG4 | ----------- (residues 20-141 of SEQ ID NO: 94) | | | | | ###IVGH##FDY |
| Germ | WGQGTLVTVSSA (SEQ ID NO: 113) | | | | | |

FIG. 4WW

Germline V=012, J=JK3
9.14.4G1
(residues 23-130 of SEQ ID NO: 26)

```
Germ        DIQMTQSPSSLSASVGDRVTITC RASQSISSYLN WYQQKPGKAPKLLIY AASSLQS GVPSRFSGSGSGTDFTLTISSLQPEDFATYYC QQSYSTPPT FGPGTKVDIKR
(SEQ ID NO: 103)   FR1                 CDR1              FR2        CDR2                 FR3                    CDR3        J
9.14.4G1    -------------------- ---P--I---L-- ------------ ---------- -------------------- --------- ----------
```

FIG. 4XX

Germline V=VH3-11, D=D7-27, J=JH4b
9.14.4G1

```
Germ        QVQLVESGGGLVKPGGSLRLSCAAS GFTFSDYYMS WIRQAPGKGLEWVS YISSSGSTIYYADSVKG RFTISRDNAKNSLYLQMNSLRAEDTAVYYCAR  HLTGDY
                   FR1                 CDR1              FR2               CDR2                    FR3                    CDR3
9.14.4G1    ------------------------ (residues 20-135 of SEQ ID NO: 102)  ---------------------------------- G------

Germ        WGQGTLVTVSSA (SEQ ID NO: 116)
                 J
```

FIG. 4YY

Germline V=A27, J=JK4
8.10.3FG1

```
Germ        EIVLTQSPGTLSLSPGERATLSC RASQSVSSSYLA WYQQKPGQAPRLLIY GASSRAT GIPDRFSGSGSGTDFTLTISRLEPEDFAVYYC
                  FR1                 CDR1              FR2         CDR2              FR3
8.10.3FG1   ----------------------- (residues 21-129 of SEQ ID NO: 114)

Germ        QQYGSSPLT FGGGTKVEIKR (SEQ ID NO: 32)
                 CDR3         J
```

FIG. 4ZZ

Germline V=VH3-48, D=D1-26, J=JH4b
8.10.3FG1 ----------- ------F-1 ------------- -------R-----S----- -----------------------------------  DPLLA-AYF---

Germ      EVQLVESGGGLVQPGGSLRLSCAAS GFTFSSYSMN WVRQAPGKGLEWVS VISSSSSTYYADSVKG RFTISRDNAKNSLYLQMNSLRAEDTAVYYCAR ##IVG#HFDY
          FR1                      CDR1       FR2            CDR2             FR3                              CDR3

8.10.3FG1 ---------- (residues 20-141 of SEQ ID NO: 98)

Germ      WGQGTLVTVSSA (SEQ ID NO: 113)

SEQUENCE LISTING

<160> NUMBER OF SEQ IDS: 117

<210> SEQ ID NO 1
<211> LENGTH: 1383
<212> TYPE: DNA
<213> ORGANISM: Homo sapiens

<400> SEQUENCE: 1

```
atggagttgg ggctgtgctg gattttcctt gttgctatta taaaaggtgt ccagtgtcag    60
gtgcagctgg tggagtctgg gggaggcttg gtcaagcctg agggtccct  gagactctcc   120 tgtgcagcct ctggattcac cttcagtgac tactacatga gctggatccg ccaggctcca   180
gggaaggggc tggagtggat ttcatacatt agtggtagtg gtagtaccat atactacgca   240
gactctgtga agggccgatt caccatctcc agggacaacg ccaagaactc actgtatctg   300
caaatgaaca gcctgagagc cgaggacacg gccgtgtatc actgtgcgag agccctgggt   360
gggatggacg tctggggcca aggaccacg  gtcaccgtct cctcagcttc caccaagggc   420
ccatccgtct tccccctggc gccctgctct agaagcacct ccgagagcac agcggccctg   480
ggctgcctgg tcaaggacta cttccccgaa ccggtgacgg tgtcgtggaa ctcaggcgct   540
ctgaccagcg gcgtgcacac cttcccagct gtcctacagt cctcaggact ctactccctc   600
agcagcgtgg tgaccgtgcc ctccagcaac ttcggcaccc agacctacac ctgcaacgta   660
gatcacaagc ccagcaacac caaggtggac aagacagttg agcgcaaatg ttgtgtcgag   720
tgcccaccgt gcccagcacc acctgtggca ggaccgtcag tcttcctctt ccccccaaaa   780
cccaaggaca cctcatgat  ctcccggacc cctgaggtca cgtgcgtggt ggtggacgtg   840
agccacgaag accccgaggt ccagttcaac tggtacgtgg acggcgtgga ggtgcataat   900
```

-continued

```
gccaagacaa agccacggga ggagcagttc aacagcacgt tccgtgtggt cagcgtcctc      960
accgttgtgc accaggactg gctgaacggc aaggagtaca agtgcaaggt ctccaacaaa     1020
ggcctcccag cccccatcga gaaaaccatc tccaaaacca agggcagcc ccgagaacca     1080 caggtgtaca ccctgccccc atcccgggag gagatgacca gaaccaggt cagcctgacc     1140 tgcctggtca aaggcttcta ccccagcgac atcgccgtgg agtgggagag caatgggcag     1200
ccggagaaca actacaagac cacacctccc atgctggact ccgacggctc cttcttcctc     1260
tacagcaagc tcaccgtgga caagagcagg tggcagcagg ggaacgtctt ctcatgctcc     1320
gtgatgcatg aggctctgca caaccactac acgcagaaga gcctctccct gtctccgggt     1380
aaa                                                                   1383
```

<210> SEQ ID NO 2
<211> LENGTH: 461
<212> TYPE: PRT
<213> ORGANISM: Homo sapiens

<400> SEQUENCE: 2

```
Met Glu Leu Gly Leu Cys Trp Ile Phe Leu Val Ala Ile Ile Lys Gly
  1               5                  10                  15

Val Gln Cys Gln Val Gln Leu Val Glu Ser Gly Gly Gly Leu Val Lys
             20                  25                  30

Pro Gly Gly Ser Leu Arg Leu Ser Cys Ala Ala Ser Gly Phe Thr Phe
         35                  40                  45

Ser Asp Tyr Tyr Met Ser Trp Ile Arg Gln Ala Pro Gly Lys Gly Leu
     50                  55                  60

Glu Trp Ile Ser Tyr Ile Ser Gly Ser Gly Ser Thr Ile Tyr Tyr Ala
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Ala Glu Asp Thr Ala Val
            100                 105                 110

Tyr His Cys Ala Arg Ala Leu Gly Gly Met Asp Val Trp Gly Gln Gly
        115                 120                 125

Thr Thr Val Thr Val Ser Ser Ala Ser Thr Lys Gly Pro Ser Val Phe
130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Gln
        275                 280                 285
```

```
Phe Asn Trp Tyr Val Asp Gly Val Glu Val His Asn Ala Lys Thr Lys
    290                 295                 300
Pro Arg Glu Glu Gln Phe Asn Ser Thr Phe Arg Val Val Ser Val Leu
305                 310                 315                 320
Thr Val Val His Gln Asp Trp Leu Asn Gly Lys Glu Tyr Lys Cys Lys
            325                 330                 335
Val Ser Asn Lys Gly Leu Pro Ala Pro Ile Glu Lys Thr Ile Ser Lys
        340                 345                 350
Thr Lys Gly Gln Pro Arg Glu Pro Gln Val Tyr Thr Leu Pro Pro Ser
    355                 360                 365
Arg Glu Glu Met Thr Lys Asn Gln Val Ser Leu Thr Cys Leu Val Lys
370                 375                 380
Gly Phe Tyr Pro Ser Asp Ile Ala Val Glu Trp Glu Ser Asn Gly Gln
385                 390                 395                 400
Pro Glu Asn Asn Tyr Lys Thr Thr Pro Pro Met Leu Asp Ser Asp Gly
            405                 410                 415
Ser Phe Phe Leu Tyr Ser Lys Leu Thr Val Asp Lys Ser Arg Trp Gln
        420                 425                 430
Gln Gly Asn Val Phe Ser Cys Ser Val Met His Glu Ala Leu His Asn
    435                 440                 445
His Tyr Thr Gln Lys Ser Leu Ser Leu Ser Pro Gly Lys
    450                 455                 460

<210> SEQ ID NO 3
<211> LENGTH: 702
<212> TYPE: DNA
<213> ORGANISM: Homo sapiens

<400> SEQUENCE: 3
atgagggtcc ctgctcagct cctggggctc ctgctactct ggctccgagg tgccagatgt      60
gacatccaga tgacccagtc tccatcctcc ctgtctgcat ctgtaggaga cagagtcacc     120
atcacttgcc gggcaagtca gagcattagc ggctttttaa attggtatca gcagaaacca     180
gggaaagccc ctaagctcct gatctatgct acatccagtt tgcaaagtgg ggtcccattc     240
aggttcagtg gcagtggatc tgggacagat ttcactctca ccatcagcag tctgcaacct     300
gaagattttg caacttatta ctgtcaacag agttacagtg tcccattcac tttcggccct     360
gggaccaaag tggatatcaa acgaactgtg gctgcaccat ctgtcttcat cttcccgcca     420
tctgatgagc agttgaaatc tggaactgct agcgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctacgcct gcgaagtcac ccatcagggc     660
ctgagctcgc ccgtcacaaa gagcttcaac aggggagagt gt                        702

<210> SEQ ID NO 4
<211> LENGTH: 234
<212> TYPE: PRT
<213> ORGANISM: Homo sapiens

<400> SEQUENCE: 4

Met Arg Val Pro Ala Gln Leu Leu Gly Leu Leu Leu Leu Trp Leu Arg
1               5                   10                  15
Gly Ala Arg Cys Asp Ile Gln Met Thr Gln Ser Pro Ser Ser Leu Ser
            20                  25                  30
```

Ala Ser Val Gly Asp Arg Val Thr Ile Thr Cys Arg Ala Ser Gln Ser
            35                  40                  45

Ile Ser Gly Phe Leu Asn Trp Tyr Gln Gln Lys Pro Gly Lys Ala Pro
    50                  55                  60

Lys Leu Leu Ile Tyr Ala Thr Ser Ser Leu Gln Ser Gly Val Pro Phe
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
            100                 105                 110

Ser Val Pro Phe Thr Phe Gly Pro Gly Thr Lys Val Asp Ile Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 5
<211> LENGTH: 1389
<212> TYPE: DNA
<213> ORGANISM: Homo sapiens

<400> SEQUENCE: 5

```
atggaatttg ggctgtgctg ggttttcctt gttgctattt tagaaggtgt ccagtgtgag      60
gtgcagctgg tggagtctgg gggaggcttg gtccagcctg ggggtccct gagactctcc     120
tgtgcagcct ctggattcac ctttagtagc tattggatga gctgggtccg ccaggctcca    180
gggaaggggc tggagtgggt ggccaacata aagcaagatg aagtgagaa atactatgtg     240
gactctgtga aggccgatt caccatctcc agagacaacg ccaagaactc actgtatctg     300
caaatgaaca gcctgagagc cgaggacacg gctgtgtatt actgtgctcc gggtatagca    360
gcagctggta gggcctactg gggccaggga accctggtca ccgtctcctc agcttccacc    420
aagggcccat ccgtcttccc cctggcgccc tgctctagaa gcacctccga gagcacagcg    480
gccctgggct gcctggtcaa ggactacttc cccgaaccgg tgacggtgtc gtggaactca    540
ggcgctctga ccagcggcgt gcacaccttc ccagctgtcc tacagtcctc aggactctac    600
tccctcagca gcgtggtgac cgtgccctcc agcaacttcg gcacccagac ctacacctgc    660
aacgtagatc acaagcccag caacaccaag gtggacaaga cagttgagcg caaatgttgt    720
gtcgagtgcc caccgtgccc agcaccacct gtggcaggac cgtcagtctt cctcttcccc    780
ccaaaaccca aggacaccct catgatctcc cggacccctg aggtcacgtg cgtggtggtg    840
gacgtgagcc acgaagaccc cgaggtccag ttcaactggt acgtggacgg cgtggaggtg    900
cataatgcca agacaaagcc acgggaggag cagttcaaca gcacgttccg tgtggtcagc    960
```

-continued

```
gtcctcaccg ttgtgcacca ggactggctg aacggcaagg agtacaagtg caaggtctcc    1020
aacaaaggcc tcccagcccc catcgagaaa accatctcca aaaccaaagg gcagccccga    1080
gaaccacagg tgtacaccct gccccatcc cgggaggaga tgaccaagaa ccaggtcagc     1140
ctgacctgcc tggtcaaagg cttctacccc agcgacatcg ccgtggagtg ggagagcaat    1200
gggcagccgg agaacaacta caagaccaca cctcccatgc tggactccga cggctccttc    1260
ttcctctaca gcaagctcac cgtggacaag agcaggtggc agcaggggaa cgtcttctca    1320
tgctccgtga tgcatgaggc tctgcacaac cactacacgc agaagagcct ctccctgtct    1380
ccgggtaaa                                                            1389
```

<210> SEQ ID NO 6
<211> LENGTH: 463
<212> TYPE: PRT
<213> ORGANISM: Homo sapiens

<400> SEQUENCE: 6

| Met | Glu | Phe | Gly | Leu | Cys | Trp | Val | Phe | Leu | Val | Ala | Ile | Leu | Glu | Gly |
|---|---|---|---|---|---|---|---|---|---|---|---|---|---|---|---|
| 1 | | | | 5 | | | | | 10 | | | | | 15 | |

| Val | Gln | Cys | Glu | Val | Gln | Leu | Val | Glu | Ser | Gly | Gly | Gly | Leu | Val | Gln |
|---|---|---|---|---|---|---|---|---|---|---|---|---|---|---|---|
| | | 20 | | | | | 25 | | | | | 30 | | | |

| Pro | Gly | Gly | Ser | Leu | Arg | Leu | Ser | Cys | Ala | Ala | Ser | Gly | Phe | Thr | Phe |
|---|---|---|---|---|---|---|---|---|---|---|---|---|---|---|---|
| | | 35 | | | | | 40 | | | | | 45 | | | |

| Ser | Ser | Tyr | Trp | Met | Ser | Trp | Val | Arg | Gln | Ala | Pro | Gly | Lys | Gly | Leu |
|---|---|---|---|---|---|---|---|---|---|---|---|---|---|---|---|
| | 50 | | | | | 55 | | | | | 60 | | | | |

| Glu | Trp | Val | Ala | Asn | Ile | Lys | Gln | Asp | Gly | Ser | Glu | Lys | Tyr | Tyr | Val |
|---|---|---|---|---|---|---|---|---|---|---|---|---|---|---|---|
| 65 | | | | | 70 | | | | | 75 | | | | | 80 |

| Asp | Ser | Val | Lys | Gly | Arg | Phe | Thr | Ile | Ser | Arg | Asp | Asn | Ala | Lys | Asn |
|---|---|---|---|---|---|---|---|---|---|---|---|---|---|---|---|
| | | | | 85 | | | | | 90 | | | | | 95 | |

| Ser | Leu | Tyr | Leu | Gln | Met | Asn | Ser | Leu | Arg | Ala | Glu | Asp | Thr | Ala | Val |
|---|---|---|---|---|---|---|---|---|---|---|---|---|---|---|---|
| | | | 100 | | | | | 105 | | | | | 110 | | |

| Tyr | Tyr | Cys | Ala | Pro | Gly | Ile | Ala | Ala | Ala | Gly | Arg | Ala | Tyr | Trp | Gly |
|---|---|---|---|---|---|---|---|---|---|---|---|---|---|---|---|
| | | 115 | | | | | 120 | | | | | 125 | | | |

| Gln | Gly | Thr | Leu | Val | Thr | Val | Ser | Ser | Ala | Ser | Thr | Lys | Gly | Pro | Ser |
|---|---|---|---|---|---|---|---|---|---|---|---|---|---|---|---|
| | 130 | | | | | 135 | | | | | 140 | | | | |

| Val | Phe | Pro | Leu | Ala | Pro | Cys | Ser | Arg | Ser | Thr | Ser | Glu | Ser | Thr | Ala |
|---|---|---|---|---|---|---|---|---|---|---|---|---|---|---|---|
| 145 | | | | | 150 | | | | | 155 | | | | | 160 |

| Ala | Leu | Gly | Cys | Leu | Val | Lys | Asp | Tyr | Phe | Pro | Glu | Pro | Val | Thr | Val |
|---|---|---|---|---|---|---|---|---|---|---|---|---|---|---|---|
| | | | | 165 | | | | | 170 | | | | | 175 | |

| Ser | Trp | Asn | Ser | Gly | Ala | Leu | Thr | Ser | Gly | Val | His | Thr | Phe | Pro | Ala |
|---|---|---|---|---|---|---|---|---|---|---|---|---|---|---|---|
| | | | 180 | | | | | 185 | | | | | 190 | | |

| Val | Leu | Gln | Ser | Ser | Gly | Leu | Tyr | Ser | Leu | Ser | Ser | Val | Val | Thr | Val |
|---|---|---|---|---|---|---|---|---|---|---|---|---|---|---|---|
| | | 195 | | | | | 200 | | | | | 205 | | | |

| Pro | Ser | Ser | Asn | Phe | Gly | Thr | Gln | Thr | Tyr | Thr | Cys | Asn | Val | Asp | His |
|---|---|---|---|---|---|---|---|---|---|---|---|---|---|---|---|
| | 210 | | | | | 215 | | | | | 220 | | | | |

| Lys | Pro | Ser | Asn | Thr | Lys | Val | Asp | Lys | Thr | Val | Glu | Arg | Lys | Cys | Cys |
|---|---|---|---|---|---|---|---|---|---|---|---|---|---|---|---|
| 225 | | | | | 230 | | | | | 235 | | | | | 240 |

| Val | Glu | Cys | Pro | Pro | Cys | Pro | Ala | Pro | Pro | Val | Ala | Gly | Pro | Ser | Val |
|---|---|---|---|---|---|---|---|---|---|---|---|---|---|---|---|
| | | | | 245 | | | | | 250 | | | | | 255 | |

| Phe | Leu | Phe | Pro | Pro | Lys | Pro | Lys | Asp | Thr | Leu | Met | Ile | Ser | Arg | Thr |
|---|---|---|---|---|---|---|---|---|---|---|---|---|---|---|---|
| | | | 260 | | | | | 265 | | | | | 270 | | |

| Pro | Glu | Val | Thr | Cys | Val | Val | Val | Asp | Val | Ser | His | Glu | Asp | Pro | Glu |
|---|---|---|---|---|---|---|---|---|---|---|---|---|---|---|---|
| | | 275 | | | | | 280 | | | | | 285 | | | |

| Val | Gln | Phe | Asn | Trp | Tyr | Val | Asp | Gly | Val | Glu | Val | His | Asn | Ala | Lys |
|---|---|---|---|---|---|---|---|---|---|---|---|---|---|---|---|
| 290 | | | | | 295 | | | | | 300 | | | | | |

Thr Lys Pro Arg Glu Glu Gln Phe Asn Ser Thr Phe Arg Val Val Ser
305 310 315 320

Val Leu Thr Val Val His Gln Asp Trp Leu Asn Gly Lys Glu Tyr Lys
325 330 335

Cys Lys Val Ser Asn Lys Gly Leu Pro Ala Pro Ile Glu Lys Thr Ile
340 345 350

Ser Lys Thr Lys Gly Gln Pro Arg Glu Pro Gln Val Tyr Thr Leu Pro
355 360 365

Pro Ser Arg Glu Glu Met Thr Lys Asn Gln Val Ser Leu Thr Cys Leu
370 375 380

Val Lys Gly Phe Tyr Pro Ser Asp Ile Ala Val Glu Trp Glu Ser Asn
385 390 395 400

Gly Gln Pro Glu Asn Asn Tyr Lys Thr Thr Pro Pro Met Leu Asp Ser
405 410 415

Asp Gly Ser Phe Phe Leu Tyr Ser Lys Leu Thr Val Asp Lys Ser Arg
420 425 430

Trp Gln Gln Gly Asn Val Phe Ser Cys Ser Val Met His Glu Ala Leu
435 440 445

His Asn His Tyr Thr Gln Lys Ser Leu Ser Leu Ser Pro Gly Lys
450 455 460

<210> SEQ ID NO 7
<211> LENGTH: 702
<212> TYPE: DNA
<213> ORGANISM: Homo sapiens

<400> SEQUENCE: 7
atgagggtcc ctgctcagct cctggggctc ctgctactct ggctccgagg tgccagatgt    60
gacatccaga tgacccagtc tccatcctcc ctgtctgcat ctgttggaga cagagtcacc   120
atcacttgcc ggccaagtca ggacattagc agttatttaa attggtatca gcagaaacca   180
gggaaagccc ctaagctcct gatctatgct catccagtt tgcaaagtgg ggtcccatta    240
aggttcagtg gcagtggatc tgggacagat ttcactctca ccatcagcag tctgcaacct   300
gaagattttg caacttacta ctgtcaacag agttacagta ccccattcac tttcggccct   360
gggaccaaag tggatatcaa acgaactgtg gctgcaccat ctgtcttcat cttcccgcca   420
tctgatgagc agttgaaatc tggaactgct agcgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag caccctgacg   600
ctgagcaaag cagactacga gaaacacaaa gtctacgcct gcgaagtcac ccatcagggc   660
ctgagctcgc ccgtcacaaa gagcttcaac aggggagagt gt                      702

<210> SEQ ID NO 8
<211> LENGTH: 234
<212> TYPE: PRT
<213> ORGANISM: Homo sapiens

<400> SEQUENCE: 8

Met Arg Val Pro Ala Gln Leu Leu Gly Leu Leu Leu Leu Trp Leu Arg
1               5                  10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Pro Ser Gln Asp
            35                  40                  45

Ile Ser Ser Tyr Leu Asn Trp Tyr Gln Gln Lys Pro Gly Lys Ala Pro
 50                  55                  60

Lys Leu Leu Ile Tyr Ala Ala Ser Ser Leu Gln Ser Gly Val Pro Leu
 65                  70                  75                  80

Arg Phe Ser Gly Ser Gly Ser Gly Thr Asp Phe Thr Leu Thr Ile Ser
                 85                  90                  95

Ser Leu Gln Pro Glu Asp Phe Ala Thr Tyr Tyr Cys Gln Gln Ser Tyr
            100                 105                 110

Ser Thr Pro Phe Thr Phe Gly Pro Gly Thr Lys Val Asp Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 9
<211> LENGTH: 1398
<212> TYPE: DNA
<213> ORGANISM: Homo sapiens

<400> SEQUENCE: 9
atggagtttg ggctccgctg gattttctt gtggctattt taaaaggtgt ccagtgtgag      60
gtgcagctgt tggagtctgg gggaggcttg gtacagcctg gggggtccct gagactctcc     120
tgtgcagcct ctggattcac ctttagcagc tatgccatga gctgggtccg ccaggctcca     180
gggaaggggc tggaatgggt ctcagctatt agtggtcgtg gtggtaggac atacttcgca     240
gactccgtga agggccggtt caccatctcc agagacaatt ccaagaacac gctgtatctg     300
caaatgaaca gcctgagagc cgaggacacg gccgtatatt tctgtgcggt agaaggctat     360
agtgggcgct acggattttt tgactactgg ggccagggaa ccctagtcac cgtctcctca     420
gcctccacca agggcccatc ggtcttcccc ctggcgccct gctctagaag cacctccgag     480
agcacagcgg ccctgggctg cctggtcaag gactacttcc ccgaaccggt gacggtgtcg     540
tggaactcag gcgctctgac cagcggcgtg cacaccttcc cagctgtcct acagtcctca     600
ggactctact ccctcagcag cgtggtgacc gtgccctcca gcaacttcgg cacccagacc     660
tacacctgca acgtagatca caagcccagc aacaccaagg tggacaagac agttgagcgc     720
aaatgttgtg tcgagtgccc accgtgccca gcaccacctg tggcaggacc gtcagtcttc     780
ctcttccccc caaaacccaa ggacaccctc atgatctccc ggaccctga ggtcacgtgc      840 gtggtggtgg acgtgagcca cgaagacccc gaggtccagt tcaactggta cgtgacggc      900 gtggaggtgc ataatgccaa gacaaagcca cgggaggagc agttcaacag cacgttccgt     960

-continued

```
gtggtcagcg tcctcaccgt tgtgcaccag gactggctga acggcaagga gtacaagtgc    1020
aaggtctcca acaaaggcct cccagccccc atcgagaaaa ccatctccaa aaccaaaggg    1080
cagccccgag aaccacaggt gtacaccctg cccccatccc gggaggagat gaccaagaac    1140
caggtcagcc tgacctgcct ggtcaaaggc ttctacccca gcgacatcgc cgtggagtgg    1200
gagagcaatg ggcagccgga gaacaactac aagaccacac ctcccatgct ggactccgac    1260
ggctccttct tcctctacag caagctcacc gtggacaaga gcaggtggca gcagggggaac    1320 gtcttctcat gctccgtgat gcatgaggct ctgcacaacc actacacgca gaagagcctc    1380
tccctgtctc cgggtaaa                                                  1398
```

<210> SEQ ID NO 10
<211> LENGTH: 466
<212> TYPE: PRT
<213> ORGANISM: Homo sapiens

<400> SEQUENCE: 10

```
Met Glu Phe Gly Leu Arg Trp Ile Phe Leu Val Ala Ile Leu Lys Gly
  1               5                  10                  15

Val Gln Cys Glu Val Gln Leu Leu Glu Ser Gly Gly Gly Leu Val Gln
             20                  25                  30

Pro Gly Gly Ser Leu Arg Leu Ser Cys Ala Ala Ser Gly Phe Thr Phe
         35                  40                  45

Ser Ser Tyr Ala Met Ser Trp Val Arg Gln Ala Pro Gly Lys Gly Leu
     50                  55                  60

Glu Trp Val Ser Ala Ile Ser Gly Arg Gly Gly Arg Thr Tyr Phe Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Phe Cys Ala Val Glu Gly Tyr Ser Gly Arg Tyr Gly Phe Phe Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
```

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
            325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
            355                 360                 365

Thr Leu Pro Pro Ser Arg Glu Glu Met Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 11
<211> LENGTH: 702
<212> TYPE: DNA
<213> ORGANISM: Homo sapiens

<400> SEQUENCE: 11
atggaagccc cagctcagct tctcttcctc ctgctactct ggctcccaga taccactgga     60
gaaatagtga tgacgcagtc tccagccacc ctgtctgtgt ctccagggga agagccacc    120
ctctcctgca gggccagtca gagtgttagc agcaacttag cctggtacca gcagaaacct    180
ggccaggctc ccaggctcct catctatggt gcatccacca gggccagtgg tatcccagac    240
aggatcagtg gcagtgggtc tggaacagag ttcactctca tcatcagcag cctgcagtct    300
gaagattttg cagtttatta ctgtcagcag tctaataact ggccattcac tttcggccct    360
gggaccaaag tggatatcaa acgaactgtg gctgcaccat ctgtcttcat cttcccgcca    420
tctgatgagc agttgaaatc tggaactgct agcgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gt                      702

<210> SEQ ID NO 12
<211> LENGTH: 234
<212> TYPE: PRT
<213> ORGANISM: Homo sapiens

<400> SEQUENCE: 12

Met Glu Ala Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser

```
            20                  25                  30
Val Ser Pro Gly Glu Arg Ala Thr Leu Ser Cys Arg Ala Ser Gln Ser
        35                  40                  45

Val Ser Ser Asn Leu Ala Trp Tyr Gln Gln Lys Pro Gly Gln Ala Pro
    50                  55                  60

Arg Leu Leu Ile Tyr Gly Ala Ser Thr Arg Ala Ser Gly Ile Pro Asp
65                  70                  75                  80

Arg Ile Ser Gly Ser Gly Ser Gly Thr Glu Phe Thr Leu Ile Ile Ser
                85                  90                  95

Ser Leu Gln Ser Glu Asp Phe Ala Val Tyr Tyr Cys Gln Gln Ser Asn
            100                 105                 110

Asn Trp Pro Phe Thr Phe Gly Pro Gly Thr Lys Val Asp Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 13

<400> SEQUENCE: 13

000

<210> SEQ ID NO 14
<211> LENGTH: 460
<212> TYPE: PRT
<213> ORGANISM: Homo sapiens

<400> SEQUENCE: 14

Met Glu Phe Gly Leu Ser Trp Val Phe Leu Val Ala Ile Ile Lys Gly
1               5                   10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Tyr Tyr Met Ser Trp Ile Arg Gln Ala Pro Gly Lys Gly Leu
    50                  55                  60

Glu Trp Phe Ser Tyr Ile Ser Ser Gly Ser Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Ser Leu Gln Met Asn Ser Leu Arg Ala Glu Asp Thr Ala Val
            100                 105                 110

Tyr Tyr Cys Ala Arg Gly Leu Thr Gly Asp Tyr Trp Gly Gln Gly Thr
        115                 120                 125
```

Leu Val Thr Val Ser Ser Ala Ser Thr Lys Gly Pro Ser Val Phe Pro
130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
                260                 265                 270

Thr Cys Val Val Val Asp Val Ser His Glu Asp Pro Glu Val Gln Phe
            275                 280                 285

Asn Trp Tyr Val Asp Gly Val Glu Val His Asn Ala Lys Thr Lys Pro
290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
                340                 345                 350

Lys Gly Gln Pro Arg Glu Pro Gln Val Tyr Thr Leu Pro Pro Ser Arg
            355                 360                 365

Glu Glu Met Thr Lys Asn Gln Val Ser Leu Thr Cys Leu Val Lys Gly
370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
450                 455                 460

<210> SEQ ID NO 15

<400> SEQUENCE: 15

000

<210> SEQ ID NO 16
<211> LENGTH: 236
<212> TYPE: PRT
<213> ORGANISM: Homo sapiens

<400> SEQUENCE: 16

```
Met Asp Met Arg Val Pro Ala Gln Leu Leu Gly Leu Leu Leu Leu Trp
  1               5                  10                  15

Phe Pro Gly Ser Arg Cys Asp Ile Gln Met Thr Gln Ser Pro Ser Ser
             20                  25                  30

Val Ser Ala Ser Val Gly Asp Arg Val Thr Ile Ser Cys Arg Ala Ser
             35                  40                  45

Gln Asp Ile Ser Gly Trp Leu Ala Trp Tyr Gln Gln Lys Pro Gly Lys
         50                  55                  60

Ala Pro Lys Leu Leu Ile Ser Ala Thr Ser Ser Leu His Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
                100                 105                 110

Thr Asn Ser Phe Pro Phe Thr Phe Gly Pro Gly Thr Lys Val Asp Ile
             115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 17

<400> SEQUENCE: 17

000

<210> SEQ ID NO 18
<211> LENGTH: 463
<212> TYPE: PRT
<213> ORGANISM: Homo sapiens

<400> SEQUENCE: 18

Met Glu Phe Gly Leu Ser Trp Val Phe Leu Val Ala Leu Leu Arg Gly
  1               5                  10                  15

Cys Gln Cys Gln Val Gln Leu Val Glu Ser Gly Gly Gly Val Val Gln
             20                  25                  30

Pro Gly Arg Ser Leu Arg Leu Ser Cys Ala Ala Ser Gly Phe Thr Phe
             35                  40                  45

Ser Ser Tyr Gly Met His Trp Val Arg Gln Ala Pro Gly Lys Gly Leu
         50                  55                  60

Glu Trp Val Ala Phe Ile Trp Tyr Asp Gly Ser Asn Lys Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
```

```
                100             105                 110
Tyr Tyr Cys Ala Arg Gly Tyr Arg Val Tyr Phe Asp Tyr Trp Gly Gln
            115                 120             125

Gly Thr Leu Val Thr Val Ser Ser Ala Ser Thr Lys Gly Pro Ser Val
        130              135             140

Phe Pro Leu Ala Pro Cys Ser Arg Ser Thr Ser Glu Ser Thr Ala Ala
145             150                  155                     160

Leu Gly Cys Leu Val Lys Asp Tyr Phe Pro Glu Pro Val Thr Val Ser
                165             170              175

Trp Asn Ser Gly Ala Leu Thr Ser Gly Val His Thr Phe Pro Ala Val
            180              185             190

Leu Gln Ser Ser Gly Leu Tyr Ser Leu Ser Ser Val Val Thr Val Pro
        195             200             205

Ser Ser Ser Leu Gly Thr Lys Thr Tyr Thr Cys Asn Val Asp His Lys
    210             215             220

Pro Ser Asn Thr Lys Val Asp Lys Arg Val Glu Ser Lys Tyr Gly Pro
225             230             235                     240

Pro Cys Pro Ser Cys Pro Ala Pro Glu Phe Leu Gly Gly Pro Ser Val
                245             250             255

Phe Leu Phe Pro Pro Lys Pro Lys Asp Thr Leu Met Ile Ser Arg Thr
            260             265             270

Pro Glu Val Thr Cys Val Val Val Asp Val Ser Gln Glu Asp Pro Glu
            275             280             285

Val Gln Phe Asn Trp Tyr Val Asp Gly Val Glu Val His Asn Ala Lys
        290             295             300

Thr Lys Pro Arg Glu Glu Gln Phe Asn Ser Thr Tyr Arg Val Val Ser
305             310             315                     320

Val Leu Thr Val Leu His Gln Asp Trp Leu Asn Gly Lys Glu Tyr Lys
                325             330             335

Cys Lys Val Ser Asn Lys Gly Leu Pro Ser Ser Ile Glu Lys Thr Ile
            340             345             350

Ser Lys Ala Lys Gly Gln Pro Arg Glu Pro Gln Val Tyr Thr Leu Pro
        355             360             365

Pro Ser Gln Glu Glu Met Thr Lys Asn Gln Val Ser Leu Thr Cys Leu
    370             375             380

Val Lys Gly Phe Tyr Pro Ser Asp Ile Ala Val Glu Trp Glu Ser Asn
385             390             395                     400

Gly Gln Pro Glu Asn Asn Tyr Lys Thr Thr Pro Pro Val Leu Asp Ser
                405             410             415

Asp Gly Ser Phe Phe Leu Tyr Ser Arg Leu Thr Val Asp Lys Ser Arg
            420             425             430

Trp Gln Glu Gly Asn Val Phe Ser Cys Ser Val Met His Glu Ala Leu
        435             440             445

His Asn His Tyr Thr Gln Lys Ser Leu Ser Leu Ser Pro Gly Lys
    450             455             460

<210> SEQ ID NO 19

<400> SEQUENCE: 19

000

<210> SEQ ID NO 20
<211> LENGTH: 236
<212> TYPE: PRT
```

<213> ORGANISM: Homo sapiens

<400> SEQUENCE: 20

```
Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Asp Ile Ser Ser Trp Leu Ala Trp Tyr Gln Arg Lys Pro Gly Lys
    50                  55                  60

Ala Pro Lys Leu Gln Ile Tyr Ala Ala Ser Leu Glu Ser Gly Val
65                  70                  75                  80

Pro Ser Arg Phe Asn Gly Ser Gly Ser Gly Thr Asp Phe Thr Leu Ser
            85                  90                  95

Ile Ser Ser Leu Gln Pro Glu Asp Phe Ala Thr Tyr Tyr Cys Gln Gln
        100                 105                 110

Thr Asn Ser Phe Pro Leu Thr Phe Gly Gly Gly Thr Lys Val Glu Ile
    115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
        180                 185                 190

Ser Thr Tyr Ser Leu Ser Ser Thr Leu Thr Leu Ser Lys Ala Asp Tyr
    195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235
```

<210> SEQ ID NO 21

<400> SEQUENCE: 21

000

<210> SEQ ID NO 22
<211> LENGTH: 464
<212> TYPE: PRT
<213> ORGANISM: Homo sapiens

<400> SEQUENCE: 22

```
Met Glu Trp Thr Trp Ser Phe Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Ile Ser Trp Val Arg Gln Ala Pro Gly Gln Gly Leu
    50                  55                  60

Glu Trp Met Gly Trp Ile Ser Ala Tyr Asn Gly Asn Thr Asn Tyr Ala
65                  70                  75                  80
```

Gln Lys Leu Gln Asp Arg Val Thr Met Thr Thr Asp Thr Ser Thr Thr
                85                  90                  95

Thr Ala Tyr Met Glu Leu Arg Ser Leu Arg Ser Asp Asp Thr Ala Val
            100                 105                 110

Tyr Tyr Cys Ala Arg Arg Ala Tyr Gly Ala Asn Phe Phe Asp Tyr Trp
            115                 120                 125

Gly Gln Gly Thr Leu Val Thr Val Ser Ser Ala Ser Thr Lys Gly Pro
            130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
            195                 200                 205

Val Pro Ser Ser Asn Phe Gly Thr Gln Thr Tyr Thr Cys Asn Val Asp
            210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr Leu Met Ile Ser Arg
                260                 265                 270

Thr Pro Glu Val Thr Cys Val Val Val Asp Val Ser His Glu Asp Pro
            275                 280                 285

Glu Val Gln Phe Asn Trp Tyr Val Asp Gly Val Glu Val His Asn Ala
290                 295                 300

Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
                325                 330                 335

Lys Cys Lys Val Ser Asn Lys Gly Leu Pro Ala Pro Ile Glu Lys Thr
            340                 345                 350

Ile Ser Lys Thr Lys Gly Gln Pro Arg Glu Pro Gln Val Tyr Thr Leu
            355                 360                 365

Pro Pro Ser Arg Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
            435                 440                 445

Leu His Asn His Tyr Thr Gln Lys Ser Leu Ser Leu Ser Pro Gly Lys
450                 455                 460

<210> SEQ ID NO 23

<400> SEQUENCE: 23

000

<210> SEQ ID NO 24
<211> LENGTH: 240
<212> TYPE: PRT
<213> ORGANISM: Homo sapiens

<400> SEQUENCE: 24

```
Met Val Leu Gln Thr Gln Val Phe Ile Ser Leu Leu Leu Trp Ile Ser
 1               5                  10                  15

Gly Ala Tyr Gly Asp Ile Val Met Thr Gln Ser Pro Asp Ser Leu Ala
             20                  25                  30

Val Ser Leu Gly Glu Arg Ala Thr Ile Asn Cys Lys Ser Ser Gln Ser
         35                  40                  45

Ile Leu Phe Phe Ser Asn Asn Lys Asn Tyr Leu Ala Trp Tyr Arg Gln
     50                  55                  60

Lys Pro Gly Gln Pro Pro Asn Leu Leu Ile Tyr Trp Ala Ser Thr Arg
 65                  70                  75                  80

Glu Ser Gly Val Pro Asp Arg Phe Ser Gly Ser Gly Ser Gly Thr Asp
                 85                  90                  95

Phe Thr Leu Thr Ile Ser Ser Leu Gln Ala Glu Asp Val Ala Val Tyr
            100                 105                 110

Tyr Cys Gln Gln Tyr Tyr Ser Ser Pro Trp Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 25
<211> LENGTH: 1380
<212> TYPE: DNA
<213> ORGANISM: Homo sapiens

<400> SEQUENCE: 25

```
atggagtttg gctgagctg ggttttcctt gttgctatta taaaaggtgt ccagtgtcag    60
gtgcagctgg tggagtctgg gggaggcttg gtcaagcctg agggtccct gagactctcc   120 tgtgcagcct ctggattcac cttcagtgac tactatatga gctggatccg ccaggctcca   180
gggaagggac tggagtgggt tcatacatt agtagtagtg gtagtaccat atactacgca   240
gactctgtga aggccgatt caccatctcc agggacaacg ccaagaactc actgtatctg   300
caaatgaaca gcctgagagc cgaggacacg gccgtgtatt actgtgcgag aggcctaact   360
ggggactact ggggccaggg aaccctggtc accgtctcct cagcttccac caagggccca   420
tccgtcttcc ccctggcgcc ctgctctaga agcacctccg agagcacagc ggccctgggc   480
tgcctggtca aggactactt ccccgaaccg gtgacggtgt cgtggaactc aggcgctctg   540
```

-continued

```
accagcggcg tgcacacctt cccagctgtc ctacagtcct caggactcta ctccctcagc   600
agcgtggtga ccgtgccctc agcaacttc  ggcacccaga cctacacctg caacgtagat   660
cacaagccca gcaacaccaa ggtggacaag acagttgagc gcaaatgttg tgtcgagtgc   720
ccaccgtgcc cagcaccacc tgtggcagga ccgtcagtct tcctcttccc cccaaaaccc   780
aaggacaccc tcatgatctc ccggacccct gaggtcacgt gcgtggtggt ggacgtgagc   840
cacgaagacc ccgaggtcca gttcaactgg tacgtggacg gcgtggaggt gcataatgcc   900
aagacaaagc cacgggagga gcagttcaac agcacgttcc gtgtggtcag cgtcctcacc   960
gttgtgcacc aggactggct gaacggcaag gagtacaagt gcaaggtctc caacaaaggc  1020
ctcccagccc ccatcgagaa aaccatctcc aaaaccaaag ggcagccccg agaaccacag  1080
gtgtacaccc tgcccccatc ccgggaggag atgaccaaga accaggtcag cctgacctgc  1140
ctggtcaaag gcttctaccc cagcgacatc gccgtggagt gggagagcaa tgggcagccg  1200
gagaacaact acaagaccac acctcccatg ctggactccg acggctcctt cttcctctac  1260
agcaagctca ccgtggacaa gagcaggtgg cagcagggga acgtcttctc atgctccgtg  1320
atgcatgagg ctctgcacaa ccactacacg cagaagagcc tctccctgtc tccgggtaaa  1380
```

<210> SEQ ID NO 26
<211> LENGTH: 460
<212> TYPE: PRT
<213> ORGANISM: Homo sapiens

<400> SEQUENCE: 26

```
Met Glu Phe Gly Leu Ser Trp Val Phe Leu Val Ala Ile Ile Lys Gly
 1               5                  10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Tyr Tyr Met Ser Trp Ile Arg Gln Ala Pro Gly Lys Gly Leu
    50                  55                  60

Glu Trp Val Ser Tyr Ile Ser Ser Ser Gly Ser Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Gly Leu Thr Gly Asp Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
```

```
                    225                 230                 235                 240
        Pro Pro Cys Pro Ala Pro Pro Val Ala Gly Pro Ser Val Phe Leu Phe
                        245                 250                 255

Pro Pro Lys Pro Lys Asp Thr Leu Met Ile Ser Arg Thr Pro Glu Val
                        260                 265                 270

Thr Cys Val Val Val Asp Val Ser His Glu Asp Pro Glu Val Gln Phe
                        275                 280                 285

Asn Trp Tyr Val Asp Gly Val Glu Val His Asn Ala Lys Thr Lys Pro
                290                 295                 300

Arg Glu Glu Gln Phe Asn Ser Thr Phe Arg Val Val Ser Val Leu Thr
        305                 310                 315                 320

Val Val His Gln Asp Trp Leu Asn Gly Lys Glu Tyr Lys Cys Lys Val
                        325                 330                 335

Ser Asn Lys Gly Leu Pro Ala Pro Ile Glu Lys Thr Ile Ser Lys Thr
                        340                 345                 350

Lys Gly Gln Pro Arg Glu Pro Gln Val Tyr Thr Leu Pro Pro Ser Arg
                        355                 360                 365

Glu Glu Met Thr Lys Asn Gln Val Ser Leu Thr Cys Leu Val Lys Gly
                370                 375                 380

Phe Tyr Pro Ser Asp Ile Ala Val Glu Trp Glu Ser Asn Gly Gln Pro
        385                 390                 395                 400

Glu Asn Asn Tyr Lys Thr Thr Pro Pro Met Leu Asp Ser Asp Gly Ser
                        405                 410                 415

Phe Phe Leu Tyr Ser Lys Leu Thr Val Asp Lys Ser Arg Trp Gln Gln
                        420                 425                 430

Gly Asn Val Phe Ser Cys Ser Val Met His Glu Ala Leu His Asn His
                        435                 440                 445

Tyr Thr Gln Lys Ser Leu Ser Leu Ser Pro Gly Lys
                        450                 455                 460

<210> SEQ ID NO 27
        <211> LENGTH: 708
        <212> TYPE: DNA
        <213> ORGANISM: Homo sapiens

<400> SEQUENCE: 27
atggacatga gggtccccgc tcagctcctg gggctcctgc tactctggct ccgaggtgcc      60
agatgtgaca tccagatgac ccagtctcca tcctccctgt ctgcatctgt cggagacaga     120
gtcaccatca cttgccggcc aagtcagatc attagcagtt attaaattg gtatcagcag      180 aaaccaggga agcccctaa gctcctgatc catgctgcat ccagtttgca aagtggggtc      240
ccatcaaggt tcagtggcag tggatctggg acagatttca ctctcaccat cagtagtctg      300
caacctgaag attttgcaac ttactactgt caacagagtt acagtacccc attcactttc      360
ggccctggga ccaaagtgga tatcaaacga actgtggctg caccatctgt cttcatcttc      420
ccgccatctg atgagcagtt gaaatctgga actgcctctg ttgtgtgcct gctgaataac      480
ttctatccca gagaggccaa agtacagtgg aaggtggata acgccctcca atcgggtaac      540
tcccaggaga gtgtcacaga gcaggacagc aaggacagca cctacagcct cagcagcacc      600
ctgacgctga gcaaagcaga ctacgagaaa cacaaagtct acgcctgcga agtcacccat      660
cagggcctga gctcgcccgt cacaaagagc ttcaacaggg gagagtgt                  708

<210> SEQ ID NO 28
        <211> LENGTH: 236
```

<212> TYPE: PRT
<213> ORGANISM: Homo sapiens

<400> SEQUENCE: 28

```
Met Asp Met Arg Val Pro Ala Gln Leu Leu Gly Leu Leu Leu Trp
 1               5                  10                  15

Leu Arg Gly Ala Arg Cys Asp Ile Gln Met Thr Gln Ser Pro Ser
             20                  25                  30

Leu Ser Ala Ser Val Gly Asp Arg Val Thr Ile Thr Cys Arg Pro Ser
         35                  40                  45

Gln Ile Ile Ser Ser Leu Leu Asn Trp Tyr Gln Gln Lys Pro Gly Lys
     50                  55                  60

Ala Pro Lys Leu Leu Ile His Ala Ala Ser Ser Leu Gln Ser Gly Val
65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
            100                 105                 110

Ser Tyr Ser Thr Pro Phe Thr Phe Gly Pro Gly Thr Lys Val Asp Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 29
<211> LENGTH: 1398
<212> TYPE: DNA
<213> ORGANISM: Homo sapiens

<400> SEQUENCE: 29

| | |
|---|---|
| atggagttgg ggctgtgctg ggttttcctt gttgctattt tagaaggtgt ccagtgtgag | 60 |
| gtgcagctgg tggagtctgg gggaggcttg gtacagcctg gggggtccct gagactctcc | 120 |
| tgtgcagcct ctggattcac cttcagtagt tttagtatga cctgggtccg ccaggctcca | 180 |
| ggaaagggc tggagtgggt ttcatacatt agtagtagaa gtagtaccat atcctacgca | 240 |
| gactctgtga agggccgatt caccatctcc agagacaatg ccaagaactc actgtatctg | 300 |
| caaatgaaca gcctgagaga cgaggacacg gctgtgtatt actgtgcgag agatcctctt | 360 |
| ctagcgggag ctaccttctt tgactactgg ggccagggaa ccctggtcac cgtctcctca | 420 |
| gcctccacca agggcccatc ggtcttcccc ctggcgccct gctccaggag cacctccgag | 480 |
| agcacagcgg ccctgggctg cctggtcaag gactacttcc ccgaaccggt gacggtgtcg | 540 |
| tggaactcag gcgctctgac cagcggcgtg cacaccttcc cagctgtcct acagtcctca | 600 |
| ggactctact ccctcagcag cgtggtgacc gtgccctcca gcaacttcgg cacccagacc | 660 |

```
tacacctgca acgtagatca caagcccagc aacaccaagg tggacaagac agttgagcgc    720
aaatgttgtg tcgagtgccc accgtgccca gcaccacctg tggcaggacc gtcagtcttc    780
ctcttcccccc caaaacccaa ggacaccctc atgatctccc ggacccctga ggtcacgtgc    840
gtggtggtgg acgtgagcca cgaagacccc gaggtccagt tcaactggta cgtggacggc    900
gtggaggtgc ataatgccaa gacaaagcca cgggaggagc agttcaacag cacgttccgt    960
gtggtcagcg tcctcaccgt tgtgcaccag gactggctga acggcaagga gtacaagtgc   1020
aaggtctcca acaaaggcct cccagccccc atcgagaaaa ccatctccaa aaccaaaggg   1080
cagccccgag aaccacaggt gtacaccctg cccccatccc gggaggagat gaccaagaac   1140
caggtcagcc tgacctgcct ggtcaaaggc ttctacccca gcgacatcgc cgtggagtgg   1200
gagagcaatg ggcagccgga gaacaactac aagaccacac ctcccatgct ggactccgac   1260
ggctccttct tcctctacag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaa                                                 1398
```

<210> SEQ ID NO 30
<211> LENGTH: 466
<212> TYPE: PRT
<213> ORGANISM: Homo sapiens

<400> SEQUENCE: 30

```
Met Glu Leu Gly Leu Cys Trp Val Phe Leu Val Ala Ile Leu Glu Gly
  1               5                  10                  15

Val Gln Cys Glu Val Gln Leu Val Glu Ser Gly Gly Gly Leu Val Gln
                 20                  25                  30

Pro Gly Gly Ser Leu Arg Leu Ser Cys Ala Ala Ser Gly Phe Thr Phe
             35                  40                  45

Ser Ser Phe Ser Met Thr Trp Val Arg Gln Ala Pro Gly Lys Gly Leu
 50                  55                  60

Glu Trp Val Ser Tyr Ile Ser Ser Arg Ser Ser Thr Ile Ser Tyr Ala
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Asp Glu Asp Thr Ala Val
            100                 105                 110

Tyr Tyr Cys Ala Arg Asp Pro Leu Leu Ala Gly Ala Thr Phe Phe Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240
```

```
Lys Cys Cys Val Glu Cys Pro Pro Cys Pro Ala Pro Val Ala Gly
                245                 250                 255
Pro Ser Val Phe Leu Phe Pro Pro Lys Pro Lys Asp Thr Leu Met Ile
            260                 265                 270
Ser Arg Thr Pro Glu Val Thr Cys Val Val Val Asp Val Ser His Glu
        275                 280                 285
Asp Pro Glu Val Gln Phe Asn Trp Tyr Val Asp Gly Val Glu Val His
    290                 295                 300
Asn Ala Lys Thr Lys Pro Arg Glu Glu Gln Phe Asn Ser Thr Phe Arg
305                 310                 315                 320
Val Val Ser Val Leu Thr Val Val His Gln Asp Trp Leu Asn Gly Lys
                325                 330                 335
Glu Tyr Lys Cys Lys Val Ser Asn Lys Gly Leu Pro Ala Pro Ile Glu
            340                 345                 350
Lys Thr Ile Ser Lys Thr Lys Gly Gln Pro Arg Glu Pro Gln Val Tyr
        355                 360                 365
Thr Leu Pro Pro Ser Arg Glu Glu Met Thr Lys Asn Gln Val Ser Leu
    370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Met
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
Glu Ala Leu His Asn His Tyr Thr Gln Lys Ser Leu Ser Leu Ser Pro
    450                 455                 460
Gly Lys
465

<210> SEQ ID NO 31
<211> LENGTH: 705
<212> TYPE: DNA
<213> ORGANISM: Homo sapiens

<400> SEQUENCE: 31
atggaaaccc cagcgcagct tctcttcctc ctgctactct ggctcccaga taccaccgga    60
gaatttgtgt tgacgcagtc tccaggcacc ctgtctttgt ctccagggga aagagccacc   120
ctctcctgca gggccagtca gagtgttagc agcagttact tagcctggta ccagcagaaa   180
cctggccagg ctcccaggct cctcatctat ggtgcatcca gcagggccac tggcatccca   240
gacaggttca gtggcagtgg gtctgggaca gacttcactc tcaccatcag cagactggag   300
cctgaagatt ttgcagtgta ttactgtcag cagtatggta gctcacctct cactttcggc   360
ggagggacca aggtggagat caaacgaact gtggctgcac catctgtctt catcttcccg   420
ccatctgatg agcagttgaa atctggaact gcctctgttg tgtgcctgct gaataacttc   480
tatcccagag aggccaaagt acagtggaag gtggataacg ccctccaatc gggtaactcc   540
caggagagtg tcacagagca ggacagcaag gacagcacct acagcctcag cagcccctg   600 acgctgagca agcagactac gagaaacac aaagtctacg cctgcgaagt cacccatcag   660
ggcctgagct cgcccgtcac aaagagcttc aacaggggag agtgt              705
```

<210> SEQ ID NO 32
<211> LENGTH: 235
<212> TYPE: PRT
<213> ORGANISM: Homo sapiens

<400> SEQUENCE: 32

Met Glu Thr Pro Ala Gln Leu Leu Phe Leu Leu Leu Leu Trp Leu Pro
1               5                   10                  15

Asp Thr Thr Gly Glu Phe Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Leu Thr Phe Gly Gly Gly Thr Lys Val Glu Ile Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
210                 215                 220

Pro Val Thr Lys Ser Phe Asn Arg Gly Glu Cys
225                 230                 235

<210> SEQ ID NO 33
<211> LENGTH: 1383
<212> TYPE: DNA
<213> ORGANISM: Homo sapiens

<400> SEQUENCE: 33

```
atggagtttg ggctgagctg ggttttcctt gttgctatta taaaaggtgt ccagtgtcag      60
gtgcagctgg tggagtctgg gggaggcttg gtcaagcctg agggtccct gagactctcc      120 tgtgcagcct ctggattcac cttcagtgac tactacatga gctggatccg ccaggctcca     180
gggaaggggc tggagtgggt tcatacatt agtagtagtg gtagtaccat atactacgca     240
gactctgtga agggccgatt caccatctcc aggacaacg ccaagaattc actgtatctg     300
caaatgaaca gcctgagagc cgaggacacg gccgtgtatt actgtgcgag cgtatagga      360 ggtatggacg tctggggcca aggaccacg gtcaccgtct cctcagcttc accaagggc      420 ccatccgtct tccccctggc gccctgctct agaagcacct ccgagagcac agcggccctg     480
ggctgcctgg tcaaggacta cttccccgaa ccggtgacg tgtcgtggaa ctcaggcgct     540
ctgaccagcg gcgtgcacac cttcccagct gtcctacagt cctcaggact ctactccctc     600
```

```
agcagcgtgg tgaccgtgcc ctccagcaac ttcggcaccc agacctacac ctgcaacgta    660
gatcacaagc ccagcaacac caaggtggac aagacagttg agcgcaaatg ttgtgtcgag    720
tgcccaccgt gcccagcacc acctgtggca ggaccgtcag tcttcctctt ccccccaaaa    780
cccaaggaca ccctcatgat ctcccggacc cctgaggtca cgtgcgtggt ggtggacgtg    840
agccacgaag accccgaggt ccagttcaac tggtacgtgg acggcgtgga ggtgcataat    900
gccaagacaa agccacggga ggagcagttc aacagcacgt tccgtgtggt cagcgtcctc    960
accgttgtgc accaggactg gctgaacggc aaggagtaca agtgcaaggt ctccaacaaa   1020
ggcctcccag cccccatcga gaaaaccatc tccaaaacca agggcagcc ccgagaacca   1080 caggtgtaca ccctgccccc atcccgggag gagatgacca agaaccaggt cagcctgacc   1140
tgcctggtca aaggcttcta ccccagcgac atcgccgtgg agtgggagag caatgggcag   1200
ccggagaaca actacaagac cacacctccc atgctggact ccgacggctc cttcttcctc   1260
tacagcaagc tcaccgtgga caagagcagg tggcagcagg ggaacgtctt ctcatgctcc   1320
gtgatgcatg aggctctgca caaccactac acgcagaaga gcctctccct gtctccgggt   1380
aaa                                                                 1383
```

<210> SEQ ID NO 34
<211> LENGTH: 461
<212> TYPE: PRT
<213> ORGANISM: Homo sapiens

<400> SEQUENCE: 34

```
Met Glu Phe Gly Leu Ser Trp Val Phe Leu Val Ala Ile Ile Lys Gly
 1               5                   10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Tyr Tyr Met Ser Trp Ile Arg Gln Ala Pro Gly Lys Gly Leu
    50                  55                  60

Glu Trp Val Ser Tyr Ile Ser Ser Gly Ser Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Arg Ile Gly Gly Met Asp Val Trp Gly Gln Gly
        115                 120                 125

Thr Thr Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220
```

-continued

```
Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
            245                 250                 255

Phe Pro Pro Lys Pro Lys Asp Thr Leu Met Ile Ser Arg Thr Pro Glu
        260                 265                 270

Val Thr Cys Val Val Val Asp Val Ser His Glu Asp Pro Glu Val Gln
    275                 280                 285

Phe Asn Trp Tyr Val Asp Gly Val Glu Val His Asn Ala Lys Thr Lys
290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
            340                 345                 350

Thr Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
450                 455                 460
```

<210> SEQ ID NO 35
<211> LENGTH: 708
<212> TYPE: DNA
<213> ORGANISM: Homo sapiens

<400> SEQUENCE: 35

```
atggacatga gggtccccgc tcagctcctg gggctcctgc tactctggct ccgaggtgcc    60
agatgtgaca tccagatgac ccagtctcca tcctccctgt ctgcatctgt aggagacaga   120
gtcaccatca cttgccgggc aagtcagagc attagcggtt ttttaatttg gtatcagcag   180
agaccaggga agcccctaa gctcctgatc tatgctacat ccagtttaca agtggggtc    240
ccatcaaggt tcagtggcag tggatctggg acagatttca ctctcaccat cagcagtctg   300
caacctgaag attttgcaac ttactactgt caacagagtt acagtacccc attcactttc   360
ggccctggga ccaaagtgga tatcaaacga actgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgt              708
```

<210> SEQ ID NO 36

-continued

<211> LENGTH: 236
<212> TYPE: PRT
<213> ORGANISM: Homo sapiens

<400> SEQUENCE: 36

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Ser Ile Ser Gly Phe Leu Ile Trp Tyr Gln Arg Pro Gly Lys
    50                  55                  60

Ala Pro Lys Leu Leu Ile Tyr Ala Thr Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ser Tyr Ser Thr Pro Phe Thr Phe Gly Pro Gly Thr Lys Val Asp Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 37
<211> LENGTH: 1383
<212> TYPE: DNA
<213> ORGANISM: Homo sapiens

<400> SEQUENCE: 37
atggagtttg ggctgagctg ggttttcctt gttgctatta taaaaggtgt ccagtgtcag     60
gtgcagctgg tggagtctgg gggaggcttg gtcaagcctg agggtccct  gagactctcc    120 tgtgcagcct ctggattcac cttcagtgac tactatatga gctggatccg ccaggctcca    180
gggaagggac tggagtgggt ttcatacatt agtagtagtg gtagtaccat atactacgca    240
gactctgtga agggccgatt caccatctcc agggacaacg ccaagaactc actgtatctg    300
caaatgaaca gcctgagagc cgaggacacg gccgtgtatt actgtgcgag aggcctaact    360
ggggactact ggggccaggg aaccctggtc accgtctcct cagcttccac caagggccca    420
tccgtcttcc ccctggcgcc ctgctctaga agcacctccg agagcacagc ggccctgggc    480
tgcctggtca aggactactt ccccgaaccg gtgacggtgt cgtggaactc aggcgctctg    540
accagcggcg tgcacacctt cccagctgtc ctacagtcct caggactcta ctccctcagc    600

```
agcgtggtga ccgtgccctc cagcagcttg ggcacgaaga cctacacctg caacgtagat    660
cacaagccca gcaacaccaa ggtggacaag agagttgagt ccaaatatgg tcccccatgc    720
ccatcatgcc cagcacctga gttcctgggg ggaccatcag tcttcctgtt ccccccaaaa    780
cccaaggaca ctctcatgat ctcccggacc cctgaggtca cgtgcgtggt ggtggacgtg    840
agccaggaag accccgaggt ccagttcaac tggtacgtgg atggcgtgga ggtgcataat    900
gccaagacaa agccgcggga ggagcagttc aacagcacgt accgtgtggt cagcgtcctc    960
accgtcctgc accaggactg gctgaacggc aaggagtaca agtgcaaggt ctccaacaaa   1020
ggcctcccgt cctccatcga gaaaaccatc tccaaagcca aagggcagcc ccgagagcca   1080
caggtgtaca ccctgccccc atcccaggag gagatgacca agaaccaggt cagcctgacc   1140
tgcctggtca aaggcttcta ccccagcgac atcgccgtgg agtgggagag caatgggcag   1200
ccggagaaca actacaagac cacgcctccc gtgctggact ccgacggctc cttcttcctc   1260
tacagcaggc taaccgtgga caagagcagg tggcaggagg gaatgtcttc tcatgctcc   1320 gtgatgcatg aggctctgca caaccactac acacagaaga gcctctccct gtctccgggt   1380
aaa                                                                 1383
```

<210> SEQ ID NO 38
<211> LENGTH: 461
<212> TYPE: PRT
<213> ORGANISM: Homo sapiens

<400> SEQUENCE: 38

```
Met Glu Phe Gly Leu Ser Trp Val Phe Leu Val Ala Ile Ile Lys Gly
  1               5                  10                  15

Val Gln Cys Gln Val Gln Leu Val Glu Ser Gly Gly Gly Leu Val Lys
             20                  25                  30

Pro Gly Gly Ser Leu Arg Leu Ser Cys Ala Ala Ser Gly Phe Thr Phe
         35                  40                  45

Ser Asp Tyr Tyr Met Ser Trp Ile Arg Gln Ala Pro Gly Lys Gly Leu
     50                  55                  60

Glu Trp Val Ser Tyr Ile Ser Ser Ser Gly Ser Thr Ile Tyr Tyr Ala
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Ala Glu Asp Thr Ala Val
            100                 105                 110

Tyr Tyr Cys Ala Arg Gly Leu Thr Gly Asp Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Lys Thr Tyr Thr Cys Asn Val Asp His Lys Pro Ser
    210                 215                 220

Asn Thr Lys Val Asp Lys Arg Val Glu Ser Lys Tyr Gly Pro Pro Cys
```

```
            225                 230                 235                 240

Pro Ser Cys Pro Ala Pro Glu Phe Leu Gly Gly Pro Ser Val Phe Leu
                        245                 250                 255

Phe Pro Pro Lys Pro Lys Asp Thr Leu Met Ile Ser Arg Thr Pro Glu
                        260                 265                 270

Val Thr Cys Val Val Val Asp Val Ser Gln Glu Asp Pro Glu Val Gln
                        275                 280                 285

Phe Asn Trp Tyr Val Asp Gly Val Glu Val His Asn Ala Lys Thr Lys
                        290                 295                 300

Pro Arg Glu Glu Gln Phe Asn Ser Thr Tyr Arg Val Val Ser Val Leu
        305                 310                 315                 320

Thr Val Leu His Gln Asp Trp Leu Asn Gly Lys Glu Tyr Lys Cys Lys
                        325                 330                 335

Val Ser Asn Lys Gly Leu Pro Ser Ser Ile Glu Lys Thr Ile Ser Lys
                        340                 345                 350

Ala Lys Gly Gln Pro Arg Glu Pro Gln Val Tyr Thr Leu Pro Pro Ser
                        355                 360                 365

Gln Glu Glu Met Thr Lys Asn Gln Val Ser Leu Thr Cys Leu Val Lys
                370                 375                 380

Gly Phe Tyr Pro Ser Asp Ile Ala Val Glu Trp Glu Ser Asn Gly Gln
        385                 390                 395                 400

Pro Glu Asn Asn Tyr Lys Thr Thr Pro Pro Val Leu Asp Ser Asp Gly
                        405                 410                 415

Ser Phe Phe Leu Tyr Ser Arg Leu Thr Val Asp Lys Ser Arg Trp Gln
                        420                 425                 430

Glu Gly Asn Val Phe Ser Cys Ser Val Met His Glu Ala Leu His Asn
                        435                 440                 445

His Tyr Thr Gln Lys Ser Leu Ser Leu Ser Pro Gly Lys
                        450                 455                 460

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43
<211> LENGTH: 705
<212> TYPE: DNA
<213> ORGANISM: Homo sapiens

<400> SEQUENCE: 43
```

```
atggaaaccc cagcgcagct tctcttcctc ctgctactct ggctcccaga taccaccgga      60
gaatttgtgt tgacgcagtc tccaggcacc ctgtctttgt ctccagggga aagagccacc     120
ctctcctgca gggccagtca gagtgttagc agcagttact tagcctggta ccagcagaaa     180
cctggccagg ctcccaggct cctcatctat ggtgcatcca gcagggccac tggcatccca     240
gacaggttca gtggcagtgg gtctgggaca gacttcactc tcaccatcag cagactggag     300
cctgaagatt ttgtagtgta ttactgtcag cagtatggta gctcacctct cactttcggc     360
ggagggacca aggtggagat caaacgaact gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca agcagactac gagaaacac aaagtctacg cctgcgaagt cacccatcag     660
ggcctgagct cgcccgtcac aaagagcttc aacaggggag agtgt                     705
```

<210> SEQ ID NO 44
<211> LENGTH: 235
<212> TYPE: PRT
<213> ORGANISM: Homo sapiens

<400> SEQUENCE: 44

```
Met Glu Thr Pro Ala Gln Leu Leu Phe Leu Leu Leu Trp Leu Pro
  1               5                  10                  15
Asp Thr Thr Gly Glu Phe Val Leu Thr Gln Ser Pro Gly Thr Leu Ser
                 20                  25                  30
Leu Ser Pro Gly Glu Arg Ala Thr Leu Ser Cys Arg Ala Ser Gln Ser
             35                  40                  45
Val Ser Ser Ser Tyr Leu Ala Trp Tyr Gln Gln Lys Pro Gly Gln Ala
         50                  55                  60
Pro Arg Leu Leu Ile Tyr Gly Ala Ser Ser Arg Ala Thr Gly Ile Pro
 65                  70                  75                  80
Asp Arg Phe Ser Gly Ser Gly Ser Gly Thr Asp Phe Thr Leu Thr Ile
                     85                  90                  95
Ser Arg Leu Glu Pro Glu Asp Phe Val Val Tyr Tyr Cys Gln Gln Tyr
                100                 105                 110
Gly Ser Ser Pro Leu Thr Phe Gly Gly Gly Thr Lys Val Glu Ile Lys
            115                 120                 125
Arg Thr Val Ala Ala Pro Ser Val Phe Ile Phe Pro Pro Ser Asp Glu
        130                 135                 140
Gln Leu Lys Ser Gly Thr Ala Ser Val Val Cys Leu Leu Asn Asn Phe
145                 150                 155                 160
Tyr Pro Arg Glu Ala Lys Val Gln Trp Lys Val Asp Asn Ala Leu Gln
                165                 170                 175
Ser Gly Asn Ser Gln Glu Ser Val Thr Glu Gln Asp Ser Lys Asp Ser
            180                 185                 190
Thr Tyr Ser Leu Ser Ser Thr Leu Thr Leu Ser Lys Ala Asp Tyr Glu
        195                 200                 205
Lys His Lys Val Tyr Ala Cys Glu Val Thr His Gln Gly Leu Ser Ser
    210                 215                 220
Pro Val Thr Lys Ser Phe Asn Arg Gly Glu Cys
225                 230                 235
```

<210> SEQ ID NO 45
<211> LENGTH: 1386
<212> TYPE: DNA
<213> ORGANISM: Homo sapiens

<400> SEQUENCE: 45

```
atggagtttg ggctgagctg ggttttcctt gttgctatta taaaaggtgt ccagtgtcag      60
gtgcagctgg tggagtctgg gggaggcttg gtcaagcctg agggtccct  gagactctcc     120
tgtgcagcct ctggattcac cttcagtgac tactacatga gctggatccg ccaggctcca     180
gggaaggggc tggagtgggt ttcatacatt agtagtagtg gtagtaccat atactacgca     240
gactctgtga aggccgatt  caccatctcc agggacaacg ccaagaattc actgtatctg     300
caaatgaaca gcctgagagc cgaggacacg gccgtgtatt actgtgcgag gcgtatagga     360
ggtatggacg tctggggcca agggaccacg gtcaccgtct cctcagcttc caccaagggc     420
ccatccgtct tccccctggc gccctgctct agaagcacct ccgagagcac agcggccctg     480
ggctgcctgg tcaaggacta cttccccgaa ccggtgacgg tgtcgtggaa ctcaggcgct     540
ctgaccagcg gcgtgcacac cttcccagct gtcctacagt cctcaggact ctactccctc     600
agcagcgtgt gaccgtgcc  ctccagcagc ttgggcacga agacctacac ctgcaacgta     660
gatcacaagc ccagcaacac caaggtggac aagagagttg agtccaaata tggtccccca     720
tgcccatcat gcccagcacc tgagttcctg ggggaccat  cagtcttcct gttcccccca     780
aaacccaagg acactctcat gatctcccgg acccctgagg tcacgtgcgt ggtggtggac     840
gtgagccagg aagaccccga ggtccagttc aactggtacg tggatggcgt ggaggtgcat     900
aatgccaaga caaagccgcg ggaggagcag ttcaacagca cgtaccgtgt ggtcagcgtc     960
ctcaccgtcc tgcaccagga ctggctgaac ggcaaggagt acaagtgcaa ggtctccaac    1020
aaaggcctcc cgtcctccat cgagaaaacc atctccaaag ccaaagggca gccccgagag    1080
ccacaggtgt acaccctgcc cccatcccag gaggagatga ccaagaacca ggtcagcctg    1140
acctgcctgg tcaaaggctt ctaccccagc gacatcgccg tggagtggga gagcaatggg    1200
cagccggaga acaactacaa gaccacgcct cccgtgctgg actccgacgg ctccttcttc    1260
ctctacagca ggctaaccgt ggacaagagc aggtggcagg aggggaatgt cttctcatgc    1320
tccgtgatgc atgaggctct gcacaaccac tacacacaga gagcctctc  cctgtctccg    1380
ggtaaa                                                               1386
```

<210> SEQ ID NO 46
<211> LENGTH: 462
<212> TYPE: PRT
<213> ORGANISM: Homo sapiens

<400> SEQUENCE: 46

```
Met Glu Phe Gly Leu Ser Trp Val Phe Leu Val Ala Ile Ile Lys Gly
 1               5                  10                  15

Val Gln Cys Gln Val Gln Leu Val Glu Ser Gly Gly Gly Leu Val Lys
             20                  25                  30

Pro Gly Gly Ser Leu Arg Leu Ser Cys Ala Ala Ser Gly Phe Thr Phe
         35                  40                  45

Ser Asp Tyr Tyr Met Ser Trp Ile Arg Gln Ala Pro Gly Lys Gly Leu
     50                  55                  60

Glu Trp Val Ser Tyr Ile Ser Ser Ser Gly Ser Thr Ile Tyr Tyr Ala
 65                  70                  75                  80

Asp Ser Val Lys Gly Arg Phe Thr Ile Ser Arg Asp Asn Ala Lys Asn
```

```
                        85                  90                  95
Ser Leu Tyr Leu Gln Met Asn Ser Leu Arg Ala Glu Asp Thr Ala Val
                100                 105                 110

Tyr Tyr Cys Ala Arg Arg Ile Gly Gly Met Asp Val Trp Gly Gln Gly
            115                 120                 125

Thr Thr Val Thr Val Ser Ser Ala Ser Thr Lys Gly Pro Ser Val Phe
        130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Lys Thr Tyr Thr Cys Asn Val Asp His Lys Pro
    210                 215                 220

Ser Asn Thr Lys Val Asp Lys Arg Val Glu Ser Lys Tyr Gly Pro Pro
225                 230                 235                 240

Cys Pro Ser Cys Pro Ala Pro Glu Phe Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser Gln Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Gly Leu Pro Ser Ser Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Gln Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
            420                 425                 430

Gln Glu Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 47
<211> LENGTH: 708
<212> TYPE: DNA
<213> ORGANISM: Homo sapiens

<400> SEQUENCE: 47
```

```
atggacatga gggtccccgc tcagctcctg gggctcctgc tactctggct ccgaggtgcc    60
agatgtgaca tccagatgac ccagtctcca tcctccctgt ctgcatctgt aggagacaga   120
gtcaccatca cttgccgggc aagtcagagc attagcggct ttttaatttg gtatcagcag   180
agaccaggga aagcccctaa gctcctgatc tatgctacat ccagtttaca aagtggggtc   240
ccattaaggt tcagtggcag tgaatctggg acagatttca ctctcaccat cagcagtctg   300
caacctgaag attttgcaac ttactactgt caacagagtt acagtacccc attcactttc   360
ggccctggga ccaaagtgga tatcaaacga actgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgt              708
```

<210> SEQ ID NO 48
<211> LENGTH: 236
<212> TYPE: PRT
<213> ORGANISM: Homo sapiens

<400> SEQUENCE: 48

```
Met Asp Met Arg Val Pro Ala Gln Leu Leu Gly Leu Leu Leu Leu Trp
 1               5                  10                  15
Leu Arg Gly Ala Arg Cys Asp Ile Gln Met Thr Gln Ser Pro Ser Ser
            20                  25                  30
Leu Ser Ala Ser Val Gly Asp Arg Val Thr Ile Thr Cys Arg Ala Ser
        35                  40                  45
Gln Ser Ile Ser Gly Phe Leu Ile Trp Tyr Gln Gln Arg Pro Gly Lys
    50                  55                  60
Ala Pro Lys Leu Leu Ile Tyr Ala Thr Ser Ser Leu Gln Ser Gly Val
65                  70                  75                  80
Pro Leu Arg Phe Ser Gly Ser Glu Ser Gly Thr Asp Phe Thr Leu Thr
                85                  90                  95
Ile Ser Ser Leu Gln Pro Glu Asp Phe Ala Thr Tyr Tyr Cys Gln Gln
            100                 105                 110
Ser Tyr Ser Thr Pro Phe Thr Phe Gly Pro Gly Thr Lys Val Asp Ile
        115                 120                 125
Lys Arg Thr Val Ala Ala Pro Ser Val Phe Ile Phe Pro Pro Ser Asp
    130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
Glu Lys His Lys Val Tyr Ala Cys Glu Val Thr His Gln Gly Leu Ser
    210                 215                 220
Ser Pro Val Thr Lys Ser Phe Asn Arg Gly Glu Cys
225                 230                 235
```

<210> SEQ ID NO 49

<400> SEQUENCE: 49

000

<210> SEQ ID NO 50
<211> LENGTH: 462
<212> TYPE: PRT
<213> ORGANISM: Homo sapiens

<400> SEQUENCE: 50

Met Glu Phe Gly Leu Ser Trp Val Phe Leu Val Ala Ile Ile Lys Gly
1               5                   10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Tyr Tyr Met Ser Trp Ile Arg Gln Ala Pro Gly Lys Gly Leu
    50                  55                  60

Glu Trp Val Ser Tyr Ile Ser Ser Ser Gly Ser Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Ile Arg Ile Gly Gly Met Asp Val Trp Gly Gln Gly
        115                 120                 125

Thr Thr Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Lys Thr Tyr Thr Cys Asn Val Asp His Lys Pro
    210                 215                 220

Ser Asn Thr Lys Val Asp Lys Arg Val Glu Ser Lys Tyr Gly Pro Pro
225                 230                 235                 240

Cys Pro Pro Cys Pro Ala Pro Glu Phe Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser Gln Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Gly Leu Pro Ser Ser Ile Glu Lys Thr Ile Ser
            340                 345                 350

Lys Ala Lys Gly Gln Pro Arg Glu Pro Gln Val Tyr Thr Leu Pro Pro
355                 360                 365

Ser Gln Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
            420                 425                 430

Gln Glu Gly Asn Val Phe Ser Cys Ser Val Met His Glu Ala Leu His
        435                 440                 445

Asn His Tyr Thr Gln Lys Ser Leu Ser Leu Ser Pro Gly Lys
450                 455                 460

<210> SEQ ID NO 51

<400> SEQUENCE: 51

000

<210> SEQ ID NO 52
<211> LENGTH: 236
<212> TYPE: PRT
<213> ORGANISM: Homo sapiens

<400> SEQUENCE: 52

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Ser Ile Ser Gly Phe Leu Ile Trp Tyr Gln Gln Lys Pro Gly Lys
    50                  55                  60

Ala Pro Lys Leu Leu Ile Tyr Ala Thr Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ser Tyr Ser Thr Pro Phe Thr Phe Gly Pro Gly Thr Lys Val Asp Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys

```
                225                 230                 235

<210> SEQ ID NO 53

<400> SEQUENCE: 53

000

<210> SEQ ID NO 54
<211> LENGTH: 461
<212> TYPE: PRT
<213> ORGANISM: Homo sapiens

<400> SEQUENCE: 54

Met Glu Phe Gly Leu Ser Trp Val Phe Leu Val Ala Ile Ile Lys Gly
  1               5                  10                  15

Val Gln Cys Gln Val Gln Leu Val Glu Ser Gly Gly Gly Leu Val Lys
             20                  25                  30

Pro Gly Gly Ser Leu Arg Leu Ser Cys Ala Ala Ser Gly Phe Thr Phe
         35                  40                  45

Ser Asp Tyr Tyr Met Ser Trp Ile Arg Gln Ala Pro Gly Lys Gly Leu
     50                  55                  60

Glu Trp Val Ser Tyr Ile Ser Ser Ser Gly Ser Thr Ile Tyr Tyr Ala
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Ala Glu Asp Thr Ala Val
            100                 105                 110

Tyr Tyr Cys Ala Arg Gly Leu Thr Gly Asp Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Lys Thr Tyr Thr Cys Asn Val Asp His Lys Pro Ser
    210                 215                 220

Asn Thr Lys Val Asp Lys Arg Val Glu Ser Lys Tyr Gly Pro Pro Cys
225                 230                 235                 240

Pro Pro Cys Pro Ala Pro Glu Phe Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335
```

-continued

```
Val Ser Asn Lys Gly Leu Pro Ser Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Gln Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Arg Leu Thr Val Asp Lys Ser Arg Trp Gln
            420                 425                 430

Glu Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460

<210> SEQ ID NO 55

<400> SEQUENCE: 55

000

<210> SEQ ID NO 56
<211> LENGTH: 236
<212> TYPE: PRT
<213> ORGANISM: Homo sapiens

<400> SEQUENCE: 56

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Pro Ser
        35                  40                  45

Gln Ile Ile Ser Ser Leu Leu Asn Trp Tyr Gln Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ser Tyr Ser Thr Pro Phe Thr Phe Gly Pro Gly Thr Lys Val Asp Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205
```

```
Glu Lys His Lys Val Tyr Ala Cys Glu Val Thr His Gln Gly Leu Ser
    210                 215                 220
Ser Pro Val Thr Lys Ser Phe Asn Arg Gly Glu Cys
225                 230                 235
```

<210> SEQ ID NO 57

<400> SEQUENCE: 57

000

<210> SEQ ID NO 58
<211> LENGTH: 467
<212> TYPE: PRT
<213> ORGANISM: Homo sapiens

<400> SEQUENCE: 58

```
Met Glu Leu Gly Leu Cys Trp Val Phe Leu Val Ala Ile Leu Glu Gly
  1                   5                  10                  15
Val Gln Cys Glu Val Gln Leu Val Glu Ser Gly Gly Gly Leu Val Gln
             20                  25                  30
Pro Gly Gly Ser Leu Arg Leu Ser Cys Ala Ala Ser Gly Phe Thr Phe
         35                  40                  45
Ser Ser Phe Ser Met Thr Trp Val Arg Gln Ala Pro Gly Lys Gly Leu
 50                  55                  60
Glu Trp Val Ser Tyr Ile Ser Ser Arg Ser Ser Thr Ile Ser Tyr Ala
 65                  70                  75                  80
Asp Ser Val Lys Gly Arg Phe Thr Ile Ser Arg Asp Asn Ala Lys Asn
                 85                  90                  95
Ser Leu Tyr Leu Gln Met Asn Ser Leu Arg Asp Glu Asp Thr Ala Val
            100                 105                 110
Tyr Tyr Cys Ala Arg Asp Pro Leu Leu Ala Gly Ala Thr Phe Phe Asp
        115                 120                 125
Tyr Trp Gly Gln Gly Thr Leu Val Thr Val Ser Ser Ala Ser Thr Lys
130                 135                 140
Gly Pro Ser Val Phe Pro Leu Ala Pro Cys Ser Arg Ser Thr Ser Glu
145                 150                 155                 160
Ser Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
            180                 185                 190
Phe Pro Ala Val Leu Gln Ser Ser Gly Leu Tyr Ser Leu Ser Ser Val
        195                 200                 205
Val Thr Val Pro Ser Ser Leu Gly Thr Lys Thr Tyr Thr Cys Asn
210                 215                 220
Val Asp His Lys Pro Ser Asn Thr Lys Val Asp Lys Arg Val Glu Ser
225                 230                 235                 240
Lys Tyr Gly Pro Pro Cys Pro Pro Cys Pro Ala Pro Glu Phe Leu Gly
                245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser Gln
        275                 280                 285
Glu Asp Pro Glu Val Gln Phe Asn Trp Tyr Val Asp Gly Val Glu Val
    290                 295                 300
His Asn Ala Lys Thr Lys Pro Arg Glu Glu Gln Phe Asn Ser Thr Tyr
```

```
                305                 310                 315                 320
        Arg Val Val Ser Val Leu Thr Val Leu His Gln Asp Trp Leu Asn Gly
                        325                 330                 335
        Lys Glu Tyr Lys Cys Lys Val Ser Asn Lys Gly Leu Pro Ser Ser Ile
                        340                 345                 350
        Glu Lys Thr Ile Ser Lys Ala Lys Gly Gln Pro Arg Glu Pro Gln Val
                        355                 360                 365
        Tyr Thr Leu Pro Pro Ser Gln Glu Glu Met Thr Lys Asn Gln Val Ser
                        370                 375                 380
        Leu Thr Cys Leu Val Lys Gly Phe Tyr Pro Ser Asp Ile Ala Val Glu
        385                 390                 395                 400
        Trp Glu Ser Asn Gly Gln Pro Glu Asn Asn Tyr Lys Thr Thr Pro Pro
                        405                 410                 415
        Val Leu Asp Ser Asp Gly Ser Phe Phe Leu Tyr Ser Arg Leu Thr Val
                        420                 425                 430
        Asp Lys Ser Arg Trp Gln Glu Gly Asn Val Phe Ser Cys Ser Val Met
                        435                 440                 445
        His Glu Ala Leu His Asn His Tyr Thr Gln Lys Ser Leu Ser Leu Ser
                        450                 455                 460
        Pro Gly Lys
        465

<210> SEQ ID NO 59

<400> SEQUENCE: 59

000

<210> SEQ ID NO 60
<211> LENGTH: 235
<212> TYPE: PRT
<213> ORGANISM: Homo sapiens

<400> SEQUENCE: 60

Met Glu Thr Pro Ala Gln Leu Leu Phe Leu Leu Leu Leu Trp Leu Pro
        1               5                   10                  15
        Asp Thr Thr Gly Glu Ile Val Leu Thr Gln Ser Pro Gly Thr Leu Ser
                        20                  25                  30
        Leu Ser Pro Gly Glu Arg Ala Thr Leu Ser Cys Arg Ala Ser Gln Ser
                        35                  40                  45
        Val Ser Ser Ser Tyr Leu Ala Trp Tyr Gln Gln Lys Pro Gly Gln Ala
                50                  55                  60
        Pro Arg Leu Leu Ile Tyr Gly Ala Ser Ser Arg Ala Thr Gly Ile Pro
        65                  70                  75                  80
        Asp Arg Phe Ser Gly Ser Gly Ser Gly Thr Asp Phe Thr Leu Thr Ile
                        85                  90                  95
        Ser Arg Leu Glu Pro Glu Asp Phe Ala Val Tyr Tyr Cys Gln Gln Tyr
                        100                 105                 110
        Gly Ser Ser Pro Leu Thr Phe Gly Gly Gly Thr Lys Val Glu Ile Lys
                        115                 120                 125
        Arg Thr Val Ala Ala Pro Ser Val Phe Ile Phe Pro Pro Ser Asp Glu
                        130                 135                 140
        Gln Leu Lys Ser Gly Thr Ala Ser Val Val Cys Leu Leu Asn Asn Phe
        145                 150                 155                 160
        Tyr Pro Arg Glu Ala Lys Val Gln Trp Lys Val Asp Asn Ala Leu Gln
                        165                 170                 175
```

-continued

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 61

<400> SEQUENCE: 61

000

<210> SEQ ID NO 62
<211> LENGTH: 466
<212> TYPE: PRT
<213> ORGANISM: Homo sapiens

<400> SEQUENCE: 62

Met Glu Leu Gly Leu Cys Trp Val Phe Leu Val Ala Ile Leu Glu Gly
  1               5                  10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Phe Ser Met Thr Trp Val Arg Gln Ala Pro Gly Lys Gly Leu
    50                  55                  60

Glu Trp Val Ser Tyr Ile Ser Ser Arg Ser Ser Thr Ile Ser Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Asp Glu Asp Thr Ala Val
            100                 105                 110

Tyr Tyr Cys Ala Arg Asp Pro Leu Leu Ala Gly Ala Thr Phe Phe Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

```
Ser Arg Thr Pro Glu Val Thr Cys Val Val Asp Val Ser His Glu
            275                 280                 285
Asp Pro Glu Val Gln Phe Asn Trp Tyr Val Asp Gly Val Glu Val His
290                 295                 300
Asn Ala Lys Thr Lys Pro Arg Glu Glu Gln Phe Asn Ser Thr Phe Arg
305                 310                 315                 320
Val Val Ser Val Leu Thr Val His Gln Asp Trp Leu Asn Gly Lys
            325                 330                 335
Glu Tyr Lys Cys Lys Val Ser Asn Lys Gly Leu Pro Ala Pro Ile Glu
            340                 345                 350
Lys Thr Ile Ser Lys Thr Lys Gly Gln Pro Arg Glu Pro Gln Val Tyr
            355                 360                 365
Thr Leu Pro Pro Ser Arg Glu Glu Met Thr Lys Asn Gln Val Ser Leu
370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Met
            405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
            435                 440                 445
Glu Ala Leu His Asn His Tyr Thr Gln Lys Ser Leu Ser Leu Ser Pro
            450                 455                 460
Gly Lys
465

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66
<211> LENGTH: 461
<212> TYPE: PRT
<213> ORGANISM: Homo sapiens

<400> SEQUENCE: 66

Met Glu Phe Gly Leu Ser Trp Val Phe Leu Val Ala Ile Ile Lys Gly
1               5                   10                  15
Val Gln Cys Gln Val Gln Leu Val Glu Ser Gly Gly Gly Leu Val Lys
            20                  25                  30
Pro Gly Gly Ser Leu Arg Leu Ser Cys Ala Ala Ser Gly Phe Thr Phe
            35                  40                  45
Ser Asp Tyr Tyr Met Ser Trp Ile Arg Gln Ala Pro Gly Lys Gly Leu
50                  55                  60
```

```
Glu Trp Val Ser Tyr Ile Ser Ser Gly Ser Thr Ile Tyr Tyr Ala
 65                  70                  75                  80

Asp Ser Val Lys Gly Arg Phe Thr Ile Ser Arg Asp Asn Ala Lys Asn
             85                  90                  95

Ser Leu Tyr Leu Gln Met Asn Ser Leu Arg Ala Glu Asp Thr Ala Val
            100                 105                 110

Tyr Tyr Cys Ala Ile Arg Ile Gly Gly Met Asp Val Trp Gly Gln Gly
            115                 120                 125

Thr Thr Val Thr Val Ser Ser Ala Ser Thr Lys Gly Pro Ser Val Phe
130             135                 140

Pro Leu Ala Pro Cys Ser Arg Ser Thr Ser Glu Ser Thr Ala Ala Leu
145             150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
            340                 345                 350

Thr Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460

<210> SEQ ID NO 67
```

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70
<211> LENGTH: 461
<212> TYPE: PRT
<213> ORGANISM: Homo sapiens

<400> SEQUENCE: 70

```
Met Glu Phe Gly Leu Ser Trp Val Phe Leu Val Ala Ile Ile Lys Gly
 1               5                   10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Tyr Tyr Met Ser Trp Ile Arg Gln Ala Pro Gly Lys Gly Leu
    50                  55                  60

Glu Trp Val Ser Tyr Ile Ser Ser Ser Gly Ser Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Ile Gly Gly Met Asp Val Trp Gly Gln Gly Thr
        115                 120                 125

Thr Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Lys Thr Tyr Thr Cys Asn Val Asp His Lys Pro Ser
    210                 215                 220

Asn Thr Lys Val Asp Lys Arg Val Glu Ser Lys Tyr Gly Pro Pro Cys
225                 230                 235                 240

Pro Ser Cys Pro Ala Pro Glu Phe Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Glu Asp Pro Glu Val Gln
        275                 280                 285
```

```
Phe Asn Trp Tyr Val Asp Gly Val Glu Val His Asn Ala Lys Thr Lys
    290                 295                 300
Pro Arg Glu Glu Gln Phe Asn Ser Thr Tyr Arg Val Val Ser Val Leu
305                 310                 315                 320
Thr Val Leu His Gln Asp Trp Leu Asn Gly Lys Glu Tyr Lys Cys Lys
            325                 330                 335
Val Ser Asn Lys Gly Leu Pro Ser Ser Ile Glu Lys Thr Ile Ser Lys
        340                 345                 350
Ala Lys Gly Gln Pro Arg Glu Pro Gln Val Tyr Thr Leu Pro Pro Ser
    355                 360                 365
Gln Glu Glu Met Thr Lys Asn Gln Val Ser Leu Thr Cys Leu Val Lys
    370                 375                 380
Gly Phe Tyr Pro Ser Asp Ile Ala Val Glu Trp Glu Ser Asn Gly Gln
385                 390                 395                 400
Pro Glu Asn Asn Tyr Lys Thr Thr Pro Pro Val Leu Asp Ser Asp Gly
            405                 410                 415
Ser Phe Phe Leu Tyr Ser Arg Leu Thr Val Asp Lys Ser Arg Trp Gln
        420                 425                 430
Glu Gly Asn Val Phe Ser Cys Ser Val Met His Glu Ala Leu His Asn
    435                 440                 445
His Tyr Thr Gln Lys Ser Leu Ser Leu Ser Pro Gly Lys
    450                 455                 460

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74
<211> LENGTH: 460
<212> TYPE: PRT
<213> ORGANISM: Homo sapiens

<400> SEQUENCE: 74

Met Glu Phe Gly Leu Ser Trp Val Phe Leu Val Ala Ile Ile Lys Gly
1               5                   10                  15
Val Gln Cys Gln Val Gln Leu Val Glu Ser Gly Gly Gly Leu Val Lys
            20                  25                  30
Pro Gly Gly Ser Leu Arg Leu Ser Cys Ala Ala Ser Gly Phe Thr Phe
        35                  40                  45
Ser Asp Tyr Tyr Met Ser Trp Ile Arg Gln Ala Pro Gly Lys Gly Leu
    50                  55                  60
Glu Trp Val Ser Tyr Ile Ser Ser Ser Gly Ser Thr Ile Tyr Tyr Ala
65                  70                  75                  80
Asp Ser Val Lys Gly Arg Phe Thr Ile Ser Arg Asp Asn Ala Lys Asn
```

```
                    85                  90                  95
Ser Leu Tyr Leu Gln Met Asn Ser Leu Arg Ala Glu Asp Thr Ala Val
                100                 105                 110
Tyr Tyr Cys Ala Arg Gly Leu Thr Gly Asp Tyr Trp Gly Gln Gly Thr
                115                 120                 125
Leu Val Thr Val Ser Ser Ala Ser Thr Lys Gly Pro Ser Val Phe Pro
            130                 135                 140
Leu Ala Pro Cys Ser Arg Ser Thr Ser Glu Ser Thr Ala Ala Leu Gly
145                 150                 155                 160
Cys Leu Val Lys Asp Tyr Phe Pro Glu Pro Val Thr Val Ser Trp Asn
                165                 170                 175
Ser Gly Ala Leu Thr Ser Gly Val His Thr Phe Pro Ala Val Leu Gln
                180                 185                 190
Ser Ser Gly Leu Tyr Ser Leu Ser Ser Val Val Thr Val Pro Ser Ser
            195                 200                 205
Asn Phe Gly Thr Gln Thr Tyr Thr Cys Asn Val Asp His Lys Pro Ser
            210                 215                 220
Asn Thr Lys Val Asp Lys Thr Val Glu Arg Lys Cys Cys Val Glu Cys
225                 230                 235                 240
Pro Pro Cys Pro Ala Pro Pro Val Ala Gly Pro Ser Val Phe Leu Phe
                245                 250                 255
Pro Pro Lys Pro Lys Asp Thr Leu Met Ile Ser Arg Thr Pro Glu Val
                260                 265                 270
Thr Cys Val Val Val Asp Val Ser His Glu Asp Pro Glu Val Gln Phe
            275                 280                 285
Asn Trp Tyr Val Asp Gly Val Glu Val His Asn Ala Lys Thr Lys Pro
            290                 295                 300
Arg Glu Glu Gln Phe Asn Ser Thr Phe Arg Val Val Ser Val Leu Thr
305                 310                 315                 320
Val Val His Gln Asp Trp Leu Asn Gly Lys Glu Tyr Lys Cys Lys Val
                325                 330                 335
Ser Asn Lys Gly Leu Pro Ala Pro Ile Glu Lys Thr Ile Ser Lys Thr
            340                 345                 350
Lys Gly Gln Pro Arg Glu Pro Gln Val Tyr Thr Leu Pro Pro Ser Arg
            355                 360                 365
Glu Glu Met Thr Lys Asn Gln Val Ser Leu Thr Cys Leu Val Lys Gly
            370                 375                 380
Phe Tyr Pro Ser Asp Ile Ala Val Glu Trp Glu Ser Asn Gly Gln Pro
385                 390                 395                 400
Glu Asn Asn Tyr Lys Thr Thr Pro Pro Met Leu Asp Ser Asp Gly Ser
                405                 410                 415
Phe Phe Leu Tyr Ser Lys Leu Thr Val Asp Lys Ser Arg Trp Gln Gln
                420                 425                 430
Gly Asn Val Phe Ser Cys Ser Val Met His Glu Ala Leu His Asn His
            435                 440                 445
Tyr Thr Gln Lys Ser Leu Ser Leu Ser Pro Gly Lys
            450                 455                 460

<210> SEQ ID NO 75

<400> SEQUENCE: 75

000
```

<210> SEQ ID NO 76

<400> SEQUENCE: 76

000

<210> SEQ ID NO 77

<400> SEQUENCE: 77

000

<210> SEQ ID NO 78
<211> LENGTH: 461
<212> TYPE: PRT
<213> ORGANISM: Homo sapiens

<400> SEQUENCE: 78

```
Met Glu Phe Gly Leu Ser Trp Val Phe Leu Val Ala Ile Ile Lys Gly
 1               5                  10                  15

Val Gln Cys Gln Val Gln Leu Val Glu Ser Gly Gly Gly Leu Val Lys
             20                  25                  30

Pro Gly Gly Ser Leu Arg Leu Ser Cys Ala Ala Ser Gly Phe Thr Phe
         35                  40                  45

Ser Asp Tyr Tyr Met Ser Trp Ile Arg Gln Ala Pro Gly Lys Gly Leu
     50                  55                  60

Glu Trp Val Ser Tyr Ile Ser Ser Ser Gly Ser Thr Ile Tyr Tyr Ala
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Ala Glu Asp Thr Ala Val
            100                 105                 110

Tyr Tyr Cys Ala Arg Gly Leu Thr Gly Asp Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Lys Thr Tyr Thr Cys Asn Val Asp His Lys Pro Ser
    210                 215                 220

Asn Thr Lys Val Asp Lys Arg Val Glu Ser Lys Tyr Gly Pro Pro Cys
225                 230                 235                 240

Pro Ser Cys Pro Ala Pro Glu Phe Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Tyr Arg Val Val Ser Val Leu
```

```
                305                 310                 315                 320
        Thr Val Leu His Gln Asp Trp Leu Asn Gly Lys Glu Tyr Lys Cys Lys
                        325                 330                 335

Val Ser Asn Lys Gly Leu Pro Ser Ser Ile Glu Lys Thr Ile Ser Lys
                        340                 345                 350

Ala Lys Gly Gln Pro Arg Glu Pro Gln Val Tyr Thr Leu Pro Pro Ser
                        355                 360                 365

Gln Glu Glu Met Thr Lys Asn Gln Val Ser Leu Thr Cys Leu Val Lys
                        370                 375                 380

Gly Phe Tyr Pro Ser Asp Ile Ala Val Glu Trp Glu Ser Asn Gly Gln
        385                 390                 395                 400

Pro Glu Asn Asn Tyr Lys Thr Thr Pro Pro Val Leu Asp Ser Asp Gly
                        405                 410                 415

Ser Phe Phe Leu Tyr Ser Arg Leu Thr Val Asp Lys Ser Arg Trp Gln
                        420                 425                 430

Glu Gly Asn Val Phe Ser Cys Ser Val Met His Glu Ala Leu His Asn
                        435                 440                 445

His Tyr Thr Gln Lys Ser Leu Ser Leu Ser Pro Gly Lys
                        450                 455                 460
```

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82
<211> LENGTH: 461
<212> TYPE: PRT
<213> ORGANISM: Homo sapiens

<400> SEQUENCE: 82

```
        Met Glu Phe Gly Leu Ser Trp Val Phe Leu Val Ala Ile Ile Lys Gly
        1               5                   10                  15

Val Gln Cys Gln Val Gln Leu Val Glu Ser Gly Gly Gly Leu Val Lys
                        20                  25                  30

Pro Gly Gly Ser Leu Arg Leu Ser Cys Ala Ala Ser Gly Phe Thr Phe
                        35                  40                  45

Ser Asp Tyr Tyr Met Ser Trp Ile Arg Gln Ala Pro Gly Lys Gly Leu
                50                  55                  60

Glu Trp Val Ser Tyr Ile Ser Ser Ser Gly Ser Thr Ile Tyr Tyr Ala
        65                  70                  75                  80

Asp Ser Val Lys Gly Arg Phe Thr Ile Ser Arg Asp Asn Ala Lys Asn
                        85                  90                  95

Ser Leu Tyr Leu Gln Met Asn Ser Leu Arg Ala Glu Asp Thr Ala Val
                        100                 105                 110
```

Tyr Tyr Cys Ala Arg Gly Leu Thr Gly Asp Tyr Trp Gly Gln Gly Thr
            115                 120                 125
Leu Val Thr Val Ser Ser Ala Ser Thr Lys Gly Pro Ser Val Phe Pro
        130                 135                 140
Leu Ala Pro Cys Ser Arg Ser Thr Ser Glu Ser Thr Ala Ala Leu Gly
145                 150                 155                 160
Cys Leu Val Lys Asp Tyr Phe Pro Glu Pro Val Thr Val Ser Trp Asn
                165                 170                 175
Ser Gly Ala Leu Thr Ser Gly Val His Thr Phe Pro Ala Val Leu Gln
            180                 185                 190
Ser Ser Gly Leu Tyr Ser Leu Ser Ser Val Val Thr Val Pro Ser Ser
        195                 200                 205
Ser Leu Gly Thr Lys Thr Tyr Thr Cys Asn Val Asp His Lys Pro Ser
        210                 215                 220
Asn Thr Lys Val Asp Lys Arg Val Glu Ser Lys Tyr Gly Pro Pro Cys
225                 230                 235                 240
Pro Pro Cys Pro Ala Pro Glu Phe Leu Gly Gly Pro Ser Val Phe Leu
                245                 250                 255
Phe Pro Pro Lys Pro Lys Asp Thr Leu Met Ile Ser Arg Thr Pro Glu
            260                 265                 270
Val Thr Cys Val Val Val Asp Val Ser Gln Glu Asp Pro Glu Val Gln
        275                 280                 285
Phe Asn Trp Tyr Val Asp Gly Val Glu Val His Asn Ala Lys Thr Lys
            290                 295                 300
Pro Arg Glu Glu Gln Phe Asn Ser Thr Tyr Arg Val Val Ser Val Leu
305                 310                 315                 320
Thr Val Leu His Gln Asp Trp Leu Asn Gly Lys Glu Tyr Lys Cys Lys
                325                 330                 335
Val Ser Asn Lys Gly Leu Pro Ser Ser Ile Glu Lys Thr Ile Ser Lys
            340                 345                 350
Ala Lys Gly Gln Pro Arg Glu Pro Gln Val Tyr Thr Leu Pro Pro Ser
        355                 360                 365
Gln Glu Glu Met Thr Lys Asn Gln Val Ser Leu Thr Cys Leu Val Lys
370                 375                 380
Gly Phe Tyr Pro Ser Asp Ile Ala Val Glu Trp Glu Ser Asn Gly Gln
385                 390                 395                 400
Pro Glu Asn Asn Tyr Lys Thr Thr Pro Pro Val Leu Asp Ser Asp Gly
                405                 410                 415
Ser Phe Phe Leu Tyr Ser Arg Leu Thr Val Asp Lys Ser Arg Trp Gln
            420                 425                 430
Glu Gly Asn Val Phe Ser Cys Ser Val Met His Glu Ala Leu His Asn
        435                 440                 445
His Tyr Thr Gln Lys Ser Leu Ser Leu Ser Pro Gly Lys
        450                 455                 460

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86
<211> LENGTH: 462
<212> TYPE: PRT
<213> ORGANISM: Homo sapiens

<400> SEQUENCE: 86

```
Met Glu Phe Gly Leu Ser Trp Val Phe Leu Val Ala Ile Ile Lys Gly
 1               5                  10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Tyr Tyr Met Ser Trp Ile Arg Gln Ala Pro Gly Lys Gly Leu
    50                  55                  60

Glu Trp Val Ser Tyr Ile Ser Ser Gly Ser Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Arg Ile Gly Gly Met Asp Val Trp Gly Gln Gly
        115                 120                 125

Thr Thr Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Lys Thr Tyr Thr Cys Asn Val Asp His Lys Pro
    210                 215                 220

Ser Asn Thr Lys Val Asp Lys Arg Val Glu Ser Lys Tyr Gly Pro Pro
225                 230                 235                 240

Cys Pro Pro Cys Pro Ala Pro Glu Phe Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser Gln Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335
```

-continued

```
Lys Val Ser Asn Lys Gly Leu Pro Ser Ser Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Gln Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
            420                 425                 430

Gln Glu Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460
```

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90
<211> LENGTH: 467
<212> TYPE: PRT
<213> ORGANISM: Homo sapiens

<400> SEQUENCE: 90

```
Met Glu Leu Gly Leu Cys Trp Val Phe Leu Val Ala Ile Leu Glu Gly
  1               5                  10                  15

Val Gln Cys Glu Val Gln Leu Val Glu Ser Gly Gly Gly Leu Val Gln
             20                  25                  30

Pro Gly Gly Ser Leu Arg Leu Ser Cys Ala Ala Ser Gly Phe Thr Phe
         35                  40                  45

Ser Ser Phe Ser Met Thr Trp Val Arg Gln Ala Pro Gly Lys Gly Leu
     50                  55                  60

Glu Trp Val Ser Tyr Ile Ser Ser Arg Ser Ser Thr Ile Ser Tyr Ala
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Asp Glu Thr Ala Val
            100                 105                 110

Tyr Tyr Cys Ala Arg Asp Pro Leu Leu Ala Gly Ala Thr Phe Phe Asp
        115                 120                 125

Tyr Trp Gly Gln Gly Thr Leu Val Thr Val Ser Ser Ala Ser Thr Lys
    130                 135                 140
```

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94
<211> LENGTH: 467
<212> TYPE: PRT
<213> ORGANISM: Homo sapiens

<400> SEQUENCE: 94

```
Met Glu Leu Gly Leu Cys Trp Val Phe Leu Val Ala Ile Leu Glu Gly
  1               5                  10                  15

Val Gln Cys Glu Val Gln Leu Val Glu Ser Gly Gly Gly Leu Val Gln
                 20                  25                  30

Pro Gly Gly Ser Leu Arg Leu Ser Cys Ala Ala Ser Gly Phe Thr Phe
             35                  40                  45

Ser Ser Phe Ser Met Thr Trp Val Arg Gln Ala Pro Gly Lys Gly Leu
 50                  55                  60

Glu Trp Val Ser Tyr Ile Ser Ser Arg Ser Ser Thr Ile Ser Tyr Ala
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Asp Glu Asp Thr Ala Val
            100                 105                 110

Tyr Tyr Cys Ala Arg Asp Pro Leu Leu Ala Gly Ala Thr Phe Phe Asp
        115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Lys Thr Tyr Thr Cys Asn
210                 215                 220

Val Asp His Lys Pro Ser Asn Thr Lys Val Asp Lys Arg Val Glu Ser
225                 230                 235                 240

Lys Tyr Gly Pro Pro Cys Pro Ser Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350
```

```
Glu Lys Thr Ile Ser Lys Ala Lys Gly Gln Pro Arg Glu Pro Gln Val
            355                 360                 365

Tyr Thr Leu Pro Pro Ser Gln Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
            435                 440                 445

His Glu Ala Leu His Asn His Tyr Thr Gln Lys Ser Leu Ser Leu Ser
    450                 455                 460

Pro Gly Lys
465

<210> SEQ ID NO 95

<400> SEQUENCE: 95

000

<210> SEQ ID NO 96

<400> SEQUENCE: 96

000

<210> SEQ ID NO 97
<211> LENGTH: 1413
<212> TYPE: DNA
<213> ORGANISM: Homo sapiens

<400> SEQUENCE: 97
atggagttgg ggctgagctg ggttttcctt gttgctatta taaaaggtgt ccagtgtgag     60
gtgcagctgg tggagtctgg gggaggcttg gtacagcctg ggggtccct gagactctcc    120 tgtgcagcct ctggattcac cttcagtagt tttagtatga cctgggtccg ccaggctcca    180 ggaaagggc tggagtgggt tcatacatt agtagtagaa gtagtaccat atcctacgca    240
gactctgtga agggccgatt caccatctcc agagacaatg ccaagaactc actgtatctg    300
caaatgaaca gcctgagaga cgaggacacg gctgtgtatt actgtgcgag agatcctctt    360
ctagcgggag ctaccttctt tgactactgg ggccagggaa ccctggtcac cgtctcctca    420
gcctccacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacatctgca acgtgaatca caagcccagc aacaccaagg tggacaagaa agttgagccc    720
aaatcttgtg acaaaactca cacatgccca ccgtgcccag cacctgaact cctggggga    780 ccgtcagtct tcctcttccc cccaaaaccc aaggacaccc tcatgatctc ccggacccct    840
gaggtcacat gcgtggtggt ggacgtgagc cacgaagacc ctgaggtcaa gttcaactgg    900
tacgtggacg gcgtggaggt gcataatgcc aagacaaagc cgcggaggga gcagtacaac    960
```

-continued

```
agcacgtacc gtgtggtcag cgtcctcacc gtcctgcacc aggactggct gaatggcaag    1020
gagtacaagt gcaaggtctc caacaaagcc ctcccagccc ccatcgagaa aaccatctcc    1080
aaagccaaag ggcagccccg agaaccacag gtgtacaccc tgccccatc ccgggatgag     1140 ctgaccaaga accaggtcag cctgacctgc ctggtcaaag gcttctatcc cagcgacatc    1200
gccgtggagt gggagagcaa tgggcagccg gagaacaact acaagaccac gcctcccgtg    1260
ctggactccg acggctcctt cttcctctac agcaagctca ccgtggacaa gagcaggtgg    1320 cagcaggga acgtcttctc atgctccgtg atgcatgagg ctctgcacaa ccactacacg     1380
cagaagagcc tctccctgtc tccgggtaaa tag                                 1413
```

```
<210> SEQ ID NO 98
<211> LENGTH: 470
<212> TYPE: PRT
<213> ORGANISM: Homo sapiens

<400> SEQUENCE: 98

Met Glu Leu Gly Leu Cys Trp Val Phe Leu Val Ala Ile Leu Glu Gly
  1               5                  10                  15

Val Gln Cys Glu Val Gln Leu Val Glu Ser Gly Gly Gly Leu Val Gln
             20                  25                  30

Pro Gly Gly Ser Leu Arg Leu Ser Cys Ala Ala Ser Gly Phe Thr Phe
         35                  40                  45

Ser Ser Phe Ser Met Thr Trp Val Arg Gln Ala Pro Gly Lys Gly Leu
     50                  55                  60

Glu Trp Val Ser Tyr Ile Ser Ser Arg Ser Ser Thr Ile Ser Tyr Ala
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Asp Glu Asp Thr Ala Val
            100                 105                 110

Tyr Tyr Cys Ala Arg Asp Pro Leu Leu Ala Gly Ala Thr Phe Phe Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
```

290			295				300
Val Glu Val His Asn Ala Lys Thr Lys Pro Arg Glu Glu Gln Tyr Asn
305					310					315					320

Ser Thr Tyr Arg Val Val Ser Val Leu Thr Val Leu His Gln Asp Trp
				325					330					335

Leu Asn Gly Lys Glu Tyr Lys Cys Lys Val Ser Asn Lys Ala Leu Pro
			340					345					350

Ala Pro Ile Glu Lys Thr Ile Ser Lys Ala Lys Gly Gln Pro Arg Glu
		355					360					365

Pro Gln Val Tyr Thr Leu Pro Pro Ser Arg Asp Glu Leu Thr Lys Asn
	370					375					380

Gln Val Ser Leu Thr Cys Leu Val Lys Gly Phe Tyr Pro Ser Asp Ile
385					390					395					400

Ala Val Glu Trp Glu Ser Asn Gly Gln Pro Glu Asn Asn Tyr Lys Thr
				405					410					415

Thr Pro Pro Val Leu Asp Ser Asp Gly Ser Phe Phe Leu Tyr Ser Lys
			420					425					430

Leu Thr Val Asp Lys Ser Arg Trp Gln Gln Gly Asn Val Phe Ser Cys
		435					440					445

Ser Val Met His Glu Ala Leu His Asn His Tyr Thr Gln Lys Ser Leu
	450					455					460

Ser Leu Ser Pro Gly Lys
465				470

<210> SEQ ID NO 99

<400> SEQUENCE: 99

000

<210> SEQ ID NO 100

<400> SEQUENCE: 100

000

<210> SEQ ID NO 101
<211> LENGTH: 1395
<212> TYPE: DNA
<213> ORGANISM: Homo sapiens

<400> SEQUENCE: 101
atggagtttg ggctgagctg ggttttcctt gttgctatta taaaaggtgt ccagtgtcag    60
gtgcagctgg tggagtctgg gggaggcttg gtcaagcctg agggtccct gagactctcc    120 tgtgcagcct ctggattcac cttcagtgac tactatatga gctggatccg ccaggctcca    180
gggaagggac tggagtgggt ttcatacatt agtagtagtg gtagtaccat atactacgca    240
gactctgtga aggccgatt caccatctcc agggacaacg ccaagaactc actgtatctg    300
caaatgaaca gcctgagagc cgaggacacg gccgtgtatt actgtgcgag aggcctaact    360
ggggactact ggggccaggg aaccctggtc accgtctcct cagcttccac caagggccca    420
tcggtcttcc ccctggcacc ctcctccaag agcacctctg gggcacagc ggccctgggc    480 tgcctggtca aggactactt ccccgaaccg gtgacggtgt cgtggaactc aggcgccctg    540
accagcggcg tgcacacctt cccggctgtc ctacagtcct caggactcta ctccctcagc    600
agcgtggtga ccgtgccctc agcagcttg ggcacccaga cctacatctg caacgtgaat    660

```
cacaagccca gcaacaccaa ggtggacaag aaagttgagc ccaaatcttg tgacaaaact    720
cacacatgcc caccgtgccc agcacctgaa ctcctggggg gaccgtcagt cttcctcttc    780
cccccaaaac ccaaggacac cctcatgatc tcccggaccc ctgaggtcac atgcgtggtg    840
gtggacgtga gccacgaaga ccctgaggtc aagttcaact ggtacgtgga cggcgtggag    900
gtgcataatg ccaagacaaa gccgcgggag gagcagtaca acagcacgta ccgtgtggtc    960
agcgtcctca ccgtcctgca ccaggactgg ctgaatggca aggagtacaa gtgcaaggtc   1020
tccaacaaag ccctcccagc ccccatcgag aaaaccatct ccaaagccaa agggcagccc   1080
cgagaaccac aggtgtacac cctgccccca tcccgggatg agctgaccaa gaaccaggtc   1140
agcctgacct gcctggtcaa aggcttctat cccagcgaca tcgccgtgga gtgggagagc   1200
aatgggcagc cggagaacaa ctacaagacc acgcctcccg tgctggactc cgacggctcc   1260
ttcttcctct acagcaagct caccgtggac aagagcaggt ggcagcaggg gaacgtcttc   1320
tcatgctccg tgatgcatga ggctctgcac aaccactaca cgcagaagag cctctccctg   1380
tctccgggta aatag                                                   1395
```

<210> SEQ ID NO 102
<211> LENGTH: 464
<212> TYPE: PRT
<213> ORGANISM: Homo sapiens

<400> SEQUENCE: 102

```
Met Glu Phe Gly Leu Ser Trp Val Phe Leu Val Ala Ile Ile Lys Gly
 1               5                  10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Tyr Tyr Met Ser Trp Ile Arg Gln Ala Pro Gly Lys Gly Leu
    50                  55                  60

Glu Trp Val Ser Tyr Ile Ser Ser Ser Gly Ser Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Gly Leu Thr Gly Asp Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240
```

His Thr Cys Pro Pro Cys Pro Ala Pro Glu Leu Leu Gly Gly Pro Ser
            245                 250                 255

Val Phe Leu Phe Pro Pro Lys Pro Lys Asp Thr Leu Met Ile Ser Arg
        260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
        290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 103
<211> LENGTH: 107
<212> TYPE: PRT
<213> ORGANISM: Homo sapiens

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105

<210> SEQ ID NO 104
<211> LENGTH: 120
<212> TYPE: PRT
<213> ORGANISM: Homo sapiens

<400> SEQUENCE: 104

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Tyr Ser Gly Ser Tyr Tyr Phe Asp Tyr Trp Gly Gln Gly
            100                 105                 110

Thr Leu Val Thr Val Ser Ser Ala
        115                 120

<210> SEQ ID NO 105
<211> LENGTH: 119
<212> TYPE: PRT
<213> ORGANISM: Homo sapiens

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Leu Arg Ala Glu Asp Thr Ala Val Tyr Tyr Cys Ala
            85                  90                  95

Arg Gly Ile Ala Ala Ala Gly Tyr Phe Asp Tyr Trp Gly Gln Gly Thr
            100                 105                 110

Leu Val Thr Val Ser Ser Ala
        115

<210> SEQ ID NO 106
<211> LENGTH: 117
<212> TYPE: PRT
<213> ORGANISM: Homo sapiens

<400> SEQUENCE: 106

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

-continued

Leu Gln Met Asn Ser Leu Arg Ala Glu Asp Thr Ala Val Tyr Tyr Cys
                    85                  90                  95

Ala Arg Ala Leu Gly Gly Met Asp Val Trp Gly Gln Gly Thr Thr Val
            100                 105                 110

Thr Val Ser Ser Ala
        115

<210> SEQ ID NO 107
<211> LENGTH: 107
<212> TYPE: PRT
<213> ORGANISM: Homo sapiens

<400> SEQUENCE: 107

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Phe
                85                  90                  95

Thr Phe Gly Pro Gly Thr Lys Val Asp Ile Lys
            100                 105

<210> SEQ ID NO 108
<211> LENGTH: 115
<212> TYPE: PRT
<213> ORGANISM: Homo sapiens

<400> SEQUENCE: 108

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Thr Gly Asp Tyr Trp Gly Gln Gly Thr Leu Val Thr Val
            100                 105                 110

Ser Ser Ala
        115

<210> SEQ ID NO 109
<211> LENGTH: 108
<212> TYPE: PRT
<213> ORGANISM: Homo sapiens -continued

<400> SEQUENCE: 109

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys Arg
            100                 105

<210> SEQ ID NO 110
<211> LENGTH: 117
<212> TYPE: PRT
<213> ORGANISM: Homo sapiens

<400> SEQUENCE: 110

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Ser Tyr Phe Asp Tyr Trp Gly Gln Gly Thr Leu Val
            100                 105                 110

Thr Val Ser Ser Ala
        115

<210> SEQ ID NO 111
<211> LENGTH: 118
<212> TYPE: PRT
<213> ORGANISM: Homo sapiens

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Asp Tyr Gly Gly Asn Tyr Phe Asp Tyr Trp Gly Gln Gly Thr Leu
        100                 105                 110

Val Thr Val Ser Ser Ala
        115

<210> SEQ ID NO 112
<211> LENGTH: 114
<212> TYPE: PRT
<213> ORGANISM: Homo sapiens

<400> SEQUENCE: 112

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

Tyr Tyr Ser Thr Pro Trp Thr Phe Gly Gln Gly Thr Lys Val Glu Ile
        100                 105                 110

Lys Arg

<210> SEQ ID NO 113
<211> LENGTH: 116
<212> TYPE: PRT
<213> ORGANISM: Homo sapiens

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
            85                  90                  95

Ala Arg Ile Val Gly Phe Asp Tyr Trp Gly Gln Gly Thr Leu Val Thr
        100                 105                 110

Val Ser Ser Ala
        115

<210> SEQ ID NO 114
<211> LENGTH: 109
<212> TYPE: PRT
<213> ORGANISM: Homo sapiens

```
<400> SEQUENCE: 114

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys Arg
            100                 105

<210> SEQ ID NO 115
<211> LENGTH: 114
<212> TYPE: PRT
<213> ORGANISM: Homo sapiens

<400> SEQUENCE: 115

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ile Gly Met Asp Val Trp Gly Gln Gly Thr Thr Val Thr Val Ser
            100                 105                 110

Ser Ala

<210> SEQ ID NO 116
<211> LENGTH: 115
<212> TYPE: PRT
<213> ORGANISM: Homo sapiens

<400> SEQUENCE: 116

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

```
Ala Arg Leu Thr Gly Asp Tyr Trp Gly Gln Gly Thr Leu Val Thr Val
            100                 105                 110

Ser Ser Ala
        115

<210> SEQ ID NO 117
<211> LENGTH: 108
<212> TYPE: PRT
<213> ORGANISM: Homo sapiens

<400> SEQUENCE: 117

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Leu
                 85                  90                  95

Thr Phe Gly Gly Gly Thr Lys Val Glu Ile Lys Arg
             100                 105
```

ANTIBODIES TO M-CSF

This application is a divisional of U.S. application Ser. No. 14/923,655, filed Oct. 27, 2015, which is a divisional of U.S. application Ser. No. 13/458,820, filed Apr. 27, 2012, which is a continuation of U.S. application Ser. No. 12/748,602, filed Mar. 29, 2010, and issued as U.S. Pat. No. 8,188,249, which is a continuation of U.S. application Ser. No. 11/894,560, filed Aug. 20, 2007 and issued as U.S. Pat. No. 7,728,113, which is a continuation of U.S. application Ser. No. 11/375,221, filed Mar. 13, 2006 and issued as U.S. Pat. No. 7,326,414, which is a continuation of U.S. application Ser. No. 10/938,353, filed Sep. 9, 2004 and issued as U.S. Pat. No. 7,592,430, which claims priority from U.S. Provisional Application 60/502,163, filed Sep. 10, 2003. The entire teachings of the above-identified applications are incorporated herein by reference.

The instant application contains a Sequence Listing which has been submitted via EFS-Web and is hereby incorporated by reference in its entirety. Said ASCII text file, created on Jun. 5, 2017, is named 000659-0052-107-SL.txt, and is 172,080 bytes in size.

BACKGROUND OF THE INVENTION

Macrophage colony stimulating factor (M-CSF) is a member of the family of proteins referred to as colony stimulating factors (CSFs). M-CSF is a secreted or a cell surface glycoprotein comprised of two subunits that are joined by a disulfide bond with a total molecular mass varying from 40 to 90 kD ((Stanley E. R., et al., *Mol. Reprod. Dev.*, 46:4-10 (1997)). Similar to other CSFs, M-CSF is produced by macrophages, monocytes, and human joint tissue cells, such as chondrocytes and synovial fibroblasts, in response to proteins such as interleukin-1 or tumor necrosis factor-alpha. M-CSF stimulates the formation of macrophage colonies from pluripotent hematopoietic progenitor stem cells (Stanley E. R., et al., *Mol. Reprod. Dev.*, 46:4-10 (1997)).

M-CSF typically bind to its receptor, c-fms, in order to exert a biological effect. c-fms contains five extracellular Ig domains, one transmembrane domain, and an intracellular domain with two kinase domains. Upon M-CSF binding to c-fms, the receptor homo-dimerizes and initiates a cascade of signal transduction pathways including the JAK/STAT, PI3K, and ERK pathways.

M-CSF is an important regulator of the function, activation, and survival of monocytes/macrophages. A number of animal models have confirmed the role of M-CSF in various diseases, including rheumatoid arthritis (RA) and cancer. Macrophages comprise key effector cells in RA. The degree of synovial macrophage infiltration in RA has been shown to closely correlate with the extent of underlying joint destruction. M-CSF, endogenously produced in the rheumatoid joint by monocytes/macrophages, fibroblasts, and endothelial cells, acts on cells of the monocyte/macrophage lineage to promote their survival and differentiation into bone destroying osteoclasts, and enhance pro-inflammatory cellular functions such as cytotoxicity, superoxide production, phagocytosis, chemotaxis and secondary cytokine production. For example, treatment with M-CSF in the rat *streptococcus agalactiae* sonicate-induced experimental arthritis model lead to enhanced pathology (Abd, A. H., et al., *Lymphokine Cytokine Res.* 10:43-50 (1991)). Similarly, subcutaneous injections of M-CSF in a murine model of collagen-induced arthritis (CIA), which is a model for RA, resulted in a significant exacerbation of the RA disease symptoms (Campbell I. K., et al., *J. Leuk. Biol.* 68:144-150 (2000)). Furthermore, MRL/lpr mice that are highly susceptible to RA and other autoimmune diseases have elevated basal M-CSF serum concentrations (Yui M. A., et al., *Am. J. Pathol.* 139:255-261 (1991)). The requirement for endogenous M-CSF in maintaining CIA was demonstrated by a significant reduction in the severity of established disease by M-CSF neutralizing mouse monoclonal antibody (Campbell I. K., et al., *J. Leuk. Biol.* 68:144-150 (2000)).

With respect to cancer, inhibition of colony stimulating factors by antisense oligonucleotides suppresses tumor growth in embryonic and colon tumor xenografts in mice by decelerating macrophage-mediated ECM breakdown (Seyedhossein, A., et al., *Cancer Research*, 62:5317-5324 (2002)).

M-CSF binding to c-fms and its subsequent activation of monocyte/macrophages is important in a number of disease states. In addition to RA and cancer, the other examples of M-CSF-related disease states include osteoporosis, destructive arthritis, atherogenesis, glomerulonephritis, Kawasaki disease, and HIV-1 infection, in which monocytes/macrophages and related cell types play a role. For instance, osteoclasts are similar to macrophages and are regulated in part by M-CSF. Growth and differentiation signals induced by M-CSF in the initial stages of osteoclast maturation are essential for their subsequent osteoclastic activity in bone.

Osteoclast mediated bone loss, in the form of both focal bone erosions and more diffuse juxta-articular osteoporosis, is a major unsolved problem in RA. The consequences of this bone loss include joint deformities, functional disability, increased risk of bone fractures and increased mortality. M-CSF is uniquely essential for osteoclastogenesis and experimental blockade of this cytokine in animal models of arthritis successfully abrogates joint destruction. Similar destructive pathways are known to operate in other forms of destructive arthritis such as psoriatic arthritis, and could represent venues for similar intervention.

Postmenopausal bone loss results from defective bone remodeling secondary to an uncoupling of bone formation from exuberant osteoclast mediated bone resorption as a consequence of estrogen deficiency. In-vivo neutralization of M-CSF using a blocking antibody has been shown in mice to completely prevent the rise in osteoclast numbers, the increase in bone resorption and the resulting bone loss induced by ovariectomy.

Several lines of evidence point to a central role for M-CSF in atherogenesis, and in proliferative intimal hyperplasia after mechanical trauma to the arterial wall. All the major cell types in atherosclerotic lesions have been shown to express M-CSF, and this is further up-regulated by exposure to oxidized lipoprotein. Blockade of M-CSF signaling with a neutralizing c-fms antibody reduces the accumulation of macrophage-derived foam cells in the aortic root of apolipoprotein E deficient mice maintained on a high fat diet.

In both experimental and human glomerulonephritis, glomerular M-CSF expression has been found to co-localize with local macrophage accumulation, activation and proliferation and correlate with the extent of glomerular injury and proteinuria. Blockade of M-CSF signaling via an antibody directed against its receptor c-fms significantly down-regulates local macrophage accumulation in mice during the renal inflammatory response induced by experimental unilateral ureteric obstruction.

Kawasaki disease (KD) is an acute, febrile, pediatric vasculitis of unknown cause. Its most common and serious complications involve the coronary vasculature in the form of aneurismal dilatation. Serum M-CSF levels are significantly elevated in acute phase Kawasaki's disease, and normalize following treatment with intravenous immunoglobulin. Giant cell arthritis (GCA) is an inflammatory vasculopathy mainly occurring in the elderly in which T cells and macrophages infiltrate the walls of medium and large arteries leading to clinical consequences that include blindness and stroke secondary to arterial occlusion. The active involvement of macrophages in GCA is evidenced by the presence of elevated levels of macrophage derived inflammatory mediators within vascular lesions.

M-CSF has been reported to render human monocyte derived macrophages more susceptible to HIV-1 infection in vitro. In a recent study, M-CSF increased the frequency with which monocyte-derived macrophages became infected, the amount of HIV mRNA expressed per infected cell, and the level of proviral DNA expressed per infected culture.

Given the role of M-CSF in various diseases, a method for inhibiting M-CSF activity is desirable.

There is a critical need for therapeutic anti-M-CSF antibodies.

SUMMARY OF THE INVENTION

The present invention provides isolated human antibodies or antigen-binding portions thereof that specifically bind human M-CSF and acts as a M-CSF antagonist and compositions comprising said antibody or portion.

The invention also provides for compositions comprising the heavy and/or light chain, the variable regions thereof, or antigen-binding portions thereof an anti-M-CSF antibody, or nucleic acid molecules encoding an antibody, antibody chain or variable region thereof the invention effective in such treatment and a pharmaceutically acceptable carrier. In certain embodiments, the compositions may further comprise another component, such as a therapeutic agent or a diagnostic agent. Diagnostic and therapeutic methods are also provided by the invention. In certain embodiments, the compositions are used in a therapeutically effective amount necessary to treat or prevent a particular disease or condition.

The invention also provides methods for treating or preventing a variety of diseases and conditions such as, but not limited to, inflammation, cancer, atherogenesis, neurological disorders and cardiac disorders with an effective amount of an anti-M-CSF antibody of the invention, or antigen binding portion thereof, nucleic acids encoding said antibody, or heavy and/or light chain, the variable regions, or antigen-binding portions thereof.

The invention provides isolated cell lines, such as a hybridomas, that produce anti-M-CSF antibodies or antigen-binding portions thereof.

The invention also provides nucleic acid molecules encoding the heavy and/or light chains of anti-M-CSF antibodies, the variable regions thereof, or the antigen-binding portions thereof.

The invention provides vectors and host cells comprising the nucleic acid molecules, as well as methods of recombinantly producing the polypeptides encoded by the nucleic acid molecules.

Non-human transgenic animals or plants that express the heavy and/or light chains, or antigen-binding portions thereof, of anti-M-CSF antibodies are also provided.

BRIEF DESCRIPTION OF THE DRAWINGS

FIG. 1A male monkeys.
FIG. 1B female monkeys.
FIGS. 2A and 2B are graphs illustrating that anti-M-CSF treatment resulted in a reduction in the percentage of CD14+ CD16+ monocytes, in male and female monkeys. 0-21 days after administration of vehicle or antibody 8.10.3 at 0, 0.1, 1 or 5 mg/kg in a dose volume of 3.79 mL/kg over an approximately 5 minute period. For each monkey tested, the percentage of monocytes within the CD14+CD16+ subset was determined after each blood draw, on days 1, 3, 7, 14 and 21 after 8.10.3 injection.

FIG. 2A male monkeys.
FIG. 2B female monkeys.
FIG. 3 is a graph illustrating that anti-M-CSF treatment resulted in a decrease in the percentage change of total monocytes at all doses of antibody 8.10.3F as compared to pre-test levels of monocytes.

FIG. 3 shows data collected from experiments using antibody 8.10.3F.

FIGS. 4A-4ZZ provide sequence alignments of the predicted amino acid sequences of light and heavy chain variable regions from twenty-six anti-M-CSF antibodies compared with the germline amino acid sequences of the corresponding variable region genes. Differences between the antibody sequences and the germline gene sequences are indicated in bold-faced type. Dashes represent no change from germline. The underlined sequences in each alignment represent, from left to right, the FR1, CDR1, FR2, CDR2, FR3, CDR3 AND FR4 sequences.

FIG. 4A shows an alignment of the predicted amino acid sequence of the light chain variable region for antibody 252 (residues 21-127 of SEQ ID NO: 4) to the germline $V_\kappa O12$, $J_\kappa 3$ sequence (SEQ ID NO: 103).

FIG. 4B shows an alignment of the predicted amino acid sequence of the light chain variable region for antibody 88 (residues 21-127 of SEQ ID NO: 8) to the germline $V_\kappa O12$, $J_\kappa 3$ sequence (SEQ ID NO: 103).

FIG. 4C shows an alignment of the predicted amino acid sequence of the light chain variable region for antibody 100 (residues 21-127 of SEQ ID NO: 12) to the germline $V_\kappa L2$, $J_\kappa 3$ sequence (SEQ ID NO: 107).

FIG. 4D shows an alignment of the predicted amino acid sequence of the light chain variable region for antibody 3.8.3 (residues 23-130 of SEQ ID NO: 16) to the germline $V_\kappa L5$, $J_\kappa 3$ sequence (SEQ ID NO: 109).

FIG. 4E shows an alignment of the predicted amino acid sequence of the light chain variable region for antibody 2.7.3 (residues 23-130 of SEQ ID NO: 20) to the germline $V_\kappa L5$, $J_\kappa 4$ sequence (SEQ ID NO: 117).

FIG. 4F shows an alignment of the predicted amino acid sequence of the light chain variable region for antibody 1.120.1 (residues 21-134 of SEQ ID NO: 24) to the germline $V_\kappa B3$, $J_\kappa 1$ sequence (SEQ ID NO: 112).

FIG. 4G shows an alignment of the predicted amino acid sequence of the heavy chain variable region for antibody 252 (residues 20-136 of SEQ ID NO: 2) to the germline $V_H 3$-11, $D_H 7$-27 $J_H 6$ sequence (SEQ ID NO: 106).

FIG. 4H shows an alignment of the predicted amino acid sequence of the heavy chain variable region for antibody 88

Figure 1A:
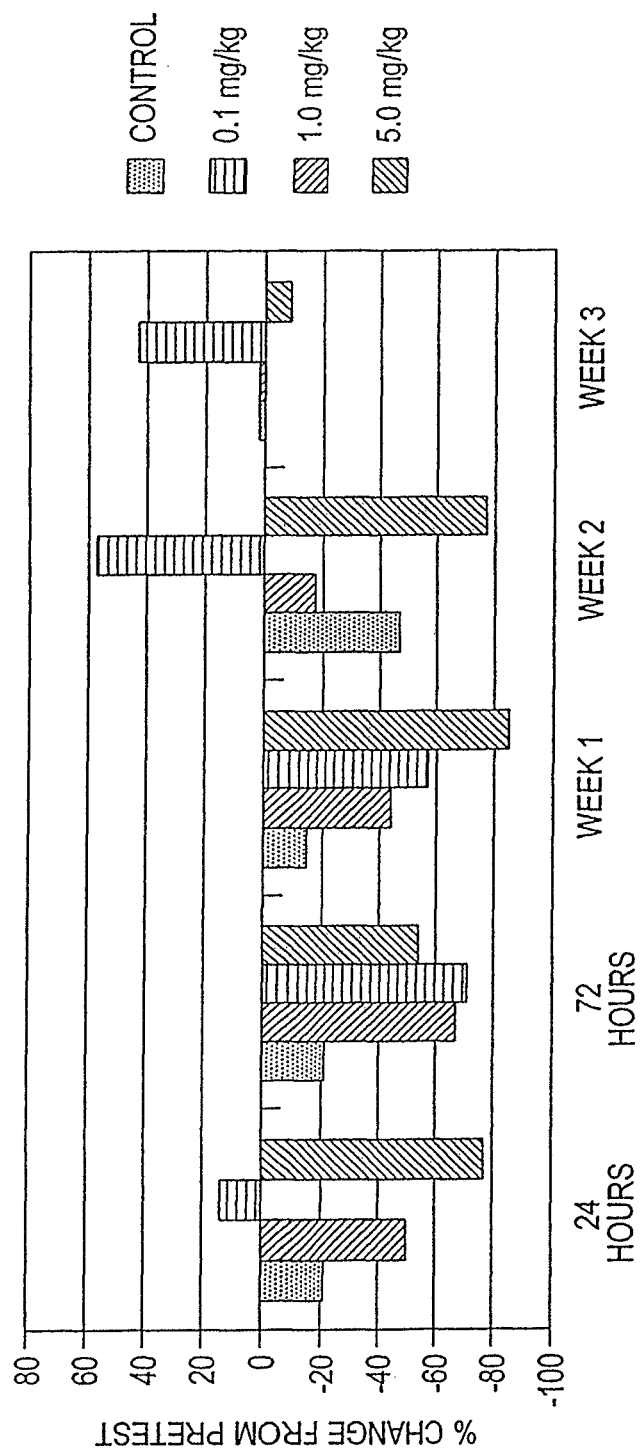
FIGS. 1A and 1B are graphs illustrating that the anti-M-CSF antibodies resulted in a dose-related decrease in total monocyte counts in male and female monkeys over time. The monocyte counts were determined by light scatter using an Abbott Diagnostics Inc. Cell Dyn system. Monocyte counts were monitored from 24 hours through 3 weeks after administration of vehicle or antibody 8.10.3 at 0, 0.1, 1 or 5 mg/kg in a dose volume of 3.79 mL/kg over an approximately 5 minute period.

(residues 20-138 of SEQ ID NO: 6) to the germline $V_H3$-7, $D_H6$-13, $J_H4$ sequence (SEQ ID NO: 105).

FIG. 4I shows the alignment of the predicted amino acid sequence of the heavy chain variable region for antibody 100 (residues 20-141 of SEQ ID NO: 10) to the germline $V_H3$-23, $D_H1$-26, $J_H4$ sequence (SEQ ID NO: 104).

FIG. 4J shows an alignment of the predicted amino acid sequence of the heavy chain variable region for antibody 3.8.3 (residues 20-135 of SEQ ID NO: 14) to the germline $V_H3$-11, $D_H7$-27, $J_H4$ sequence (SEQ ID NO: 108).

FIG. 4K shows an alignment of the predicted amino acid sequence of the heavy chain variable region for antibody 2.7.3 (residues 20-137 of SEQ ID NO: 18) to the germline $V_H3$-33, $D_H1$-26, $J_H4$ sequence (SEQ ID NO: 110).

FIG. 4L shows an alignment of the predicted amino acid sequence of the heavy chain variable region for antibody 1.120.1 (residues 20-139 of SEQ ID NO: 22) to the germline $V_H1$-18, $D_H4$-23, $J_H4$ sequence (SEQ ID NO: 111).

FIG. 4M shows an alignment of the predicted amino acid sequence of the light chain variable region for antibody 8.10.3 (residues 21-129 of SEQ ID NO: 44) to the germline $V_\kappa A27$, $J_\kappa 4$ sequence (SEQ ID NO: 114).

FIG. 4N shows an alignment of the predicted amino acid sequence of the heavy chain variable region for antibody 8.10.3 (residues 20-141 of SEQ ID NO: 30) to the germline $V_H3$-48, $D_H1$-26, $J_H4b$ sequence (SEQ ID NO: 113).

FIG. 4O shows an alignment of the predicted amino acid sequence of the light chain variable region for antibody 9.14.4 (residues 23-130 of SEQ ID NO: 28) to the germline $V_\kappa O12$, $J_\kappa 3$ sequence (SEQ ID NO: 103).

FIG. 4P shows an alignment of the predicted amino acid sequence of the heavy chain variable region for antibody 9.14.4 (residues 20-135 of SEQ ID NO: 38) to the germline $V_H3$-11, $D_H7$-27, $J_H4b$ sequence (SEQ ID NO: 116).

FIG. 4Q shows an alignment of the predicted amino acid sequence of the light chain variable region for antibody 9.7.2 (residues 23-130 of SEQ ID NO: 48) to the germline $V_\kappa O12$, $J_\kappa 3$ sequence (SEQ ID NO: 103).

FIG. 4R shows an alignment of the predicted amino acid sequence of the heavy chain variable region for antibody 9.7.2 (residues 20-136 of SEQ ID NO: 46) to the germline $V_H3$-11, $D_H6$-13, $J_H6b$ sequence (SEQ ID NO: 115).

FIG. 4S shows an alignment of the predicted amino acid sequence of the light chain variable region for antibody 9.14.4I (residues 23-130 of SEQ ID NO: 28) to the germline $V_\kappa O12$ $J_\kappa 3$ sequence (SEQ ID NO: 103).

FIG. 4T shows an alignment of the predicted amino acid sequence of the heavy chain variable region for antibody 9.14.4I (residues 20-135 of SEQ ID NO: 26) to the germline $V_H3$-11, $D_H7$-27, $J_H4b$ sequence (SEQ ID NO: 116).

FIG. 4U shows an alignment of the predicted amino acid sequence of the light chain variable region for antibody 8.10.3F (residues 21-129 of SEQ ID NO: 32) to the germline $V_\kappa A27$, $J_\kappa 4$ sequence (SEQ ID NO: 114).

FIG. 4V shows an alignment of the predicted amino acid sequence of the heavy chain variable region for antibody 8.10.3F (residues 20-141 of SEQ ID NO: 30) to the germline $V_H3$-48, $D_H1$-26, $J_H4b$ sequence (SEQ ID NO: 113).

FIG. 4W shows an alignment of the predicted amino acid sequence of the light chain variable region for antibody 9.7.2IF (residues 23-130 of SEQ ID NO: 36) to the germline $V_\kappa O12$, $J_\kappa 3$ sequence (SEQ ID NO: 103).

FIG. 4X shows an alignment of the predicted amino acid sequence of the heavy chain variable region for antibody 9.7.2IF (residues 20-136 of SEQ ID NO: 34) to the germline $V_H3$-11, $D_H6$-13, $J_H6b$ sequence (SEQ ID NO: 115).

FIG. 4Y shows an alignment of the predicted amino acid sequence of the light chain variable region for antibody 9.7.2C-Ser (residues 23-130 of SEQ ID NO: 52) to the germline $V_\kappa O12$, $J_\kappa 3$ sequence (SEQ ID NO: 103).

FIG. 4Z shows an alignment of the predicted amino acid sequence of the heavy chain variable region for antibody 9.7.2C-Ser (residues 20-136 of SEQ ID NO: 50) to the germline $V_H3$-11, $D_H6$-13, $J_H6b$ sequence (SEQ ID NO: 115).

FIG. 4AA shows an alignment of the predicted amino acid sequence of the light chain variable region for antibody 9.14.4C-Ser (residues 23-130 of SEQ ID NO: 56) to the germline $V_\kappa O12$, $J_\kappa 3$ sequence (SEQ ID NO: 103).

FIG. 4BB shows an alignment of the predicted amino acid sequence of the heavy chain variable region for antibody 9.14.4C-Ser (residues 20-135 of SEQ ID NO: 54) to the germline $V_H3$-11, $D_H7$-27, $J_H4b$ sequence (SEQ ID NO: 116).

FIG. 4CC shows an alignment of the predicted amino acid sequence of the light chain variable region for antibody 8.10.3C-Ser (residues 21-129 of SEQ ID NO: 60) to the germline $V_\kappa A27$, $J_\kappa 4$ sequence (SEQ ID NO: 114).

FIG. 4DD shows an alignment of the predicted amino acid sequence of the heavy chain variable region for antibody 8.10.3C-Ser (residues 20-141 of SEQ ID NO: 58) to the germline $V_H3$-48, $D_H1$-26, $J_H4b$ sequence (SEQ ID NO: 113).

FIG. 4EE shows an alignment of the predicted amino acid sequence of the light chain variable region for antibody 8.10.3-CG2 (residues 21-129 of SEQ ID NO: 60) to the germline $V_\kappa A27$, $J_\kappa 4$ sequence (SEQ ID NO: 114).

FIG. 4FF shows an alignment of the predicted amino acid sequence of the heavy chain variable region for antibody 8.10.3-CG2 (residues 20-141 of SEQ ID NO: 62) to the germline $V_H3$-48, $D_H1$-26, $J_H4b$ sequence (SEQ ID NO: 113).

FIG. 4GG shows an alignment of the predicted amino acid sequence of the light chain variable region for antibody 9.7.2-CG2 (residues 23-130 of SEQ ID NO: 52) to the germline $V_\kappa O12$, $J_\kappa 3$ sequence (SEQ ID NO: 103).

FIG. 4HH shows an alignment of the predicted amino acid sequence of the heavy chain variable region for antibody 9.7.2-CG2 (residues 20-136 of SEQ ID NO: 66) to the germline $V_H3$-11, $D_H6$-13, $J_H6b$ sequence (SEQ ID NO: 115).

FIG. 4II shows an alignment of the predicted amino acid sequence of the light chain variable region for antibody 9.7.2-CG4 (residues 23-130 of SEQ ID NO: 52) to the germline $V_\kappa O12$, $J_\kappa 3$ sequence (SEQ ID NO: 103).

FIG. 4JJ shows an alignment of the predicted amino acid sequence of the heavy chain variable region for antibody 9.7.2-CG4 (residues 20-135 of SEQ ID NO: 70) to the germline $V_H3$-11, $D_H6$-13, $J_H6b$ sequence (SEQ ID NO: 115).

FIG. 4KK shows an alignment of the predicted amino acid sequence of the light chain variable region for antibody 9.14.4-CG2 (residues 23-130 of SEQ ID NO: 56) to the germline $V_\kappa O12$, $J_\kappa 3$ sequence (SEQ ID NO: 103).

FIG. 4LL shows an alignment of the predicted amino acid sequence of the heavy chain variable region for antibody 9.14.4-CG2 (residues 20-135 of SEQ ID NO: 74) to the germline $V_H3$-11, $D_H7$-27, $J_H4b$ sequence (SEQ ID NO: 116).

FIG. 4MM shows an alignment of the predicted amino acid sequence of the light chain variable region for antibody 9.14.4-CG4 (residues 23-130 of SEQ ID NO: 56) to the germline $V_\kappa O12$, $J_\kappa 3$ sequence (SEQ ID NO: 103).

FIG. 4NN shows an alignment of the predicted amino acid sequence of the heavy chain variable region for antibody 9.14.4-CG4 (residues 20-135 of SEQ ID NO: 78) to the germline $V_H3$-11, $D_H7$-27, $J_H4b$ sequence (SEQ ID NO: 116).

FIG. 4OO shows an alignment of the predicted amino acid sequence of the light chain variable region for antibody 9.14.4-Ser (residues 23-130 of SEQ ID NO: 28) to the germline $V_\kappa O12$, $J_\kappa 3$ sequence (SEQ ID NO: 103).

FIG. 4PP shows an alignment of the predicted amino acid sequence of the heavy chain variable region for antibody 9.14.4-Ser (residues 20-135 of SEQ ID NO: 82) to the germline $V_H3$-11, $D_H7$-27, $J_H4b$ sequence (SEQ ID NO: 116).

FIG. 4QQ shows an alignment of the predicted amino acid sequence of the light chain variable region for antibody 9.7.2-Ser (residues 23-130 of SEQ ID NO: 48) to the germline $V_\kappa O12$, $J_\kappa 3$ sequence (SEQ ID NO: 103).

FIG. 4RR shows an alignment of the predicted amino acid sequence of the heavy chain variable region for antibody 9.7.2-Ser (residues 20-136 of SEQ ID NO: 86) to the germline $V_H3$-11, $D_H6$-13, $J_H6b$ sequence (SEQ ID NO: 115).

FIG. 4SS shows an alignment of the predicted amino acid sequence of the light chain variable region for antibody 8.10.3-Ser (residues 21-129 of SEQ ID NO: 44) to the germline $V_\kappa A27$, $J_\kappa 4$ sequence (SEQ ID NO: 114).

FIG. 4TT shows an alignment of the predicted amino acid sequence of the heavy chain variable region for antibody 8.10.3-Ser (residues 20-141 of SEQ ID NO: 90) to the germline $V_H3$-48, $D_H1$-26, $J_H4b$ sequence (SEQ ID NO: 113).

FIG. 4UU shows an alignment of the predicted amino acid sequence of the light chain variable region for antibody 8.10.3-CG4 (residues 21-129 of SEQ ID NO: 60) to the germline $V_\kappa A27$, $J_\kappa 4$ sequence (SEQ ID NO: 114).

FIG. 4VV shows an alignment of the predicted amino acid sequence of the heavy chain variable region for antibody 8.10.3-CG4 (residues 20-141 of SEQ ID NO: 94) to the germline $V_H3$-48, $D_H1$-26, $J_H4b$ sequence (SEQ ID NO: 113).

FIG. 4WW shows an alignment of the predicted amino acid sequence of the light chain variable region for antibody 9.14.4G1 (residues 23-130 of SEQ ID NO: 28) to the germline $V_\kappa O12$ $J_\kappa 3$ sequence (SEQ ID NO: 103).

FIG. 4XX shows an alignment of the predicted amino acid sequence of the heavy chain variable region for antibody 9.14.4G1 (residues 20-135 of SEQ ID NO: 102) to the germline $V_H3$-11, $D_H7$-27, $J_H4b$ sequence (SEQ ID NO: 116).

FIG. 4YY shows an alignment of the predicted amino acid sequence of the light chain variable region for antibody 8.10.3FG1 (residues 21-129 of SEQ ID NO:32) to the germline $V_\kappa A27$, $J_\kappa 4$ sequence (SEQ ID NO: 114).

FIG. 4ZZ shows an alignment of the predicted amino acid sequence of the heavy chain variable region for antibody 8.10.3FG1 (residues 20-141 of SEQ ID NO: 98) to the germline $V_H3$-48, $D_H1$-26, $J_H4b$ sequence (SEQ ID NO: 113).

DETAILED DESCRIPTION OF THE INVENTION

Definitions and General Techniques

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook et al., *Molecular Cloning: A Laboratory Manual*, 2d ed., Cold Spring Harbor Laboratory Press, Cold Spring Harbor, N.Y. (1989) and Ausubel et al., *Current Protocols in Molecular Biology*, Greene Publishing Associates (1992), and Harlow and Lane *Antibodies: A Laboratory Manual*, Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following terms, unless otherwise indicated, shall be understood to have the following meanings:

The term "polypeptide" encompasses native or artificial proteins, protein fragments and polypeptide analogs of a protein sequence. A polypeptide may be monomeric or polymeric.

The term "isolated protein", "isolated polypeptide" or "isolated antibody" is a protein, polypeptide or antibody that by virtue of its origin or source of derivation has one to four of the following: (1) is not associated with naturally associated components that accompany it in its native state, (2) is free of other proteins from the same species, (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

Examples of isolated antibodies include an anti-M-CSF antibody that has been affinity purified using M-CSF, an anti-M-CSF antibody that has been synthesized by a hybridoma or other cell line in vitro, and a human anti-M-CSF antibody derived from a transgenic mouse.

A protein or polypeptide is "substantially pure," "substantially homogeneous," or "substantially purified" when at least about 60 to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "polypeptide fragment" as used herein refers to a polypeptide that has an amino-terminal and/or carboxy-terminal deletion, but where the remaining amino acid sequence is identical to the corresponding positions in the naturally-occurring sequence. In some embodiments, fragments are at least 5, 6, 8 or 10 amino acids long. In other embodiments, the fragments are at least 14, at least 20, at least 50, or at least 70, 80, 90, 100, 150 or 200 amino acids long.

The term "polypeptide analog" as used herein refers to a polypeptide that comprises a segment that has substantial identity to a portion of an amino acid sequence and that has at least one of the following properties: (1) specific binding to M-CSF under suitable binding conditions, (2) ability to inhibit M-CSF.

Typically, polypeptide analogs comprise a conservative amino acid substitution (or insertion or deletion) with respect to the normally-occurring sequence. Analogs typically are at least 20 or 25 amino acids long, preferably at least 50, 60, 70, 80, 90, 100, 150 or 200 amino acids long or longer, and can often be as long as a full-length polypeptide.

In certain embodiments, amino acid substitutions of the antibody or antigen-binding portion thereof are those which: (1) reduce susceptibility to proteolysis, (2) reduce susceptibility to oxidation, (3) alter binding affinity for forming protein complexes, or (4) confer or modify other physicochemical or functional properties of such analogs. Analogs can include various muteins of a sequence other than the normally-occurring peptide sequence. For example, single or multiple amino acid substitutions (preferably conservative amino acid substitutions) may be made in the normally-occurring sequence, preferably in the portion of the polypeptide outside the domain(s) forming intermolecular contacts.

A conservative amino acid substitution should not substantially change the structural characteristics of the parent sequence; e.g., a replacement amino acid should not alter the anti-parallel β-sheet that makes up the immunoglobulin binding domain that occurs in the parent sequence, or disrupt other types of secondary structure that characterizes the parent sequence. In general, glycine and proline analogs would not be used in an anti-parallel β-sheet. Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et al., *Nature* 354:105 (1991), which are each incorporated herein by reference.

Non-peptide analogs are commonly used in the pharmaceutical industry as drugs with properties analogous to those of the template peptide. These types of non-peptide compound are termed "peptide mimetics" or "peptidomimetics." Fauchere, *J. Adv. Drug Res.* 15:29 (1986); Veber and Freidinger, *TINS* p. 392 (1985); and Evans et al., *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a desired biochemical property or pharmacological activity), such as a human antibody, but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, —CH(OH) $CH_2$—, and —$CH_2SO$—, by methods well known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch, *Ann. Rev. Biochem.* 61:387 (1992), incorporated herein by reference); for example, by adding internal cysteine residues capable of forming intramolecular disulfide bridges which cyclize the peptide.

An "antibody" refers to an intact antibody or an antigen-binding portion that competes with the intact antibody for specific binding. See generally, *Fundamental Immunology*, Ch. 7 (Paul, W., ed., 2nd ed. Raven Press, N.Y. (1989)) (incorporated by reference in its entirety for all purposes). Antigen-binding portions may be produced by recombinant DNA techniques or by enzymatic or chemical cleavage of intact antibodies. In some embodiments, antigen-binding portions include Fab, Fab', F(ab')$_2$, Fd, Fv, dAb, and complementarity determining region (CDR) fragments, single-chain antibodies (scFv), chimeric antibodies, diabodies and polypeptides that contain at least a portion of an antibody that is sufficient to confer specific antigen binding to the polypeptide.

From N-terminus to C-terminus, both the mature light and heavy chain variable domains comprise the regions FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md. (1987 and 1991)), Chothia & Lesk, *J. Mol. Biol.* 196:901-917 (1987), or Chothia et al., *Nature* 342:878-883 (1989).

As used herein, an antibody that is referred to by number is the same as a monoclonal antibody that is obtained from the hybridoma of the same number. For example, monoclonal antibody 3.8.3 is the same antibody as one obtained from hybridoma 3.8.3.

As used herein, a Fd fragment means an antibody fragment that consists of the $V_H$ and $C_H 1$ domains; an Fv fragment consists of the $V_L$ and $V_H$ domains of a single arm of an antibody; and a dAb fragment (Ward et al., *Nature* 341:544-546 (1989)) consists of a $V_H$ domain.

In some embodiments, the antibody is a single-chain antibody (scFv) in which a $V_L$ and $V_H$ domains are paired to form a monovalent molecules via a synthetic linker that enables them to be made as a single protein chain. (Bird et al., *Science* 242:423-426 (1988) and Huston et al., *Proc. Natl. Acad. Sci. USA* 85:5879-5883 (1988).) In some embodiments, the antibodies are diabodies, i.e., are bivalent antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites. (See e.g., Holliger P. et al., *Proc. Natl. Acad. Sci. USA* 90:6444-6448 (1993), and Poljak R. J. et al., *Structure* 2:1121-1123 (1994).) In some embodiments, one or more CDRs from an antibody of the invention may be incorporated into a molecule either covalently or noncovalently to make it an immunoadhesin that specifically binds to M-CSF. In such embodiments, the CDR(s) may be incorporated as part of a larger polypeptide chain, may be covalently linked to another polypeptide chain, or may be incorporated noncovalently.

In embodiments having one or more binding sites, the binding sites may be identical to one another or may be different.

As used herein, the term "human antibody" means any antibody in which the variable and constant domain sequences are human sequences. The term encompasses antibodies with sequences derived from human genes, but which have been changed, e.g. to decrease possible immunogenicity, increase affinity, eliminate cysteines that might cause undesirable folding, etc. The term emcompasses such antibodies produced recombinantly in non-human cells, which might impart glycosylation not typical of human cells. These antibodies may be prepared in a variety of ways, as described below.

The term "chimeric antibody" as used herein means an antibody that comprises regions from two or more different antibodies. In one embodiment, one or more of the CDRs are derived from a human anti-M-CSF antibody. In another embodiment, all of the CDRs are derived from a human anti-M-CSF antibody. In another embodiment, the CDRs from more than one human anti-M-CSF antibodies are combined in a chimeric antibody. For instance, a chimeric antibody may comprise a CDR1 from the light chain of a first human anti-M-CSF antibody, a CDR2 from the light chain of a second human anti-M-CSF antibody and a CDR3 from the light chain of a third human anti-M-CSF antibody, and the CDRs from the heavy chain may be derived from one or more other anti-M-CSF antibodies. Further, the framework regions may be derived from one of the anti-M-CSF antibodies from which one or more of the CDRs are taken or from one or more different human antibodies.

Fragments or analogs of antibodies or immunoglobulin molecules can be readily prepared by those of ordinary skill in the art following the teachings of this specification. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. See Bowie et al., *Science* 253:164 (1991).

The term "surface plasmon resonance", as used herein, refers to an optical phenomenon that allows for the analysis of real-time biospecific interactions by detection of alterations in protein concentrations within a biosensor matrix, for example using the BIACORE® protein interaction analysis equipment (Pharmacia Biosensor AB, Uppsala, Sweden and Piscataway, N.J.). For further descriptions, see Jonsson U. et al., *Ann. Biol. Clin.* 51:19-26 (1993); Jonsson U. et al., *Biotechniques* 11:620-627 (1991); Jonsson B. et al., *J. Mol. Recognit.* 8:125-131 (1995); and Johnsson B. et al., *Anal. Biochem.* 198:268-277 (1991).

The term "$K_D$" refers to the equilibrium dissociation constant of a particular antibody-antigen interaction.

The term "epitope" includes any protein determinant capable of specific binding to an immunoglobulin or T-cell receptor or otherwise interacting with a molecule. Epitopic determinants generally consist of chemically active surface groupings of molecules such as amino acids or sugar side chains and generally have specific three dimensional structural characteristics, as well as specific charge characteristics. An epitope may be "linear" or "conformational." In a linear epitope, all of the points of interaction between the protein and the interacting molecule (such as an antibody) occur linearally along the primary amino acid sequence of the protein. In a conformational epitope, the points of interaction occur across amino acid residues on the protein that are separated from one another. An antibody is said to specifically bind an antigen when the dissociation constant is ≤1 mM, preferably ≤100 nM and most preferably ≤10 nM. In certain embodiments, the $K_D$ is 1 pM to 500 pM. In other embodiments, the $K_D$ is between 500 pM to 1 μM. In other embodiments, the $K_D$ is between 1 μM to 100 nM. In other embodiments, the $K_D$ is between 100 mM to 10 nM. Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, e.g., the antibodies compete for binding to the antigen. A high throughout process for "binning" antibodies based upon their cross-competition is described in International Patent Application No. WO 03/48731.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference.

The term "polynucleotide" as referred to herein means a polymeric form of nucleotides of at least 10 bases in length, either ribonucleotides or deoxynucleotides or a modified form of either type of nucleotide. The term includes single and double stranded forms.

The term "isolated polynucleotide" as used herein means a polynucleotide of genomic, cDNA, or synthetic origin or some combination thereof, which by virtue of its origin or source of derivation, the "isolated polynucleotide" has one to three of the following: (1) is not associated with all or a portion of a polynucleotides with which the "isolated polynucleotide" is found in nature, (2) is operably linked to a polynucleotide to which it is not linked in nature, or (3) does not occur in nature as part of a larger sequence.

The term "oligonucleotide" as used herein includes naturally occurring, and modified nucleotides linked together by naturally occurring and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g. for primers and probes; although oligonucleotides may be double stranded, e.g. for use in the construction of a gene mutant. Oligonucleotides of the invention can be either sense or antisense oligonucleotides.

The term "naturally occurring nucleotides" as used herein includes deoxyribonucleotides and ribonucleotides. The term "modified nucleotides" as used herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche et al., *Nucl. Acids Res.* 14:9081 (1986); Stec et al., *J. Am. Chem. Soc.* 106:6077 (1984); Stein et al., *Nucl. Acids Res.* 16:3209 (1988); Zon et al., *Anti-Cancer Drug Design* 6:539 (1991); Zon et al., *Oligonucleotides and Analogues: A Practical Approach*, pp. 87-108 (F. Eckstein, Ed., Oxford University Press, Oxford England (1991)); U.S. Pat. No. 5,151,510; Uhlmann and Peyman, *Chemical Reviews* 90:543 (1990), the disclosures of which are hereby incorporated by reference. An oligonucleotide can include a label for detection, if desired.

"Operably linked" sequences include both expression control sequences that are contiguous with the gene of interest and expression control sequences that act in trans or at a distance to control the gene of interest. The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, means a nucleic acid molecule capable of transporting another nucleic acid to which it has been linked. In some embodiments, the vector is a plasmid, i.e., a circular double stranded DNA loop into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The term "recombinant host cell" (or simply "host cell"), as used herein, means a cell into which a recombinant expression vector has been introduced. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. "High stringency" or "highly stringent" conditions can be used to achieve selective hybridization conditions as known in the art and discussed herein. One example of "high stringency" or "highly stringent" conditions is the incubation of a polynucleotide with another polynucleotide, wherein one polynucleotide may be affixed to a solid surface such as a membrane, in a hybridization buffer of 6×SSPE or SSC, 50% formamide, 5×Denhardt's reagent, 0.5% SDS, 100 µg/ml denatured, fragmented salmon sperm DNA at a hybridization temperature of 42° C. for 12-16 hours, followed by twice washing at 55° C. using a wash buffer of 1×SSC, 0.5% SDS. See also Sambrook et al., supra, pp. 9.50-9.55.

The term "percent sequence identity" in the context of nucleic acid sequences means the percent of residues when a first contiguous sequence is compared and aligned for maximum correspondence to a second contiguous sequence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, *Methods Enzymol.* 183:63-98 (1990); Pearson, *Methods Mol. Biol.* 132:185-219 (2000); Pearson, *Methods Enzymol.* 266:227-258 (1996); Pearson, *J. Mol. Biol.* 276:71-84 (1998); herein incorporated by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference.

A reference to a nucleotide sequence encompasses its complement unless otherwise specified. Thus, a reference to a nucleic acid having a particular sequence should be understood to encompass its complementary strand, with its complementary sequence.

The term "percent sequence identity" means a ratio, expressed as a percent of the number of identical residues over the number of residues compared.

The term "substantial similarity" or "substantial sequence similarity," when referring to a nucleic acid or fragment thereof, means that when optimally aligned with appropriate nucleotide insertions or deletions with another nucleic acid (or its complementary strand), there is nucleotide sequence identity in at least about 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

As applied to polypeptides, the term "substantial identity" means that two peptide sequences, when optimally aligned, such as by the programs GAP or BESTFIT using default gap weights, as supplied with the programs, share at least 70%, 75% or 80% sequence identity, preferably at least 90% or 95% sequence identity, and more preferably at least 97%, 98% or 99% sequence identity. In certain embodiments, residue positions that are not identical differ by conservative amino acid substitutions. A "conservative amino acid substitution" is one in which an amino acid residue is substituted by another amino acid residue having a side chain R group with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity may be adjusted upwards to correct for the conservative nature of the substitution. Means for making this adjustment are well-known to those of skill in the art. See, e.g., Pearson, *Methods Mol. Biol.* 243:307-31 (1994). Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., *Science* 256:1443-45 (1992), herein incorporated by reference. A "moderately conservative" replacement is any change having a nonnegative value in the PAM250 log-likelihood matrix.

Sequence identity for polypeptides, is typically measured using sequence analysis software. Protein analysis software matches sequences using measures of similarity assigned to various substitutions, deletions and other modifications, including conservative amino acid substitutions. For instance, GCG contains programs such as "Gap" and "Bestfit" which can be used with default parameters, as specified with the programs, to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, see GCG Version 6.1. (University of Wisconsin WI) FASTA (e.g., FASTA2 and FASTA3) provides alignments and percent sequence identity of the regions of the best overlap between the query and search sequences (Pearson, *Methods Enzymol.* 183:63-98 (1990); Pearson, *Methods Mol. Biol.* 132:185-219 (2000)). Another preferred algorithm when comparing a sequence of the invention to a database containing a large number of sequences from different organisms is the computer program BLAST, especially blastp or tblastn, using default parameters, as supplied with the programs. See, e.g., Altschul et al., *J. Mol. Biol.* 215:403-410 (1990); Altschul et al., *Nucleic Acids Res.* 25:3389-402 (1997).

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences.

As used herein, the terms "label" or "labeled" refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

Throughout this specification and claims, the word "comprise," or variations such as "comprises" or "comprising," will be understood to imply the inclusion of a stated integer or group of integers but not the exclusion of any other integer or group of integers.

Human Anti-M-CSF Antibodies and Characterization Thereof

In one embodiment, the invention provides humanized anti-M-CSF antibodies. In another embodiment, the invention provides human anti-M-CSF antibodies. In some embodiments, human anti-M-CSF antibodies are produced by immunizing a non-human transgenic animal, e.g., a rodent, whose genome comprises human immunoglobulin genes so that the rodent produces human antibodies.

An anti-M-CSF antibody of the invention can comprise a human kappa or a human lamda light chain or an amino acid sequence derived therefrom. In some embodiments comprising a kappa light chain, the light chain variable domain ($V_L$) is encoded in part by a human $V_\kappa O12$, $V_\kappa L2$, $V_\kappa L5$, $V_\kappa A27$ or $V_\kappa B3$ gene and a $J_\kappa 1$, $J_\kappa 2$, $J_\kappa 3$, or $J_\kappa 4$ gene. In particular embodiments of the invention, the light chain variable domain is encoded by $V_\kappa O12/J\kappa 3$, $V_\kappa L2/J\kappa 3$, $V_\kappa L5/J\kappa 3$, $V_\kappa L5/J\kappa 4$, $V_\kappa A27/J\kappa 4$ or $V_\kappa B3/J\kappa 1$ gene.

In some embodiments, the $V_L$ of the M-CSF antibody comprises one or more amino acid substitutions relative to the germline amino acid sequence. In some embodiments, the $V_L$ of the anti-M-CSF antibody comprises 1, 2, 3, 4, 5, 6, 7, 8, 9, or 10 amino acid substitutions relative to the germline amino acid sequence. In some embodiments, one or more of those substitutions from germline is in the CDR regions of the light chain. In some embodiments, the amino acid substitutions relative to germline are at one or more of the same positions as the substitutions relative to germline in any one or more of the $V_L$ of antibodies 252, 88, 100, 3.8.3, 2.7.3, 1.120.1, 9.14.4I, 8.10.3F, 9.7.2IF, 9.14.4, 8.10.3, 9.7.2, 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4, 8.10.3FG1 or 9.14.4G1. For example, the $V_L$ of the anti-M-CSF antibody may contain one or more amino acid substitutions compared to germline found in the $V_L$ of antibody 88, and other amino acid substitutions compared to germline found in the $V_L$ of antibody 252 which utilizes the same $V_K$ gene as antibody 88. In some embodiments, the amino acid changes are at one or more of the same positions but involve a different mutation than in the reference antibody.

In some embodiments, amino acid changes relative to germline occur at one or more of the same positions as in any of the $V_L$ of antibodies 252, 88, 100, 3.8.3, 2.7.3, 1.120.1, 9.14.4I, 8.10.3F, 9.7.2IF, 9.14.4, 8.10.3, 9.7.2, 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4, 8.10.3FG1 or 9.14.4G1, but the changes may represent conservative amino acid substitutions at such position(s) relative to the amino acid in the reference antibody. For example, if a particular position in one of these antibodies is changed relative to germline and is glutamate, one may substitute aspartate at that position. Similarly, if an amino acid substitution compared to germline is serine, one may substitute threonine for serine at that position. Conservative amino acid substitutions are discussed supra.

In some embodiments, the light chain of the human anti-M-CSF antibody comprises the amino acid sequence that is the same as the amino acid sequence of the $V_L$ of antibody 252 (SEQ ID NO: 4), 88 (SEQ ID NO: 8), 100 (SEQ ID NO: 12), 3.8.3 (SEQ ID NO: 16), 2.7.3 (SEQ ID NO: 20), 1.120.1 (SEQ ID NO: 24), 9.14.4I (SEQ ID NO: 28), 8.10.3F (SEQ ID NO: 32), 9.7.2IF (SEQ ID NO: 36), 9.14.4 (SEQ ID NO: 28), 8.10.3 (SEQ ID NO: 44), 9.7.2 (SEQ ID NO: 48), 9.7.2C-Ser (SEQ ID NO: 52), 9.14.4C-Ser (SEQ ID NO: 56), 8.10.3C-Ser (SEQ ID NO: 60), 8.10.3-CG2 (SEQ ID NO: 60), 9.7.2-CG2 (SEQ ID NO: 52), 9.7.2-CG4 (SEQ ID NO: 52), 9.14.4-CG2 (SEQ ID NO: 56), 9.14.4-CG4 (SEQ ID NO: 56), 9.14.4-Ser (SEQ ID NO: 28), 9.7.2-Ser (SEQ ID NO: 48), 8.10.3-Ser (SEQ ID NO: 44), 8.10.3-CG4 (SEQ ID NO: 60) 8.10.3FG1 (SEQ ID NO: 32) or 9.14.4G1 (SEQ ID NO: 28), or said amino acid sequence having up to 1, 2, 3, 4, 5, 6, 7, 8, 9, or 10 conservative amino acid substitutions and/or a total of up to 3 non-conservative amino acid substitutions. In some embodiments, the light chain comprises the amino acid sequence from the beginning of the CDR1 to the end of the CDR3 of any one of the foregoing antibodies.

In some embodiments, the light chain of the anti-M-CSF antibody comprises at least the light chain CDR1, CDR2 or CDR3 of a germline or antibody sequence, as described herein. In another embodiment, the light chain may comprise a CDR1, CDR2 or CDR3 regions of an antibody independently selected from 252, 88, 100, 3.8.3, 2.7.3, 1.120.1, 9.14.4I, 8.10.3F, 9.7.2IF, 9.14.4, 8.10.3, 9.7.2, 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4, 8.10.3FG1 or 9.14.4G1, or CDR regions each having less than 4 or less than 3 conservative amino acid substitutions and/or a total of three or fewer non-conservative amino acid substitutions. In other embodiments, the light chain of the anti-M-CSF antibody comprises the light chain CDR1, CDR2 or CDR3, each of which are independently selected from the CDR1, CDR2 and CDR3 regions of an antibody having a light chain variable region comprising the amino acid sequence of the $V_L$ region selected from SEQ ID NOS: 4, 8, 12, 16, 20, 24, 28, 32, 36, 44, 48, 52, 56 or 60, or encoded by a nucleic acid molecule encoding the $V_L$ region selected from SEQ ID NOS: 3, 7, 11, 27, 31, 35, 43 or 47. The light chain of the anti-M-CSF antibody may comprise the CDR1, CDR2 and CDR3 regions of an antibody comprising the amino acid sequence of the $V_L$ region selected from 252, 88, 100, 3.8.3, 2.7.3, 1.120.1, 9.14.4I, 8.10.3F, 9.7.2IF, 9.14.4, 8.10.3, 9.7.2, 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4, 8.10.3FG1 or 9.14.4G1 or SEQ ID NOS: 4, 8, 12, 16, 20, 24, 28, 32, 36, 44, 48, 52, 56 or 60.

In some embodiments, the light chain comprises the CDR1, CDR2 and CDR3 regions of antibody 252, 88, 100, 3.8.3, 2.7.3, 1.120.1, 9.14.4I, 8.10.3F, 9.7.2IF, 9.14.4, 8.10.3, 9.7.2, 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4, 8.10.3FG1 or 9.14.4G1, or said CDR regions each having less than 4 or less than 3 conservative amino acid substitutions and/or a total of three or fewer non-conservative amino acid substitutions.

With regard to the heavy chain, in some embodiments, the variable region of the heavy chain amino acid sequence is encoded in part by a human $V_H3$-11, $V_H3$-23, $V_H3$-7, $V_H1$-18, $V_H3$-33, $V_H3$-48 gene and a $J_H4$, $J_H6$, $J_H4b$, or $J_H6b$ gene. In a particular embodiment of the invention, the heavy chain variable region is encoded by $V_H3$-11/$D_H7$-27/$J_H6$, $V_H3$-7/$D_H6$-13/$J_H4$, $V_H3$-23/$D_H1$-26/$J_H4$, $V_H3$-11/$D_H7$-27/$J_H4$, $V_H3$-33/$D_H1$-26/$J_H4$, $V_H1$-18/$D_H4$-23/$J_H4$, $V_H3$-11/$D_H7$-27/$J_H4b$, $V_H3$-48/$D_H1$-26/$J_H4b$, $V_H3$-11/$D_H6$-13/$J_H6b$, $V_H3$-11/$D_H7$-27/$J_H4b$, $V_H3$-48/$D_H1$-6/$J_H4b$, or $V_H3$-11/$D_H6$-13/$J_H6b$ gene. In some embodiments, the $V_H$ of the anti-M-CSF antibody contains one or more amino acid substitutions, deletions or insertions (additions) relative to the germline amino acid sequence. In some embodiments, the variable domain of the heavy chain comprises 1, 2, 3, 4, 5, 6, 7, 8, 9, 10, 11, 12, 13, 14, 15, 16, 17, or 18 mutations from the germline amino acid sequence. In some embodiments, the mutation(s) are non-conservative substitutions compared to the germline amino acid sequence. In some embodiments, the mutations are in the CDR regions of the heavy chain. In some embodiments, the amino acid changes are made at one or more of the same positions as the mutations from germline in any one or more of the $V_H$ of antibodies 252, 88, 100, 3.8.3, 2.7.3, 1.120.1, 9.14.4I, 8.10.3F, 9.7.2IF, 9.14.4, 8.10.3, 9.7.2, 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4, 8.10.3FG1 or 9.14.4G1. In other embodiments, the amino acid changes are at one or more of the same positions but involve a different mutation than in the reference antibody.

In some embodiments, the heavy chain comprises an amino acid sequence of the variable domain ($V_H$) of antibody 252 (SEQ ID NO: 2), 88 (SEQ ID NO: 6), 100 (SEQ ID NO: 10), 3.8.3 (SEQ ID NO: 14), 2.7.3 (SEQ. ID NO: 18), 1.120.1 (SEQ. ID NO: 22), 9.14.4I (SEQ ID NO: 26), 8.10.3F (SEQ ID NO: 30), 9.7.2IF (SEQ ID NO: 34), 9.14.4 (SEQ ID NO: 38), 8.10.3 (SEQ ID NO: 30), 9.7.2 (SEQ ID NO: 46), 9.7.2C-Ser (SEQ ID NO: 50), 9.14.4C-Ser (SEQ ID NO: 54), 8.10.3C-Ser (SEQ ID NO: 58), 8.10.3-CG2

(SEQ ID NO: 62), 9.7.2-CG2 (SEQ ID NO: 66), 9.7.2-CG4 (SEQ ID NO: 70), 9.14.4-CG2 (SEQ ID NO: 74), 9.14.4-CG4 (SEQ ID NO: 78), 9.14.4-Ser (SEQ ID NO: 82), 9.7.2-Ser (SEQ ID NO: 86), 8.10.3-Ser (SEQ ID NO: 90) 8.10.3-CG4 (SEQ ID NO: 94), 8.10.3FG1 (SEQ ID NO: 98) or 9.14.4G1 (SEQ ID NO: 102), or said amino acid sequence having up to 1, 2, 3, 4, 5, 6, 7, 8, 9, or 10 conservative amino acid substitutions and/or a total of up to 3 non-conservative amino acid substitutions. In some embodiments, the heavy chain comprises the amino acid sequence from the beginning of the CDR1 to the end of the CDR3 of any one of the foregoing antibodies.

In some embodiments, the heavy chain comprises the heavy chain CDR1, CDR2 and CDR3 regions of antibody 252, 88, 100, 3.8.3, 2.7.3, 1.120.1, 9.14.4I, 8.10.3F, 9.7.2IF, 9.14.4, 8.10.3, 9.7.2, 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4, 8.10.3FG1 or 9.14.4G1, or said CDR regions each having less than 8, less than 6, less than 4, or less than 3 conservative amino acid substitutions and/or a total of three or fewer non-conservative amino acid substitutions.

In some embodiments, the heavy chain comprises a germline or antibody CDR3, as described above, of an antibody sequence as described herein, and may also comprise the CDR1 and CDR2 regions of a germline sequence, or may comprise a CDR1 and CDR2 of an antibody sequence, each of which are independently selected from an antibody comprising a heavy chain of an antibody selected from 252, 88, 100, 3.8.3, 2.7.3, 1.120.1, 9.14.4I, 8.10.3F, 9.7.2IF, 9.14.4, 8.10.3, 9.7.2, 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4, 8.10.3FG1 or 9.14.4G1. In another embodiment, the heavy chain comprises a CDR3 of an antibody sequence as described herein, and may also comprise the CDR1 and CDR2 regions, each of which are independently selected from a CDR1 and CDR2 region of a heavy chain variable region comprising an amino acid sequence of the $V_H$ region selected from SEQ ID NOS: 2, 6, 10, 14, 18, 22, 26, 30, 34, 38, 46, 50, 54, 58, 62, 66, 70, 74, 78, 82, 86, 90, 94, 98 or 102, or encoded by a nucleic acid sequence encoding the $V_H$ region selected from SEQ ID NOS: 1, 5, 9, 25, 29, 33, 37, 45, 97 or 101. In another embodiment, the antibody comprises a light chain as disclosed above and a heavy chain as disclosed above.

One type of amino acid substitution that may be made is to change one or more cysteines in the antibody, which may be chemically reactive, to another residue, such as, without limitation, alanine or serine. In one embodiment, there is a substitution of a non-canonical cysteine. The substitution can be in a framework region of a variable domain or in the constant domain of an antibody. In another embodiment, the cysteine is in a non-canonical region of the antibody.

Another type of amino acid substitution that may be made is to remove any potential proteolytic sites in the antibody, particularly those that are in a CDR or framework region of a variable domain or in the constant domain of an antibody. Substitution of cysteine residues and removal of proteolytic sites may decrease the risk of any heterogeneity in the antibody product and thus increase its homogeneity. Another type of amino acid substitution is elimination of asparagine-glycine pairs, which form potential deamidation sites, by altering one or both of the residues.

In some embodiments, the C-terminal lysine of the heavy chain of the anti-M-CSF antibody of the invention is not present (Lewis D. A., et al., *Anal. Chem*, 66(5): 585-95 (1994)). In various embodiments of the invention, the heavy and light chains of the anti-M-CSF antibodies may optionally include a signal sequence.

In one aspect, the invention relates to inhibiting human anti-M-CSF monoclonal antibodies and the cell lines engineered to produce them. Table 1 lists the sequence identifiers (SEQ ID NOS) of the nucleic acids that encode the variable region of the heavy and light chains and the corresponding predicted amino acid sequences for the monoclonal antibodies: 252, 88, 100, 3.8.3, 2.7.3, 1.120.1, 9.14.4I, 8.10.3F, 9.7.2IF, 9.14.4, 8.10.3 and 9.7.2. Additional variant antibodies 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4 8.10.3FG1 or 9.14.4G1 could be made by methods known to one skilled in the art.

TABLE 1

HUMAN ANTI-M-CSF ANTIBODIES

| | SEQUENCE IDENTIFIER (SEQ ID NOS:) Full Length | | | |
|---|---|---|---|---|
| | Heavy | | Light | |
| MAb | DNA | Protein | DNA | Protein |
| 252 | 1 | 2 | 3 | 4 |
| 88 | 5 | 6 | 7 | 8 |
| 100 | 9 | 10 | 11 | 12 |
| 3.8.3 | | 14 | | 16 |
| 2.7.3 | | 18 | | 20 |
| 1.120.1 | | 22 | | 24 |
| 9.14.4I | 25 | 26 | 27 | 28 |
| 9.14.4 | 37 | 38 | 27 | 28 |
| 9.14.4C-Ser | | 54 | | 56 |
| 9.14.4-CG2 | | 74 | | 56 |
| 9.14.4-CG4 | | 78 | | 56 |
| 9.14.4-Ser | | 82 | 27 | 28 |
| 9.14.4-G1 | 101 | 102 | 27 | 28 |
| 8.10.3F | 29 | 30 | 31 | 32 |
| 8.10.3 | 29 | 30 | 43 | 44 |
| 8.10.3C-Ser | | 58 | | 60 |
| 8.10.3-CG2 | | 62 | | 60 |
| 8.10.3-Ser | | 90 | 43 | 44 |
| 8.10.3-CG4 | | 94 | | 60 |
| 8.10.3FG1 | 97 | 98 | 31 | 32 |
| 9.7.2IF | 33 | 34 | 35 | 36 |
| 9.7.2 | 45 | 46 | 47 | 48 |
| 9.7.2C-Ser | | 50 | | 52 |
| 9.7.2-CG2 | | 66 | | 52 |
| 9.7.2-CG4 | | 70 | | 52 |
| 9.7.2-Ser | | 86 | 47 | 48 |

Class and Subclass of Anti-M-CSF Antibodies

The class and subclass of anti-M-CSF antibodies may be determined by any method known in the art. In general, the class and subclass of an antibody may be determined using antibodies that are specific for a particular class and subclass of antibody. Such antibodies are commercially available. The class and subclass can be determined by ELISA, or Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies.

In some embodiments, the anti-M-CSF antibody is a monoclonal antibody. The anti-M-CSF antibody can be an IgG, an IgM, an IgE, an IgA, or an IgD molecule. In preferred embodiments, the anti-M-CSF antibody is an IgG and is an IgG1, IgG2, IgG3 or IgG4 subclass. In other preferred embodiments, the antibody is subclass IgG2 or IgG4. In another preferred embodiment, the antibody is subclass IgG1.

Species and Molecular Selectivity

In another aspect of the invention, the anti-M-CSF antibodies demonstrate both species and molecule selectivity. In some embodiments, the anti-M-CSF antibody binds to human, cynomologus monkey and mouse M-CSF. Following the teachings of the specification, one may determine the species selectivity for the anti-M-CSF antibody using methods well known in the art. For instance, one may determine the species selectivity using Western blot, FACS, ELISA, RIA, a cell proliferation assay, or a M-CSF receptor binding assay. In a preferred embodiment, one may determine the species selectivity using a cell proliferation assay or ELISA. In some embodiments, the anti-M-CSF antibodies bind to human secreted isoforms of M-CSF and membrane bound isoforms of M-CSF.

In another embodiment, the anti-M-CSF antibody has a selectivity for M-CSF that is at least 100 times greater than its selectivity for GM-/G-CSF. In some embodiments, the anti-M-CSF antibody does not exhibit any appreciable specific binding to any other protein other than M-CSF. One can determine the selectivity of the anti-M-CSF antibody for M-CSF using methods well known in the art following the teachings of the specification. For instance one can determine the selectivity using Western blot, FACS, ELISA, or RIA.

Identification of M-CSF Epitopes Recognized by Anti-M-CSF Antibodies

The invention provides a human anti-M-CSF monoclonal antibody that binds to M-CSF and competes with, cross-competes with and/or binds the same epitope and/or binds to M-CSF with the same $K_D$ as (a) an antibody selected from 252, 88, 100, 3.8.3, 2.7.3, 1.120.1, 9.14.4I, 8.10.3F, 9.7.2IF, 9.14.4, 8.10.3, 9.7.2, 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4, 8.10.3FG1 or 9.14.4G1; (b) an antibody that comprises a heavy chain variable region having an amino acid sequence of SEQ ID NO: 2, 6, 10, 14, 18, 22, 26, 30, 34, 38, 46, 50, 54, 58, 62, 66, 70, 74, 78, 82, 86, 90, 94, 98 or 102; (c) an antibody that comprises a light chain variable region having a an amino acid sequence of SEQ ID NO: 4, 8, 12, 16, 20, 24, 28, 32, 36, 44, 48, 52, 56 or 60; (d) an antibody that comprises both a heavy chain variable region as defined in (b) and a light chain variable region as defined in (c).

One can determine whether an antibody binds to the same epitope, competes for binding with, cross competes for binding with or has the same $K_D$ an anti-M-CSF antibody by using methods known in the art. In one embodiment, one allows the anti-M-CSF antibody of the invention to bind to M-CSF under saturating conditions and then measures the ability of the test antibody to bind to M-CSF. If the test antibody is able to bind to M-CSF at the same time as the anti-M-CSF antibody, then the test antibody binds to a different epitope as the anti-M-CSF antibody. However, if the test antibody is not able to bind to M-CSF at the same time, then the test antibody binds to the same epitope, an overlapping epitope, or an epitope that is in close proximity to the epitope bound by the human anti-M-CSF antibody. This experiment can be performed using ELISA, RIA, or FACS. In a preferred embodiment, the experiment is performed using BIACORE® protein interaction analysis equipment.

Binding Affinity of Anti-M-CSF Antibodies to M-CSF

In some embodiments of the invention, the anti-M-CSF antibodies bind to M-CSF with high affinity. In some embodiments, the anti-M-CSF antibody binds to M-CSF with a $K_D$ of $1\times10^{-7}$M or less. In other preferred embodiments, the antibody binds to M-CSF with a $K_D$ of $1\times10^{-8}$ M, $1\times10^{-9}$ M, $1\times10^{-10}$ M, $1\times10^{-11}$ M, $1\times10^{-12}$M or less. In certain embodiments, the $K_D$ is 1 pM to 500 pM. In other embodiments, the $K_D$ is between 500 pM to 1 µM. In other embodiments, the $K_D$ is between 1 µM to 100 nM. In other embodiments, the $K_D$ is between 100 mM to 10 nM. In an even more preferred embodiment, the antibody binds to M-CSF with substantially the same $K_D$ as an antibody selected from 252, 88, 100, 3.8.3, 2.7.3, 1.120.1, 9.14.4I, 8.10.3F, 9.7.2IF, 9.14.4, 8.10.3, 9.7.2, 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4, 8.10.3FG1 or 9.14.4G1. In another preferred embodiment, the antibody binds to M-CSF with substantially the same $K_D$ as an antibody that comprises a CDR2 of a light chain, and/or a CDR3 of a heavy chain from an antibody selected from 252, 88, 100, 3.8.3, 2.7.3, 1.120.1, 9.14.4I, 8.10.3F, 9.7.2IF, 9.14.4, 8.10.3, 9.7.2, 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4, 8.10.3FG1 or 9.14.4G1. In still another preferred embodiment, the antibody binds to M-CSF with substantially the same $K_D$ as an antibody that comprises a heavy chain variable region having an amino acid sequence of SEQ ID NO: 2, 6, 10, 14, 18, 22, 26, 30, 34, 38, 46, 50, 54, 58, 62, 66, 70, 74, 78, 82, 86, 90, 94, 98 or 102, or that comprises a light chain variable region having an amino acid sequence of SEQ ID NO: 4, 8, 12, 16, 20, 24, 28, 32, 36, 44, 48, 52, 56 or 60. In another preferred embodiment, the antibody binds to M-CSF with substantially the same $K_D$ as an antibody that comprises a CDR2, and may optionally comprise a CDR1 and/or CDR3, of a light chain variable region having an amino acid sequence of the $V_L$ region of SEQ ID NO: 4, 8, 12, 16, 20, 24, 28, 32, 36, 44, 48, 52, 56 or 60, or that comprises a CDR3, and may optionally comprise a CDR1 and/or CDR2, of a heavy chain variable region having an amino acid sequence of the $V_H$ region of SEQ ID NO: 2, 6, 10, 14, 18, 22, 26, 30, 34, 38, 46, 50, 54, 58, 62, 66, 70, 74, 78, 82, 86, 90, 94, 98 or 102.

In some embodiments, the anti-M-CSF antibody has a low dissociation rate. In some embodiments, the anti-M-CSF antibody has an $k_{off}$ of $2.0\times10^{-4}$ s$^{-1}$ or lower. In other preferred embodiments, the antibody binds to M-CSF with a $k_{off}$ of $2.0\times10^{-5}$ or a $k_{off}$ $2.0\times10^{-6}$ s$^{-1}$ or lower. In some embodiments, the $k_{off}$ is substantially the same as an antibody described herein, such as an antibody selected from 252, 88, 100, 3.8.3, 2.7.3, 1.120.1, 9.14.4I, 8.10.3F, 9.7.2IF, 9.14.4, 8.10.3, 9.7.2, 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4, 8.10.3FG1 or 9.14.4G1. In some embodiments, the antibody binds to M-CSF with substantially the same $k_{off}$ as an antibody that comprises (a) a CDR3, and may optionally comprise a CDR1 and/or CDR2, of a heavy chain of an antibody selected from 252, 88, 100, 3.8.3, 2.7.3, 1.120.1, 9.14.4I, 8.10.3F, 9.7.2IF, 9.14.4, 8.10.3, 9.7.2, 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4, 8.10.3FG1 or 9.14.4G1; or (b) a CDR2, and may optionally comprise a CDR1 and/or CDR3, of a light chain from an antibody selected from 252, 88, 100, 3.8.3, 2.7.3, 1.120.1, 9.14.4I, 8.10.3F, 9.7.2IF, 9.14.4, 8.10.3, 9.7.2, 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4, 8.10.3FG1 or 9.14.4G1. In some embodiments, the antibody binds to M-CSF with substantially the same $k_{off}$ as an antibody that comprises a heavy chain variable region having an amino acid sequence of SEQ ID NO: 2, 6, 10, 14, 18, 22, 26, 30, 34, 38, 46, 50, 54, 58, 62, 66, 70, 74, 78, 82, 86, 90, 94, 98 or 102; or that comprises a light chain variable region having an amino acid sequence of SEQ ID NO: 4, 8, 12, 16, 20, 24, 28, 32, 36, 44, 48, 52, 56 or 60; In another preferred embodiment, the antibody binds to M-CSF with substantially the same $k_{off}$ as an antibody that comprises a CDR2, and may optionally comprise a CDR1 and/or CDR3, of a light chain variable region having an amino acid sequence of SEQ ID NO: 4, 8, 12, 16, 20, 24, 28, 32, 36, 44, 48, 52, 56 or 60; or a CDR3, and may optionally comprise a CDR1 and/or CDR2, of a heavy chain variable region having an amino acid sequence of SEQ ID NO: 2, 6, 10, 14, 18, 22, 26, 30, 34, 38, 46, 50, 54, 58, 62, 66, 70, 74, 78, 82, 86, 90, 94, 98 or 102.

The binding affinity and dissociation rate of an anti-M-CSF antibody to a M-CSF can be determined by methods known in the art. The binding affinity can be measured by competitive ELISAs, RIAs, surface plasmon resonance (e.g., by using BIACORE® protein interaction analysis equipment). The dissociation rate can be measured by surface plasmon resonance. Preferably, the binding affinity and dissociation rate is measured by surface plasmon resonance. More preferably, the binding affinity and dissociation rate are measured using BIACORE® protein interaction analysis equipment. Example VI exemplifies a method for determining affinity constants of anti-M-CSF monoclonal antibodies by BIACORE® protein interaction analysis equipment.

Inhibition of M-CSF Activity by Anti-M-CSF Antibody
Inhibition of M-CSF Binding to c-Fms In another embodiment, the invention provides an anti-M-CSF antibody that inhibits the binding of a M-CSF to c-fms receptor and blocks or prevents activation of c-fms. In an preferred embodiment, the M-CSF is human. In another preferred embodiment, the anti-M-CSF antibody is a human antibody. The $IC_{50}$ can be measured by ELISA, RIA, and cell based assays such as a cell proliferation assay, a whole blood monocyte shape change assay, or a receptor binding inhibition assay. In one embodiment, the antibody or portion thereof inhibits cell proliferation with an $IC_{50}$ of no more than $8.0 \times 10^{-7}$ M, preferably no more than $3 \times 10^{-7}$ M, or more preferably no more than $8 \times 10^{-8}$ M as measured by a cell proliferation assay. In another embodiment, the $IC_{50}$ as measured by a monocyte shape change assay is no more than $2 \times 10^{-6}$ M, preferably no more than $9.0 \times 10^{-7}$ M, or more preferably no more than $9 \times 10^{-8}$ M. In another preferred embodiment, the $IC_{50}$ as measured by a receptor binding assay is no more than $2 \times 10^{-6}$ M, preferably no more than $8.0 \times 10^{-7}$ M, or more preferably no more than $7.0 \times 10^{-8}$ M. Examples III, IV, and V exemplify various types of assays.

In another aspect anti-M-CSF antibodies of the invention inhibit monocyte/macrophage cell proliferation in response to a M-CSF by at least 20%, more preferably 40%, 45%, 50%, 55%, 60%, 65%, 70%, 80%, 85%, 90%, 95% or 100% compared to the proliferation of cell in the absence of antibody.

Methods of Producing Antibodies and Antibody Producing Cell Lines
Immunization

In some embodiments, human antibodies are produced by immunizing a non-human animal comprising in its genome some or all of human immunoglobulin heavy chain and light chain loci with a M-CSF antigen. In a preferred embodiment, the non-human animal is a XENOMOUSE® transgenic mouse that makes human antibodies (Abgenix Inc., Fremont, Calif.). Another non-human animal that may be used is a transgenic mouse produced by Medarex (Medarex, Inc., Princeton, N.J.).

XENOMOUSE® transgenic mice that make human antibodies are engineered mouse strains that comprise large fragments of human immunoglobulin heavy chain and light chain loci and are deficient in mouse antibody production. See, e.g., Green et al., Nature Genetics 7:13-21 (1994) and U.S. Pat. Nos. 5,916,771, 5,939,598, 5,985,615, 5,998,209, 6,075,181, 6,091,001, 6,114,598, 6,130,364, 6,162,963 and 6,150,584. See also WO 91/10741, WO 94/02602, WO 96/34096, WO 96/33735, WO 98/16654, WO 98/24893, WO 98/50433, WO 99/45031, WO 99/53049, WO 00/09560, and WO 00/037504.

In another aspect, the invention provides a method for making anti-M-CSF antibodies from non-human, non-mouse animals by immunizing non-human transgenic animals that comprise human immunoglobulin loci with a M-CSF antigen. One can produce such animals using the methods described in the above-cited documents. The methods disclosed in these documents can be modified as described in U.S. Pat. No. 5,994,619. U.S. Pat. No. 5,994,619 describes methods for producing novel cultural inner cell mass (CICM) cells and cell lines, derived from pigs and cows, and transgenic CICM cells into which heterologous DNA has been inserted. CICM transgenic cells can be used to produce cloned transgenic embryos, fetuses, and offspring. The '619 patent also describes the methods of producing the transgenic animals, that are capable of transmitting the heterologous DNA to their progeny. In preferred embodiments, the non-human animals are rats, sheep, pigs, goats, cattle or horses.

XENOMOUSE® transgenic mice that make human antibodies produce an adult-like human repertoire of fully human antibodies and generate antigen-specific human antibodies. In some embodiments, the XENOMOUSE® transgenic mice that make human antibodies contain approximately 80% of the human antibody V gene repertoire through introduction of megabase sized, germline configuration yeast artificial chromosome (YAC) fragments of the human heavy chain loci and kappa light chain loci. In other embodiments, XENOMOUSE® transgenic mice that make human antibodies further contain approximately all of the lambda light chain locus. See Mendez et al., Nature Genetics 15:146-156 (1997), Green and Jakobovits, J. Exp. Med. 188:483-495 (1998), and WO 98/24893, the disclosures of which are hereby incorporated by reference.

In some embodiments, the non-human animal comprising human immunoglobulin genes are animals that have a human immunoglobulin "minilocus". In the minilocus approach, an exogenous Ig locus is mimicked through the inclusion of individual genes from the Ig locus. Thus, one or more $V_H$ genes, one or more $D_H$ genes, one or more $J_H$ genes, a mu constant domain, and a second constant domain (preferably a gamma constant domain) are formed into a construct for insertion into an animal. This approach is described, inter alia, in U.S. Pat. Nos. 5,545,807, 5,545,806, 5,569,825, 5,625,126, 5,633,425, 5,661,016, 5,770,429, 5,789,650, 5,814,318, 5,591,669, 5,612,205, 5,721,367, 5,789,215, and 5,643,763, hereby incorporated by reference.

In another aspect, the invention provides a method for making humanized anti-M-CSF antibodies. In some embodiments, non-human animals are immunized with a M-CSF antigen as described below under conditions that permit antibody production. Antibody-producing cells are isolated from the animals, fused with myelomas to produce hybridomas, and nucleic acids encoding the heavy and light chains of an anti-M-CSF antibody of interest are isolated. These nucleic acids are subsequently engineered using techniques known to those of skill in the art and as described further below to reduce the amount of non-human sequence, i.e., to humanize the antibody to reduce the immune response in humans In some embodiments, the M-CSF antigen is isolated and/or purified M-CSF. In a preferred embodiment, the M-CSF antigen is human M-CSF. In some embodiments, the M-CSF antigen is a fragment of M-CSF. In some embodiments, the M-CSF fragment is the extracellular domain of M-CSF. In some embodiments, the M-CSF fragment comprises at least one epitope of M-CSF. In other embodiments, the M-CSF antigen is a cell that expresses or overexpresses M-CSF or an immunogenic fragment thereof on its surface. In some embodiments, the M-CSF antigen is a M-CSF fusion protein. M-CSF can be purified from natural sources using known techniques. Recombinant M-CSF is commercially available.

Immunization of animals can be by any method known in the art. See, e.g., Harlow and Lane, *Antibodies: A Laboratory Manual*, New York: Cold Spring Harbor Press, 1990. Methods for immunizing non-human animals such as mice, rats, sheep, goats, pigs, cattle and horses are well known in the art. See, e.g., Harlow and Lane, supra, and U.S. Pat. No. 5,994,619. In a preferred embodiment, the M-CSF antigen is administered with an adjuvant to stimulate the immune response. Exemplary adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks. Example I exemplifies a method for producing anti-M-CSF monoclonal antibodies in XENOMOUSE® transgenic mice that make human antibodies.

Production of Antibodies and Antibody-Producing Cell Lines

After immunization of an animal with a M-CSF antigen, antibodies and/or antibody-producing cells can be obtained from the animal. In some embodiments, anti-M-CSF antibody-containing serum is obtained from the animal by bleeding or sacrificing the animal. The serum may be used as it is obtained from the animal, an immunoglobulin fraction may be obtained from the serum, or the anti-M-CSF antibodies may be purified from the serum.

In some embodiments, antibody-producing immortalized cell lines are prepared from cells isolated from the immunized animal. After immunization, the animal is sacrificed and lymph node and/or splenic B cells are immortalized. Methods of immortalizing cells include, but are not limited to, transfecting them with oncogenes, infecting them with an oncogenic virus, cultivating them under conditions that select for immortalized cells, subjecting them to carcinogenic or mutating compounds, fusing them with an immortalized cell, e.g., a myeloma cell, and inactivating a tumor suppressor gene. See, e.g., Harlow and Lane, supra. If fusion with myeloma cells is used, the myeloma cells preferably do not secrete immunoglobulin polypeptides (a non-secretory cell line). Immortalized cells are screened using M-CSF, a portion thereof, or a cell expressing M-CSF. In a preferred embodiment, the initial screening is performed using an enzyme-linked immunoassay (ELISA) or a radioimmunoassay. An example of ELISA screening is provided in WO 00/37504, incorporated herein by reference.

Anti-M-CSF antibody-producing cells, e.g., hybridomas, are selected, cloned and further screened for desirable characteristics, including robust growth, high antibody production and desirable antibody characteristics, as discussed further below. Hybridomas can be expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, the immunized animal is a non-human animal that expresses human immunoglobulin genes and the splenic B cells are fused to a myeloma cell line from the same species as the non-human animal. In a more preferred embodiment, the immunized animal is a XENOMOUSE® transgenic mouse that makes human antibodies and the myeloma cell line is a non-secretory mouse myeloma. In an even more preferred embodiment, the myeloma cell line is P3-X63-AG8-653. See, e.g., Example I.

Thus, in one embodiment, the invention provides methods of producing a cell line that produces a human monoclonal antibody or a fragment thereof directed to M-CSF comprising (a) immunizing a non-human transgenic animal described herein with M-CSF, a portion of M-CSF or a cell or tissue expressing M-CSF; (b) allowing the transgenic animal to mount an immune response to M-CSF; (c) isolating B lymphocytes from a transgenic animal; (d) immortalizing the B lymphocytes; (e) creating individual monoclonal populations of the immortalized B lymphocytes; and (f) screening the immortalized B lymphocytes to identify an antibody directed to M-CSF.

In another aspect, the invention provides hybridomas that produce an human anti-M-CSF antibody. In a preferred embodiment, the hybridomas are mouse hybridomas, as described above. In other embodiments, the hybridomas are produced in a non-human, non-mouse species such as rats, sheep, pigs, goats, cattle or horses. In another embodiment, the hybridomas are human hybridomas.

In another preferred embodiment, a transgenic animal is immunized with M-CSF, primary cells, e.g., spleen or peripheral blood cells, are isolated from an immunized transgenic animal and individual cells producing antibodies specific for the desired antigen are identified. Polyadenylated mRNA from each individual cell is isolated and reverse transcription polymerase chain reaction (RT-PCR) is performed using sense primers that anneal to variable region sequences, e.g., degenerate primers that recognize most or all of the FR1 regions of human heavy and light chain variable region genes and antisense primers that anneal to constant or joining region sequences. cDNAs of the heavy and light chain variable regions are then cloned and expressed in any suitable host cell, e.g., a myeloma cell, as chimeric antibodies with respective immunoglobulin constant regions, such as the heavy chain and κ or λ, constant domains. See Babcook, J. S. et al., *Proc. Natl. Acad. Sci. USA* 93:7843-48, 1996, herein incorporated by reference. Anti M-CSF antibodies may then be identified and isolated as described herein.

In another embodiment, phage display techniques can be used to provide libraries containing a repertoire of antibodies with varying affinities for M-CSF. For production of such repertoires, it is unnecessary to immortalize the B cells from the immunized animal. Rather, the primary B cells can be used directly as a source of DNA. The mixture of cDNAs obtained from B cell, e.g., derived from spleens, is used to prepare an expression library, for example, a phage display library transfected into E. coli. The resulting cells are tested for immunoreactivity to M-CSF. Techniques for the identification of high affinity human antibodies from such libraries are described by Griffiths et al., EMBO J., 13:3245-3260 (1994); Nissim et al., ibid, pp. 692-698 and by Griffiths et al., ibid, 12:725-734. Ultimately, clones from the library are identified which produce binding affinities of a desired magnitude for the antigen and the DNA encoding the product responsible for such binding is recovered and manipulated for standard recombinant expression. Phage display libraries may also be constructed using previously manipulated nucleotide sequences and screened in a similar fashion. In general, the cDNAs encoding heavy and light chains are independently supplied or linked to form Fv analogs for production in the phage library.

The phage library is then screened for the antibodies with the highest affinities for M-CSF and the genetic material recovered from the appropriate clone. Further rounds of screening can increase affinity of the original antibody isolated.

In another aspect, the invention provides hybridomas that produce an human anti-M-CSF antibody. In a preferred embodiment, the hybridomas are mouse hybridomas, as described above. In other embodiments, the hybridomas are produced in a non-human, non-mouse species such as rats, sheep, pigs, goats, cattle or horses. In another embodiment, the hybridomas are human hybridomas.

Nucleic Acids, Vectors, Host Cells, and Recombinant Methods of Making Antibodies Nucleic Acids The present invention also encompasses nucleic acid molecules encoding anti-M-CSF antibodies. In some embodiments, different nucleic acid molecules encode a heavy chain and a light chain of an anti-M-CSF immunoglobulin. In other embodiments, the same nucleic acid molecule encodes a heavy chain an a light chain of an anti-M-CSF immunoglobulin. In one embodiment, the nucleic acid encodes a M-CSF antibody of the invention.

In some embodiments, the nucleic acid molecule encoding the variable domain of the light chain comprises a human $V_\kappa L5$, O12, L2, B3, A27 gene and a Jκ1, Jκ2, Jκ3, or Jκ4 gene.

In some embodiments, the nucleic acid molecule encoding the light chain, encodes an amino acid sequence comprising 1, 2, 3, 4, 5, 6, 7, 8, 9, or 10 mutations from the germline amino acid sequence. In some embodiments, the nucleic acid molecule comprises a nucleotide sequence that encodes a $V_L$ amino acid sequence comprising 1, 2, 3, 4, 5, 6, 7, 8, 9, or 10 non-conservative amino acid substitutions and/or 1, 2, or 3 non-conservative substitutions compared to germline sequence. Substitutions may be in the CDR regions, the framework regions, or in the constant domain.

In some embodiments, the nucleic acid molecule encodes a $V_L$ amino acid sequence comprising one or more variants compared to germline sequence that are identical to the variations found in the $V_L$ of one of the antibodies 252, 88, 100, 3.8.3, 2.7.3, 1.120.1, 9.14.4I, 8.10.3F, 9.7.2IF, 9.14.4, 8.10.3, 9.7.2, 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4, 8.10.3FG1 or 9.14.4G1.

In some embodiments, the nucleic acid molecule encodes at least three amino acid mutations compared to the germline sequence found in the $V_L$ of one of the antibodies 252, 88, 100, 3.8.3, 2.7.3, 1.120.1, 9.14.4, 8.10.3, or 9.7.2.

In some embodiments, the nucleic acid molecule comprises a nucleotide sequence that encodes the $V_L$ amino acid sequence of monoclonal antibody 252 (SEQ ID NO: 4), 88 (SEQ ID NO: 8), 100 (SEQ ID NO: 12), 3.8.3 (SEQ ID NO: 16), 2.7.3 (SEQ ID NO: 20), 1.120.1 (SEQ ID NO: 24), 9.14.4I (SEQ ID NO: 28), 8.10.3F (SEQ ID NO: 32), 9.7.2IF (SEQ ID NO: 36), 9.14.4 (SEQ ID NO: 28), 8.10.3 (SEQ ID NO: 44), 9.7.2 (SEQ ID NO: 48), 9.7.2C-Ser (SEQ ID NO: 52), 9.14.4C-Ser (SEQ ID NO: 56), 8.10.3C-Ser (SEQ ID NO: 60), 8.10.3-CG2 (SEQ ID NO: 60), 9.7.2-CG2 (SEQ ID NO: 52), 9.7.2-CG4 (SEQ ID NO: 52), 9.14.4-CG2 (SEQ ID NO: 56), 9.14.4-CG4 (SEQ ID NO: 56), 9.14.4-Ser (SEQ ID NO: 28), 9.7.2-Ser (SEQ ID NO: 48), 8.10.3-Ser (SEQ ID NO: 44), 8.10.3-CG4 (SEQ ID NO: 60) 8.10.3FG1 (SEQ ID NO: 32) or 9.14.4G1 (SEQ ID NO: 28), or a portion thereof. In some embodiments, said portion comprises at least the CDR2 region. In some embodiments, the nucleic acid encodes the amino acid sequence of the light chain CDRs of said antibody. In some embodiments, said portion is a contiguous portion comprising CDR1-CDR3.

In some embodiments, the nucleic acid molecule comprises a nucleotide sequence that encodes the light chain amino acid sequence of one of SEQ ID NOS: 4, 8, 12, 16, 20, 24, 28, 32, 36, 44, 48, 52, 56 or 60. In some preferred embodiments, the nucleic acid molecule comprises the light chain nucleotide sequence of SEQ ID NOS: 3, 7, 11, 27, 31, 35, 43 or 47, or a portion thereof.

Figure 1B:
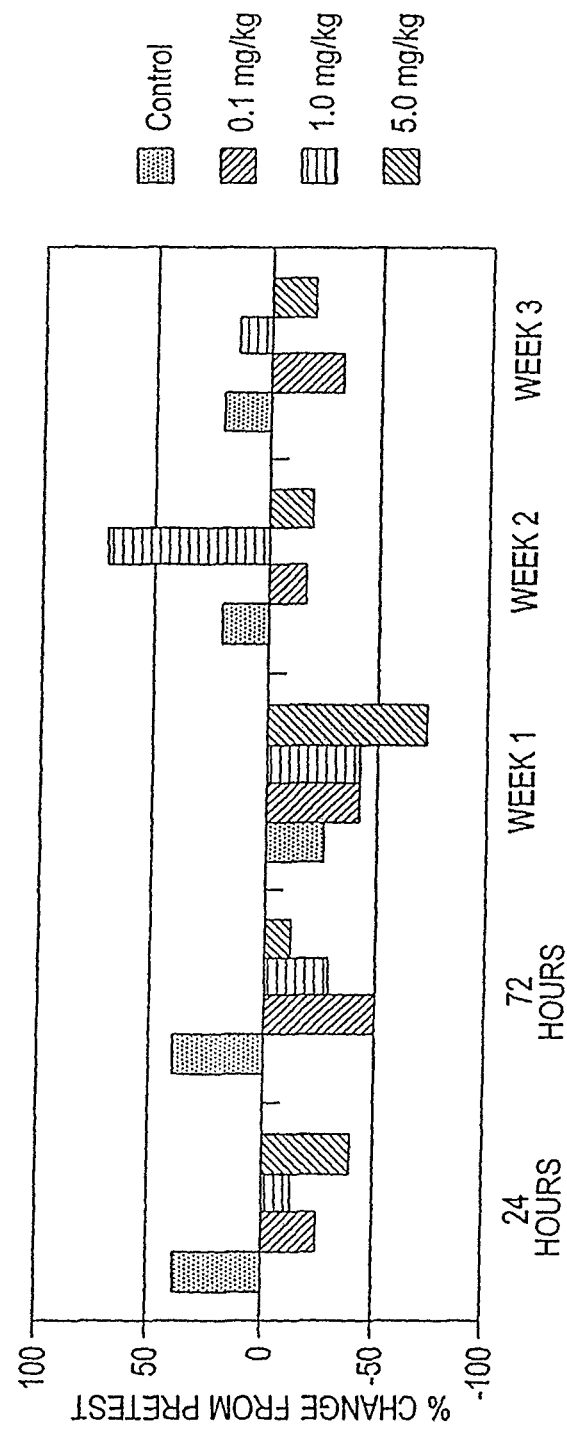

In some embodiments, the nucleic acid molecule encodes a $V_L$ amino acid sequence that is at least 70%, 75%, 80%, 85%, 90%, 95%, 97%, 98% or 99% identical to a $V_L$ amino acid sequence shown in FIG. 1 or to a $V_L$ amino acid sequences of any one of antibodies 252, 88, 100, 3.8.3, 2.7.3, 1.120.1, 9.14.4I, 8.10.3F, 9.7.2IF, 9.14.4, 8.10.3, 9.7.2, 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4, 8.10.3FG1 or 9.14.4G1, or an amino acid sequence of any one of SEQ ID NOS: 4, 8, 12, 16, 20, 24, 28, 32, 36, 44, 48, 52, 56 or 60. Nucleic acid molecules of the invention include nucleic acids that hybridize under highly stringent conditions, such as those described above, to a nucleic acid sequence encoding the light chain amino acid sequence of SEQ ID NOS: 4, 8, 12, 16, 20, 24, 28, 32, 36, 44, 48, 52, 56 or 60, or that has the light chain nucleotide sequence of SEQ ID NOS: 3, 7, 11, 27, 31, 35, 43 or 47.

In another embodiment, the nucleic acid encodes a full-length light chain of an antibody selected from 252, 88, 100, 3.8.3, 2.7.3, 1.120.1, 9.14.4I, 8.10.3F, 9.7.2IF, 9.14.4, 8.10.3, 9.7.2, 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4, 8.10.3FG1 or 9.14.4G1, or a light chain comprising the amino acid sequence of SEQ ID NOS: 4, 8, 12, 16, 20, 24, 28, 32, 36, 44, 48, 52, 56 or 60 and a constant region of a light chain, or a light chain comprising a mutation. Further, the nucleic acid may comprise the light chain nucleotide sequence of SEQ ID NOS: 3, 7, 11, 27, 31, 35, 43 or 47 and the nucleotide sequence encoding a constant region of a light chain, or a nucleic acid molecule encoding a light chain comprise a mutation.

In another preferred embodiment, the nucleic acid molecule encodes the variable domain of the heavy chain ($V_H$) that comprises a human $V_H$ 1-18, 3-33, 3-11, 3-23, 3-48, or 3-7 gene sequence or a sequence derived therefrom. In various embodiments, the nucleic acid molecule comprises a human $V_H$ 1-18 gene, a $D_H$4-23 gene and a human $J_H$4 gene; a human $V_H$ 3-33 gene, a human $D_H$1-26 gene and a human $J_H$4 gene; a human $V_H$ 3-11 gene, a human $D_H$7-27 gene and a human $J_H$4 gene; a human $V_H$3-11 gene, a human $D_H$7-27 gene and a human $J_H$6 gene; a human $V_H$3-23 gene, a human $D_H$1-26 gene and a human $J_H$4 gene; a human $V_H$ 3-7 gene, a human $D_H$6-13 gene and a human $J_H$4 gene; a human $V_H$3-11 gene, a human $D_H$7-27 gene, and a human $J_H$4b gene; a human $V_H$3-48 gene, a human $D_H$1-26 gene, and a human $J_H$4b gene; a human $V_H$3-11 gene, a human $D_H$6-13 gene, and a human $J_H$6b gene, or a sequence derived from the human genes.

In some embodiments, the nucleic acid molecule encodes an amino acid sequence comprising 1, 2, 3, 4, 5, 6, 7, 8, 9, 10, 11, 12, 13, 14, 15, 16, 17 or 18 mutations compared to the germline amino acid sequence of the human V, D or J genes. In some embodiments, said mutations are in the $V_H$ region. In some embodiments, said mutations are in the CDR regions.

In some embodiments, the nucleic acid molecule encodes one or more amino acid mutations compared to the germline sequence that are identical to amino acid mutations found in the $V_H$ of monoclonal antibody 252, 88, 100, 3.8.3, 2.7.3, 1.120.1, 9.14.4I, 8.10.3F, 9.7.2IF, 9.14.4, 8.10.3, 9.7.2, 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4, 8.10.3FG1 or 9.14.4G1. In some embodiments, the nucleic acid encodes at least three amino acid mutations compared to the germline sequences that are identical to at least three amino acid mutations found in one of the above-listed monoclonal antibodies.

In some embodiments, the nucleic acid molecule comprises a nucleotide sequence that encodes at least a portion of the $V_H$ amino acid sequence of antibody 252 (SEQ ID NO: 2), 88 (SEQ ID NO: 6), 100 (SEQ ID NO: 10), 3.8.3 (SEQ ID NO: 14), 2.7.3 (SEQ ID NO: 18), 1.120.1 (SEQ ID NO: 22), 9.14.4I (SEQ ID NO: 26), 8.10.3F (SEQ ID NO: 30), 9.7.2IF (SEQ ID NO: 34), 9.14.4 (SEQ ID NO: 38), 8.10.3 (SEQ ID NO: 30), 9.7.2 (SEQ ID NO: 46), 9.7.2C-Ser (SEQ ID NO: 50), 9.14.4C-Ser (SEQ ID NO: 54), 8.10.3C-Ser (SEQ ID NO: 58), 8.10.3-CG2 (SEQ ID NO: 62), 9.7.2-CG2 (SEQ ID NO: 66), 9.7.2-CG4 (SEQ ID NO: 70), 9.14.4-CG2 (SEQ ID NO: 74), 9.14.4-CG4 (SEQ ID NO: 78), 9.14.4-Ser (SEQ ID NO: 82), 9.7.2-Ser (SEQ ID NO: 86), 8.10.3-Ser (SEQ ID NO: 90), 8.10.3-CG4 (SEQ ID NO: 94), 8.10.3FG1 (SEQ ID NO: 98) or 9.14.4-G1 (SEQ ID NO: 102), or said sequence having conservative amino acid mutations and/or a total of three or fewer non-conservative amino acid substitutions. In various embodiments the sequence encodes one or more CDR regions, preferably a CDR3 region, all three CDR regions, a contiguous portion including CDR1-CDR3, or the entire $V_H$ region.

In some embodiments, the nucleic acid molecule comprises a heavy chain nucleotide sequence that encodes the amino acid sequence of one of SEQ ID NOS: 2, 6, 10, 14, 18, 22, 26, 30, 34, 38, 46, 50, 54, 58, 62, 66, 70, 74, 78, 82, 86, 90, 94, 98 or 102. In some preferred embodiments, the nucleic acid molecule comprises at least a portion of the heavy chain nucleotide sequence of SEQ ID NO: 1, 5, 9, 25, 29, 33, 37, 45, 97 or 101. In some embodiments, said portion encodes the $V_H$ region, a CDR3 region, all three CDR regions, or a contiguous region including CDR1-CDR3.

In some embodiments, the nucleic acid molecule encodes a $V_H$ amino acid sequence that is at least 70%, 75%, 80%, 85%, 90%, 95%, 97%, 98% or 99% identical to the $V_H$ amino acid sequences shown in FIGS. 4A-4ZZ or to a $V_H$ amino acid sequence of any one of SEQ ID NOS: 2, 6, 10, 14, 18, 22, 26, 30, 34, 38, 46, 50, 54, 58, 62, 66, 70, 74, 78, 82, 86, 90, 94, 98 or 102. Nucleic acid molecules of the invention include nucleic acids that hybridize under highly stringent conditions, such as those described above, to a nucleotide sequence encoding the heavy chain amino acid sequence of SEQ ID NOS: 2, 6, 10, 14, 18, 22, 26, 30, 34, 38, 46, 50, 54, 58, 62, 66, 70, 74, 78, 82, 86, 90, 94, 98 or 102 or that has the nucleotide sequence of SEQ ID NOS: 1, 5, 9, 25, 29, 33, 37, 45, 97 or 101.

In another embodiment, the nucleic acid encodes a full-length heavy chain of an antibody selected from 252, 88, 100, 3.8.3, 2.7.3, 1.120.1, 9.14.4I, 8.10.3F, 9.7.2IF, 9.14.4, 8.10.3, 9.7.2, 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4, 8.10.3FG1 or 9.14.4G1, or a heavy chain having the amino acid sequence of SEQ ID NOS: 2, 6, 10, 14, 18, 22, 26, 30, 34, 38, 46, 50, 54, 58, 62, 66, 70, 74, 78, 82, 86, 90, 94, 98 or 102 and a constant region of a heavy chain, or a heavy chain comprising a mutation. Further, the nucleic acid may comprise the heavy chain nucleotide sequence of SEQ ID NOS: 1, 5, 9, 25, 29, 33, 37, 45, 97 or 101 and a nucleotide sequence encoding a constant region of a light chain, or a nucleic acid molecule encoding a heavy chain comprising a mutation.

A nucleic acid molecule encoding the heavy or entire light chain of an anti-M-CSF antibody or portions thereof can be isolated from any source that produces such antibody. In various embodiments, the nucleic acid molecules are isolated from a B cell isolated from an animal immunized with M-CSF or from an immortalized cell derived from such a B cell that expresses an anti-M-CSF antibody. Methods of isolating mRNA encoding an antibody are well-known in the art. See, e.g., Sambrook et al. The mRNA may be used to produce cDNA for use in the polymerase chain reaction (PCR) or cDNA cloning of antibody genes. In a preferred embodiment, the nucleic acid molecule is isolated from a hybridoma that has as one of its fusion partners a human immunoglobulin-producing cell from a non-human transgenic animal. In an even more preferred embodiment, the human immunoglobulin producing cell is isolated from a XENOMOUSE® transgenic mouse that makes human antibodies. In another embodiment, the human immunoglobulin-producing cell is from a non-human, non-mouse transgenic animal, as described above. In another embodiment, the nucleic acid is isolated from a non-human, non-transgenic animal. The nucleic acid molecules isolated from a non-human, non-transgenic animal may be used, e.g., for humanized antibodies.

In some embodiments, a nucleic acid encoding a heavy chain of an anti-M-CSF antibody of the invention can comprise a nucleotide sequence encoding a $V_H$ domain of the invention joined in-frame to a nucleotide sequence encoding a heavy chain constant domain from any source. Similarly, a nucleic acid molecule encoding a light chain of an anti-M-CSF antibody of the invention can comprise a nucleotide sequence encoding a $V_L$ domain of the invention joined in-frame to a nucleotide sequence encoding a light chain constant domain from any source.

In a further aspect of the invention, nucleic acid molecules encoding the variable domain of the heavy ($V_H$) and light ($V_L$) chains are "converted" to full-length antibody genes. In one embodiment, nucleic acid molecules encoding the $V_H$ or $V_L$ domains are converted to full-length antibody genes by insertion into an expression vector already encoding heavy chain constant ($C_H$) or light chain ($C_L$) constant domains, respectively, such that the $V_H$ segment is operatively linked to the $C_H$ segment(s) within the vector, and the $V_L$ segment is operatively linked to the $C_L$ segment within the vector. In another embodiment, nucleic acid molecules encoding the $V_H$ and/or $V_L$ domains are converted into full-length antibody genes by linking, e.g., ligating, a nucleic acid molecule encoding a $V_H$ and/or $V_L$ domains to a nucleic acid molecule encoding a $C_H$ and/or $C_L$ domain using standard molecular biological techniques. Nucleic acid sequences of human heavy and light chain immunoglobulin constant domain genes are known in the art. See, e.g., Kabat et al., *Sequences of Proteins of Immunological Interest*, 5th Ed., NIH Publ. No. 91-3242, 1991. Nucleic acid molecules encoding the full-length heavy and/or light chains may then be expressed from a cell into which they have been introduced and the anti-M-CSF antibody isolated.

The nucleic acid molecules may be used to recombinantly express large quantities of anti-M-CSF antibodies. The nucleic acid molecules also may be used to produce chimeric antibodies, bispecific antibodies, single chain antibodies, immunoadhesins, diabodies, mutated antibodies and antibody derivatives, as described further below. If the nucleic acid molecules are derived from a non-human, non-transgenic animal, the nucleic acid molecules may be used for antibody humanization, also as described below.

In another embodiment, a nucleic acid molecule of the invention is used as a probe or PCR primer for a specific antibody sequence. For instance, the nucleic acid can be used as a probe in diagnostic methods or as a PCR primer to amplify regions of DNA that could be used, inter alia, to isolate additional nucleic acid molecules encoding variable domains of anti-M-CSF antibodies. In some embodiments, the nucleic acid molecules are oligonucleotides. In some embodiments, the oligonucleotides are from highly variable regions of the heavy and light chains of the antibody of interest. In some embodiments, the oligonucleotides encode all or a part of one or more of the CDRs of antibody 252, 88, 100, 3.8.3, 2.7.3, or 1.120.1, or variants thereof described herein.

Vectors

The invention provides vectors comprising nucleic acid molecules that encode the heavy chain of an anti-M-CSF antibody of the invention or an antigen-binding portion thereof. The invention also provides vectors comprising nucleic acid molecules that encode the light chain of such antibodies or antigen-binding portion thereof. The invention further provides vectors comprising nucleic acid molecules encoding fusion proteins, modified antibodies, antibody fragments, and probes thereof.

In some embodiments, the anti-M-CSF antibodies, or antigen-binding portions of the invention are expressed by inserting DNAs encoding partial or full-length light and heavy chains, obtained as described above, into expression vectors such that the genes are operatively linked to necessary expression control sequences such as transcriptional and transnational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The antibody gene is ligated into a vector such that transcriptional and transnational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors. In a preferred embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human $C_H$ or $C_L$ immunoglobulin sequence, with appropriate restriction sites engineered so that any $V_H$ or $V_L$ sequence can easily be inserted and expressed, as described above. In such vectors, splicing usually occurs between the splice donor site in the inserted J region and the splice acceptor site preceding the human C domain, and also at the splice regions that occur within the human $C_H$ exons. Polyadenylation and transcription termination occur at native chromosomal sites downstream of the coding regions. The recombinant expression vector also can encode a signal peptide that facilitates secretion of the antibody chain from a host cell. The antibody chain gene may be cloned into the vector such that the signal peptide is linked in-frame to the amino terminus of the immunoglobulin chain. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. No. 5,168,062, U.S. Pat. No. 4,510,245 and U.S. Pat. No. 4,968,615. Methods for expressing antibodies in plants, including a description of promoters and vectors, as well as transformation of plants is known in the art. See, e.g., U.S. Pat. No. 6,517,529, herein incorporated by reference. Methods of expressing polypeptides in bacterial cells or fungal cells, e.g., yeast cells, are also well known in the art.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification), the neomycin resistance gene (for G418 selection), and the glutamate synthetase gene.

Non-Hybridoma Host Cells and Methods of Recombinantly Producing Protein

Nucleic acid molecules encoding anti-M-CSF antibodies and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455 (which patents are hereby incorporated herein by reference). Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, and a number of other cell lines. Cell lines of particular preference are selected through determining which cell lines have high expression levels. Other cell lines that may be used are insect cell lines, such as Sf9 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Plant host cells include, e.g., *Nicotiana, Arabidopsis*, duckweed, corn, wheat, potato, etc. Bacterial host cells include *E. coli* and *Streptomyces* species. Yeast host cells include *Schizosaccharomyces pombe, Saccharomyces cerevisiae* and *Pichia pastoris*.

Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

It is possible that antibodies expressed by different cell lines or in transgenic animals will have different glycosylation from each other. However, all antibodies encoded by the nucleic acid molecules provided herein, or comprising the amino acid sequences provided herein are part of the instant invention, regardless of the glycosylation state or pattern or modification of the antibodies.

Transgenic Animals and Plants

Anti-M-CSF antibodies of the invention also can be produced transgenically through the generation of a mammal or plant that is transgenic for the immunoglobulin heavy and light chain sequences of interest and production of the antibody in a recoverable form therefrom. In connection with the transgenic production in mammals, anti-M-CSF antibodies can be produced in, and recovered from, the milk of goats, cows, or other mammals. See, e.g., U.S. Pat. Nos. 5,827,690, 5,756,687, 5,750,172, and 5,741,957. In some embodiments, non-human transgenic animals that comprise human immunoglobulin loci are immunized with M-CSF or an immunogenic portion thereof, as described above. Methods for making antibodies in plants, yeast or fungi/algae are described, e.g., in U.S. Pat. No. 6,046,037 and U.S. Pat. No. 5,959,177.

In some embodiments, non-human transgenic animals or plants are produced by introducing one or more nucleic acid molecules encoding an anti-M-CSF antibody of the invention into the animal or plant by standard transgenic techniques. See Hogan and U.S. Pat. No. 6,417,429, supra. The transgenic cells used for making the transgenic animal can be embryonic stem cells or somatic cells. The transgenic non-human organisms can be chimeric, nonchimeric heterozygotes, and nonchimeric homozygotes. See, e.g., Hogan et al., *Manipulating the Mouse Embryo: A Laboratory Manual* 2ed., Cold Spring Harbor Press (1999); Jackson et al., *Mouse Genetics and Transgenics: A Practical Approach*, Oxford University Press (2000); and Pinkert, *Transgenic Animal Technology: A Laboratory Handbook*, Academic Press (1999). In some embodiments, the transgenic non-human animals have a targeted disruption and replacement by a targeting construct that encodes a heavy chain and/or a light chain of interest. In a preferred embodiment, the transgenic animals comprise and express nucleic acid molecules encoding heavy and light chains that specifically bind to M-CSF, preferably human M-CSF. In some embodiments, the transgenic animals comprise nucleic acid molecules encoding a modified antibody such as a single-chain antibody, a chimeric antibody or a humanized antibody. The anti-M-CSF antibodies may be made in any transgenic animal. In a preferred embodiment, the non-human animals are mice, rats, sheep, pigs, goats, cattle or horses. The non-human transgenic animal expresses said encoded polypeptides in blood, milk, urine, saliva, tears, mucus and other bodily fluids.

Phage Display Libraries

The invention provides a method for producing an anti-M-CSF antibody or antigen-binding portion thereof comprising the steps of synthesizing a library of human antibodies on phage, screening the library with M-CSF or a portion thereof, isolating phage that bind M-CSF, and obtaining the antibody from the phage. By way of example, one method for preparing the library of antibodies for use in phage display techniques comprises the steps of immunizing a non-human animal comprising human immunoglobulin loci with M-CSF or an antigenic portion thereof to create an immune response, extracting antibody producing cells from the immunized animal; isolating RNA from the extracted cells, reverse transcribing the RNA to produce cDNA, amplifying the cDNA using a primer, and inserting the cDNA into a phage display vector such that antibodies are expressed on the phage. Recombinant anti-M-CSF antibodies of the invention may be obtained in this way.

Recombinant anti-M-CSF human antibodies of the invention can be isolated by screening a recombinant combinatorial antibody library. Preferably the library is a scFv phage display library, generated using human $V_L$ and $V_H$ cDNAs prepared from mRNA isolated from B cells. Methodologies for preparing and screening such libraries are known in the art. There are commercially available kits for generating phage display libraries (e.g., the Pharmacia Recombinant Phage Antibody System, catalog no. 27-9400-01; and the Stratagene SURFZAP® phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., *Bio/Technology* 9:1370-1372 (1991); Hay et al., *Hum. Antibod. Hybridomas* 3:81-85 (1992); Huse et al., *Science* 246:1275-1281 (1989); McCafferty et al., *Nature* 348:552-554 (1990); Griffiths et al., *EMBO J.* 12:725-734 (1993); Hawkins et al., *J. Mol. Biol.* 226:889-896 (1992); Clackson et al., *Nature* 352:624-628 (1991); Gram et al., *Proc. Natl. Acad. Sci. USA* 89:3576-3580 (1992); Garrad et al., *Bio/Technology* 9:1373-1377 (1991); Hoogenboom et al., *Nuc. Acid Res.* 19:4133-4137 (1991); and Barbas et al., *Proc. Natl. Acad. Sci. USA* 88:7978-7982 (1991).

In one embodiment, to isolate human anti-M-CSF antibodies with the desired characteristics, a human anti-M-CSF antibody as described herein is first used to select human heavy and light chain sequences having similar binding activity toward M-CSF, using the epitope imprinting methods described in PCT Publication No. WO 93/06213. The antibody libraries used in this method are preferably scFv libraries prepared and screened as described in PCT Publication No. WO 92/01047, McCafferty et al., *Nature* 348: 552-554 (1990); and Griffiths et al., *EMBO J.* 12:725-734 (1993). The scFv antibody libraries preferably are screened using human M-CSF as the antigen.

Once initial human $V_L$ and $V_H$ domains are selected, "mix and match" experiments are performed, in which different pairs of the initially selected $V_L$ and $V_H$ segments are screened for M-CSF binding to select preferred $V_L/V_H$ pair combinations. Additionally, to further improve the quality of the antibody, the $V_L$ and $V_H$ segments of the preferred $V_L/V_H$ pair(s) can be randomly mutated, preferably within the CDR3 region of $V_H$ and/or $V_L$, in a process analogous to the in vivo somatic mutation process responsible for affinity maturation of antibodies during a natural immune response. This in vitro affinity maturation can be accomplished by amplifying $V_H$ and $V_L$ domains using PCR primers complimentary to the $V_H$ CDR3 or $V_L$ CDR3, respectively, which primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be re-screened for binding to M-CSF.

Following screening and isolation of an anti-M-CSF antibody of the invention from a recombinant immunoglobulin display library, nucleic acids encoding the selected antibody can be recovered from the display package (e.g., from the phage genome) and subcloned into other expression vectors by standard recombinant DNA techniques. If desired, the nucleic acid can further be manipulated to create other antibody forms of the invention, as described below. To express a recombinant human antibody isolated by screening of a combinatorial library, the DNA encoding the antibody is cloned into a recombinant expression vector and introduced into a mammalian host cells, as described above.

Class Switching

Another aspect of the invention provides a method for converting the class or subclass of an anti-M-CSF antibody to another class or subclass. In some embodiments, a nucleic acid molecule encoding a $V_L$ or $V_H$ that does not include any nucleic acid sequences encoding $C_L$ or $C_H$ is isolated using methods well-known in the art. The nucleic acid molecule then is operatively linked to a nucleic acid sequence encoding a $C_L$ or $C_H$ from a desired immunoglobulin class or subclass. This can be achieved using a vector or nucleic acid molecule that comprises a $C_L$ or $C_H$ chain, as described above. For example, an anti-M-CSF antibody that was originally IgM can be class switched to an IgG. Further, the class switching may be used to convert one IgG subclass to another, e.g., from IgG1 to IgG2. Another method for producing an antibody of the invention comprising a desired isotype comprises the steps of isolating a nucleic acid encoding a heavy chain of an anti-M-CSF antibody and a nucleic acid encoding a light chain of an anti-M-CSF antibody, isolating the sequence encoding the $V_H$ region, ligating the $V_H$ sequence to a sequence encoding a heavy chain constant domain of the desired isotype, expressing the light chain gene and the heavy chain construct in a cell, and collecting the anti-M-CSF antibody with the desired isotype.

In some embodiments, anti-M-CSF antibodies of the invention have the serine at position 228 (according to the EU-numbering convention) of the heavy chain changed to a proline. Accordingly, the CPSC sub-sequence in the $F_C$ region of IgG4 becomes CPPC, which is the sub-sequence in IgG1. (Aalberse, R. C. and Schuurman, J., *Immunology*, 105:9-19 (2002)). For example, the serine at residue 243 SEQ ID NO: 46 (which corresponds to reside 228 in the EU-numbering convention) would become proline. Similarly, the serine at residue 242 of SEQ ID NO: 38 (which corresponds to reside 228 in the EU-numbering convention) would become proline. In some embodiments, the framework region of the IgG4 antibody can be back-mutated to the germline framework sequence. Some embodiments comprise both the back-mutates framework region and the serine to proline change in the $F_C$ region. See, e.g., SEQ ID NO: 54 (antibody 9.14.4C-Ser) and SEQ ID NO: 58 (antibody 8.10.3C-Ser) in Table 1.

Deimmunized Antibodies

Another way of producing antibodies with reduced immunogenicity is the deimmunization of antibodies. In another aspect of the invention, the antibody may be deimmunized using the techniques described in, e.g., PCT Publication Nos. WO98/52976 and WO00/34317 (which incorporated herein by reference in their entirety).

Mutated Antibodies

In another embodiment, the nucleic acid molecules, vectors and host cells may be used to make mutated anti-M-CSF antibodies. The antibodies may be mutated in the variable domains of the heavy and/or light chains, e.g., to alter a binding property of the antibody. For example, a mutation may be made in one or more of the CDR regions to increase or decrease the $K_D$ of the antibody for M-CSF, to increase or decrease $k_{off}$, or to alter the binding specificity of the antibody. Techniques in site-directed mutagenesis are well-known in the art. See, e.g., Sambrook et al. and Ausubel et al., supra. In a preferred embodiment, mutations are made at an amino acid residue that is known to be changed compared to germline in a variable domain of an anti-M-CSF antibody. In another embodiment, one or more mutations are made at an amino acid residue that is known to be changed compared to the germline in a CDR region or framework region of a variable domain, or in a constant domain of a monoclonal antibody 252, 88, 100, 3.8.3, 2.7.3, 1.120.1, 9.14.4I, 8.10.3F, 9.7.2IF, 9.14.4, 8.10.3, 9.7.2, 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4, 8.10.3FG1 or 9.14.4G1. In another embodiment, one or more mutations are made at an amino acid residue that is known to be changed compared to the germline in a CDR region or framework region of a variable domain of a heavy chain amino acid sequence selected from SEQ ID NOS: 2, 6, 10, 14, 18, 22, 26, 30, 34, 38, 46, 50, 54, 58, 62, 66, 70, 74, 78, 82, 86, 90, 94, 98 or 102, or whose heavy chain nucleotide sequence is presented in SEQ ID NOS: 1, 5, 9, 25, 29, 33, 37, 45, 97 or 101. In another embodiment, one or more mutations are made at an amino acid residue that is known to be changed compared to the germline in a CDR region or framework region of a variable domain of a light chain amino acid sequence selected from SEQ ID NOS: 4, 8, 12, 16, 20, 24, 28, 32, 36, 44, 48, 52, 56 or 60, or whose light chain nucleotide sequence is presented in SEQ ID NOS: 3, 7, 11, 27, 31, 35, 43 or 47.

In one embodiment, the framework region is mutated so that the resulting framework region(s) have the amino acid sequence of the corresponding germline gene. A mutation may be made in a framework region or constant domain to increase the half-life of the anti-M-CSF antibody. See, e.g., PCT Publication No. WO 00/09560, herein incorporated by reference. A mutation in a framework region or constant domain also can be made to alter the immunogenicity of the antibody, to provide a site for covalent or non-covalent binding to another molecule, or to alter such properties as complement fixation, FcR binding and antibody-dependent cell-mediated cytotoxicity (ADCC). According to the invention, a single antibody may have mutations in any one or more of the CDRs or framework regions of the variable domain or in the constant domain.

In some embodiments, there are from 1 to 8 including any number in between, amino acid mutations in either the $V_H$ or $V_L$ domains of the mutated anti-M-CSF antibody compared to the anti-M-CSF antibody prior to mutation. In any of the above, the mutations may occur in one or more CDR regions. Further, any of the mutations can be conservative amino acid substitutions. In some embodiments, there are no more than 5, 4, 3, 2, or 1 amino acid changes in the constant domains.

Modified Antibodies

In another embodiment, a fusion antibody or immunoadhesin may be made that comprises all or a portion of an anti-M-CSF antibody of the invention linked to another polypeptide. In a preferred embodiment, only the variable domains of the anti-M-CSF antibody are linked to the polypeptide. In another preferred embodiment, the $V_H$ domain of an anti-M-CSF antibody is linked to a first polypeptide, while the $V_L$ domain of an anti-M-CSF antibody is linked to a second polypeptide that associates with the first polypeptide in a manner such that the $V_H$ and $V_L$ domains can interact with one another to form an antibody binding site. In another preferred embodiment, the $V_H$ domain is separated from the $V_L$ domain by a linker such that the $V_H$ and $V_L$ domains can interact with one another (see below under Single Chain Antibodies). The $V_H$-linker-$V_L$ antibody is then linked to the polypeptide of interest. The fusion antibody is useful for directing a polypeptide to a M-CSF-expressing cell or tissue. The polypeptide may be a therapeutic agent, such as a toxin, growth factor or other regulatory protein, or may be a diagnostic agent, such as an enzyme that may be easily visualized, such as horseradish peroxidase. In addition, fusion antibodies can be created in which two (or more) single-chain antibodies are linked to one another. This is useful if one wants to create a divalent or polyvalent antibody on a single polypeptide chain, or if one wants to create a bispecific antibody.

To create a single chain antibody, (scFv) the $V_H$- and $V_L$-encoding DNA fragments are operatively linked to another fragment encoding a flexible linker, e.g., encoding the amino acid sequence $(Gly_4-Ser)_3$, such that the $V_H$ and $V_L$ sequences can be expressed as a contiguous single-chain protein, with the $V_L$ and $V_H$ domains joined by the flexible linker. See, e.g., Bird et al., Science 242:423-426 (1988); Huston et al., Proc. Natl. Acad. Sci. USA 85:5879-5883 (1988); McCafferty et al., Nature 348:552-554 (1990). The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to M-CSF and to another molecule.

In other embodiments, other modified antibodies may be prepared using anti-M-CSF antibody-encoding nucleic acid molecules. For instance, "Kappa bodies" (Ill et al., Protein Eng. 10: 949-57 (1997)), "Minibodies" (Martin et al., EMBO J. 13: 5303-9 (1994)), "Diabodies" (Holliger et al., Proc. Natl. Acad. Sci. USA 90: 6444-6448 (1993)), or "Janusins" (Traunecker et al., EMBO J. 10:3655-3659 (1991) and Traunecker et al., Int. J. Cancer (Suppl.) 7:51-52 (1992)) may be prepared using standard molecular biological techniques following the teachings of the specification.

Bispecific antibodies or antigen-binding fragments can be produced by a variety of methods including fusion of hybridomas or linking of Fab' fragments. See, e.g., Songsivilai & Lachmann, Clin. Exp. Immunol. 79: 315-321 (1990), Kostelny et al., J. Immunol. 148:1547-1553 (1992). In addition, bispecific antibodies may be formed as "diabodies" or "Janusins." In some embodiments, the bispecific antibody binds to two different epitopes of M-CSF. In some embodiments, the bispecific antibody has a first heavy chain and a first light chain from monoclonal antibody 252, 88, 100, 3.8.3, 2.7.3, 1.120.1, 9.14.4I, 8.10.3F, 9.7.2IF, 9.14.4, 8.10.3, or 9.7.2 and an additional antibody heavy chain and light chain. In some embodiments, the additional light chain and heavy chain also are from one of the above-identified monoclonal antibodies, but are different from the first heavy and light chains.

In some embodiments, the modified antibodies described above are prepared using one or more of the variable domains or CDR regions from a human anti-M-CSF monoclonal antibody provided herein, from an amino acid sequence of said monoclonal antibody, or from a heavy chain or light chain encoded by a nucleic acid sequence encoding said monoclonal antibody.

Derivatized and Labeled Antibodies

An anti-M-CSF antibody or antigen-binding portion of the invention can be derivatized or linked to another molecule (e.g., another peptide or protein). In general, the antibodies or portion thereof is derivatized such that the M-CSF binding is not affected adversely by the derivatization or labeling. Accordingly, the antibodies and antibody portions of the invention are intended to include both intact and modified forms of the human anti-M-CSF antibodies described herein. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detection agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Another type of derivatized antibody is a labeled antibody. Useful detection agents with which an antibody or antigen-binding portion of the invention may be derivatized include fluorescent compounds, including fluorescein, fluorescein isothiocyanate, rhodamine, 5-dimethylamine-1-napthalenesulfonyl chloride, phycoerythrin, lanthanide phosphors and the like. An antibody can also be labeled with enzymes that are useful for detection, such as horseradish peroxidase, β-galactosidase, luciferase, alkaline phosphatase, glucose oxidase and the like. When an antibody is labeled with a detectable enzyme, it is detected by adding additional reagents that the enzyme uses to produce a reaction product that can be discerned. For example, when the agent horseradish peroxidase is present, the addition of hydrogen peroxide and diaminobenzidine leads to a colored reaction product, which is detectable. An antibody can also be labeled with biotin, and detected through indirect measurement of avidin or streptavidin binding. An antibody can also be labeled with a predetermined polypeptide epitope recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

An anti-M-CSF antibody can also be labeled with a radiolabeled amino acid. The radiolabeled anti-M-CSF antibody can be used for both diagnostic and therapeutic purposes. For instance, the radiolabeled anti-M-CSF antibody can be used to detect M-CSF-expressing tumors by x-ray or other diagnostic techniques. Further, the radiolabeled anti-M-CSF antibody can be used therapeutically as a toxin for cancerous cells or tumors. Examples of labels for polypeptides include, but are not limited to, the following radioisotopes or radionuclides—$^{3}$H, $^{14}$C, $^{15}$N, $^{35}$S, $^{90}$Y, $^{99}$Tc, $^{111}$In, $^{125}$I, and $^{131}$I.

An anti-M-CSF antibody can also be derivatized with a chemical group such as polyethylene glycol (PEG), a methyl or ethyl group, or a carbohydrate group. These groups are useful to improve the biological characteristics of the antibody, e.g., to increase serum half-life or to increase tissue binding.

Pharmaceutical Compositions and Kits

The invention also relates to compositions comprising a human anti-M-CSF antagonist antibody for the treatment of subjects in need of treatment for rheumatoid arthritis, osteoporosis, or atherosclerosis. In some embodiments, the subject of treatment is a human. In other embodiments, the subject is a veterinary subject. Hyperproliferative disorders where monocytes play a role that may be treated by an antagonist anti-M-CSF antibody of the invention can involve any tissue or organ and include but are not limited to brain, lung, squamous cell, bladder, gastric, pancreatic, breast, head, neck, liver, renal, ovarian, prostate, colorectal, esophageal, gynecological, nasopharynx, or thyroid cancers, melanomas, lymphomas, leukemias or multiple myelomas. In particular, human antagonist anti-M-CSF antibodies of the invention are useful to treat or prevent carcinomas of the breast, prostate, colon and lung.

This invention also encompasses compositions for the treatment of a condition selected from the group consisting of arthritis, psoriatic arthritis, Reiter's syndrome, gout, traumatic arthritis, rubella arthritis and acute synovitis, rheumatoid arthritis, rheumatoid spondylitis, ankylosing spondylitis, osteoarthritis, gouty arthritis and other arthritic conditions, sepsis, septic shock, endotoxic shock, gram negative sepsis, toxic shock syndrome, Alzheimer's disease, stroke, neurotrauma, asthma, adult respiratory distress syndrome, cerebral malaria, chronic pulmonary inflammatory disease, silicosis, pulmonary sarcoidosis, bone resorption disease, osteoporosis, restenosis, cardiac and renal reperfusion injury, thrombosis, glomerularonephritis, diabetes, graft vs. host reaction, allograft rejection, inflammatory bowel disease, Crohn's disease, ulcerative colitis, multiple sclerosis, muscle degeneration, eczema, contact dermatitis, psoriasis, sunburn, or conjunctivitis shock in a mammal, including a human, comprising an amount of a human anti-M-CSF monoclonal antibody of the invention effective in such treatment and a pharmaceutically acceptable carrier.

Treatment may involve administration of one or more antagonist anti-M-CSF monoclonal antibodies of the invention, or antigen-binding fragments thereof, alone or with a pharmaceutically acceptable carrier. As used herein, "pharmaceutically acceptable carrier" means any and all solvents, dispersion media, coatings, antibacterial and antifungal agents, isotonic and absorption delaying agents, and the like that are physiologically compatible. Some examples of pharmaceutically acceptable carriers are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

Anti-M-CSF antibodies of the invention and compositions comprising them, can be administered in combination with one or more other therapeutic, diagnostic or prophylactic agents. Additional therapeutic agents include other anti-neoplastic, anti-tumor, anti-angiogenic or chemotherapeutic agents. Such additional agents may be included in the same composition or administered separately. In some embodiments, one or more inhibitory anti-M-CSF antibodies of the invention can be used as a vaccine or as adjuvants to a vaccine.

The compositions of this invention may be in a variety of forms, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection. In another embodiment, the invention includes a method of treating a subject in need thereof with an antibody or an antigen-binding portion thereof that specifically binds to M-CSF comprising the steps of: (a) administering an effective amount of an isolated nucleic acid molecule encoding the heavy chain or the antigen-binding portion thereof, an isolated nucleic acid molecule encoding the light chain or the antigen-binding portion thereof, or both the nucleic acid molecules encoding the light chain and the heavy chain or antigen-binding portions thereof; and (b) expressing the nucleic acid molecule.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the anti-M-CSF antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies of the present invention can be administered by a variety of methods known in the art, although for many therapeutic applications, the preferred route/mode of administration is subcutaneous, intramuscular, or intravenous infusion. As will be appreciated by the skilled artisan, the route and/or mode of administration will vary depending upon the desired results.

In certain embodiments, the antibody compositions active compound may be prepared with a carrier that will protect the antibody against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems* (J. R. Robinson, ed., Marcel Dekker, Inc., New York, 1978).

In certain embodiments, an anti-M-CSF antibody of the invention can be orally administered, for example, with an inert diluent or an assimilable edible carrier. The compound (and other ingredients, if desired) can also be enclosed in a hard or soft shell gelatin capsule, compressed into tablets, or incorporated directly into the subject's diet. For oral therapeutic administration, the anti-M-CSF antibodies can be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Additional active compounds also can be incorporated into the compositions. In certain embodiments, an anti-M-CSF antibody of the invention is co-formulated with and/or co-administered with one or more additional therapeutic agents. These agents include antibodies that bind other targets, antineoplastic agents, antitumor agents, chemotherapeutic agents, peptide analogues that inhibit M-CSF, soluble c-fms that can bind M-CSF, one or more chemical agents that inhibit M-CSF, anti-inflammatory agents, anti-coagulants, agents that lower blood pressure (i.e, angiotensin-converting enzyme (ACE) inhibitors). Such combination therapies may require lower dosages of the anti-M-CSF antibody as well as the co-administered agents, thus avoiding possible toxicities or complications associated with the various monotherapies.

Inhibitory anti-M-CSF antibodies of the invention and compositions comprising them also may be administered in combination with other therapeutic regimens, in particular in combination with radiation treatment for cancer. The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, farnesyl transferase inhibitors, VEGF inhibitors, and antimetabolites such as methotrexate.

The compounds of the invention may also be used in combination with antiviral agents such as VIRACEPT® (nelfinavir mesylate), AZT, aciclovir and famciclovir, and antisepsis compounds such as Valant.

The compositions of the invention may include a "therapeutically effective amount" or a "prophylactically effective amount" of an antibody or antigen-binding portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens can be adjusted to provide the optimum desired response (e.g., a therapeutic or prophylactic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier The specification for the dosage unit forms of the invention are dictated by and directly dependent on (a) the unique characteristics of the anti-M-CSF antibody or portion and the particular therapeutic or prophylactic effect to be achieved, and (b) the limitations inherent in the art of compounding such an antibody for the treatment of sensitivity in individuals.

An exemplary, non-limiting range for a therapeutically or prophylactically effective amount of an antibody or antibody portion of the invention is 0.025 to 50 mg/kg, more preferably 0.1 to 50 mg/kg, more preferably 0.1-25, 0.1 to 10 or 0.1 to 3 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Another aspect of the present invention provides kits comprising an anti-M-CSF antibody or antigen-binding portion of the invention or a composition comprising such an antibody or portion. A kit may include, in addition to the antibody or composition, diagnostic or therapeutic agents. A kit also can include instructions for use in a diagnostic or therapeutic method. In a preferred embodiment, the kit includes the antibody or a composition comprising it and a diagnostic agent that can be used in a method described below. In another preferred embodiment, the kit includes the antibody or a composition comprising it and one or more therapeutic agents that can be used in a method described below. One embodiment of the invention is a kit comprising a container, instructions on the administration of an anti-M-CSF antibody to a human suffering from an inflammatory disease, or instructions for measuring the number of CD14+ CD16+ monocytes in a biological sample and an anti-M-CSF antibody.

This invention also relates to compositions for inhibiting abnormal cell growth in a mammal comprising an amount of an antibody of the invention in combination with an amount of a chemotherapeutic agent, wherein the amounts of the compound, salt, solvate, or prodrug, and of the chemotherapeutic agent are together effective in inhibiting abnormal cell growth. Many chemotherapeutic agents are known in the art. In some embodiments, the chemotherapeutic agent is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, e.g. anti-androgens, and anti-angiogenesis agents.

Anti-angiogenic agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with an anti-M-CSF antibody of the invention. Examples of useful COX-II inhibitors include CELEBREX® (celecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP inhibitors are those that do not demonstrate arthralgia. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, RS 13-0830, and the compounds recited in the following list: 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo [3.2.1]octane-3-carboxylic acid hydroxyamide; 3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of said compounds.

A compound comprising a human anti-M-CSF monoclonal antibody of the invention can also be used with signal transduction inhibitors, such as agents that can inhibit EGF-R (epidermal growth factor receptor) responses, such as EGF-R antibodies, EGF antibodies, and molecules that are EGF-R inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN® (trastuzumab) (Genentech, Inc.). EGF-R inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated), ABX-EGF (Abgenix/Cell Genesys), EMD-7200 (Merck KgaA), EMD-5590 (Merck KgaA), MDX-447/H-477 (Medarex Inc. and Merck KgaA), and the compounds ZD-1834, ZD-1838 and ZD-1839 (AstraZeneca), PKI-166 (Novartis), PKI-166/CGP-75166 (Novartis), PTK 787 (Novartis), CP 701 (Cephalon), leflunomide (Pharmacia/Sugen), CI-1033 (Warner Lambert Parke Davis), CI-1033/PD 183, 805 (Warner Lambert Parke Davis), CL-387,785 (Wyeth-Ayerst), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co.), VRCTC-310 (Ventech Research), EGF fusion toxin (Seragen Inc.), DAB-389 (Seragen/Lilgand), ZM-252808 (Imperial Cancer Research Fund), RG-50864 (INSERM), LFM-A12 (Parker Hughes Cancer Center), WHI-P97 (Parker Hughes Cancer Center), GW-282974 (Glaxo), KT-8391 (Kyowa Hakko) and EGF-R Vaccine (York Medical/Centro de Immunologia Molecular (CIM)). These and other EGF-R-inhibiting agents can be used in the present invention.

VEGF inhibitors, for example SU-5416 and SU-6668 (Sugen Inc.), AVASTIN® (bevacizumab) (Genentech), SH-268 (Schering), and NX-1838 (NeXstar) can also be combined with the compound of the present invention. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc.); anti-VEGF monoclonal antibody of Genentech, Inc.; and angiozyme, a synthetic ribozyme from Ribozyme and Chiron. These and other VEGF inhibitors can be used in the present invention as described herein. ErbB2 receptor inhibitors, such as GW-282974 (Glaxo Wellcome plc), and the monoclonal antibodies AR-209 (Aronex Pharmaceuticals Inc.) and 2B-1 (Chiron), can furthermore be combined with the compound of the invention, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Pat. No. 6,465,449 (issued Oct. 15, 2002), and in U.S. Pat. No. 6,284,764 (issued Sep. 4, 2001), both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with the compound of the present invention in accordance with the present invention.

Anti-survival agents include anti-IGF-IR antibodies and anti-integrin agents, such as anti-integrin antibodies.

Anti-inflammatory agents can be used in conjunction with an anti-M-CSF antibody of the invention. For the treatment of rheumatoid arthritis, the human anti-M-CSF antibodies of the invention may be combined with agents such as TNF-α inhibitors such as TNF drugs (such as REMICADE® (infliximab), CDP-870 and HUMIRA® (adalimumab)) and TNF receptor immunoglobulin molecules (such as ENBREL® (etanercept)), IL-1 inhibitors, receptor antagonists or soluble IL-1ra (e.g. KINERET® (anakinra) or ICE inhibitors), COX-2 inhibitors (such as celecoxib, rofecoxib, valdecoxib and etoricoxib), metalloprotease inhibitors (preferably MMP-13 selective inhibitors), p2X7 inhibitors, α2δ ligands (such as NEUROTIN® (gabapentin) and LYRICA® (pregabalin), low dose methotrexate, leflunomide, hydroxychloroquine, d-penicillamine, auranofin or parenteral or oral gold. The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc.

Anti-coagulant agents can be used in conjunction with an anti-M-CSF antibody of the invention. Examples of anti-coagulant agents include, but are not limited to, COUMADIN® (warfarin sodium), heparin, and LOVENOX® (enoxaparin sodium).

The human anti-M-CSF antibodies of the present invention may also be used in combination with cardiovascular agents such as calcium channel blockers, lipid lowering agents such as statins, fibrates, beta-blockers, Ace inhibitors, Angiotensin-2 receptor antagonists and platelet aggregation inhibitors. The compounds of the present invention may also be used in combination with CNS agents such as antidepressants (such as sertraline), anti-Parkinsonian drugs (such as deprenyl, L-dopa, REQUIP® (ropinirole HCl), MIRAPEX® (pramipexole dihydrochloride), MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, α2δ LIGANDS (such as NEUROTIN® (gabapentin) and LYRICA® (pregabalin)) inhibitors, COX-2 inhibitors, propentofylline or metryfonate.

The human anti-M-CSF antibodies of the present invention may also be used in combination with osteoporosis agents such as roloxifene, droloxifene, lasofoxifene or fosomax and immunosuppressant agents such as FK-506 and rapamycin.

Diagnostic Methods of Use

In another aspect, the invention provides diagnostic methods. The anti-M-CSF antibodies can be used to detect M-CSF in a biological sample in vitro or in vivo. In one embodiment, the invention provides a method for diagnosing the presence or location of a M-CSF-expressing tumor in a subject in need thereof, comprising the steps of injecting the antibody into the subject, determining the expression of M-CSF in the subject by localizing where the antibody has bound, comparing the expression in the subject with that of a normal reference subject or standard, and diagnosing the presence or location of the tumor.

The anti-M-CSF antibodies can be used in a conventional immunoassay, including, without limitation, an ELISA, an RIA, FACS, tissue immunohistochemistry, Western blot or immunoprecipitation. The anti-M-CSF antibodies of the invention can be used to detect M-CSF from humans. In another embodiment, the anti-M-CSF antibodies can be used to detect M-CSF from primates such as cynomologus monkey, rhesus monkeys, chimpanzees or apes. The invention provides a method for detecting M-CSF in a biological sample comprising contacting a biological sample with an anti-M-CSF antibody of the invention and detecting the bound antibody. In one embodiment, the anti-M-CSF antibody is directly labeled with a detectable label. In another embodiment, the anti-M-CSF antibody (the first antibody) is unlabeled and a second antibody or other molecule that can bind the anti-M-CSF antibody is labeled. As is well known to one of skill in the art, a second antibody is chosen that is able to specifically bind the particular species and class of the first antibody. For example, if the anti-M-CSF antibody is a human IgG, then the secondary antibody could be an anti-human-IgG. Other molecules that can bind to antibodies include, without limitation, Protein A and Protein G, both of which are available commercially, e.g., from Pierce Chemical Co.

Suitable labels for the antibody or secondary antibody have been disclosed supra, and include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{135}$S or $^{3}$H.

In other embodiments, M-CSF can be assayed in a biological sample by a competition immunoassay utilizing M-CSF standards labeled with a detectable substance and an unlabeled anti-M-CSF antibody. In this assay, the biological sample, the labeled M-CSF standards and the anti-M-CSF antibody are combined and the amount of labeled M-CSF standard bound to the unlabeled antibody is determined. The amount of M-CSF in the biological sample is inversely proportional to the amount of labeled M-CSF standard bound to the anti-M-CSF antibody.

One can use the immunoassays disclosed above for a number of purposes. For example, the anti-M-CSF antibodies can be used to detect M-CSF in cells or on the surface of cells in cell culture, or secreted into the tissue culture medium. The anti-M-CSF antibodies can be used to determine the amount of M-CSF on the surface of cells or secreted into the tissue culture medium that have been treated with various compounds. This method can be used to identify compounds that are useful to inhibit or activate M-CSF expression or secretion. According to this method, one sample of cells is treated with a test compound for a period of time while another sample is left untreated. If the total level of M-CSF is to be measured, the cells are lysed and the total M-CSF level is measured using one of the immunoassays described above. The total level of M-CSF in the treated versus the untreated cells is compared to determine the effect of the test compound.

An immunoassay for measuring total M-CSF levels is an ELISA or Western blot. If the cell surface level of M-CSF is to be measured, the cells are not lysed, and the M-CSF cell surface levels can be measured using one of the immunoassays described above. An immunoassay for determining cell surface levels of M-CSF can include the steps of labeling the cell surface proteins with a detectable label, such as biotin or $^{125}$I, immunoprecipitating the M-CSF with an anti-M-CSF antibody and then detecting the labeled M-CSF. Another immunoassay for determining the localization of M-CSF, e.g., cell surface levels, can be immunohistochemistry. Methods such as ELISA, RIA, Western blot, immunohistochemistry, cell surface labeling of integral membrane proteins and immunoprecipitation are well known in the art. See, e.g., Harlow and Lane, supra. In addition, the immunoassays can be scaled up for high throughput screening in order to test a large number of compounds for inhibition or activation of M-CSF.

Another example of an immunoassay for measuring secreted M-CSF levels can be an antigen capture assay, ELISA, immunohistochemistry assay, Western blot and the like using antibodies of the invention. If secreted M-CSF is to be measured, cell culture media or body fluid, such as blood serum, urine, or synovial fluid, can be assayed for secreted M-CSF and/or cells can be lysed to release produced, but not yet secreted M-CSF. An immunoassay for determining secreted levels of M-CSF includes the steps of labeling the secreted proteins with a detectable label, such as biotin or $^{125}$I, immunoprecipitating the M-CSF with an anti-M-CSF antibody and then detecting the labeled M-CSF. Another immunoassay for determining secreted levels of M-CSF can include the steps of (a) pre-binding anti-M-CSF antibodies to the surface of a microtiter plate; (b) adding tissue culture cell media or body fluid containing the secreted M-CSF to the wells of the microtiter plate to bind to the anti-M-CSF antibodies; (c) adding an antibody that will detect the anti-M-CSF antibody, e.g., anti-M-CSF labeled with digoxigenin that binds to an epitope of M-CSF different from the anti-M-CSF antibody of step (a); (d) adding an antibody to digoxigenin conjugated to peroxidase; and (e) adding a peroxidase substrate that will yield a colored reaction product that can be quantitated to determine the level of secreted M-CSF in tissue culture cell media or a body fluid sample. Methods such as ELISA, RIA, Western blot, immunohistochemistry, and antigen capture assay are well known in the art. See, e.g., Harlow and Lane, supra. In addition, the immunoassays can be scaled up for high throughput screening in order to test a large number of compounds for inhibition or activation of M-CSF.

The anti-M-CSF antibodies of the invention can also be used to determine the levels of cell surface M-CSF in a tissue or in cells derived from the tissue. In some embodiments, the tissue is from a diseased tissue. In some embodiments, the tissue can be a tumor or a biopsy thereof. In some embodiments of the method, a tissue or a biopsy thereof can be excised from a patient. The tissue or biopsy can then be used in an immunoassay to determine, e.g., total M-CSF levels, cell surface levels of M-CSF, or localization of M-CSF by the methods discussed above.

The method can comprise the steps of administering a detectably labeled anti-M-CSF antibody or a composition comprising them to a patient in need of such a diagnostic test and subjecting the patient to imaging analysis to determine the location of the M-CSF-expressing tissues. Imaging analysis is well known in the medical art, and includes, without limitation, x-ray analysis, magnetic resonance imaging (MRI) or computed tomography (CE). The antibody can be labeled with any agent suitable for in vivo imaging, for example a contrast agent, such as barium, which can be used for x-ray analysis, or a magnetic contrast agent, such as a gadolinium chelate, which can be used for MRI or CE. Other labeling agents include, without limitation, radioisotopes, such as $^{99}$Tc. In another embodiment, the anti-M-CSF antibody will be unlabeled and will be imaged by administering a second antibody or other molecule that is detectable and that can bind the anti-M-CSF antibody. In an embodiment, a biopsy is obtained from the patient to determine whether the tissue of interest expresses M-CSF.

The anti-M-CSF antibodies of the invention can also be used to determine the secreted levels of M-CSF in a body fluid such as blood serum, urine, or synovial fluid derived from a tissue. In some embodiments, the body fluid is from a diseased tissue. In some embodiments, the body fluid is from a tumor or a biopsy thereof. In some embodiments of the method, body fluid is removed from a patient. The body fluid is then used in an immunoassay to determine secreted M-CSF levels by the methods discussed above. One embodiment of the invention is a method of assaying for the activity of a M-CSF antagonist comprising: administering a M-CSF antagonist to a primate or human subject and measuring the number of CD14+CD16+ monocytes in a biological sample.

Therapeutic Methods of Use

In another embodiment, the invention provides a method for inhibiting M-CSF activity by administering an anti-M-CSF antibody to a patient in need thereof. Any of the types of antibodies described herein may be used therapeutically. In a preferred embodiment, the anti-M-CSF antibody is a human, chimeric or humanized antibody. In another preferred embodiment, the M-CSF is human and the patient is a human patient. Alternatively, the patient may be a mammal that expresses a M-CSF that the anti-M-CSF antibody cross-reacts with. The antibody may be administered to a non-human mammal expressing a M-CSF with which the antibody cross-reacts (i.e. a primate) for veterinary purposes or as an animal model of human disease. Such animal models may be useful for evaluating the therapeutic efficacy of antibodies of this invention.

As used herein, the term "a disorder in which M-CSF activity is detrimental" is intended to include diseases and other disorders in which the presence of high levels of M-CSF in a subject suffering from the disorder has been shown to be or is suspected of being either responsible for the pathophysiology of the disorder or a factor that contributes to a worsening of the disorder. Such disorders may be evidenced, for example, by an increase in the levels of M-CSF secreted and/or on the cell surface or increased tyrosine autophosphorylation of c-fms in the affected cells or tissues of a subject suffering from the disorder. The increase in M-CSF levels may be detected, for example, using an anti-M-CSF antibody as described above.

In one embodiment, an anti-M-CSF antibody may be administered to a patient who has a c-fms-expressing tumor or a tumor that secretes M-CSF and/or that expresses M-CSF on its cell surface. Preferably, the tumor expresses a level of c-fms or M-CSF that is higher than a normal tissue. The tumor may be a solid tumor or may be a non-solid tumor, such as a lymphoma. In a more preferred embodiment, an anti-M-CSF antibody may be administered to a patient who has a c-fms-expressing tumor, a M-CSF-expressing tumor, or a tumor that secretes M-CSF that is cancerous. Further, the tumor may be cancerous. In an even more preferred embodiment, the tumor is a cancer of lung, breast, prostate or colon. In another preferred embodiment, the anti-M-CSF antibody administered to a patient results in M-CSF no longer bound to the c-fms receptor. In a highly preferred embodiment, the method causes the tumor not to increase in weight or volume or to decrease in weight or volume. In another embodiment, the method causes c-fms on tumor cells to not be bound by M-CSF. In another embodiment, the method causes M-CSF on tumor cells to not be bound to c-fms. In another embodiment, the method causes secreted M-CSF of the tumor cells to not be bound to c-fms. In a preferred embodiment, the antibody is selected from 252, 88, 100, 3.8.3, 2.7.3, 1.120.1, 9.14.4I, 8.10.3F, 9.7.2IF, 9.14.4, 8.10.3, 9.7.2, 9.7.2C-Ser, 9.14.4C-Ser, 8.10.3C-Ser, 8.10.3-CG2, 9.7.2-CG2, 9.7.2-CG4, 9.14.4-CG2, 9.14.4-CG4, 9.14.4-Ser, 9.7.2-Ser, 8.10.3-Ser, 8.10.3-CG4, 8.10.3FG1 or 9.14.4G1, or comprises a heavy chain, light chain or antigen binding region thereof.

In another preferred embodiment, an anti-M-CSF antibody may be administered to a patient who expresses inappropriately high levels of M-CSF. It is known in the art that high-level expression of M-CSF can lead to a variety of common cancers. In one embodiment, said method relates to the treatment of cancer such as brain, squamous cell, bladder, gastric, pancreatic, breast, head, neck, esophageal, prostate, colorectal, lung, renal, kidney, ovarian, gynecological or thyroid cancer. Patients that can be treated with a compounds of the invention according to the methods of this invention include, for example, patients that have been diagnosed as having lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors (e.g., sarcomas, carcinomas or lymphomas that are cancers of body tissues other than blood, bone marrow or the lymphatic system), solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas). In a more preferred embodiment, the anti-M-CSF antibody is administered to a patient with breast cancer, prostate cancer, lung cancer or colon cancer. In an even more preferred embodiment, the method causes the cancer to stop proliferating abnormally, or not to increase in weight or volume or to decrease in weight or volume.

The antibody may be administered once, but more preferably is administered multiple times. For example, the antibody may be administered from three times daily to once every six months or longer. The administering may be on a schedule such as three times daily, twice daily, once daily, once every two days, once every three days, once weekly, once every two weeks, once every month, once every two months, once every three months and once every six months. The antibody may also be administered continuously via a minipump. The antibody may be administered via an oral, mucosal, buccal, intranasal, inhalable, intravenous, subcutaneous, intramuscular, parenteral, intratumor or topical route. The antibody may be administered at the site of the tumor or inflamed body part, into the tumor or inflamed body part, or at a site distant from the site of the tumor or inflamed body part. The antibody may be administered once, at least twice or for at least the period of time until the condition is treated, palliated or cured. The antibody generally will be administered for as long as the tumor is present provided that the antibody causes the tumor or cancer to stop growing or to decrease in weight or volume or until the inflamed body part is healed. The antibody will generally be administered as part of a pharmaceutical composition as described supra. The dosage of antibody will generally be in the range of 0.1-100 mg/kg, more preferably 0.5-50 mg/kg, more preferably 1-20 mg/kg, and even more preferably 1-10 mg/kg. The serum concentration of the antibody may be measured by any method known in the art.

In another aspect, the anti-M-CSF antibody may be co-administered with other therapeutic agents, such as anti-inflammatory agents, anti-coagulant agents, agents that will lower or reduce blood pressure, anti-neoplastic drugs or molecules, to a patient who has a hyperproliferative disorder, such as cancer or a tumor. In one aspect, the invention relates to a method for the treatment of the hyperproliferative disorder in a mammal comprising administering to said mammal a therapeutically effective amount of a compound of the invention in combination with an anti-tumor agent selected from the group consisting of, but not limited to, mitotic inhibitors, alkylating agents, anti-metabolites, intercalating agents, growth factor inhibitors, cell cycle inhibitors, enzymes, topoisomerase inhibitors, biological response modifiers, anti-hormones, kinase inhibitors, matrix metalloprotease inhibitors, genetic therapeutics and anti-androgens. In a more preferred embodiment, the antibody may be administered with an antineoplastic agent, such as adriamycin or taxol. In another preferred embodiment, the antibody or combination therapy is administered along with radiotherapy, chemotherapy, photodynamic therapy, surgery or other immunotherapy. In yet another preferred embodiment, the antibody will be administered with another antibody. For example, the anti-M-CSF antibody may be administered with an antibody or other agent that is known to inhibit tumor or cancer cell proliferation, e.g., an antibody or agent that inhibits erbB2 receptor, EGF-R, CD20 or VEGF.

Co-administration of the antibody with an additional therapeutic agent (combination therapy) encompasses administering a pharmaceutical composition comprising the anti-M-CSF antibody and the additional therapeutic agent and administering two or more separate pharmaceutical compositions, one comprising the anti-M-CSF antibody and the other(s) comprising the additional therapeutic agent(s). Further, although co-administration or combination therapy generally means that the antibody and additional therapeutic agents are administered at the same time as one another, it also encompasses instances in which the antibody and additional therapeutic agents are administered at different times. For instance, the antibody may be administered once every three days, while the additional therapeutic agent is administered once daily. Alternatively, the antibody may be administered prior to or subsequent to treatment of the disorder with the additional therapeutic agent. Similarly, administration of the anti-M-CSF antibody may be administered prior to or subsequent to other therapy, such as radiotherapy, chemotherapy, photodynamic therapy, surgery or other immunotherapy The antibody and one or more additional therapeutic agents (the combination therapy) may be administered once, twice or at least the period of time until the condition is treated, palliated or cured. Preferably, the combination therapy is administered multiple times. The combination therapy may be administered from three times daily to once every six months. The administering may be on a schedule such as three times daily, twice daily, once daily, once every two days, once every three days, once weekly, once every two weeks, once every month, once every two months, once every three months and once every six months, or may be administered continuously via a minipump. The combination therapy may be administered via an oral, mucosal, buccal, intranasal, inhalable, intravenous, subcutaneous, intramuscular, parenteral, intratumor or topical route. The combination therapy may be administered at a site distant from the site of the tumor. The combination therapy generally will be administered for as long as the tumor is present provided that the antibody causes the tumor or cancer to stop growing or to decrease in weight or volume.

In a still further embodiment, the anti-M-CSF antibody is labeled with a radiolabel, an immunotoxin or a toxin, or is a fusion protein comprising a toxic peptide. The anti-M-CSF antibody or anti-M-CSF antibody fusion protein directs the radiolabel, immunotoxin, toxin or toxic peptide to the M-CSF-expressing cell. In a preferred embodiment, the radiolabel, immunotoxin, toxin or toxic peptide is internalized after the anti-M-CSF antibody binds to the M-CSF on the surface of the target cell.

In another aspect, the anti-M-CSF antibody may be used to treat noncancerous states in which high levels of M-CSF and/or M-CSF have been associated with the noncancerous state or disease. In one embodiment, the method comprises the step of administering an anti-M-CSF antibody to a patient who has a noncancerous pathological state caused or exacerbated by high levels of M-CSF and/or M-CSF levels or activity. In a more preferred embodiment, the anti-M-CSF antibody slows the progress of the noncancerous pathological state. In a more preferred embodiment, the anti-M-CSF antibody stops or reverses, at least in part, the noncancerous pathological state.

Gene Therapy

The nucleic acid molecules of the instant invention can be administered to a patient in need thereof via gene therapy. The therapy may be either in vivo or ex vivo. In a preferred embodiment, nucleic acid molecules encoding both a heavy chain and a light chain are administered to a patient. In a more preferred embodiment, the nucleic acid molecules are administered such that they are stably integrated into chromosomes of B cells because these cells are specialized for producing antibodies. In a preferred embodiment, precursor B cells are transfected or infected ex vivo and re-transplanted into a patient in need thereof. In another embodiment, precursor B cells or other cells are infected in vivo using a virus known to infect the cell type of interest. Typical vectors used for gene therapy include liposomes, plasmids and viral vectors. Exemplary viral vectors are retroviruses, adenoviruses and adeno-associated viruses. After infection either in vivo or ex vivo, levels of antibody expression can be monitored by taking a sample from the treated patient and using any immunoassay known in the art or discussed herein.

In a preferred embodiment, the gene therapy method comprises the steps of administering an isolated nucleic acid molecule encoding the heavy chain or an antigen-binding portion thereof of an anti-M-CSF antibody and expressing the nucleic acid molecule. In another embodiment, the gene therapy method comprises the steps of administering an isolated nucleic acid molecule encoding the light chain or an antigen-binding portion thereof of an anti-M-CSF antibody and expressing the nucleic acid molecule. In a more preferred method, the gene therapy method comprises the steps of administering of an isolated nucleic acid molecule encoding the heavy chain or an antigen-binding portion thereof and an isolated nucleic acid molecule encoding the light chain or the antigen-binding portion thereof of an anti-M-CSF antibody of the invention and expressing the nucleic acid molecules. The gene therapy method may also comprise the step of administering another anti-cancer agent, such as taxol or adriamycin.

In order that this invention may be better understood, the following examples are set forth. These examples are for purposes of illustration only and are not to be construed as limiting the scope of the invention in any manner.

EXAMPLE I

Generation of Cell Lines Producing Anti-M-CSF Antibody

Antibodies of the invention were prepared, selected, and assayed as follows:

Immunization and Hybridoma Generation

Eight to ten week old XENOMOUSE® transgenic mice that make human antibodies were immunized intraperitoneally or in their hind footpads with human M-CSF (10 µg/dose/mouse). This dose was repeated five to seven times over a three to eight week period. Four days before fusion, the mice were given a final injection of human M-CSF in PBS. The spleen and lymph node lymphocytes from immunized mice were fused with the non-secretory myeloma P3-X63-Ag8.653 cell line, and the fused cells were subjected to HAT selection as previously described (Galfre and Milstein, *Methods Enzymol.* 73:3-46, 1981). A panel of hybridomas all secreting M-CSF specific human IgG2 and IgG4 antibodies was recovered. Antibodies also were generated using XENOMAX® antibody selection technology as described in Babcook, J. S. et al., *Proc. Natl. Acad. Sci. USA* 93:7843-48, 1996. Nine cell lines engineered to produce antibodies of the invention were selected for further study and designated 252, 88, 100, 3.8.3, 2.7.3, 1.120.1, 9.14.4, 8.10.3 and 9.7.2. The hybridomas were deposited under terms in accordance with the Budapest Treaty with the American Type Culture Collection (ATCC), 10801 University Blvd., Manassas, Va. 20110-2209 on Aug. 8, 2003. The hybridomas have been assigned the following accession numbers:

| Hybridoma 3.8.3 (LN 15891) | PTA-5390 |
| Hybridoma 2.7.3 (LN 15892) | PTA-5391 |
| Hybridoma 1.120.1 (LN 15893) | PTA-5392 |
| Hybridoma 9.7.2 (LN 15894) | PTA-5393 |
| Hybridoma 9.14.4 (LN 15895) | PTA-5394 |
| Hybridoma 8.10.3 (LN 15896) | PTA-5395 |
| Hybridoma 88-gamma (UC 25489) | PTA-5396 |
| Hybridoma 88-kappa (UC 25490) | PTA-5397 |
| Hybridoma 100-gamma (UC 25491) | PTA-5398 |
| Hybridoma 100-kappa (UC 25492) | PTA-5399 |
| Hybridoma 252-gamma (UC 25493) | PTA-5400 |
| Hybridoma 252-kappa (UC 25494) | PTA-5401 |

EXAMPLE II

Gene Utilization Analysis

DNA encoding the heavy and light chains of monoclonal antibodies 252, 88, 100, 3.8.3, 2.7.3, 1,120.1, 9.14.4, 8.10.3 and 9.7.2 was cloned from the respective hybridoma cell lines and the DNA sequences were determined by methods known to one skilled in the art. Additionally, DNA from the hybridoma cell lines 9.14.4, 8.10.3 and 9.7.2 was mutated at specific framework regions in the variable domain and/or isotype-switched to obtain, for example, 9.14.4I, 8.10.3F, and 9.7.2IF, respectively. From nucleic acid sequence and predicted amino acid sequence of the antibodies, the identity of the gene usage for each antibody chain was determined ("VBASE"). Table 2 sets forth the gene utilization of selected antibodies in accordance with the invention:

TABLE 2

Heavy and Light Chain Gene Utilization

| | Heavy Chain | | | | Kappa Light Chain | | |
|---|---|---|---|---|---|---|---|
| Clone | SEQ ID NO: $V_H$ | $D_H$ | $J_H$ | | SEQ ID NO: $V_K$ | | $J_K$ |
| 252 | 1, 2 | 3-11 | 7-27 | 6 | 3, 4 | O12 | 3 |
| 88 | 5, 6 | 3-7 | 6-13 | 4 | 7, 8 | O12 | 3 |
| 100 | 9, 10 | 3-23 | 1-26 | 4 | 11, 12 | L2 | 3 |
| 3.8.3 | 14 | 3-11 | 7-27 | 4 | 16 | L5 | 3 |
| 2.7.3 | 18 | 3-33 | 1-26 | 4 | 20 | L5 | 4 |
| 1.120.1 | 22 | 1-18 | 4-23 | 4 | 24 | B3 | 1 |
| 9.14.4I | 25, 26 | 3-11 | 7-27 | 4b | 27, 28 | O12 | 3 |
| 8.10.3F | 29, 30 | 3-48 | 1-26 | 4b | 31, 32 | A27 | 4 |
| 9.7.2IF | 33, 34 | 3-11 | 6-13 | 6b | 35, 36 | O12 | 3 |
| 9.14.4 | 37, 38 | 3-11 | 7-27 | 4b | 27, 28 | O12 | 3 |
| 8.10.3 | 29, 30 | 3-48 | 1-26 | 4b | 43, 44 | A27 | 4 |
| 9.7.2 | 45, 46 | 3-11 | 6-13 | 6b | 47, 48 | O12 | 3 |
| 8.10.3FG1 | 97, 98 | 3-48 | 1-26 | 4b | 31, 32 | A27 | 4 |
| 9.14.4G1 | 101, 102 | 3-11 | 7-27 | 4b | 27, 28 | O12 | 3 |
| 9.14.4C-Ser | 54 | 3-11 | 7-27 | 4b | 56 | O12 | 3 |
| 9.14.4-CG2 | 74 | 3-11 | 7-27 | 4b | 56 | O12 | 3 |
| 9.14.4-CG4 | 78 | 3-11 | 7-27 | 4b | 56 | O12 | 3 |
| 8.10.3C-Ser | 58 | 3-48 | 1-26 | 4b | 60 | A27 | 4 |
| 8.10.3-CG2 | 62 | 3-48 | 1-26 | 4b | 60 | A27 | 4 |
| 8.10.3-CG4 | 94 | 3-48 | 1-26 | 4b | 60 | A27 | 4 |
| 8.10.3-Ser | 90 | 3-48 | 1-26 | 4b | 43, 44 | A27 | 4 |
| 9.7.2C-Ser | 50 | 3-11 | 6-13 | 6b | 52 | O12 | 3 |
| 9.7.2-CG2 | 66 | 3-11 | 6-13 | 6b | 52 | O12 | 3 |
| 9.7.2-CG4 | 70 | 3-11 | 6-13 | 6b | 52 | O12 | 3 |
| 9.7.2-Ser | 86 | 3-11 | 6-13 | 6b | 47, 48 | O12 | 3 |
| 9.14.4-Ser | 82 | 3-11 | 7-27 | 4b | 27, 28 | O12 | 3 |

Mutagenesis of specific residues of the heavy and light chains was carried out by designing primers and using the QuickChange Site Directed Mutagenesis Kit from Stratagene, according to the manufacturer's instructions. Mutations were confirmed by automated sequencing, and mutagenized inserts were subcloned into expression vectors. The expression vectors were transfected into HEK293 cells to produce enough of the antibodies for characterization.

EXAMPLE III

M-CSF Mouse Monocytic Cell Proliferation Assay

In vitro assays were conducted to measure M-CSF-dependent mouse monocytic cell proliferation in the presence of anti-M-CSF antibodies to determine the degree of inhibition by anti-M-CSF antibodies.

Mouse monocytic cells, M-NFS-60 cells, from American Type Culture Collection (ATCC) (Manassas, Va.), were obtained and maintained in RPMI-1640 medium containing 2 mM L-glutamine (ATCC), 10% heat inactivated fetal bovine serum (FBS) (Invitrogen, Carlsbad, Calif.), 0.05 mM 2-mercaptoethanol (Sigma, St. Louis Mo.) (assay medium), with 15 ng/ml human M-CSF. M-NSF-60 cells were split to $5 \times 10^4$ for next day use or to $2.5 \times 10^4$ for use in 2 days. Prior to use in the assay, the cells were washed three times with RPMI-1640, counted and the volume adjusted with assay medium to yield $2 \times 10^5$ cells/ml. All conditions were conducted in triplicate in 96-well treated tissue culture plates (Corning, Corning, N.Y.). To each well 50 µl of the washed cells, either 100 pM or 1000 pM M-CSF in a volume of 25 µl and test or control antibody at various concentrations in a volume of 25 µl in acetate buffer (140 mM sodium chloride, 20 mM sodium acetate, and 0.2 mg/ml polysorbate 80, pH 5.5) to a final volume of 100 µl was added. Antibodies of the invention were tested alone and with human M-CFS. The plates were incubated for 24 hours (hrs) at 37° C. with 5% $CO_2$.

After 24 hrs, 10 µl/well of 0.5 µCi $^3$H-thymidine (Amersham Biosciences, Piscataway, N.J.) was added and pulsed with the cells for 3 hrs. To detect the amount of incorporated thymidine, the cells were harvested onto pre-wet unifilter GF/C filterplates (Packard, Meriden, Conn.) and washed 10 times with water. The plates were allowed to dry overnight. Bottom seals were added to the filterplates. Next, 45 µl Microscint 20 (Packard, Meriden, Conn.) per well was added. After a top seal was added, the plates were counted in a Trilux microbeta counter (Wallac, Norton, Ohio).

These experiments demonstrate that anti-M-CSF antibodies of the invention inhibit mouse monocytic cell proliferation in response to M-CSF. Further, by using various concentrations of antibodies, the $IC_{50}$ for inhibition of mouse nonocytic cell proliferation was determined for antibodies 252, 88, 100, 3.8.3, 2.7.3, 1.120.1, 9.14.4I, 8.10.3F, 9.7.2IF, 9.14.4, 8.10.3, and 9.7.2 (Cell Proliferation Assay, Table 3a and Table 3b).

$CaCl_2$) was added and the plates were incubated for 10 minutes at room temperature. For each sample, 180 µl from each well and 1 ml of Red Cell Lysis Buffer were mixed. The tubes were vortexed for 2 seconds. Next, the samples were incubated at 37° C. for 5 minutes in a shaking water bath to lyse the red blood cells, but to leave monocytes intact. Immediately following this incubation, the samples were read on a fluorescence-activated cell scanning (FACS) machine (BD Beckman FACS) and data was analyzed using FACS Station Software Version 3.4.

These experiments demonstrate that anti-M-CSF antibodies of the invention inhibit monocyte shape changes compared to control samples. Using the monocyte shape change assay, the $IC_{50}$ was determined for antibodies 252, 88, 100, 3.8.3, 2.7.3, 1.120.1, 9.14.4I, 8.10.3F, 9.7.2IF, 9.14.4, 8.10.3, and 9.7.2 (Human Whole Blood Monocyte Activation, Table 3a and Table 3b).

EXAMPLE V c-Fms Receptor Binding Inhibition Assay

In vitro assays were conducted to measure M-CSF binding to c-fms receptor in the presence of anti-M-CSF anti- TABLE 3a

| Antibody | 252 | 88 | 100 | 3.8.3 | 2.7.3 | 1.120.1 |
|---|---|---|---|---|---|---|
| M-CSF Mouse Monocytic Cell Proliferation Assay [$IC_{50}$, M] | $1.86 \times 10^{-10}$ | $2.31 \times 10^{-10}$ | $7.44 \times 10^{-10}$ | $7.3 \times 10^{-11}$ | $1.96 \times 10^{-10}$ | $1.99 \times 10^{-10}$ |
| Human Whole Blood Monocyte Activation Assay [$IC_{50}$, M] | $8.67 \times 10^{-10}$ | $5.80 \times 10^{-10}$ | $1.53 \times 10^{-10}$ | $8.6 \times 10^{-11}$ | $7.15 \times 10^{-10}$ | $8.85 \times 10^{-10}$ |
| Receptor Binding Inhibition Assay [$IC_{50}$, M] | $7.47 \times 10^{-10}$ | $4.45 \times 10^{-10}$ | $1.252 \times 10^{-9}$ | $7.0 \times 10^{-11}$ | $3.08 \times 10^{-10}$ | $1.57 \times 10^{-10}$ |

TABLE 3b

| Antibody | 9.14.4I | 8.10.3F | 9.7.2IF | 9.14.4 | 8.10.3 | 9.7.2 |
|---|---|---|---|---|---|---|
| M-CSF Mouse Monocytic Cell Proliferation Assay [$IC_{50}$, M] | $2.02 \times 10^{-10}$ | $4.13 \times 10^{-10}$ | $7.37 \times 10^{-10}$ | $2.02 \times 10^{-10}$ | $4.13 \times 10^{-10}$ | $7.37 \times 10^{-10}$ |
| Human Whole Blood Monocyte Activation Assay [$IC_{50}$, M] | $2.49 \times 10^{-10}$ | $4.46 \times 10^{-10}$ | $1.125 \times 10^{-9}$ | $6.48 \times 10^{-10}$ | $2.8 \times 10^{-10}$ | $1.98 \times 10^{-10}$ |
| Receptor Binding Inhibition Assay [$IC_{50}$, M ] | $2.97 \times 10^{-10}$ | $9.8 \times 10^{-11}$ | $5.29 \times 10^{-10}$ | $4.1 \times 10^{-11}$ | $1.5 \times 10^{-9}$ | $6 \times 10^{-12}$ |

EXAMPLE IV

Human Whole Blood Monocyte Activation Assay

In vitro assays were conducted to measure M-CSF dependent monocyte shape changes in the presence of anti-M-CSF antibodies to determine if the anti-M-CSF antibodies were capable of inhibiting whole blood monocyte activation and their degree of inhibition of monocyte shape changes.

In individual wells of a 96-well tissue culture plate, 6 µl of 1.7 nM anti-M-CSF and 94 µl of whole human blood for a final concentration of 102 pM anti-M-CSF antibody were mixed. The plates were incubated at 37° C. in a $CO_2$ tissue culture incubator. Next, the plates were removed from the incubator. To each well, 100 µl of a fixative solution (0.5% formalin in phosphate buffered saline without $MgCl_2$ or bodies to determine if the anti-M-CSF antibodies were capable of inhibiting M-CSF binding to c-fms receptor and their degree of inhibition.

NIH-3T3 cells transfected with human c-fms or M-NSF-60 cells maintained in Dulbecco's phosphate buffered saline without magnesium or calcium were washed. NIH-3T3 cells were removed from tissue culture plates with 5 mM ethylene-diamine-tetra-acetate (EDTA), pH 7.4. The NIH-3T3 cells were returned to the tissue culture incubator for 1-2 minutes and the flask(s) were tapped to loosen the cells. The NIH-3T3 cells and the M-NSF-60 cells were transferred to 50 ml tubes and washed twice with reaction buffer (lx RPMI without sodium bicarbonate containing 50 mM N-2-Hydroxyethylpiperazine-N'-2-ethanesulfonic acid (HEPES), pH 7.4). Next, the NIH-3T3 cells were resuspended in reaction buffer for a final concentration of $1.5 \times 10^5$ cell/ml.

The M-NSF-60 cells were resuspended in a reaction buffer for a final concentration of $2.5 \times 10^6$ cells/ml.

For the assay, 9 µl of a sterile 0.4 M sucrose solution, 100 µl of $^{125}$I-M-CSF (Amersham, IMQ7228v) at a final concentration of 200 pM in RPMI-1640 containing 50 mM HEPES (pH 7.4), 0.2% bovine serum albumin, and 100 µl of unlabeled M-CSF at a final concentration of 200 nM were mixed in a binding tube. Next, 50 µl/tube of increasing concentrations of a test antibody was added. In order to determine non-specific binding of the antibodies, we included samples to which we also added 200 nM M-CSF. To control tubes, we did not add antibody. Next, 15,000 NIH-3T3 cells or 250,000 M-NSF-60 cells were added per tube. All tubes were incubated at room temperature for 3 hrs and subjected to centrifugation at 10,000 rpm for 2 min. The tips of the tubes containing the cell pellets were cut off and the amount of M-CSF bound to the cells was determined using a Packard Cobra II Gamma counter. The specific binding was determined by subtracting non-specific binding from total binding. All assays were performed in duplicate. The binding data was analyzed using the computer program, Graph Pad Prism 2.01.

These experiments demonstrate that anti-M-CSF antibodies of the invention inhibit the binding of M-CSF to c-fms receptor compared to control samples. Further, by using various concentrations of antibodies, the $IC_{50}$ for inhibition of receptor binding was determined for antibodies 252, 88, 100, 3.8.3, 2.7.3, 1.120.1, 9.14.4I, 8.10.3F, 9.7.2IF, 9.14.4, 8.10.3, and 9.7.2 (Receptor Binding Inhibition Assay, Table 3a and Table 3b).

EXAMPLE VI

Determination of Affinity Constants ($K_D$) of Anti-M-CSF Monoclonal Antibodies by BIACORE™

Affinity measures of purified antibodies were performed by surface plasmon resonance using the BIACORE™ 3000 instrument, following the manufacturer's protocols.

For antibodies 3.8.3, 2.7.3 and 1.120.1, the experiments were performed in a BIACORE™ 3000 instrument at 25° C. in Dulbecco's phosphate buffered saline containing 0.0005% Tween-20. Protein concentrations were obtained from sedimentation velocity experiments or by measuring the wavelength of the sample at 280 nm using theoretical extinction coefficients derived from amino acid sequences. For experiments measuring the binding of antibody to immobilized antigens, M-CSF was immobilized on a B1 chip by standard direct amine coupling procedures. Antibody samples were prepared at 0.69 µM for 3.8.3, 2.7.3 and 1.120.1. These samples were diluted 3-fold serially to 8.5 nM or 2.8 nM for roughly a 100-fold range in concentrations. For each concentration, the samples were injected in duplicate at 5 µl/min flow for 4 min. The dissociation was monitored for 2000 seconds. The data were fit globally to a simple 1:1 binding model using BIACORE™ Biaevaluation software. In all cases, this method was used to obtain $k_{off}$ and it was found that this data set compared well to data obtained from global fit of association and dissociation data.

For antibodies 252, 88 and 100, the experiments were performed in a BIACORE™ 3000 instrument at 25° C. in HBS-EP Buffer (0.01M HEPES, pH 7.4, 0.15 M NaCl, 3 mM EDTA, 0.005% Surfactant P20). For experiments measuring the binding of antibody to immobilized antigens, a M-CSF was immobilized on a CM5 Research Grade Sensor chip by standard direct amine coupling procedures. Antibody samples were prepared at 12.5 nM for antibodies 252 and 100 and at 25.0 nM for antibody 88. These samples were two-fold serially diluted to 0.78 nM for roughly a 15-30 fold range in concentrations. For each concentration, the samples were injected in duplicate in random order at 30 µl/min flow for 3 min. The dissociation was monitored for 300 sec. The data were fit globally to a simple 1:1 binding model using BIACORE™ Biaevaluation software. In all cases, this method was used to obtain $k_{off}$ and it was found that this data set compared well to data obtained from global fit of association and dissociation data.

Table 4 shows results for antibodies 252, 88, 100, 3.8.3, 2.7.3 and 1.120.1.

TABLE 4

|  | 252 | 88 | 100 | 3.8.3 | 2.7.3 | 1.120.1 |
| --- | --- | --- | --- | --- | --- | --- |
| $K_D$ (M) | $1.33 \times 10^{-11}$ | $1.33 \times 10^{-9}$ | $2.0 \times 10^{-11}$ | $4.0 \times 10^{-10}$ | $4.7 \times 10^{-19}$ | $5.4 \times 10^{-9}$ |
| $k_{off}$ (1/s) | $1.03 \times 10^{-6}$ | $7.3 \times 10^{-5}$ | $1.7 \times 10^{-5}$ | | | |

EXAMPLE VII

Production of 8.10.3 Antibodies from 8.10.3 Hybridoma Cells

Antibody 8.10.3 was produced in 3 L sparged spinners. The 3 L sparged spinner flask is a glass vessel where cultures are mixed with an impeller controlled by a magnetic platform. The spinner is connected to gas lines to provide 5% $CO_2$ and air. 8.10.3 hybridoma cells were initially thawed into T-25 cell culture flasks. The cells were progressively expanded until there was a sufficient number of cells to seed the sparged spinners.

Two 3 L sparged spinner flasks were seeded with 8.10.3 hybridoma cells in Hybridoma Serum-Free Medium with the additions noted on Table 5, for the two sparged flasks. The concentrations for Ultra low IgG serum (Gibco cat#16250-078), L-glutamine (JRH Biosciences cat#59202-500M), Non-Essential Amino Acids (Gibco cat#11140-050), Peptone (Difco cat#211693), glucose (In-house stock prepared from JT Baker cat#1920-07), and Anti-foam C (Sigma cat.# A-8011) are given at their final concentrations in the media. The balance of the volume in each reactor is Hybridoma Serum-Free Medium.

TABLE 5

Conditions for Growing Hybridoma 8.10.3 in two 3L sparged spinners.

| Conditions | Spinner 1 | Spinner 2 |
| --- | --- | --- |
| Seeding density ($1 \times 10^6$ cells/ml) | 0.16 ml | 0.16 ml |
| Hybridoma Serum-Free Medium (Gibco cat# 12045-076) | Balance | Balance |
| Ultra low IgG serum (Gibco cat# 16250-078) | 5% | 5% |
| L-glutamine (JRH Biosciences cat# 59202-500M) | 8 mmol/L | 8 mmol/L |
| Non-Essential Amino Acids (Gibco cat# 11140-050) | 1% | 1% |
| Peptone (Difco cat# 211693) | 1 g/L | 1 g/L |
| 2M glucose (In-house stock prepared from JT Baker cat# 1920-07) | 8 g/L | 8 g/L |
| Anti-foam C (Sigma cat.# A-8011) | 1 ml/L | 1 ml/L |

The cultures were grown for 15 days and were harvested when the viability was below 20%. Viability was determined by trypan blue exclusion method with an automated cell counter (Cedex, Innovatis). Harvesting was accomplished by centrifugation and subsequent filtration. Clarified supernatant was obtained after centrifugation for 15 minutes at 7000 rpm and subsequent filtration with a sterile 0.22 μm 4" Opticap Millipore filter (cat# KVSCO4HB3) into a 10 L sterile TC-Tech bag (cat # P/N 12420 Bag Style CC-10-112420). The filtrate was then purified in the following example.

EXAMPLE VIII

Purification of an Anti-M-CSF Antibody

A Protein A column (Amersham Pharmacia) was prepped by washing with 3 column volumes of 8M Urea, followed by an equilibration wash with 20 mM Tris (pH 8). The final filtrate from Example VII was spiked with 2% v/v of 1M Tris pH 8.3 and 0.02% $NaN_3$ before being loaded onto the Protein A column via gravity-drip mode. After load was complete, the resin was washed with 5 column volumes of 20 mM Tris (pH 8), followed by 5 column volumes of the elution buffer (0.1 M Glycine pH 3.0). Any precipitation was noted, and then a 10% v/v spike of 1M Tris pH 8.3 was added to the eluted antibody. The eluted protein was then dialyzed into 100 fold the volume amount of eluted material of dialysis buffer (140 mM NaCl/20 mM Sodium Acetate pH 5.5). Following dialysis, the antibody was sterile filtered with a 0.22 μm filter and stored until further use.

EXAMPLE IX

Monkey Treatment and Monocyte Counts

One male and one female cynomolgus monkey per dosage group were intravenously administered vehicle or antibody 8.10.3 (produced as describe in Examples VII and VIII) at 0, 0.1, 1, or 5 mg/kg in a dose volume of 3.79 mL/kg over an approximately 5 minute period. Blood samples for clinical laboratory analysis were collected at 24 and 72 hours postdose and weekly for 3 weeks. The monocyte counts were determined by light scatter using an Abbott Diagnostics Inc. Cell Dyn system (Abbott Park, Ill.).

A dose-related decrease (~25% to 85%) in total monocytes at all doses (FIGS. 1A and 1B) was observed. Monocyte counts at the 0.1 and 1 mg/kg appeared to rebound to near control levels by week 2, while monocyte counts at 5 mg/kg were still decreased at 3 weeks.

CD14+CD16+ Monocyte Subset Analysis

Primate whole blood was drawn into Vacutainer tubes containing sodium heparin. 0.2 ml of each blood sample was added to a 15 ml conical polypropylene centrifuge tube containing 10 ml of red blood cell lysis buffer (Sigma), and incubated in a 37° C. water bath for 15 minutes. The tubes were then centrifuged in a Sorvall RT7 centrifuge for 5 minutes at 1,200 rpm. The supernatant was aspirated, the pellet resuspended in 10 ml of 4° C. FACS buffer (Hanks' Balanced Salt Solution/2% FBS/0.02% sodium azide), and the tube centrifuged again for 5 minutes at 1,200 rpm. The supernatant was aspirated and the pellet resuspended in an antibody cocktail consisting of 80 μl 4° C. FACS buffer, 10 μl FITC-conjugated anti-human CD14 monoclonal antibody (BD Biosciences, San Diego, Calif.), 0.5 μl Cy5-PE-conjugated anti-human CD16 monoclonal antibody (BD Biosciences, San Diego, Calif.), and 10 μl PE-conjugated anti-human CD89 monoclonal antibody (BD Biosciences, San Diego, Calif.). The cell suspension was incubated on ice for 20 minutes, after which 10 ml of 4° C. FACS buffer was added and the cells centrifuged as before. The supernatant was aspirated, and the cell pellet resuspended in 400 μl FACS buffer and the cells analyzed on a FACSCaliber flow cytometer (BD Biosciences, San Jose, Calif.). Data for 30,000 cells were collected from each sample.

The monocyte population was identified by a combination of forward angle light scatter and orthogonal light scatter. Cells within the monocyte gate were further analyzed for expression of CD14 and CD16. Two distinct population of monocytes were observed, one expressing high levels of CD14 with little or no CD16 expression (CD14++CD16−) and the other expressing lower levels of CD14, but high levels of CD16 (CD14+CD16+), similar to the two monocyte subsets previously described in human peripheral blood (Ziegler-Heitbrock H. W., *Immunology Today* 17:424-428 (1996)). For each primate tested, the percentage of monocytes within the CD14+CD16+ subset was determined after each blood draw, on days 1, 3, 7, 14, and 21 after 8.10.3 injection.

In general, 8.10.3 treatment resulted in a reduction in the percentage of CD14+CD16+ monocytes (see FIGS. 2A and 2B). Monkeys not receiving 8.10.3 Antibody demonstrated relatively stable CD14+CD16+ monocyte levels. CD14+CD16+ monocytes have been termed "proinflammatory" because they produce higher levels of TNF-α and other inflammatory cytokines (Frankenberger, M. T., et al., *Blood* 87:373-377 (1996)). It has also been reported that the differentiation of monocytes from the conventional CD14++CD16− phenotype to the proinflammatory phenotype is dependent on M-CSF (Saleh M. N., et al., *Blood* 85: 2910-2917 (1995)).

EXAMPLE X

Monkey Treatment and Monocyte Counts

Three male cynomolgus monkeys per dosage group were intravenously administered vehicle (20 mM Sodium acetate, pH 5.5, 140 mM NaCl), purified antibody 8.10.3F, or purified antibody 9.14.4I at 0, 1, or 5 mg/kg in a dose volume of 3.79 mL/kg over an approximately 5 minute period. The monkeys were 4 to 9 years of age and weighed 6 to 10 kg. Blood samples for clinical laboratory analysis were collected at 2, 4, 8, 15, 23, and 29 days. Monocyte counts were determined by light scatter using an Abbott Diagnostics Inc. Cell Dyn system (Abbott Park, Ill.).

A decrease in the percentage change in total monocytes at all doses of antibody 8.10.3F as compared to pre-test levels of monocytes (FIG. 3) was observed (see e.g., day 4, 8, 15, and 23 in FIG. 3).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

| SEQUENCES |
| --- |

SEQ ID NO: 1
252 Heavy Chain [Gamma chain] nucleotide sequence
<u>atggagttggggctgtgctggattaccttgttgctattataaaaggtgtccagtgt</u>CAGGTGCAGCTGGTG
GAGTCTGGGGGAGGCTTGGTCAAGCCTGGAGGGTCCCTGAGACTCTCC
TGTGCAGCCTCT<u>GGATTCACCTTCAGTGACTACTACATGAGC</u>TGGATCC
GCCAGGCTCCAGGGAAGGGGCTGGAGTGG<u>A</u>TTTCA<u>TACATTAGTGGTA</u>
<u>GTGGTAGTACCATATACTACGCAGACTCTGTGAAGGGC</u>CGATTCACCAT
CTCCAGGGACAACGCCAAGAACTCACTGTATCTGCAAATGAACAGCCT
GAGAGCCGAGGACACGGCCGTGTATCACTGTGCGAGA<u>GCCCTGGGTGG</u>
<u>GATGGACGTC</u>TGGGGCCAAGGGACCACGGTCACCGTCTCCTCAGCTcca
ccaagggcccatccgtcttcccctggcgccctgctctagaagcacctccgagagcacagcggccctgggctgcctg
gtcaaggactacttccccgaaccggtgacggtgtcgtggaactcaggcgctctgaccagcggcgtgcacaccttccc
agctgtcctacagtcctcaggactctactccctcagcagcgtggtgaccgtgccctccagcaacttcggcacccagac
ctacacctgcaacgtagatcacaagcccagcaacaccaaggtggacaagacagttgagcgcaaatgagtgtcgagt
gcccaccgtgcccagcaccacctgtggcaggaccgtcagtcttcctcttccccccaaaacccaaggacaccctcatga
tctcccggacccctgaggtcacgtccgtggtggtggacgtgagccacgaagaccccgaggtccagttcaactggtac
gtggacggcgtggaggtgcataatgccaagacaaagccacgggaggagcagttcaacagcacgttccgtgtggtca
gcgtcctcaccgttgtgcaccaggactggctgaacggcaaggagtacaagtgcaaggtctccaacaaagcctccca
gcccccatcgagaaaaccatctccaaaaccaaagggcagccccgagaaccacaggtgtacaccctgcccccatccc
gggaggagatgaccaagaaccaggtcagcctgacctgcctggtcaaaggcttctaccccagcgacatcgccgtggga
gtgggagagcaatgggcagccggagaacaactacaagaccacacctcccatgctggactccgacggctccttcttcc
tctacagcaagctcaccgtggacaagagcaggtggcagcaggggaacgtcttctcatgctccgtgatgcatgaggct
ctgcacaaccactacacgcagaagagcctctccctgtctccgggtaaa SEQ ID NO: 2
252 Heavy Chain [Gamma chain] protein sequence
<u>melglcwiflvaiikgvqc</u>QVQLVESGGGLVKPGGSLRLSCAAS<u>GFTFSDYYMS</u>WIR
QAPGKGLEWI<u>SYISGSGSTIYYADS</u>VKGRFTISRDNAKNSLYLQMNSLRAE
DTAVYHCAR<u>ALGGMDV</u>WGQGTTVTVSSAstkgpsvfplapcsrstsestaalgclvkdyfp
epvtvswnsgaltsgvhtfpavlqssglyslssvvtvpssnfgtqtytcnvdhkpsntkvdktverkccvecppcp
appvagpsvflfppkpkdtlmisrtpevtcvvvdvshedpevqfnwyvdgvevhnaktkpreeqfnstfrvvsv
ltvvhqdwlngkeykckvsnkglpapiektisktkgqprepqvytlppsreemtknqvsltclvkgfypsdiave
wesngqpennykttppmldsdgsfflyskltvdksrwqqgnvfscsvmhealhnhytqkslslspgk SEQ ID NO: 3
252 Light Chain [Kappa chain] nucleotide sequence
<u>atgagggtccctgctcagctcctggggctcctgctactctggctccgaggtgccagatgt</u>GACATCCAGAT
GACCCAGTCTCCATCCTCCCTGTCTGCATCTGTAGGAGACAGAGTCACC
ATCACTTGC<u>CGGGCAAGTCAGAGCATTAGCGGCTTTTTAAAT</u>TGGTATC
AGCAGAAACCAGGGAAAGCCCCTAAGCTCCTGATCTATG<u>CTACATCCA</u>
<u>GTTTGCAAAGT</u>GGGGTCCCATTCAGG<u>TT</u>CAGTGGCAGTGGATCTGGGA
CAGATTTCACTCTCACCATCAGCAGTCTGCAACCTGAAGATTTTGCAAC
TTATTACTGT<u>CAACAGAGTTACAGTGT</u>CCCATTCACTTTCGGCCCTGGG
ACCAAAGTGGATATCAAACGAactgtggctgcaccatctgtcttcatcttcccgccatctgatgagc
agttgaaatctggaactgctagcgttgtgtgcctgctgaataacttctatcccagagaggccaaagtacagtggaaggt
ggataacgcctccaatcgggtaactcccaggagagtgtcacagagcaggacagcaaggacagcacctacagcctc
agcagcaccctgacgctgagcaaagcagactacgagaaacacaaagtctacgcctgcgaagtcacccatcagggcc
tgagctcgcccgtcacaaagagcttcaacaggggagagtgt SEQ ID NO: 4
252 Light Chain [Kappa chain] protein sequence
<u>mrvpaqllqllllwlrgarc</u>DIQMTQSPSSLSASVGDRVTITC<u>RASQSISGFLN</u>WYQQK
PGKAPKLLIY<u>ATSSLQS</u>GVPFRFSGSGSGTD<u>F</u>TLTISSLQPEDFATYYC<u>QQS</u>
<u>YSVPFT</u>FGPGTKVDIKRtvaapsvfifppsdeqlksgtasvvcllnnfypreakvqwkvdnalqsgns
qesvteqdskdstyslsstltlskadyekhkvyacevthqglsspvtksfnrgec SEQ ID NO: 5
88 Heavy Chain [Gamma chain] nucleotide sequence
<u>atggaatttgggctgtgctgggttttccttgttgctattttagaaggtgtccagtgt</u>GAGGTGCAGCTGGTG
GAGTCTGGGGGAGGCTTGGTCCAGCCTGGGGGGTCCCTGAGACTCTCC
TGTGCAGCCTCT<u>GGATTCACCTTTAGTAGCTATTGGATGAGC</u>TGGGTCC
GCCAGGCTCCAGGGAAGGGGCTGGAGTGGGTGGCC<u>AACATAAAGCAA</u>
<u>GATGGAAGTGAGAAATACTATGTGGACTCTGTGAAGGGC</u>CGATTCACC
ATCTCCAGAGACAACGCCAAGAACTCACTGTATCTGCAAATGAACAGC
CTGAGAGCCGAGGACACGGCTGTGTATTACTGTGCT<u>CCGGGTATAGCA</u>
<u>GCAGCTGGTAGGGCCTAC</u>TGGGGCCAGGGAACCCTGGTCACCGTCTCC
TCAGCTtccaccaagggcccatccgtcttcccctggcgccctgctctagaagcacctccgagagcacagcggc
cctgggctgcctggtcaaggactacttccccgaaccggtgacggtgtcgtggaactcaggcgctctgaccagcggcg
tgcacaccttcccagctgtcctacagtcctcaggactctactccctcagcagcgtggtgaccgtgccctccagcaacttc
ggcacccagacctacacctgcaacgtagatcacaagcccagcaacaccaaggtggacaagacagttgagcgcaaat
gttgtgtcgagtgcccaccgtgcccagcaccacctgtggcaggaccgtcagtcttcctcttccccccaaaacccaagg
acaccctcatgatctcccggacccctgaggtcacgtcgcgtggtggtggacgtgagccacgaagaccccgaggtcca
gttcaactggtacgtggacggcgtggaggtgcataatgccaagacaaagccacgggaggagcagttcaacagcacg
ttccgtgtggtcagcgtcctcaccgttgtgcaccaggactggctgaacggcaaggagtacaagtgcaaggtctccaac
aaagcctcccagccccatcgagaaaaccatctccaaaaccaaagggcagccccgagaaccacaggtgtacaccc
tgcccccatcccgggaggagatgaccaagaaccaggtcagcctgacctgcctggtcaaaggcttctacccccagcg
acatcgccgtggagtgggagagcaatgggcagccggagaacaactacaagaccacacctcccatgctggactccg
acggctccttcttcctctacagcaagctcaccgtggacaagagcaggtggcagcaggggaacgtcttctcatgctccg
tgatgcatgaggctctgcacaaccactacacgcagaagagcctctccctgtctccgggtaaa

SEQUENCES

SEQ ID NO: 6
88 Heavy Chain [Gamma chain] protein sequence
mefglcwvflvailegvqcEVQLVESGGGLVQPGGSLRLSCAAS<u>GFTFSSYWMS</u>WV
RQAPGKGLEWVA<u>NIKQDGSEKYYVDSVKG</u>RFTISRDNAKNSLYLQMNSL
RAEDTAVYYCA<u>PGIAAAGRAY</u>VVGQGTLVTVSSAstkgpsvfplapcsrstsestaalgcl
vkdyfpepvtvswnsgaltsgvhtfpavlqssglyslssvvtypssnfgtqtytcnvdhkpsntkvdktverkccv
ecppcpappvagpsvflfppkpkdtlmisrtpevtcvvvdvshedpevqfnwyvdgvevhnaktkpreeqfns
tfrvvsvltvvhqdwlngkeykckvsnkglpapiektisktkgqprepqvytlppsreemtknqvsltclvkgfyp
sdiavewesngqpennykttppmldsdgsfflyskltvdksrwqqgnvfscsvmhealhnhytqkslslspgk SEQ ID NO: 7
88 Light Chain [Kappa chain] nucleotide sequence
<u>atgagggtccctgctcagctcctggggctcctgctactctggctcccagaggtgccagatgt</u>GACATCCAGAT
GACCCAGTCTCCATCCTCCCTGTCTGCATCTGTTGGAGACAGAGTCACC
ATCACTTGC<u>CGGCCAAGTCAGGA</u>CATTAGCAGTTATTTAAATTGGTATC
AGCAGAAACCAGGGAAAGCCCCTAAGCTCCTGATCTAT<u>GCTGCATCCA</u>
<u>GTTTGCAAAGT</u>GGGGTCCCATTAAGGTTCAGTGGCAGTGGATCTGGGA
CAGATTTCACTCTCACCATCAGCAGTCTGCAACCTGAAGATTTTGCAAC
TTACTACTGT<u>CAACAGAGTTACAGTACCCCATTCACTTT</u>CGGCCCTGGG
ACCAAAGTGGATATCAAACGAactgtggctgcaccatctgtcttcatcttcccgccatctgatgagc
agttganatctggaactgctagcgttgtgtgcctgctgaataacttctatcccagagaggccaaagtacagtggaaggt
ggataacgccctccaatcgggtaactcccaggagagtgtcacagagcaggacagcaaggacagcacctacagcctc
agcagcaccctgacgctgagcaaagcagactacgagaaacacaaagtctacgcctgcgaagtcacccatcagggcc
tgagctcgcccgtcacaaagagcttcaacaggggagagtgt SEQ ID NO: 8
88 Light Chain [Kappa chain] protein sequence
mrvpaqllglllllwlrgarcDIQMTQSPSSLSASVGDRVTITCR<u>PSQDISSYLN</u>WYQQK
PGKAPKLLIY<u>AASSLQSGVP</u>LRFSGSGSGTDFTLTISSLQPEDFATYYC<u>QQS</u>
<u>YSTPFT</u>FGPGTKVDIKRtvaapsvfifppsdeqlksgtasvvcllnnfypreakvqwkvdnalqsgns
qesvteqdskdstyslsstltlskadyekhkvyacevthqglsspvtksfnrgec SEQ ID NO: 9
100 Heavy Chain [Gamma chain] nucleotide sequence
<u>atggagtttgggctccgctggattttttcttgtggctattttaaaaggtgtccagtgt</u>GAGGTGCAGCTGTTG
GAGTCTGGGGGAGGCTTGGTACAGCCTGGGGGGTCCCTGAGACTCTCC
TGTGCAGCCTCT<u>GGATTCACCTTTAGCAGCTATGCCATGAGC</u>TGGGTCC
GCCAGGCTCCAGGGAAGGGGCTGGAATGGGTCTC<u>AGCTATTAGTGGTC</u>
<u>GTGGTGGTAGGA</u>CATACTTCGCAGACTCCGTGAAGGGCCGGTTCACCA
TCTCCAGAGACAATTCCAAGAACACGCTGTATCTGCAAATGAACAGCC
TGAGAGCCGAGGACACGGCCGTATATT<u>CTGTGCGGTAGAAGGCTATA</u>
<u>GTGGGCGCTACGGATTTTTTGACTAC</u>GGGGCCAGGGAACCCTAGTCAC
CGTCTCCTCAGCCtccaccaagggcccatcggtcttccccctggcgccctgctctagaagcacctccgag
agcacagcggccctgggctgcctggtcaaggactacttccccgaaccggtgacggtgtcgtggaactcaggcgctct
gaccagcggcgtgcacaccttcccagctgtcctacagtcctcaggactctactccctcagcagcgtggtgaccgtgcc
ctccagcaacttcggcacccagacctacacctgcaacgtagatcacaagcccagcaacaccaaggtggacaagaca
gttgagcgcaaatgttgtgtcgagtgcccaccgtgcccagcaccacctgtggcaggaccgtcagtcttcctcttccccc
caaaacccaaggacaccctcatgatctcccggacccctgaggtcacgtgcgtggtggtggacgtgagccacgaaga
ccccgaggtccagttcaactggtacgtggacggcgtggaggtgcataatgccaagacaaagccacgggaggagca
gttcaacagcacgttccgtgtggtcagcgtcctcaccgttgtgcaccaggactggctgaacggcaaggagtacaagtg
caaggtctccaacaaaggcctcccagcccccatcgagaaaaccatctctccaaaaccaaagggcagccccgagaacc
acaggtgtacaccctgcccccatcccgggaggagatgaccaagaaccaggtcagcctgacctgcctggtcaaaggc
ttctaccccagcgacatcgccgtggagtgggagagcaatgggcagccggagaacaactacaagaccacctccca
tgctggactccgacggctccttcttcctctacagcaagctcaccgtggacaagagccaggtggcagcaggggaacgtc
ttctcatgctccgtgatgcatgaggctctgcacaaccactacacgcagaagagcctctccctgtctccgggtaaa SEQ ID NO: 10
100 Heavy Chain [Gamma chain] protein sequence
mefglrwiflvailkgvqcEVQLLESGGGLVQPGGSLRLSCAAS<u>GFTFSSYAMS</u>WVR
QAPGKGLEWVS<u>AISGRGGRTYF</u>ADSVKGRFTISRDNSKNTLYLQMNSLRA
EDTAVYFCAV<u>EGYSGRYGFFD</u>YWGQGTLVTVSSAstkgpsvfplapcsrstsestaal
gclvkdyfpepvtvswnsgaltsgvhtfpavlqssglyslssvvtvpssnfgtqtytcnvdhkpsntkvdktverkc
cvecppcpappvagpsvflfppkpkdtlmisrtpevtcvvvdvshedpevqfnwyvdgvevhnaktkpreeqf
nstfrvvsyltvvhqdwingkeykckvsnkglpapiektisktkgqprepqvytlppsreemtknqvsltclvkgf
ypsdiavewesngqpennykttppmldsdgsfflyskltvdksrwqqgnvfscsvmhealhnhytqkslslspg
k SEQ ID NO: 11
100 Light Chain [Kappa chain] nucleotide sequence
<u>atggaagcccccagctcagcnctcttcctcctgctactctggctcccagataccactgga</u>GAAATAGTGATG
ACGCAGTCTCCAGCCACCCTGTCTGTGTCTCAGGGGAAAGAGCCACC
CTCTCCTGC<u>AGGGCCAGTCAGAGTGTTAGCAGCAACTT</u>AGCCTGGTACC
AGCAGAAACCTGGCCAGGCTCCCAGGCTCCTCATCTAT<u>GGTGCATCCAC</u>
<u>CAGGGCCAGT</u>GGTATCCCAGACAGGATCAGTGGCAGTGGGTCTGGAAC
AGAGTTCACTCTCATCATCAGCAGCCTGCAGTCTGAAGATTTTGCAGTT
TATTACTGT<u>CAGCAGTCTAATAACTGGCCATTCACTTT</u>CGGCCCTGGGA
CCAAAGTGGATATCAAACGAactgtggctgcaccatctgtcttcatcttcccgccatctgatgagca

| SEQUENCES |
|---|
| gttgaaatctggaactgctagcgttgtgtgcctgctgaataacttctatcccagagaggccaaagtacagtggaaggtg<br>gataacgccctccaatcgggtaactcccaggagagtgtcacagagcaggacagcaaggacagcacctacagcctca<br>gcagcaccctgacgctgagcaaagcagactacgagaaacacaaagtctacgcctgcgaagtcacccatcagggcct<br>gagctcgcccgtcacaaagagcttcaacaggggagagtgt |
| SEQ ID NO: 12<br>100 Light Chain [Kappa chain] protein sequence<br><u>meapaqllflllllwlpdttg</u>EIVMTQSPATLSVSPGERATLSC<u>RASQSVSSNLAWYQQ</u><br>KPGQAPRLLIY<u>GASTRASG</u>IP<u>DR</u>ISGSGSGTEFTLIISSLQSEDFAVYYC<u>QQS<br>NNWPFT</u>FGPGTKVDIKRtvaapsvfifppsdeqlksgtasvvcllnnfypreakvqwkvdnalqsgn<br>sqesvteqdskdstyslsstltlskadyekhkvyacevthqglsspvtksfnrgec |
| SEQ ID NO: 14<br>3.8.3 Heavy Chain [Gamma chain] protein sequence<br><u>mefglswvflvaiikqvqc</u>QVQLVESGGGLVKPGGSLRLSCAAS<u>GFTFSDYYMS</u>WI<br>RQAPGKGLEW<u>F</u>S<u>YISSSGSTIYY</u>ADSVKGRFTISRDNAKN<u>SL</u>S<u>L</u>QMNSLRA<br>EDTAVYYCAR<u>GLTGDY</u>WGQGTLVTVSSAstkgpsvfplapcsrstsestaalgclvkdyfpe<br>pvtvswnsgaltsgvhtfpavlqssglyslssvvtvpssnfgtqtytcnvdhkpsntkvdktverkccvecppcpa<br>ppvagpsvflfppkpkdtlmisrtpevtcvvvdvshedpevqfnwyvdgvevhnaktkpreeqfnstfrvvsylt<br>vvhqdwlngkeykckvsnkglpapiektisktkgqprepqvytlppsreemtknqvsltclvkgfypsdiavew<br>esngqpennykttppmldsdgsfflyskltvdksrwqqgnvfscsvmhealhnhytqkslslspgk |
| SEQ ID NO: 16<br>3.8.3 Light Chain [Kappa chain] protein sequence<br><u>mdmrvpaqllqlllllwfpqsrc</u>DIQMTQSPSSVSASVGDRVTISC<u>RASQDISGWLA</u>WY<br>QQKPGKAPKLLIS<u>ATSSLH</u>SGVPSRFSGSGSGTDFTLTISSLQPEDFATYYC<br><u>QQTNSFPFT</u>FGPGTKVDIKRtvaapsvfifppsdeqlksgtasvvcllnnfypreakvqwkvdnalq<br>sgnsqesvteqdskdstyslsstltlskadyekhkvyacevthqglsspvtksfnrgec |
| SEQ ID NO: 18<br>2.7.3 Heavy Chain [Gamma chain] protein sequence<br><u>mefglswvflvallrgcqc</u>QVQLVESGGGVVQPGRSLRLSCAAS<u>GFTFSSYGMH</u>WV<br>RQAPGKGLEWVA<u>F</u>I<u>WYDGSNKYY</u>ADSVKGRFTISRDNSKNTLYLQMNSL<br>RAEDTAVYYCAR<u>GYRVYFDY</u>WGQGTLVTVSSAstkgpsvfplapcsrstsestaalgcl<br>vkdyfpepvtyswnsgaltsgyhtfpaylqssglyslssyytypssslgtktytcnvdhkpsntkvdkrveskygp<br>pcpscpapeflggpsvflfppkpkdtlmisrtpevtcvvvdvsqedpevqfnwyvdgvevhnaktkpreeqfns<br>tyrvvsyltvlhqdwingkeykckvsnkglpssiektiskakgqprepqvytlppsqeemtknqvsltclykgfy<br>psdiavewesngqpennykttppvldsdgsfflysrltvdksrwqegnvfscsvmhealhnhytqkslslspgk |
| SEQ ID NO: 20<br>2.7.3 Light Chain [Kappa chain] protein sequence<br><u>mdmrypaqllqlllllwfpqsrc</u>DIQMTQSPSSVSASVGDRVTITC<u>RASQDISSWLA</u>WY<br>QRKPGKAPK<u>LQ</u>IYA<u>ASSLE</u>SGVPSRF<u>N</u>GSGSGTDFTL<u>S</u>ISSLQPEDFATYYC<br><u>QQTNSFPLT</u>FGGGTKVEIKRtvaapsyfifppsdeqlksgtasATvcllnnfypreakvqwkvdnal<br>qsgnsqesvteqdskdstyslsstltlskadyekhkvyaceythqglsspytksfnrgec |
| SEQ ID NO: 22<br>1.120.1 Heavy Chain [Gamma chain] protein sequence<br><u>mewtwsflflvaaatgahs</u>QVQLVQSGAEVKKPGASVKVSCKAS<u>GYTFTSYGIS</u>WV<br>RQAPGQGLEWMG<u>WISAYNGNTNYAQKLQ</u>DRVTMTTDTS<u>TTT</u>AYMELRS<br>LRSDDTAVYYC<u>ARRAYGANFF</u>DYWGQGTLVTVSSAstkgpsvfplapcsrstsestaa<br>lgclvkdyfpepvtvswnsgaltsgvhtfpavlqssglyslssvvtypssnfgtqtytcnvdhkpsntkvdktverk<br>ccvecppcpappvagpsvflfppkpkdtlmisrtpevtcvvvdvshedpevqfnwyvdgvevhnaktkpree<br>qfnstfrvvsyltvvhqdwlngkeykckvsnkglpapiektisktkgqprepqvytlppsreemtknqvsltclvk<br>gfypsdiavewesngqpennykttppmldsdgsfflyskltvdksrwqqgnvfscsvmhealhnhytqkslsls<br>pgk |
| SEQ ID NO: 24<br>1.120.1 Light Chain [Kappa chain] protein sequence<br><u>mylqtqvfislllwisqayq</u>DIVMTQSPDSLAVSLGERATINC<u>KSSQSILFFSNNKNYL</u><br>AWYRQKPGQPP<u>N</u>LLIY<u>WASTRES</u>GVPDRFSGSGSGTDFTLTISSLQAEDVA<br>VYYC<u>QQYYSSPWT</u>FGQGTKVEIKRtvaapsvfifppsdeqlksgtasvvcllnnfypreakvq<br>wkvdnalqsgnsqesvteqdskdstyslsstltlskadyekhkvyacevthqglsspvtksfnrgec |
| SEQ ID NO: 25<br>9.14.41 Heavy Chain [Gamma Chain] nucleotide sequence<br><u>atggagtttgggctgagctggttttccttgttgctattataaaaggtgt</u>CCAGTGTCAGGTGCAGCTG<br>GTGGAGTCTGGGGGAGGCTTGGTCAAGCCTGGAGGGTCCCTGAGACTC<br>TCCTGTGCAGCCTCTGGATTCACCTTCAGT<u>GACTACTATATGAGC</u>TGGA<br>TCCGCCAGGCTCCAGGGAAGGGACTGGAGTGGGTTTCA<u>TACATTAGTA<br>GTAGTGGTAGTACCATATACTACGCAGACTCTGTGAAGGGC</u>CGATTCA<br>CCATCTCCAGGGACAACGCCAAGAACTCACTGTATCTGCAAATGAACA<br>GCCTGAGAGCCGAGGACACGGCCGTGTATTACTGTGCGAGA<u>GGCCTAA<br>CTGGGGACTAC</u>TGGGGCCAGGGAACCCTGGTCACCGTCTCCTCAGCTtcc<br>accaagggcccatccgtcttccccctggcgccctgctctagaagcacctccgagagcacagcggccctgggctgcct<br>ggtcaaggactacttccccgaaccggtgacggtgtcgtggaactcaggcgctctgaccagcggcgtgcacaccttcc<br>cagctgtcctacagtcctcaggactctactccctcagcagcgtggtgaccgtgccctccagcaacttcggcacccaga |

SEQUENCES

```
cctacacctgcaacgtagatcacaagcccagcaacaccaaggtggacaagacagttgagcgcaaatgttgtgtcgag
tgcccaccgtgcccagcaccacctgtggcaggaccgtcagtcttcctcttccccccaaaacccaaggacaccctcatg
atctcccggacccctgaggtcacgtgcgtggtggtggacgtgagccacgaagaccccgaggtccagttcaactggta
cgtggacggcgtggaggtgcataatgccaagacaaagccacgggaggagcagttcaacagcacgttccgtgtggtc
agcgtcctcaccgttgtgcaccaggactggctgaacggcaaggagtacaagtgcaaggtctccaacaaaggcctcc
cagcccccatcgagaaaaccatctccaaaaccaaagggcagccccgagaaccacaggtgtacaccctgcccccatcc
cgggaggagatgaccaagaaccaggtcagcctgacctgcctggtcaaaggcttctaccccagcgacatcgccgtgg
agtgggagagcaatgggcagccggagaacaactacaagaccacacctcccatgctggactccgacggctccttcttc
ctctacagcaagctcaccgtggacaagagcaggtggcagcaggggaacgtcttctcatgctccgtgatgcatgagc
tctgcacaaccactacacgcagaagagcctctccctgtctccgggtaaa SEQ ID NO: 26
9.14.4I Heavy Chain [Gamma Chain] protein sequence
mefglswvflvaiikgvqcQVQLVESGGGLVKPGGSLRLSCAASGFTFSDYYMSWI
RQAPGKGLEWVSYISSSGSTIYYADSVKGRFTISRDNAKNSLYLQMNSLRA
EDTAVYYCARGLTGDYWGQGTLVTVSSAstkgpsvfplapcsrstsestaalgclvkdyfpe
pvtvswnsgaltsgvhtfpavlqssglyslssvvtvpssnfgtqtytcnvdhkpsntkvdktverkccvecppcpa
ppvagpsvflfppkpkdtlmisrtpevtcvvvdvshedpevqfnwyvdgvevhnaktkpreeqfnstfrvvsvlt
vvhqdwlngkeykckvsnkglpapiektisktkgqprepqvytlppsreemtknqvsltclvkgfypsdiavew
esngqpennykttppmldsdgsfflysktvdksrwqqgnvfscsvmhealhnhytqkslslspgk SEQ ID NO: 27
9.14.4, 9.14.4I, 9.14.4-Ser and 9.14.4-G1 Light Chain [Kappa Chain] nucleotide
sequence
atggacatgagggtccccgctcagctcctggggctcctgctactctggctccgaggtgccagatgTGACATCC
AGATGACCCAGTCTCCATCCTCCCTGTCTGCATCTGTCGGAGACAGAGT
CACCATCACTTGCCGGCCAAGTCAGATCATTAGCAGTTTATTAAATTGG
TATCAGCAGAAACCAGGGAAAGCCCCTAAGCTCCTGATCCATGCTGCA
TCCAGTTTGCAAAGTGGGGTCCCATCAAGGTTCAGTGGCAGTGGATCTG
GGACAGATTTCACTCTCACCATCAGTAGTCTGCAACCTGAAGATTTTGC
AACTTACTACTGTCAACAGAGTTACAGTACCCCATTCACTTTCGGCCCT
GGGACCAAAGTGGATATCAAACGAactgtggctgcaccatctgtcttcccgccatctga
tgagcagttgaaatctggaactgcctctgttgtgtgcctgctgaataacttctatcccagagaggccaaagtacagtgga
aggtggataacgccctccaatcgggtaactcccaggagagtgtcacagagcaggacagcaaggacagcacctaca
gcctcagcagcaccctgacgctgagcaaagcagactacgagaaacacaaagtctacgcctgcgaagtcacccatca
gggcctgagctcgcccgtcacaaagagcttcaacaggggagagtgt SEQ ID NO: 28
9.14.4, 9.14.4I, 9.14.4-Ser and 9.14.4-G1 Light Chain [Kappa Chain] protein
sequence
mdmrvpaqllqlllllwlrqarcDIQMTQSPSSLSASVGDRVTITCRPSQIISSLLNWYQ
QKPGKAPKLLIHAASSLQSGVPSRFSGSGSGTDFTLTISSLQPEDFATYYCQ
QSYSTPFTFGPGTKVDIKRtvaapsvfifppsdeqlksgtasvvcllnnfypreakvqwkvdnalqs
gnsqesvteqdskdstyslsstltlskadyekhkvyacevthqglsspvtksfnrgec SEQ ID NO: 37
9.14.4 Heavy Chain [Gamma Chain] nucleotide sequence
atggagtttgggctgagctgggttttccttgttgctattataaaaggtgtCCAGTGTCAGGTGCAGCTG
GTGGAGTCTGGGGGAGGCTTGGTCAAGCCTGGAGGGTCCCTGAGACTC
TCCTGTGCAGCCTCTGGATTCACCTTCAGTGACTACTATATGAGCTGGA
TCCGCCAGGCTCCAGGGAAGGGACTGGAGTGGGTTTCATACATTAGTA
GTAGTGGTAGTACCATATACTACGCAGACTCTGTGAAGGGCCGATTCA
CCATCTCCAGGGACAACGCCAAGAACTCACTGTATCTGCAAATGAACA
GCCTGAGAGCCGAGGACACGGCCGTGTATTACTGTGCGAGAGGCCTAA
CTGGGGACTACTGGGGCCAGGGAACCCTGGTCACCGTCTCCTCAGCTtcc
accaagggcccatccgtcttccccctggcgccctgctctagaagcacctccgagagcacagcggccctgggctgcct
ggtcaaggactacttccccgaaccggtgacggtgtcgtggaactcaggcgctctgaccagcggcgtgcacaccttcc
cagctgtcctacagtcctcaggactctactccctcagcagcgtggtgaccgtgccctccagcagcttgggcacgaaga
cctacacctgcaacgtagatcacaagcccagcaacaccaaggtggacaagagagttgagtccaaatatggtccccca
tgcccatcatgcccagcacctgagttcctggggggaccatcagtcttcctgttccccccaaaacccaaggacactctca
tgatctcccggacccctgaggtcacgtgcgtggtggtggacgtgagccaggaagaccccgaggtccagttcaactgg
tacgtggatggcgtggaggtgcataatgccaagacaaagccgcgggaggagcagttcaacagcacgtaccgtgtgg
tcagcgtcctcaccgtcctgcaccaggactggctgaacggcaaggagtacaagtgcaaggtctccaacaaaggcctc
ccgtcctccatcgagaaaaccatctccaaagccaaagggcagccccgagagccacaggtgtacaccctgcccccat
cccaggaggagatgaccaagaaccaggtcagcctgacctgcctggtcaaaggcttctaccccagcgacatcgccgt
ggagtgggagagcaatgggcagccggagaacaactacaagaccacgcctcccgtgctggactccgacggctccttc
ttcctctacagcaggctaaccgtggacaagagcaggtggcaggaggggaatgtcttctcatgctccgtgatgcatgag
gctctgcacaaccactacacacagaagagcctctccctgtctccgggtaaa SEQ ID NO: 38
9.14.4 Heavy Chain [Gamma Chain] protein sequence
mefglswvflvaiikgvqcQVQLVESGGGLVKPGGSLRLSCAASGFTFSDYYMSWI
RQAPGKGLEWVSYISSSGSTIYYADSVKGRFTISRDNAKNSLYLQMNSLRA
EDTAVYYCARGLTGDYWGQGTLVTVSSAstkgpsvfplapcsrstsestaalgclvkdyfpe
pvtvswnsgaltsgvhtfpavlqssglyslssvvtvpsssslgtktytcnvdhkpsntkvdkrveskygppcpscpa
peflggpsvflfppkpkdtlmisrtpevtcvvvdvsqedpevqfnwyvdgvevhnaktkpreeqfnstyrvvsvl
``` tvlhqdwlngkeykckvsnkglpssiektiskakgqprepqvytlppsqeemtknqvsltclvkgfypsdiave
wesngqpennykttppvldsdgsfflysrltvdksrwqegnvfscsvmhealhnhytqkslslspgk SEQ ID NO: 54
9.14.4C-Ser Heavy Chain [Gamma chain] protein sequence
<u>mefglswvflvaiikqvqc</u>QVQLVESGGGLVKPGGSLRLSCAAS<u>GFTFSDYYMS</u>WI
RQAPGKGLEWVS<u>YISSSGSTIYYADSVK</u>GRFTISRDNAKNSLYLQMNSLRA
EDTAVYYCAR<u>GLTGDY</u>WGQGTLVTVSSAstkgpsvfplapcsrstsestaalgclvkdyfpe
pvtvswnsgaltsgvhtfpavlqssglyslssvvtvpssslgtktytcnvdhkpsntkvdkrveskygppcpcpa
peflggpsvflfppkpkdtlmisrtpevtcvvvdvsqedpevqfnwyydgvevhnaktkpreeqfnstyrvvsvl
tylhqdwlngkeykckvsnkglpssiektiskakgqprepqvytlppsqeemtknqvsltclvkgfypsdiave
wesngqpennykttppvldsdgsfflysrltvdksrwqegnvfscsvmhealhnhytqkslslspgk SEQ ID NO: 56
9.14.4C-Ser, 9.14.4-CG2 and 9.14.4-CG4 Light Chain [Kappa chain] protein
sequence
<u>mdmrvpaqllqllllwlrgarc</u>DIQMTQSPSSLSASVGDRVTITCR<u>PSQIISSLL</u>NWYQ
QKPGKAPKLLIY<u>AASSLQS</u>GVPSRFSGSGSGTDFTLTISSLQPEDFATYYC<u>Q</u>
<u>QSYSTPF</u>TFGPGTKVDIKRtvaapsvfifppsdeqlksgtasvvcllnnfypreakvqwkvdnalqs
gnsqesvteqdskdstyslsstltlskadyekhkvyacevthqglsspvtksfnrgec SEQ ID NO: 74
9.14.4-CG2 Heavy Chain [Gamma chain] protein sequence
mefglswvflvaiikqvqcQVQLVESGGGLVKPGGSLRLSCAASGFTFS<u>DYYMS</u>WI
RQAPGKGLEWVS<u>YISSSGSTIYYADSVK</u>GRFTISRDNAKNSLYLQMNSLRA
EDTAVYYCAR<u>GLTGDY</u>WGQGTLVTVSSAstkgpsvfplapcsrstsestaalgclvkdyfpe
pvtvswnsgaltsgvhtfpavlqssglyslssvvtvpssnfgtqtytcnvdhkpsntkvdktverkccvecppcpa
ppvagpsvflfppkpkdtlmisrtpevtcvvvdvshedpevqfnwyvdgvevhnaktkpreeqfnstfrvvsvlt
vvhqdwlngkeykckvsnkglpapiektisktkgqprepqvytlppsreemtknqvsltclvkgfypsdiavew
esngqpennykttppmldsdgsfflyskltvdksrwqqgnvfscsvmhealhnhytqkslslspgk SEQ ID NO: 78
9.14.4-CG4 Heavy Chain [Gamma chain] protein sequence
<u>mefglswvflvaiikqvqc</u>QVQLVESGGGLVKPGGSLRLSCAAS<u>GFTFSDYYMS</u>WI
RQAPGKGLEWVS<u>YISSSGSTIYYADSVK</u>GRFTISRDNAKNSLYLQMNSLRA
EDTAVYYCAR<u>GLTGDY</u>WGQGTLVTVSSAstkgpsvfplapcsrstsestaalgclvkdyfpe
pvtvswnsgaltsgvhtfpavlqssglyslssvvtvpssslgtktytcnvdhkpsntkvdkryeskygppcpscpa
peflggpsvflfppkpkdtlmisrtpevtcvvvdvsqedpevqfnwyvdgvevhnaktkpreeqfnstyrvvsvl
tvlhqdwlngkeykckvsnkglpssiektiskakgqprepqvytlppsqeemtknqvsltclvkgfypsdiave
wesngqpennykttppvldsdgsfflysrltvdksrwqegnvfscsvmhealhnhytqkslslspgk SEQ ID NO: 82
9.14.4-Ser Heavy Chain [Gamma chain] protein sequence
<u>mefglswvflvaiikqvqc</u>QVQLVESGGGLVKPGGSLRLSCAAS<u>GFTFSDYYMS</u>WI
RQAPGKGLEWVS<u>YISSSGSTIYYADSVK</u>GRFTISRDNAKNSLYLQMNSLRA
EDTAVYYCAR<u>GLTGDY</u>WGQGTLVTVSSAstkgpsvfplapcsrstsestaalgclvkdyfpe
pvtvswnsgaltsgvhtfpavlqssglyslssvvtvpssslgtktytcnvdhkpsntkvdkrveskygppcppcpa
peflggpsvflfppkpkdtlmisrtpevtcvvvdvsqedpevqfnwyvdgvevhnaktkpreeqfnstyrvvsvl
tvlhqdwlngkeykckvsnkglpssiektiskakgqprepqvytlppsqeemtknqvsltclvkgfypsdiave
wesngqpennykttppvldsdgsfflysrltvdksrwqegnvfscsvmhealhnhytqkslslspgk SEQ ID NO. 101
9.14.4G1 Heavy chain (gamma chain) nucleotide sequence
<u>atggagtttgggctgagctgggttttccttgttgctattataaaaggtgtccagtgt</u>CAGGTGCAGCTGGTG
GAGTCTGGGGGAGGCTTGGTCAAGCCTGGAGGGTCCCTGAGACTCTCC
TGTGCAGCCTCTGGATTCACCTTCAGTGACTACTATATGAGCTGGATCC
GCCAGGCTCCAGGGAAGGGACTGGAGTGGGTTTCATACATTAGTAGTA
GTGGTAGTACCATATACTACGCAGACTCTGTGAAGGGCCGATTCACCAT
CTCCAGGGACAACGCCAAGAACTCACTGTATCTGCAAATGAACAGCCT
GAGAGCCGAGGACACGGCCGTGTATTACTGTGCGAGAGGCCTAACTGG
GGACTACTGGGGCCAGGGAACCCTGGTCACCGTCTCCTCAGCTtccaccaag
ggcccatcggtcttccccctggcaccctcctccaagagcacctctgggggcacagcggccctgggctgcctggtcaa
ggactacttccccgaaccggtgacggtgtcgtggaactcaggcgccctgaccagcggcgtgcacaccttcccggctg
tcctacagtcctcaggactctactccctcagcagcgtggtgaccgtgccctccagcagcttgggcacccagacctacat
ctgcaacgtgaatcacaagcccagcaacaccaaggtggacaagaaagttgagcccaaatcttgtgacaaaactcaca
catgcccaccgtgcccagcacctgaactcctggggggaccgtcagtcttcctcttccccccaaaacccaaggacacc
ctcatgatctcccggacccctgaggtcacatgcgtggtggtggacgtgagccacgaagaccctgaggtcaagttcaa
ctggtacgtggacggcgtggaggtgcataatgccaagacaaagccgcgggaggagcagtacaacagcacgtaccg
tgtggtcagcgtcctcaccgtcctgcaccaggactggctgaaggcaaggagtacaagtgcaaggtctccaacaaag
ccctcccagcccccatcgagaaaaccatctccaaagccaaagggcagccccgagaaccacaggtgtacaccctgcc
cccatcccgggatgagctgaccaagaaccaggtcagcctgacctgcctggtcaaaggcttctatcccagcgacatcg
ccgtggagtgggagagcaatgggcagccggagaacaactacaagaccacgcctcccgtgctggactccgacggct
ccttcttcctctacagcaagctcaccgtggacaagagcaggtggcagcaggggaacgtcttctcatgctccgtgatgc
atgaggctctgcacaaccactacacgcagaagagcctctccctgtctccgggtaaatag -continued

SEQUENCES

SEQ ID NO 102
9.14.4G1 Heavy chain (gamma chain) protein sequence
mefglswvflvaiikqvqcQVQLVESGGGLVKPGGSLRLSCAASGFTFSDYYMSWI
RQAPGKGLEWVSYISSSGSTIYYADSVKGRFTISRDNAKNSLYLQMNSLRA
EDTAVYYCARGLTGDYWGQGTLVTVSSAstkgpsvfplapsskstsggtaalgclvkdyfp
epvtvswnsgaltsgvhtfpavlqssglyslssvvtvpssslgtqtyicnvnhkpsntkvdkkvepkscdkthtcpp
cpapellggpsvflfppkpkdtlmisrtpevtcvvvdvshedpevkfnwyvdgvevhnaktkpreeqynstyrv
vsvltvlhqdwlngkeykckvsnkalpapiektiskakgqprepqvytlppsrdeltknqvsltclvkgfypsdia
vewesngqpennykttppvldsdgsfflysktltvdksrwqqgnvfscsvmhealhnhytqkslslspgk SEQ ID NO: 29
8.10.3 and 8.10.3F Heavy Chain [Gamma chain] nucleotide sequence
atggagttgggctgtgctgggttttccttgagctatttagaaggtgtccagtgtGAGGTGCAGCTGGTG
GAGTCTGGGGGAGGCTTGGTACAGCCTGGGGGGTCCCTGAGACTCTCC
TGTGCAGCCTCTGGATTCACCTTCAGTAGTTTTAGTATGACCTGGGTCC
GCCAGGCTCCAGGAAAGGGGCTGGAGTGGGTTTCATACATTAGTAGTA
GAAGTAGTACCATATCCTACGCAGACTCTGTGAAGGGCCGATTCACCA
TCTCCAGAGACAATGCCAAGAACTCACTGTATCTGCAAATGAACAGCC
TGAGAGACGAGGACACGGCTGTGTATTACTGTGCGAGAGATCCTCTTCT
AGCGGGAGCTACCTTCTTTGACTACTGGGGCCAGGGAACCCTGGTCAC
CGTCTCCTCAGCCtccaccaagggcccatcggtcttccccctggcgccctgctccaggagcacctccgag
agcacagcggccctgggctgcctggtcaaggactacttccccgaaccggtgacggtgtcgtggaactcaggcgctct
gaccagcggcgtgcacaccttcccagctgtcctacagtcctcaggactctactccctcagcagcgtggtgaccgtgcc
ctccagcaacttcggcacccagacctacacctgcaacgtagatcacaagcccagcaacaccaaggtggacaagaca
gttgagcgcaaatgttgtgtcgagtgcccaccgtgcccagcaccacctgtggcaggaccgtcagtcttcctcttccccc
caaaacccaaggacaccctcatgatctcccggaccctgaggtcacgtgcgtggtggtggacgtgagccacgaaga
ccccgaggtccagttcaactggtacgtggacggcgtggaggtgcataatgccaagacaaagccacgggaggagca
gttcaacagcacgttccgtgtggtcagcgtcctcaccgttgtgcaccaggactggctgaacggcaaggagtacaagtg
caaggtctccaacaaaggcctcccagcccccatcgagaaaaccatctccaaaaccaaagggcagccccgagaacc
acaggtgtacaccctgcccccatcccgggaggagatgaccaagaaccaggtcagcctgacctgcctggtcaaaggc
ttctaccccagcgacatcgccgtggagtgggagagcaatgggcagccggagaacaactacaagaccacacctccca
tgctggactccgacggctccttcttcctctacagcaagctcaccgtggacaagagcaggtggcagcaggggaacgtc
ttctcatgctccgtgatgcatgaggctctgcacaaccactacacgcagaagagcctctccctgtctccgggtaaa SEQ ID NO: 30
8.10.3 and 8.10.3F Heavy Chain [Gamma chain] protein sequence
melqlcwvflvaileqvqcEVQLVESGGGLVQPGGSLRLSCAASGFTFSSFSMTWV
RQAPGKGLEWVSYISSRSSTISYADSVKGRFTISRDNAKNSLYLQMNSLRD
EDTAVYYCARDPLLAGATFFDYWGQGTLVTVSSAstkgpsvfplapcsrstsestaalg
clvkdyfpepvtvswnsgaltsgvhtfpavlqssglyslssvvtvpssnfgtqtytcnvdhkpsntkvdktverkcc
vecppcpappvagpsvflfppkpkdtlmisrtpevtcvvvdvshedpevqfnwyvqfngvevhnaktkpreeqfn
stfrvvsyltvvhqdwlngkeykckvsnkglpapiektisktkgqprepqvytlppsreemtknqvsltclvkgfy
psdiavewesngqpennykttppmldsdgsfflysktltvdksrwqqgnvfscsvmhealhnhytqkslslspgk SEQ ID NO: 31
8.10.3FG1 and 8.10.3F Light Chain [Kappa chain] nucleotide sequence
atggaaaccccagcgcagcttctcttcctcctgctactctggctcccagataccaccggaGAATTTGTGTTG
ACGCAGTCTCCAGGCACCCTGTCTTTGTCTCCAGGGGAAAGAGCCACCC
TCTCCTGCAGGGCCAGTCAGAGTGTTAGCAGCAGTTACTTAGCCTGGTA
CCAGCAGAAACCTGGCCAGGCTCCCAGGCTCCTCATCTATGGTGCATCC
AGCAGGGCCACTGGCATCCCAGACAGGTTCAGTGGCAGTGGGTCTGGG
ACAGACTTCACTCTCACCATCAGCAGACTGGAGCCTGAAGATTTTGCAG
TGTATTACTGTCAGCAGTATGGTAGCTCACCTCTCACTTTCGGCGGAGG
GACCAAGGTGGAGATCAAACGAactgtggctgcaccatctgtcttcatcttcccgccatctgatga
gcagttgaaatctggaactgcctctgttgtgtgcctgctgaataacttctatcccagagaggccaaagtacagtggaag
gtggataacgccctccaatcgggtaactcccaggagagtgtcacagagcaggacagcaaggacagcacctacagcc
tcagcagcaccctgacgctgagcaaagcagactacgagaaacacaaagtctacgcctgcgaagtcacccatcaggg
cctgagctcgcccgtcacaaagagcttcaacaggggagagtgt SEQ ID NO: 32
8.10.3FG1 and 8.10.3F Light Chain [Kappa chain] protein sequence
metpaqllflllwlpdttgEFVLTQSPGTLSLSPGERATLSCRASQSVSSSYLAWYQQ
KPGQAPRLLIYGASSRATGIPDRFSGSGSGTDFTLTISRLEPEDFAVYYCQQ
YGSSPLTFGGGTKVEIKRtvaapsvfifppsdeqlksgtasvvcllnnfypreakvqwkvdnalqsg
nsqesvteqdskdstyslsstltlskadyekhkvyacevthqglsspvtksfnrgec SEQ ID NO: 43
8.10.3 and 8.10.3-Ser Light Chain [Kappa chain] nucleotide sequence
atggaaaccccagcgcagcttctcttcctcctgctactctggctcccagataccaccggaGAATTTGTGTTG
ACGCAGTCTCCAGGCACCCTGTCTTTGTCTCCAGGGGAAAGAGCCACCC
TCTCCTGCAGGGCCAGTCAGAGTGTTAGCAGCAGTTACTTAGCCTGGTA
CCAGCAGAAACCTGGCCAGGCTCCCAGGCTCCTCATCTATGGTGCATCC
AGCAGGGCCACTGGCATCCCAGACAGGTTCAGTGGCAGTGGGTCTGGG
ACAGACTTCACTCTCACCATCAGCAGACTGGAGCCTGAAGATTTTGTAG
TGTATTACTGTCAGCAGTATGGTAGCTCACCTCTCACTTTCGGCGGAGG
GACCAAGGTGGAGATCAAACGAactgtggctgcaccatctgtcttcatcttcccgccatctgatga
gcagttgaaatctggaactgcctctgttgtgtgcctgctgaataacttctatcccagagaggccaaagtacagtggaag

| SEQUENCES |
| --- |
| gtggataacgccctccaatcgggtaactcccaggagagtgtcacagagcaggacagcaaggacagcacctacagcc<br>tcagcagcaccctgacgctgagcaaagcagactacgagaaacacaaagtctacgcctgcgaagtcacccatcaggg<br>cctgagctcgcccgtcacaaagagcttcaacaggggagagtgt<br><br>SEQ ID NO: 44<br>8.10.3 and 8.10.3-Ser Light Chain [Kappa chain] protein sequence<br>metpaqllflllllwlpdttgEFVLTQSPGTLSLSPGERATLSCRASQSVSSSYLAWYQQ<br>KPGQAPRLLIYGASSRATGIPDRFSGSGSGTDFTLTISRLEPEDFVVYYCQQ<br>YGSSPLTFGGGTKVEIKRtvaapsvfifppsdeqlksgtasvvcllnnfypreakvqwkvdnalqsg<br>nsqesvteqdskdstyslsstltlskadyekhkvyacevthqglsspvtksfnrgec<br><br>SEQ ID NO: 58<br>8.10.3C-Ser Heavy Chain [Gamma chain] protein sequence<br>melglcwvflvailegvqcEVQLVESGGGLVQPGGSLRLSCAASGFTFSSFSMTWV<br>RQAPGKGLEWVSYISSRSSTISYADSVKGRFTISRDNAKNSLYLQMNSLRD<br>EDTAVYYCARDPLLAGATFFDYWGQGTLVTVSSAstkgpsvfplapcsrstsestaalg<br>clykdyfpepytvswnsgaltsgvhtfpavlqssglyslssvvtvpssslgtktytcnvdhkpsntkvdkrveskyg<br>ppcpPcpapeflggpsvflfppkpkdtlmisrtpevtcvvvdvsqedpevqfnwyvdgvevhnaktkpreeqf<br>nstyrvvsvltvlhqdwingkeykckvsnkglpssiektiskakgqprepqvytlppsqeemtknqvsltclykgf<br>ypsdiavewesngqpennykttppvldsdgsffflysrltvdksrwqegnyfscsvmhealhnhytqkslslspgk<br><br>SEQ ID NO: 60<br>8.10.3-CG2, 8.10.3-CG4 and 8.10.3C-Ser Light Chain [kappa chain] protein<br>sequence<br>metpaqllflllllwlpdttgEIVLTQSPGTLSLSPGERATLSCRASQSVSSSYLAWYQQ<br>KPGQAPRLLIYGASSRATGIPDRFSGSGSGTDFTLTISRLEPEDFAVYYCQQ<br>YGSSPLTFGGGTKVEIKRtvaapsvfifppsdeqlksgtasvvcllnnfypreakvqwkvdnalqsg<br>nsqesvteqdskdstyslsstltlskadyekhkvyaceythqglsspytksfnrgec<br><br>SEQ ID NO: 62<br>8.10.3-CG2 Heavy Chain [Gamma chain] protein sequence<br>melglcwvflvailegvqcEVQLVESGGGLVQPGGSLRLSCAASGFTFSSFSMTWV<br>RQAPGKGLEWVSYISSRSSTISYADSVKGRFTISRDNAKNSLYLQMNSLRD<br>EDTAVYYCARDPLLAGATFFDYWGQGTLVTVSSAstkgpsvfplapcsrstsestaalg<br>clykdyfpepytyswnsgaltsgyhtfpaylqssglyslssyytypssnfgtqtytcnvdhkpsntkvdktverkcc<br>vecppcpappyagpsvflfppkpkdtlmisrtpevtcvvvdvshedpevqfnwyydgvevhnaktkpreeqfn<br>stfrvvsvltvvhqdwingkeykckvsnkglpapiektisktkgqprepqvytlppsreemtknqvsltclvkgfy<br>psdiavewesngqpennykttppmldsdgsffflyskltvdksrwqqgnvfscsvmhealhnhytqkslslspgk<br><br>SEQ ID NO: 90<br>8.10.3-Ser Heavy Chain [Gamma chain] protein sequence<br>melglcwvflvailegvqcEVQLVESGGGLVQPGGSLRLSCAASGFTFSSFSMTWV<br>RQAPGKGLEWVSYISSRSSTISYADSVKGRFTISRDNAKNSLYLQMNSLRD<br>EDTAVYYCARDPLLAGATFFDYWGQGTLVTVSSAstkgpsvfplapcsrstsestaalg<br>clykdyfpepytyswnsgaltsgyhtfpavlqssglyslssvvtypssslgtktytcnvdhkpsntkvdkrveskyg<br>ppcpPcpapeflggpsvflfppkpkdtlmisrtpevtcvvvdvsqedpevqfnwyvdgvevhnaktkpreeqf<br>nstyrvvsyltylhqdwingkeykckvsnkglpssiektiskakgqprepqvytlppsqeemtknqvsltclykgf<br>ypsdiavewesngqpennykttppvldsdgsffflysrltvdksrwqegnyfscsvmhealhnhytqkslslspgk<br><br>SEQ ID NO: 94<br>8.10.3-CG4 Heavy Chain [Gamma chain] protein sequence<br>melglcwvflvailegvqcEVQLVESGGGLVQPGGSLRLSCAASGFTFSSFSMTWV<br>RQAPGKGLEWVSYISSRSSTISYADSVKGRFTISRDNAKNSLYLQMNSLRD<br>EDTAVYYCARDPLLAGATFFDYWGQGTLVTVSSAstkgpsvfplapcsrstsestaalg<br>clvkdyfpepvtvswnsgaltsgvhtfpavlqssglyslssvvtvpssslgtktytcnvdhkpsntkvdkryeskyg<br>ppcpscpapeflggpsvflfppkpkdtlmisrtpevtcvvvdvsqedpevqfnwyvdgvevhnaktkpreeqf<br>nstyrvvsvltvlhqdwlngkeykckvsnkglpssiektiskakgqprepqvytlppsqeemtknqvsltclvkgf<br>ypsdiavewesngqpennykttppvldsdgsffflysrltvdksrwqegnyfscsvmhealhnhytqkslslspgk<br><br>SEQ ID NO: 97<br>8.10.3FG1 Heavy Chain nucleotide sequence<br>atggagttggggctgagctggttttccttgttgctattataaaaggtgtccagtgtGAGGTGCAGCTGGTG<br>GAGTCTGGGGGAGGCTTGGTACAGCCTGGGGGTCCCTGAGACTCTCC<br>TGTGCAGCCTCTGGATTCACCTTCAGTAGTTTTAGTATGACCTGGGTCC<br>GCCAGGCTCCAGGAAAGGGGCTGGAGTGGGTTTCATACATTAGTAGTA<br>GAAGTAGTACCATATCCTACGCAGACTCTGTGAAGGGCCGATTCACCA<br>TCTCCAGAGACAATGCCAAGAACTCACTGTATCTGCAAATGAACAGCC<br>TGAGAGACGAGGACACGGCTGTGTATTACTGTGCGAGAGATCCTCTTCT<br>AGCGGGAGCTACCTTCTTTGACTACTGGGGCCAGGGAACCCTGGTCAC<br>CGTCTCCTCAGCCtccaccaagggcccatcggtcttccccctggcaccctcctccaagagcacctctggg<br>ggcacagcggccctgggctgcctggtcaaggactacttccccgaaccggtgacggtgtcgtggaactcaggcgccc<br>tgaccagcggcgtgcacaccttcccggctgtcctacagtcctcaggactctactccctcagcagcgtggtgaccgtgc<br>cctccagcagcttgggcacccagacctacatctgcaacgtgaatcacaagcccagcaacaccaaggtggacaagaa<br>agttgagcccaaatcttgtgacaaaactcacacatgcccaccgtgcccagcacctgaactcctggggggaccgtcagt<br>cttcctcttccccccaaaacccaaggacaccctcatgatctcccggacccctgaggtcacatgcgtggtggtggacgtg |

-continued

| SEQUENCES |
|---|
| agccacgaagaccctgaggtcaagttcaactggtacgtggacggcgtggaggtgcataatgccaagacaaagccgc
gggaggagcagtacaacagcacgtaccgtgtggtcagcgtcctcaccgtcctgcaccaggactggctgaatggcaa
ggagtacaagtgcaaggtctccaacaaagccctcccagccccatcgagaaaaccatctccaaagccaaagggcag
ccccgagaaccacaggtgtacaccctgcccccatcccgggatgagctgaccaagaaccaggtcagcctgacctgcc
tggtcaaaggcttctatcccagcgacatcgccgtggagtgggagagcaatgggcagccggagaacaactacaagac
cacgcctcccgtgctggactccgacggctccttcttcctctacagcaagctcaccgtggacaagagcaggtggcagca
ggggaacgtcnctcatgctccgtgatgcatgaggctctgcacaaccactacacgcagaagagcctctccctgtctccg
ggtaaatag |

SEQ ID NO: 98
8.10.3FG1 Heavy chain (gamma chain) protein sequence
melqlcwvflvaileqvqcEVQLVESGGGLVQPGGSLRLSCAASGFTFSSFSMTWV
RQAPGKGLEWVSYISSRSSTISYADSVKGRFTISRDNAKNSLYLQMNSLRD
EDTAVYYCARDPLLAGATFFDYWGQGTLVTVSSAstkgpsvfplapssksts ggtaal
gclvkdyfpepvtvswnsgaltsgvhtfpavlqssglyslssvvtvpssslgtqtyicnvnhkpsntkvdkkvepk
scdkthtcppcpapellggpsvflfppkpkdtlmisrtpevtcvvvdvshedpevkfnwyvdgvevhnaktkpr
eeqynstyrvvsyltvlhqdwlngkeykckvsnkalpapiektiskakgqprepqvytlppsrdeltknqvsltclv
kgfypsdiavewesngqpennykttppvldsdgsfflysltvdksrwqqgnvfscsvmhealhnhytqkslsls
pgk SEQ ID NO: 33
9.7.2IF Heavy Chain [Gamma chain] nucleotide sequence
atggagtttgggctgagctgggttttccttgttgctattataaaaggtgtccagtgtcAGGTGCAGCTGGTG
GAGTCTGGGGGAGGCTTGGTCAAGCCTGGAGGGTCCCTGAGACTCTCC
TGTGCAGCCTCTGGATTCACCTTCAGT<u>GACTACTACATGAGC</u>TGGATCC
GCCAGGCTCCAGGGAAGGGGCTGGAGTGGGTTTCA<u>TACATTAGTAGTA
GTGGTAGTACCATATACTACGCAGACTCTGTGAAGGGC</u>CGATTCACCAT
CTCCAGGGACAACGCCAAGAATTCACTGTATCTGCAAATGAACAGCCT
GAGAGCCGAGGACACGGCCGTGTATTACTGTGCGAGG<u>CGTATAGGAGG
TATGGACGTC</u>TGGGGCCAAGGGACCACGGTCACCGTCTCCTCAGCTtcca
ccaagggcccatccgtcttccccctggcgccctgctctagaagcacctccgagagcacagcggccctgggctgcctg
gtcaaggactacttccccgaaccggtgacggtgtcgtggaactcaggcgctctgaccagcggcgtgcacaccttccc
agctgtcctacagtcctcaggactctactccctcagcagcgtggtgaccgtgccctccagcaacttcggcacccagac
ctacacctgcaacgtagatcacaagcccagcaacaccaaggtggacaagacagttgagcgcaaatgttgtgtcgagt
gcccaccgtgcccagcaccacctgtggcaggaccgtcagtcttcctcttccccaaaacccaaggacaccctcatga
tctcccggacccctgaggtcacgtgcgtggtggtggacgtgagccacgaagaccccgaggtccagttcaactggtac
gtggacggcgtggaggtgcataatgccaagacaaagccacgggaggagcagttcaacagcacgttccgtgtggtca
gcgtcctcaccgttgtgcaccaggactggctgaacggcaaggagtacaagtgcaaggtctccaacaaaggcctccca
gcccccatcgagaaaaccatctccaaaaccaaagggcagccccgagaaccacaggtgtacaccctgcccccatccc
gggaggagatgaccaagaaccaggtcagcctgacctgcctggtcaaaggcttctaccccagcgacatcgccgtgga
gtgggagagcaatgggcagccggagaacaactacaagaccacacctcccatgctggactccgacggctccttcttcc
tctacagcaagctcaccgtggacaagagcaggtggcagcaggggaacgtcttctcatgctccgtgatgcatgaggct
ctgcacaaccactacacgcagaagagcctctccctgtctccgggtaaa SEQ ID NO: 34
9.7.2IF Heavy Chain [Gamma Chain] protein sequence
mefqlswvflvaiikqvqcQVQLVESGGGLVKPGGSLRLSCAASGFTFSDYYMSWI
RQAPGKGLEWVSYISSSGSTIYYADSVKGRFTISRDNAKNSLYLQMNSLRA
EDTAVYYCARRRIGGMDVWGQGTTVTVSSAstkgpsvfplapcsrstsestaalgclvkdyf
pepvtvswnsgaltsgvhtfpavlqssglyslssvvtvpssnfgtqtytcnvdhkpsntkvdktverkccvecppc
pappvagpsvflfppkpkdtlmisrtpevtcvvvdvshedpevqfnwyvdgvevhnaktkpreeqfnstfrvvs
vltvvhqdwlngkeykckvsnkglpapiektisktkgqprepqvytlppsreemtknqvsltclvkgfypsdiav
ewesngqpennykttppmldsdgsfflyskltvdksrwqqgnvfscsvmhealhnhytqkslslspgk SEQ ID NO: 35
9.7.2IF Light Chain [Kappa chain] nucleotide sequence
atggacatgagggtccccgctcagctcctggggctcctgctactctggctccgaggtgccagatgtGACATCC
AGATGACCCAGTCTCCATCCTCCCTGTCTGCATCTGTAGGAGACAGAGT
CACCATCACTTGC<u>CGGGCAAGTCAGAGCATTAGCGGCTTTTTAATT</u>TGG
TATCAGCAGAGACCAGGGAAAGCCCCTAAGCTCCTGATCTAT<u>GCTACA
TCCAGTTTACAAAGT</u>GGGGTCCCATCAAGGTTCAGTGGCAGTGGATCTG
GGACAGATTTCACTCTCACCATCAGCAGTCTGCAACCTGAAGATTTTGC
AACTTACTACTGT<u>CAACAGAGTTACAGTACCCC</u>ATTCACTTTCGGCCCT
GGGACCAAAGTGGATATCAAACGAactgtggctgcaccatctgtcttcatcttcccgccatctga
tgagcagttgaaatctggaactgcctctgttgtgtgcctgctgaataacttctatcccagagaggccaaagtacagtgga
aggtggataacgccctccaatcgggtaactcccaggagagtgtcacagagcaggacagcaaggacagcacctaca
gcctcagcagcaccctgacgctgagcaaacagactacgagaaacacaaagtctacgcctgcgaagtcacccatca
gggcctgagctcgcccgtcacaaagagcttcaacaggggagagtgt SEQ ID NO: 36
9.7.2IF Light Chain [Kappa chain] protein sequence
mdmrvpaqllqllllwlrqarcDIQMTQSPSSLSASVGDRVTITC<u>RASQSISGFLI</u>WYQ
QRPGKAPKLLIY<u>ATSSLQS</u>GVPSRFSGSGSGTDFTLTISSLQPEDFATYYC<u>Q
QSYSTP</u>FTFGPGTKVDIKRtvaapsvfifppsdeqlksgtasvvcllnnfypreakvqwkvdnalqs
gnsqesvteqdskdstyslsstltlskadyekhkvyacevthqglsspvtksfnrgec SEQ ID NO: 45
9.7.2 Heavy Chain [Gamma chain] nucleotide sequence
atggagtttgggctgagctgggttttccttgttgctattataaaaggtgtccagtgtcAGGTGCAGCTGGTG
GAGTCTGGGGGAGGCTTGGTCAAGCCTGGAGGGTCCCTGAGACTCTCC
TGTGCAGCCTCTGGATTCACCTTCAGTGACTACTACATGAGCTGGATCC
GCCAGGCTCCAGGGAAGGGGCTGGAGTGGGTTTCATACATTAGTAGTA
GTGGTAGTACCATATACTACGCAGACTCTGTGAAGGGCCGATTCACCAT
CTCCAGGGACAACGCCAAGAATTCACTGTATCTGCAAATGAACAGCCT
GAGAGCCGAGGACACGGCCGTGTATTACTGTGCGAGGCGTATAGGAGG
TATGGACGTCTGGGGCCAAGGGACCACGGTCACCGTCTCCTCAGCTtcca
ccaagggcccatccgtcttcccctggcgccctgctctagaagcacctccgagagcacagcggccctgggctgcctg
gtcaaggactacttccccgaaccggtgacggtgtcgtggaactcaggcgctctgaccagcggcgtgcacacctccc
agctgtcctacagtcctcaggactctactccctcagcagcgtggtgaccgtgccctccagcagcttgggcacgaagac
ctacacctgcaacgtagatcacaagcccagcaacaccaaggtggacaagagagttgagtccaaatatggtccccat
gcccatcatgcccagcacctgagttcctgggggaccatcagtcttcctgttccccccaaaacccaaggacactctcat
gatctcccggacccctgaggtcacgtgcgtggtggtggacgtgagccaggaagaccccgaggtccagttcaactggt
acgtggatggcgtggaggtgcataatgccaagacaaagccgcgggaggagcagttcaacagcacgtaccgtgtggt
cagcgtcctcaccgtcctgcaccaggactggctgaacggcaaggagtacaagtgcaaggtctccaacaaaggcctc
ccgtcctccatcgagaaaaccatctccaaagccaaagggcagccccgagagccacaggtgtacaccctgcccccat
cccgaggagatgaccaagaaccaggtcagcctgacctgcctggtcaaaggcttctatcccagcgacatcgccgt
ggagtgggagagcaatgggcagccggagaacaactacaagaccacgcctcccgtgctggactccgacggctccttc
ttcctctacagcaggctaaccgtggacaagagcaggtggcaggaggggaatgtcttctcatgctccgtgatgcatgag
gctctgcacaaccactacacacagaagagcctctccctgtctccgggtaaa SEQ ID NO: 46
9.7.2 Heavy Chain [Gamma Chain] protein sequence
mefglswvflvaiikgvqcQVQLVESGGGLVKPGGSLRLSCAASGFTFSDYYMSWI
RQAPGKGLEWVSYISSSGSTIYYADSVKGRFTISRDNAKNSLYLQMNSLRA
EDTAVYYCARRIGGMDVWGQGTTVTVSSAstkgpsvfplapcsrstsestaalgclvkdyf
pepvtvswnsgaltsgvhtfpavlqssglyslssvvtvpssslgtktytcnvdhkpsntkvdkrveskygppcpsc
papeflggpsvflfppkpkdtlmisrtpevtcvvvdvsqedpevqfnwyvdgvevhnaktkpreeqfnstyrvv
svltvlhqdwlngkeykckvsnkglpssiektiskakgqprepqvytlppsqeemtknqvsltclvkgfypsdia
vewesngqpennykttppvldsdgsfflysrltvdksrwqegnvfscsvmhealhnhytqkslslspgk SEQ ID NO: 47
9.7.2 and 9.7.2-Ser Light Chain [Kappa chain] nucleotide sequence
atggacatgagggtccccgctcagctcctggggctcctgctactctggctcccagaggtgccagatgtGACATCC
AGATGACCCAGTCTCCATCCTCCCTGTCTGCATCTGTAGGAGACAGAGT
CACCATCACTTGCCGGGCAAGTCAGAGCATTAGCGGCTTTTTAATTTGG
TATCAGCAGAGACCAGGGAAAGCCCCTAAGCTCCTGATCTATGCTACA
TCCAGTTTACAAAGTGGGGTCCCATTAAGGTTCAGTGGCAGTGGAATCTG
GGACAGATTTCACTCTCACCATCAGCAGTCTGCAACCTGAAGATTTTGC
AACTTACTACTGTCAACAGAGTTACAGTACCCCATTCACTTTCGGCCCT
GGGACCAAAGTGGATATCAAACGAactgtggctgcaccatctgtcttcatcttcccgccatctga
tgagcagttgaaatctggaactgcctctgttgtgtgcctgctgaataacttctatcccagagaggccaaagtacagtgga
aggtggataacgccctccaatcgggtaactcccaggagagtgtcacagagcaggacagcaaggacagcacctaca
gcctcagcagcaccctgacgctgagcaaagcagactacgagaaacacaaagtctacgcctgcgaagtcacccatca
gggcctgagctcgcccgtcacaaagagcttcaacaggggagagtgt SEQ ID NO: 48
9.7.2 and 9.7.2-Ser Light Chain [Kappa chain] protein sequence
mdmrvpaqllqllllwlrqarcDIQMTQSPSSLSASVGDRVTITCRASQSISGFLIWYQ
QRPGKAPKLLIYATSSLQSGVPLRFSGSESGTDFTLTISSLQPEDFATYYCQ
QSYSTPFTFGPGTKVDIKRtvaapsvfifppsdeqlksgtasvvcllnnfypreakvqwkvdnalqs
gnsqesvteqdskdstyslsstltlskadyekhkvyacevthqglsspvtksfnrgec SEQ ID NO: 50
9.7.2C-Ser Heavy Chain [Gamma chain] protein sequence
mefglswvflvaiikgvqcQVQLVESGGGLVKPGGSLRLSCAASGFTFSDYYMSWI
RQAPGKGLEWVSYISSSGSTIYYADSVKGRFTISRDNAKNSLYLQMNSLRA
EDTAVYYCAIRIGGMDVWGQGTTVTVSSAstkgpsvfplapcsrstsestaalgclvkdyfp
epvtvswnsgaltsgvhtfpavlqssglyslssvvtvpssslgtktytcnvdhkpsntkvdkryeskygppcppcp
apeflggpsvflfppkpkdtlmisrtpevtcvvvdvsqedpevqfnwyvdgvevhnaktkpreeqfnstyrvvs
vltvlhqdwlngkeykckvsnkglpssiektiskakgqprepqvytlppsqeemtknqvsltclvkgfypsdiav
ewesngqpennykttppvldsdgsfflysrltvdksrwqegnvfscsvmhealhnhytqkslslspgk SEQ ID NO: 52
9.7.2C-Ser, 9.7.2-CG2 and 9.7.2-CG4 Light Chain [Kappa chain] protein sequence
mdmrvpaqllqllllwlrqarcDIQMTQSPSSLSASVGDRVTITCRASQSISGFLIWYQ
QKPGKAPKLLIYATSSLQSGVPSRFSGSGSGTDFTLTISSLQPEDFATYYCQ
QSYSTPFTFGPGTKVDIKRtvaapsvfifppsdeqlksgtasvvcllnnfypreakvqwkvdnalqs
gnsqesvteqdskdstyslsstltlskadyekhkvyacevthqglsspvtksfnrgec SEQ ID NO: 66
9.7.2-CG2 Heavy Chain [Gamma chain] protein sequence
mefglswvflvaiikgvqcQVQLVESGGGLVKPGGSLRLSCAASGFTFSDYYMSWI
RQAPGKGLEWVSYISSSGSTIYYADSVKGRFTISRDNAKNSLYLQMNSLRA

| SEQUENCES |
|---|
| EDTAVYYCAI<u>RIG</u>GMDVWGQGTTVTVSSAstkgpsvfplapcsrstsestaalgclvkdyfp<br>epytyswnsgaltsgyhtfpavlqssglysissvvtypssnfgtqtytcnvdhkpsntkvdktverkccvecppcp<br>appvagpsvflfppkpkdtlmisrtpevtcvvvdvshedpevqfnwyydgvevhnaktkpreeqfnstfrvvsv<br>ltvvhqdwingkeykckvsnkglpapiektisktkgqprepqvytlppsreemtknqvsltclvkgfypsdiave<br>wesngqpennykttppmldsdgsfflyskltvdksrwqqgnvfscsvmhealhnhytqkslslspgk<br><br>SEQ ID NO: 70<br>9.7.2-CG4 Heavy Chain [Gamma chain] protein sequence<br><u>mefglswvflvaiikgvqc</u>QVQLVESGGGLVKPGGSLRLSCAAS<u>GFTFSDYYMSWI</u><br><u>RQAPGKGLEWVSYISSSGSTIYYADSVK</u>GRFTISRDNAKNSLYLQMNSLRA<br>EDTAVYYCA<u>RIG</u>GMDVWGQGTTVTVSSAstkgpsvfplapcsrstsestaalgclvkdyfp<br>epvtvswnsgaltsgyhtfpaylqssglysissvvtypsssslgtktytcnvdhkpsntkvdkrveskygppcpscp<br>apeflgpsvflfppkpkdtlmisrtpevtcvvvdvsqedpevqfnwyvdgvevhnaktkpreeqfnstvrvvs<br>vltvlhqdwingkeykckvsnkglpssiektiskakgqprepqvytlppsqeemtknqvsltclvkgfypsdiav<br>ewesngqpennykttppvldsdgsfflysrltydksrwqegnvfscsvmhealhnhytqkslslspgk<br><br>SEQ ID NO: 86<br>9.7.2-Ser Heavy Chain [Gamma chain] protein sequence<br><u>mefglswvflvaiikgvqc</u>QVQLVESGGGLVKPGGSLRLSCAAS<u>GFTFSDYYMSWI</u><br><u>RQAPGKGLEWVSYISSSGSTIYYADSVK</u>GRFTISRDNAKNSLYLQMNSLRA<br>EDTAVYYCAR<u>RIG</u>GMDVWGQGTTVTVSSAstkgpsvfplapcsrstsestaalgclvkdyf<br>pepvtvswnsgaltsgyhtfpavlqssglyslssvvtypssslgtktytcnvdhkpsntkvdkrveskygppcppc<br>papeflgpsvflfppkpkdtlmisrtpevtcvvvdvsqedpevqfnwyvdgvevhnaktkpreeqfnstvrvv<br>svltvlhqdwingkeykckvsnkglpssiektiskakgqprepqvytlppsqeemtknqvsltclvkgfypsdia<br>vewesngqpennykttppvldsdgsfflysrltvdksrwqegnvfscsvmhealhnhytqkslslspgk |

Key:
Signal peptide: underlined lower case
CDRs 1,2,3: underlined UPPERCASE
Variable domain: UPPER CASE
Constant domain: lower case
Mutations from germline in bold

What is claimed:

1. A monoclonal antibody or an antigen-binding fragment thereof that specifically binds macrophage colony stimulating factor (M-CSF), wherein the antibody comprises the amino acid sequences of the complementarity determining region (CDR) 1, CDR2 and CDR3 in SEQ ID NO: 34 and the amino acid sequences of the CDR1, CDR2 and CDR3 in SEQ ID NO: 36.

2. The monoclonal antibody or antigen-binding fragment according to claim 1, wherein the antibody comprises the heavy chain variable domain in SEQ ID NO: 34 without the signal sequence, and the light chain variable domain in SEQ ID NO: 36 without the signal sequence.

3. The monoclonal antibody or antigen-binding fragment according to claim 2, wherein the heavy chain amino acid sequence of the monoclonal antibody is SEQ ID NO: 34 without the signal sequence, and the light chain amino acid sequence of the monoclonal antibody is SEQ ID NO: 36 without the signal sequence.

4. The monoclonal antibody or antigen-binding fragment according to claim 1, wherein the antibody is an IgG molecule.

5. The monoclonal antibody or antigen-binding fragment according to claim 2, wherein the antibody is an IgG molecule.

6. The antigen-binding fragment according to claim 1, wherein the fragment is selected from the group consisting of: an Fab fragment, an F(ab')$_2$ fragment and an Fv fragment.

7. The antigen-binding fragment according to claim 2, wherein the fragment is selected from the group consisting of: an Fab fragment, an F(ab')$_2$ fragment and an Fv fragment.

8. A pharmaceutical composition comprising the monoclonal antibody according to claim 1 and a pharmaceutically acceptable carrier.

9. The pharmaceutical composition according to claim 8, wherein the antibody comprises the heavy chain variable domain in SEQ ID NO: 34 without the signal sequence, and the light chain variable domain in SEQ ID NO: 36 without the signal sequence.

10. The pharmaceutical composition according to claim 9, wherein the heavy chain amino acid sequence of the monoclonal antibody is SEQ ID NO: 34 without the signal sequence, and the light chain amino acid sequence of the monoclonal antibody is SEQ ID NO: 36 without the signal sequence.

11. The pharmaceutical composition according to claim 8, wherein the antibody is an IgG molecule.

12. The pharmaceutical composition according to claim 8, wherein the fragment is selected from the group consisting of: an Fab fragment, an F(ab')$_2$ fragment and an Fv fragment.

* * * * *